(12) United States Patent
Saito et al.

(10) Patent No.: US 8,420,810 B2
(45) Date of Patent: Apr. 16, 2013

(54) BICYCLIC HETEROCYCLIC COMPOUND

(75) Inventors: Tetsuji Saito, Osaka (JP); Tetsuo Obitsu, Osaka (JP); Yoshifumi Kagamiishi, Osaka (JP)

(73) Assignee: Ono Pharmaceutical, Co., Ltd., Osaka (JP)

( * ) Notice: Subject to any disclaimer, the term of this patent is extended or adjusted under 35 U.S.C. 154(b) by 247 days.

(21) Appl. No.: 12/597,302

(22) PCT Filed: Apr. 25, 2008

(86) PCT No.: PCT/JP2008/058014
§ 371 (c)(1),
(2), (4) Date: Oct. 23, 2009

(87) PCT Pub. No.: WO2008/136377
PCT Pub. Date: Nov. 13, 2008

(65) Prior Publication Data
US 2010/0137318 A1    Jun. 3, 2010

(30) Foreign Application Priority Data

Apr. 26, 2007 (JP) ................................ 2007-117757
Nov. 13, 2007 (JP) ................................ 2007-294024
Feb. 6, 2008 (JP) ................................ 2008-026456

(51) Int. Cl.
| C07D 487/04 | (2006.01) |
| A61K 31/53 | (2006.01) |
| A61P 3/04 | (2006.01) |
| A61P 15/12 | (2006.01) |
| A61P 25/18 | (2006.01) |
| A61P 25/22 | (2006.01) |
| A61P 25/24 | (2006.01) |
| A61P 25/30 | (2006.01) |
| A61P 25/32 | (2006.01) |

(52) U.S. Cl.
USPC ............................................ 544/183; 514/243

(58) Field of Classification Search ................ 544/183; 514/243
See application file for complete search history.

(56) References Cited

U.S. PATENT DOCUMENTS
2004/0242587 A1    12/2004    Fu

FOREIGN PATENT DOCUMENTS
| JP | 2006-525309 A | 11/2006 |
| WO | WO 03/099286 A1 | 12/2003 |
| WO | WO 2004/009601 A1 | 1/2004 |
| WO | WO 2004/009784 A2 | 1/2004 |
| WO | WO 2004/099213 A2 | 11/2004 |

OTHER PUBLICATIONS

Zorrilla, E.P., et al., Drug Discov Today. May 2010; 15(9-10): 371-383.*
Nielsen, Life Sciences, 78, 909-919, 2006.*
Mitchell, Neurosci. Biobehav. Rev. 22(5); 635-651, 1998.*
Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
International Search Report [PCT/ISA/210] for PCT/JP2008/058014 issued Jul. 22, 2008.
Extended European Search Report dated Dec. 5, 2011, issued by the European Patent Office in corresponding European Patent Application No. 08752088.8.

* cited by examiner

*Primary Examiner* — Venkataraman Balasubramanian
(74) *Attorney, Agent, or Firm* — Sughrue Mion, PLLC

(57) ABSTRACT

A compound of a formula (I):

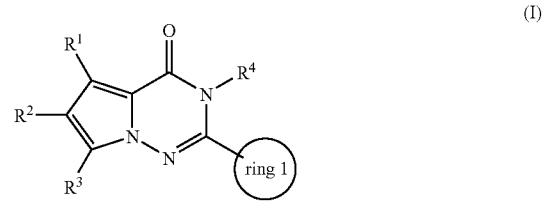

wherein $R^1$ represents a C3-10 branched alkyl group which may be substituted; $R^2$ represents a hydrogen atom or a C1-4 alkyl group which may be substituted; $R^3$ represents a C1-4 alkyl group which may be substituted or a halogen atom; $R^4$ represents a C1-4 alkyl group which may be substituted; and ring 1 represents a cyclic group which has planarity and may have a substituent group, a salt thereof, an N-oxide thereof or a solvate thereof, or a prodrug thereof, is useful as a medicinal component having CRF antagonistic activity for the prevention and/or treatment of a neuropsychiatric disease, a peripheral organ disease and the like.

18 Claims, No Drawings

BICYCLIC HETEROCYCLIC COMPOUND

TECHNICAL FIELD

The present invention relates to a novel bicyclic heterocyclic ring compound or a salt thereof, and a pharmaceutical containing as an active ingredient the same. More specifically, the present invention relates to a novel bicyclic heterocyclic ring compound represented by the formula (I), a salt thereof, an N-oxide thereof, a solvate thereof, or a prodrug thereof, and a pharmaceutical containing as an active ingredient the same:

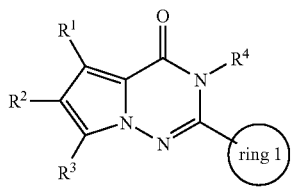

(I)

wherein all symbols represent the same meanings as described hereinafter.

BACKGROUND ART

Corticotropin Releasing Factor (CRF) is a peptide including 41 amino acid isolated from ovine hypothalamic in 1981. It was suggested that CRF was released from hypothalamic and controlled a secretion of adrenocorticotropic hormone (ACTH) from hypophysis [Science, 218, 377-379 (1982)].

ACTH, which is released by a stimulation of CRF, stimulates a secretion of cortisol from adrenal cortex, and relates to a systemic action for reproduction, growth, gastrointestinal function, inflammation, immune system, nervous system, etc. Consequently, CRF is believed to plays a role as a regulator of these functions. In view of those things, an involvement of CRF with neuropsychiatric diseases, digestive diseases has received attention.

On the other hand, the depression patients and the anxiety disorder patients increase, and the number also of depression patients with the slight illness increases recently. Moreover, an aged patient is commanding a majority in the depression patient. Under these circumstances, from the earliness of the appearance of the effect and in view of the side effect, neuropsychiatric disease treatment which can be easily used is requested more and more.

Currently, for the treatment of neuropsychiatric diseases, for example, tricyclic antidepressants, tetracyclic antidepressants, monoamine oxidase inhibitors, serotonin and noradrenaline reuptake inhibitors (SNRI), selective serotonin reuptake inhibitors (SSRI), etc. as antidepressant are used. However, the therapeutic gain is not enough; it will take a long time by the time the effect appears; drowsiness, a dryness of the mouth, constipation, difficulty feelings in micturition, etc. are seen as a side effect. As an antianxiety agent, such as benzodiazepine anxiolytic, thienodiazepine anxiolytic, non-benzodiazepine anxiolytic etc. are used. However, the therapeutic gain is not also enough; decrease in mental movement function and decrease in concentration and attention power, drowsiness, stagger, dizziness, headache, amnesia, etc. are seen as a side effect.

In WO2003/099286, it is described that a compound of a formula (A):

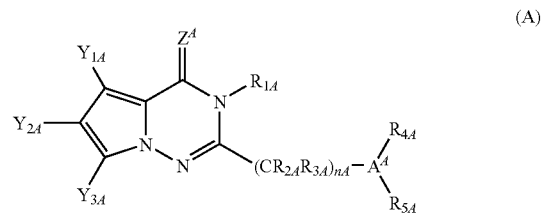

(A)

wherein $Y_{1A}$, $Y_{2A}$ and $Y_{3A}$ are each independently a hydrogen atom, halogen, —CN, alkyl or the like; $Z^A$ is an oxygen atom or a sulfur atom; $R_{1A}$ is a hydrogen atom, alkyl, substituted alkyl, cycloalkyl, substituted cycloalkyl or the like; $R_{2A}$ and $R_{3A}$ are each independently a hydrogen atom, halogen, alkyl or the like; nA is 0 to 4; $A^A$ represents an oxygen atom, a sulfur atom or a nitrogen atom, but when $A^A$ is an oxygen atom or a sulfur atom, $R_{5A}$ is not present; and $R_{4A}$ and $R_{5A}$ each independently represent a hydrogen atom, alkyl or the like, in this connection, necessary parts were extracted from the description of groups, has the action to control Eg5 motor protein and becomes a therapeutic agent for a proliferative disease such as a cancer (cf. Patent Reference 1).

In WO2004/009784, it is described that a compound of a formula (B):

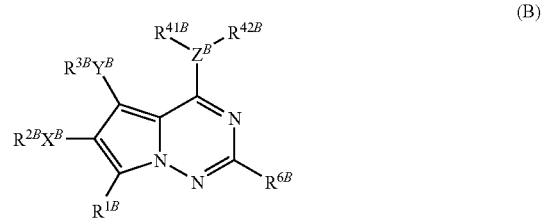

(B)

wherein $Z^B$ is selected from the group consisting of an oxygen atom, a sulfur atom, a nitrogen atom, a hydroxyl group and a chlorine atom, and when $Z^B$ is a hydroxyl group or a chlorine atom, $R^{41B}$ and $R^{42B}$ are not present; $X^B$ and $Y^B$ are each independently selected from the group consisting of —O—, —OCO— and the like or not present; $R^{1B}$ is a hydrogen atom, methyl or the like; $R^{2B}$ and $R^{3B}$ are each independently a hydrogen atom, alkyl or the like; and $R^{6B}$ represents a hydrogen atom, alkyl, substituted alkyl, aryl, substituted aryl, heterocyclo, substituted heterocyclo or the like, in this connection necessary parts were extracted from the description of groups, has a tyrosine kinase inhibitory activity and is useful as an antitumor agent (cf. Patent Reference 2).

In WO2005/026126, it is described that a compound of a formula (C):

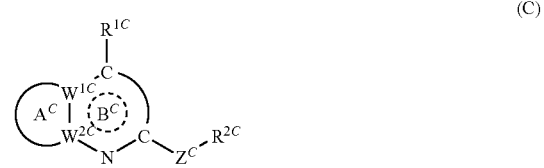

(C)

wherein $A^C$ ring is a 5- or 6-membered single ring which may be substituted by 1 to 3 substituent groups; $B^C$ ring is a 5- to 7-membered monocyclic unsaturated heterocyclic ring which may further contain, other than a nitrogen atom, $W^{1C}$ and $W^{2C}$, 1 or 2 hetero atoms selected from a nitrogen atom, an oxygen atom and/or a sulfur atom which may be oxidized, and may be further substituted; $W^{1C}$ and $W^{2C}$ are each independently a carbon atom or a nitrogen atom; $Z^C$ is —$NR^{3C}$—, an oxygen atom, a sulfur atom which may be oxidized or —$CR^{4C}R^{5C}$— wherein $R^{4C}$ and $R^{5C}$ each independently represent a hydrogen atom, C1-6 alkyl, C2-6 alkenyl or C2-6 alkynyl which may be substituted, or $R^{4C}$ and $R^{5C}$ may together represent (i) an oxo group, (ii) a C2-5 alkylene group wherein one carbon atom may be replaced with one oxygen atom, nitrogen atom, or sulfur atom which may be oxidized wherein the C2-5 alkylene group may be substituted with a substituent group or (iii) a C1-6 alkylidene group which may be substituted; $R^{1C}$ represents (i) C1-15 alkyl, C2-15 alkenyl or C2-15 alkynyl which may be substituted, (ii) amino which may be protected, (iii) hydroxyl which may be protected, (iv) mercapto which may be protected, (v) —$S(O)_n{}_CR^{6C}$, (vi) —$COR^{7C}$ or (vii) a cyclic group which may be substituted; and $R^{2C}$ represents an unsaturated cyclic group which may be substituted, in this connection necessary parts were extracted from the description of groups, has a CRF antagonistic activity (cf. Patent Reference 3).

In WO2007/069565, it is described that a compound of a formula (D):

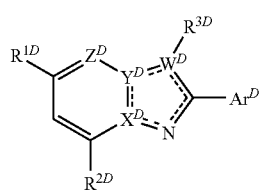

(D)

wherein $X^D$, $Y^D$ and $W^D$ each independently represent carbon atom or nitrogen atom and $Z^D$ is CH or a nitrogen atom; ===== is a single bond or a double bond; $R^{1D}$ is (1) a C3-10 branched alkyl group which may be substituted or (2) a —$(CH_2)_{mD}$—$NR^{4D}R^{5D}$ group; $R^{2D}$ and $R^{3D}$ are each independently (1) a hydrogen atom, (2) a halogen atom, hydroxy which may be protected, amino which may be protected or C1-4 alkyl group which may be substituted with carboxyl which may be protected, (3) a C2-4 alkenyl group, (4) a C2-4 alkynyl group, (5) a nitrile group, (6) $COOR^{6D}$ group, (7) $CONR^{7D}R^{8D}$ group, (8) $COR^{101D}$ group, (9) $S(O)_{nD}R^{102D}$ group or (10) a halogen atom; and $Ar^D$ represents an aromatic cyclic group which may be substituted; in this connection, necessary parts were extracted from the description of groups, has a CRF antagonistic activity (cf. Patent Reference 4).

In WO2007/069671, it is described that a compound of a formula (E):

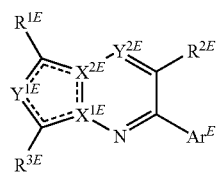

(E)

wherein $X^{1E}$ is a nitrogen atom and $X^{2E}$ is a carbon atom, or $X^{1E}$ is a carbon atom and $X^{2E}$ is a nitrogen atom; $Y^{1E}$ is $CR^{4E}$ or a nitrogen atom; $Y^{2E}$ is CH or a nitrogen atom; wherein $Y^1$ and $Y^2$ do not represent a nitrogen atom at the same time:

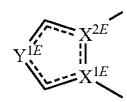

represents

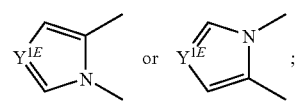

$R^{1E}$ is (1) a C3-10 branched alkyl group which may be substituted or (2) —$(CH2)_{mE}$—$NR^{5E}R^{6E}$ group; $R^{2E}$, $R^{3E}$ and $R^{4E}$ are each independently a hydrogen atom, a C1-4 alkyl group which may be substituted with a halogen atom, a C2-4 alkenyl group, a C2-4 alkynyl group, a nitrile group, $COOR^{7E}$ group, $CONR^{8E}R^{9E}$ group or a halogen atom; $R^{5E}$ and $R^{6E}$ are each independently C1-6 alkyl group which may be substituted, or $R^{5E}$ is a hydrogen atom and $R^{6E}$ is a C3-6 branched alkyl group which may be substituted; mE is 0 or an integer of 1 to 3; $R^{7E}$ is a hydrogen atom or a C1-4 alkyl group; $R^{8E}$ and $R^{9E}$ are each independently a hydrogen atom or a C1-4 alkyl group; and $Ar^E$ represents an aromatic cyclic group which may be substituted, has a CRF antagonistic activity (cf. Patent Reference 5).

[Patent Document 1] WO 2003/099286
[Patent Document 2] WO 2004/009784
[Patent Document 3] WO 2005/026126
[Patent Document 4] WO 2007/069565
[Patent Document 5] WO 2007/069671

DISCLOSURE OF THE INVENTION

Problem to be Solved by the Invention

Although the CRF antagonistic compounds have sufficient activity, their separation from toxicity was not sufficient and they have problems in terms of solubility and stability. Thus, regarding neuropsychiatric diseases or digestive diseases or the like, an agent which is easy to handle, has further strong preventive and/or therapeutic effects, has all of the properties important as a pharmaceutical (e.g., solubility, chemical stability, biological stability and the like) and also has further alleviated side effects (e.g., hepatotoxicity and the like) is desired.

Means for Solving the Problem

The inventors of the present invention studied intensively in order to solve the above problems, and as a result, found that the object can be achieved by a bicyclic heterocyclic compound.

That is, the present invention relates to:

(1) a compound of a formula (I):

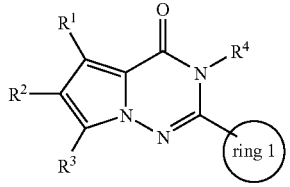

(I)

wherein R¹ represents (1) a C3-10 branched alkyl group which may be substituted or (2) a —(CH₂)$_m$—NR⁵R⁶ group;

R⁵ and R⁶ each independently represent a C1-6 alkyl group which may be substituted, or R⁵ represents a hydrogen atom and R⁶ represents a C3-6 branched alkyl group which may be substituted;

m represents 0 or an integer of 1 to 3;

R² represents a hydrogen atom or a C1-4 alkyl group which may be substituted;

R³ represents a C1-4 alkyl group which may be substituted or a halogen atom;

R⁴ represents a C1-4 alkyl group which may be substituted or a C3-6 cycloalkyl group which may be substituted; and ring 1 represents a cyclic group which has planarity and may have a substituent group, a salt thereof, an N-oxide thereof or a solvate thereof, or a prodrug thereof;

(2) the compound according to (1), wherein the ring 1 is

wherein ring 1$^x$ represents a cyclic group which has planarity; binds to pyrrolo[2,1-f][1,2,4]triazin-4(3H)-one ring through the carbon atom; and may have a substituent group;

(3) the compound according to (1), wherein R¹ is isopropyl, 1-methylbutyl, 1-ethylpropyl, 1-methylpentyl, 1-ethylbutyl, 1-methylhexyl, 1-ethylpentyl, 1-propylbutyl, 1-methylheptyl, 1-ethylhexyl, 1-propylpentyl, (1S)-1-methylbutyl or (1R)-1-methylbutyl;

(4) the compound according to (2), wherein ring 1 is benzene, indane, imidazole, pyrazole, pyrazine, pyridine, pyrimidine, pyridazine, thiophene, oxazole, thiazole, isothiazole, indole, benzothiophene, benzoxazole, benzothiazole, benzimidazole, benzofurazan, benzothiadiazole or benzotriazole having 1-3 substituent(s);

(5) the compound according to (4), wherein ring 1 is benzene, pyridine, pyrimidine or thiazole having 1-3 substituent(s);

(6) the compound according to (5), wherein ring 1 represents the ring represented by one of the following formulae:

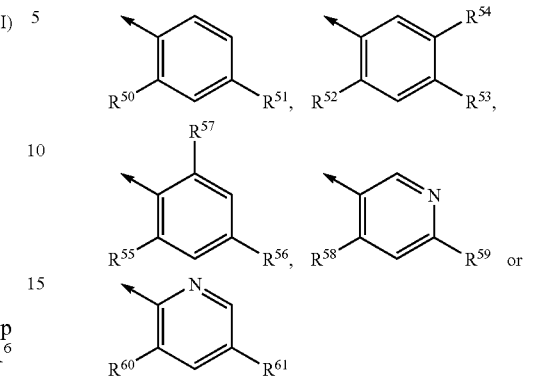

wherein R⁵⁰, R⁵¹, R⁵², R⁵³, R⁵⁴, R⁵⁵, R⁵⁶, R⁵⁷, R⁵⁸, R⁵⁹, R⁶⁰ and R⁶¹ represent the substituent of ring 1, and arrowhead represents a bond with pyrrolo[2,1-f][1,2,4]triazin-4-(3H)-one ring;

(7) the compound according to (6), wherein R⁵⁰, R⁵¹, R⁵², R⁵³, R⁵⁴, R⁵⁵, R⁵⁶, R⁵⁷, R⁵⁸, R⁵⁹, R⁶⁰ and R⁶¹ are each independently C1-6 alkyl, C1-6 alkoxy, difluoromethoxy, trifluoromethoxy, C1-6 alkylthio, a halogen atom, or a cyclic group which may be substituted;

(8) the compound according to (1), wherein the compound is:

<1> 2-[6-(difluoromethoxy)-4-methyl-3-pyridinyl]-5-(1-ethylpropyl)-3,7-dimethylpyrrolo[2,1-f][1,2,4]triazin-4 (3H)-one, <2> 2-[2-chloro-4-(trifluoromethoxy)phenyl]-5-isopropyl-3,7-dimethylpyrrolo[2,1-f][1,2,4]triazin-4(3H)-one, <3> 2-[2-chloro-4-(methylthio)phenyl]-3-ethyl-5-isopropyl-7-methylpyrrolo[2,1-f][1,2,4]triazin-4(3H)-one, <4> 2-[2-chloro-4-(trifluoromethoxy)phenyl]-5-(1-ethylpropyl)-3,7-dimethylpyrrolo[2,1-f][1,2,4]triazin-4(3H)-one, <5> 3-ethyl-5-isopropyl-7-methyl-2-[2-methyl-4-(methylthio)phenyl]pyrrolo[2,1-f][1,2,4]triazin-4(3H)-one, <6> 2-[2-chloro-4-(methylthio)phenyl]-3,7-dimethyl-5-(1-methylbutyl)pyrrolo[2,1-f][1,2,4]triazin-4(3H)-one, <7> 5-(1-ethylpropyl)-2-(5-fluoro-4-methoxy-2-methylphenyl)-3,7-dimethylpyrrolo[2,1-f][1,2,4]triazin-4(3H)-one, <8> 2-(4-chloro-2-methylphenyl)-5-(1-ethylpropyl)-3,7-dimethylpyrrolo[2,1-f][1,2,4]triazin-4(3H)-one, <9> 2-[2-chloro-4-(difluoromethoxy)phenyl]-5-(1-ethylpropyl)-3,7-dimethylpyrrolo[2,1-f][1,2,4]triazin-4(3H)-one, <10> 2-(2-ethyl-4-methoxyphenyl)-5-(1-ethylpropyl)-3,7-dimethylpyrrolo[2,1-f][1,2,4]triazin-4(3H)-one, <11> 5-(1-ethylpropyl)-3,7-dimethyl-2-[2-methyl-4-(1H-pyrazol-1-yl)phenyl]pyrrolo[2,1-f][1,2,4]triazin-4(3H)-one, <12> 2-[2-chloro-4-(methylthio)phenyl]-5-(1-ethylpropyl)-3,7-dimethylpyrrolo[2,1-f][1,2,4]triazin-4(3H)-one, <13> 2-(2-chloro-4-methoxyphenyl)-3-cyclopropyl-5-(1-ethylpropyl)-7-methylpyrrolo[2,1-f][1,2,4]triazin-4(3H)-one, <14> 2-(2-chloro-4-methoxy-6-methylphenyl)-5-(1-ethylpropyl)-3,7-dimethylpyrrolo[2,1-f][1,2,4]triazin-4(3H)-one, <15> 5-(1-ethylpropyl)-2-[4-(1H-imidazol-1-yl)-2-methylphenyl]-3,7-dimethylpyrrolo[2,1-f][1,2,4]triazin-4 (3H)-one, <16> 2-(3-chloro-5-methoxy-2-pyridinyl)-5-(1-ethylpropyl)-3,7-dimethylpyrrolo[2,1-f][1,2,4]triazin-4(3H)-one,
<17> 2-(2-chloro-5-fluoro-4-methoxyphenyl)-5-(1-ethylpropyl)-3,7-dimethylpyrrolo[2,1-f][1,2,4]triazin-4(3H)-one,
<18> 3-ethyl-5-(1-ethylpropyl)-2-(2-fluoro-4-methoxyphenyl)-7-methylpyrrolo[2,1-f][1,2,4]triazin-4(3H)-one,
<19> 5-sec-butyl-2-(2-chloro-5-fluoro-4-methoxyphenyl)-3,7-dimethylpyrrolo[2,1-f][1,2,4]triazin-4(3H)-one,
<20> 5-sec-butyl-2-[2-chloro-4-(difluoromethoxy)phenyl]-3,7-dimethylpyrrolo[2,1-f][1,2,4]triazin-4(3H)-one,
<21> 2-[4-(difluoromethoxy)-5-fluoro-2-methylphenyl]-3-ethyl-5-isopropyl-7-methypyrrolo[2,1-f][1,2,4]triazin-4(3H)-one,
<22> 2-[4-(difluoromethoxy)-2-methylphenyl]-3-ethyl-5-isopropyl-7-methylpyrrolo[2,1-f][1,2,4]triazin-4(3H)-one,
<23> 2-[2-chloro-4-(difluoromethoxy)-6-fluorophenyl]-3-ethyl-5-isopropyl-7-methylpyrrolo[2,1-f][1,2,4]triazin-4(3H)-one,
<24> 2-[2-chloro-4-(difluoromethoxy)phenyl]-3,7-dimethyl-5-(1-methylbutyl)pyrrolo[2,1-f][1,2,4]triazin-4(3H)-one,
<25> 2-(2-chloro-5-fluoro-4-methoxyphenyl)-3,7-dimethyl-5-(1-methylbutyl)pyrrolo[2,1-f][1,2,4]triazin-4(3H)-one,
<26> 2-[6-(difluoromethoxy)-4-methyl-3-pyridinyl]-3,7-dimethyl-5-(1-methylbutyl)pyrrolo[2,1-f][1,2,4]triazin-4(3H)-one,
<27> 2-[5-chloro-4-(difluoromethoxy)-2-methylphenyl]-3-ethyl-5-isopropyl-7-methylpyrrolo[2,1-f][1,2,4]triazin-4(3H)-one,
<28> 2-[2-chloro-4-(methylthio)phenyl]-3,7-dimethyl-5-[(1S)-1-methylbutyl]pyrrolo[2,1-f][1,2,4]triazin-4(3H)-one, or
<29> 2-[2-chloro-4-(methylthio)phenyl]-3,7-dimethyl-5-[(1R)-1-methylbutyl]pyrrolo[2,1-f][1,2,4]triazin-4(3H)-one;

(9) a pharmaceutical composition containing as an active ingredient the compound of the formula (I) described in (1), a salt thereof, an N-oxide thereof, a solvate thereof, or a prodrug thereof;

(10) the pharmaceutical composition according to (9), which is a CRF antagonist;

(11) the pharmaceutical composition according to (9), which is an agent for preventing and/or treating CRF mediated diseases;

(12) the pharmaceutical composition according to (11), wherein the CRF mediated diseases are neuropsychiatric diseases or digestive diseases;

(13) the pharmaceutical composition according to (12), wherein the neuropsychiatric diseases or the digestive diseases are mood disorder, anxiety disorder, adjustment disorder, stress-related disorder, eating disorder, symptom caused by psychotropic substance or dependency thereon, organic mental disorder, schizophrenic disorder, attention-deficit hyperactivity disorder, irritable bowel syndrome, or gastrointestinal disorder caused by stress;

(14) the pharmaceutical composition according to (13), wherein the mood disorders are depression, bipolar disorder, indefinite complaint, premenstrual dysphoric disorder, postpartum mood disorder, or perimenopausal or menopausal dysphoric disorder, and the anxiety disorders are generalized anxiety disorder, panic disorder, posttraumatic stress disorder, obsessive compulsive disorder, social anxiety disorder, or phobic disorder;

(15) a pharmaceutical composition comprising the compound of the formula (I) described in (1), a salt thereof, an N-oxide thereof, a solvate thereof, or a prodrug thereof in combination with at least one kind selected from a tricyclic antidepressant, a tetracyclic antidepressant, a monoamine oxidase inhibitor, a serotonin and noradrenaline reuptake inhibitor, a selective serotonin reuptake inhibitor, a serotonin reuptake inhibitor, a psychostimulant, an antianxiety agent, an antipsychotic agent, a mitochondrial benzodiazepine receptor ligand, a neurokinin 1 antagonist, a gastrointestinal promotility agent, a proton pump inhibitor, a histamine $H_2$ receptor antagonist, a 5-$HT_3$ antagonist, a 5-$HT_4$ agonist, an anticholinergic agent, an antidiarrheal drug, a laxative, and an autonomic modulating agent;

(16) a method of preventing and/or treating CRF mediated diseases, comprising administering to a mammal an effective amount of the compound of the formula (I) described in (1), a salt thereof, an N-oxide thereof, a solvate thereof, or a prodrug thereof;

(17) a use of the compound of the formula (I) described in (1), a salt thereof, an N-oxide thereof, a solvate thereof, or a prodrug thereof for manufacturing an agent for preventing and/or treating CRF mediated diseases; and

(18) the compound of the formula (I) described in (1), a salt thereof, an N-oxide thereof, a solvate thereof, or a prodrug thereof for preventing and/or treating CRF mediated diseases.

In the present invention, "C3-10 branched alkyl which may be substituted" represented by $R^1$ is "C3-10 branched alkyl substituted with a substituent(s)" or "unsubstituted C3-10 branched alkyl".

In the present invention, "C3-10 branched alkyl" in "C3-10 branched alkyl which may be substituted", "C3-10 branched alkyl substituted with a substituent(s)", and "unsubstituted C3-10 branched alkyl" includes branched propyl, butyl, pentyl, hexyl, octyl, nonyl, and decyl.

Specifically, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methylpentyl, 1,1-diethylbutyl, 1-methyloctyl, 2-methyloctyl, 7-methyloctyl, 1-ethylheptyl, 2-ethylheptyl, 1-propylhexyl, 2-propylhexyl, 3-ethylheptyl, 3-propylhexyl, 1-butylpentyl, 1,6-dimethylheptyl, 1-ethyl-5-methylhexyl, 1-propyl-4-methylpentyl, 1-butyl-3-methylbutyl, 1,1-dimethylheptyl, 1-ethyl-1-methylhexyl, 1,1-diethylpentyl, 1-ethyl-1-propylbutyl, 1-methylnonyl, 2-methylnonyl, 1-ethyloctyl, 2-ethyloctyl, 3-ethyloctyl, 1-propylheptyl, 2-propylheptyl, 3-propylheptyl, 1-butylhexyl, 2-butylhexyl, 3-butylhexyl, 1,8-dimethyloctyl, 1-ethyl-6-methylheptyl, 1-propyl-5-methylhexyl, 1-butyl-4-methylpentyl, 1,1-dimethyloctyl, 1-ethyl-1-methylheptyl, 1-ethyl-1-propylpentyl, 1,1-dipropylbutyl, and the like are given.

In the present invention, as the "substituent(s)" in "the C3-10 branched alkyl substituted with a substituent(s)" include hydroxyl, C1-4 alkoxy, a halogen atom, —$CF_3$, —OCF$_3$, C3-6 cycloalkyl, —O—(C3-6 cycloalkyl), C5-6 monocyclic unsaturated carbocyclic ring, —O—(C5-6 monocyclic unsaturated carbocyclic ring), a 3-6 membered monocyclic heterocyclic ring, —O-(3-6 membered monocyclic heterocyclic ring). Those substituents may be arbitrary substituted in the C3-10 branched alkyl at substitutable positions, but 1 to 4 substitutable positions are preferred.

In the present invention, "C1-4 alkoxy" includes methoxy, ethoxy, propoxy, isopropyloxy, butoxy, isobutoxy, sec-butoxy or tert-butoxy.

In the present invention, the "halogen atom" includes fluorine, chlorine, bromine and iodine.

In the present invention, "C3-6 cycloalkyl" in the "C3-6 cycloalkyl" and "—O—(C3-6 cycloalkyl)" includes cyclopropyl, cyclobutyl, cyclopentyl, or cyclohexyl.

In the present invention, "C5-6 monocyclic unsaturated carbocyclic ring" in the "C5-6 monocyclic unsaturated carbocyclic ring" and "—O—(C5-6 monocyclic unsaturated carbocyclic ring)" means a C5-6 unsaturated or partially saturated monocyclic carbocyclic ring, and for example, cyclopentene, cyclohexene, cyclopentadiene, cyclohexadiene, and benzene are given.

In the present invention, the "3-6 membered monocyclic heterocyclic ring" in the "3-6 membered monocyclic heterocyclic ring" and "—O—(3-6 membered monocyclic heterocyclic ring) means a 3-6 membered saturated, partially saturated or unsaturated monocyclic heterocyclic ring containing 1-2 heteroatom selected from a nitrogen atom, an oxygen atom and/or a sulfur atom which may be oxidized, and for example, oxirane, thiirane, aziridine, oxetane, thietane, azetidine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydroxazole(oxazolidine), dihydroisooxazole, tetrahydroisooxazole(isooxazolidine), dihydrothiazole, tetrahydrothiazole(thiazolidine), dihydroisothiazole, tetrahydroisothiazole(isothiazolidine), dihydrooxazine, tetrahydrooxazine, dihydrothiazine, tetrahydrothiazine, morpholine, thiomorpholine, oxathiane, pyrrole, imidazole, pyrazole, pyridine, pyrazine, pyrimidine, pyridazine, furan, pyran, thiophene, thiopyran, oxazole, isooxazole, thiazole, isothiazole, oxazine, and thiazine are given.

In the present invention, "C1-6 alkyl which may be substituted" represented by R$^5$ or R$^6$ is "C1-6 alkyl substituted with a substituent(s)", or "unsubstituted C1-6 alkyl".

In the present invention, the "C1-6 alkyl" in the "C1-6 alkyl which may be substituted", "C1-6 alkyl substituted with a substituent(s)" and "unsubstituted C1-6 alkyl" represents straight or branched C1-6 alkyl, and includes methyl, ethyl, n-propyl, isopropyl, n-butyl, isobutyl, sec-butyl, tert-butyl, pentyl, hexyl, and isomers thereof.

In the present invention, the "substituent(s)" in the "C1-6 alkyl substituted with a substituent(s)" includes hydroxyl, C1-4 alkoxy, a halogen atom, —CF$_3$, —OCF$_3$, C3-6 cycloalkyl, —O—(C3-6 cycloalkyl), C5-6 monocyclic unsaturated carbocyclic ring, —O—(C5-6 monocyclic unsaturated carbocyclic ring), a 3-6 membered monocyclic heterocyclic ring and —O-(3-6 membered monocyclic heterocyclic ring). Those substituents may be arbitrary substituted in the C1-6 alkyl at substitutable positions, but 1 to 4 substitutable positions are preferred.

In the present invention, "C3-6 branched alkyl which may be substituted" represented by R$^6$ is "C3-6 branched alkyl substituted with a substituent(s)" or "unsubstituted C3-6 branched alkyl".

In the present invention, the "C3-6 branched alkyl" in the "C3-6 branched alkyl which may be substituted", "C3-6 branched alkyl substituted with a substituent(s)" and "unsubstituted C3-6 branched alkyl" represents branched propyl, butyl, pentyl, and hexyl. For example, isopropyl, sec-butyl, tert-butyl, 1-methylbutyl, 1-ethylpropyl, 1,1-dimethylpropyl, 1,2-dimethylpropyl, 1-methylpentyl, 1-ethylbutyl, 1-ethyl-1-methylpropyl, 1-ethyl-2-methylpropyl, 1,1-dimethylbutyl, 1,2-dimethylbutyl, and 1,3-dimethylbutyl are given.

In the present invention, as the "substituent(s)" in the "C3-6 branched alkyl substituted with a substituent(s)", hydroxyl, C1-4 alkoxy, a halogen atom, —CF$_3$, —OCF$_3$, C3-6 cycloalkyl, —O—(C3-6 cycloalkyl), C5-6 monocyclic unsaturated carbocyclic ring, —O—(C5-6 monocyclic unsaturated carbocyclic ring), a 3-6 membered monocyclic heterocyclic ring, and —O-(3-6 membered monocyclic heterocyclic ring) are given. Those substituents may be arbitrary substituted in the C3-6 branched alkyl at substitutable positions, but 1 to 4 substitutable positions are preferred.

In the present invention, the "C1-4 alkyl which may be substituted" represented by R$^2$ is "C1-4 alkyl substituted with a substituent(s)" or "unsubstituted C1-4 alkyl".

In the present invention, the "C1-4 alkyl" in the "C1-4 alkyl which may be substituted", "C1-4 alkyl substituted with a substituent(s)", and "unsubstituted C1-4 alkyl" represents straight or branched C1-4 alkyl, and includes methyl, ethyl, n-propyl, isopropyl, n-butyl, isobutyl, sec-butyl, and tert-butyl.

In the present invention, as the "substituent(s)" in the "C1-4 alkyl substituted with a substituent(s)" represented by R$^2$, hydroxyl, C1-4 alkoxy, a halogen atom, —CF$_3$, —OCF$_3$, C3-6 cycloalkyl, —O—(C3-6 cycloalkyl), C5-6 monocyclic unsaturated carbocyclic ring, —O—(C5-6 monocyclic unsaturated carbocyclic ring), a 3-6 membered monocyclic heterocyclic ring, and —O-(3-6 membered monocyclic heterocyclic ring) are given. Those substituents may be arbitrary substituted in the C1-4 alkyl at substitutable positions, but 1 to 4 substitutable positions are preferred.

In the present invention, the "C1-4 alkyl which may be substituted" represented by R$^3$ represents the same meaning described as the "C1-4 alkyl which may be substituted" represented by R$^2$.

In the present invention, the "C1-4 alkyl which may be substituted" represented by R$^4$ is "C1-4 alkyl substituted with a substituent(s)" or "unsubstituted C1-4 alkyl".

In the present invention, as the "substituent(s)" in the "C1-4 alkyl substituted with a substituent(s)" represented by R$^4$, hydroxyl, C1-4 alkoxy, a halogen atom, —CF$_3$, —OCF$_3$, C1-4 alkoxycarbonyl (for example, methoxycarbonyl, ethoxycarbonyl, etc.), C2-8 acyloxy (for example, acetyloxy, benzoyloxy, etc.), —O-(phosphate which may be protected) (for example, —O—P=O(OH)$_2$, —O—P=O(OCH$_3$)$_2$, etc.), amino which may be protected (for example, amino, methylamino, ethylamino, dimethylamino, diethylamino, etc.), carbamoyl, dialkylaminocarbonyloxy (for example, dimethylaminocarbonyloxy, etc.), C3-6 cycloalkyl, —O—(C3-6 cycloalkyl), C5-6 monocyclic unsaturated carbocyclic ring, —O—(C5-6 monocyclic unsaturated carbocyclic ring), a 3-6 membered monocyclic heterocyclic ring, and —O-(3-6 membered monocyclic heterocyclic ring) are given. Those substituents may be arbitrary substituted in the C1-4 alkyl at substitutable positions, but 1 to 4 substitutable positions are preferred.

In the present invention, the "C3-6 cycloalkyl which may be substituted" represented by $R^4$ is "C3-6 cycloalkyl substituted with a substituent(s)" or "unsubstituted C3-6 cycloalkyl".

In the present invention, the "C3-6 cycloalkyl" in the "C3-6 cycloalkyl which may be substituted", "C3-6 cycloalkyl substituted with a substituent(s)" and "unsubstituted C3-6 cycloalkyl" represents cyclopropyl, cyclobutyl, cyclopentyl, or cyclohexyl.

In the present invention, as the "substituent(s)" in the "C3-6 cycloalkyl substituted with a substituent(s)", hydroxyl, C1-4 alkoxy, a halogen atom, —$CF_3$, —$OCF_3$, C3-6 cycloalkyl, —O—(C3-6 cycloalkyl), C5-6 monocyclic unsaturated carbocyclic ring, —O—(C5-6 monocyclic unsaturated carbocyclic ring), a 3-6 membered monocyclic heterocyclic ring, and —O-(3-6 membered monocyclic heterocyclic ring) are given. Those substituents may be arbitrary substituted in the C3-6 cycloalkyl at substitutable positions, but 1 to 4 substitutable positions are preferred.

In the present invention, "a cyclic group which has planarity and may have a substituent group" represented by ring 1 means a 5-12 membered monocyclic or bicyclic aromatic cyclic group being unsubstituted or having 1-3 substituent(s), which may contain 1-4 heteroatom(s) selected from a nitrogen atom, an oxygen atom and/or a sulfur atom which may be oxidized. As the aromatic cyclic group, an aromatic carbocyclic group or an aromatic heterocyclic group containing 1-4 heteroatom(s) selected from a nitrogen atom, an oxygen atom and/or a sulfur atom which may be oxidized, is included.

The "aromatic carbocyclic group" in ring 1 represents a 5-12 membered monocyclic or bicyclic aromatic carbocyclic group, and includes a monocyclic aromatic carbocyclic ring, a bicyclic aromatic carbocyclic ring, or a bicyclic fused ring formed of a monocyclic aromatic carbocyclic ring and an unsaturated or saturated monocyclic carbocyclic ring. For example, benzene, indene, indan, naphthalene, dihydronaphthalene, tetrahydronaphthalene, and azulene rings are given. However, in the case of an indene, indan, dihydronaphthalene, and tetrahydronaphthalene rings, a benzene ring among those rings binds to pyrrolo[2,1-f][1,2,4]triazin-4(3H)-one.

The "aromatic heterocyclic group containing 1-4 heteroatom(s) selected from a nitrogen atom, an oxygen atom and/or a sulfur atom which may be oxidized" in ring 1 represents a 5-12 membered monocyclic or bicyclic aromatic heterocyclic group containing 1-4 heteroatom(s) selected from a nitrogen atom, an oxygen atom and/or a sulfur atom which may be oxidized, and includes a monocyclic aromatic heterocyclic ring, a bicyclic aromatic heterocyclic ring, a bicyclic fused ring formed of a monocyclic aromatic heterocyclic ring and an unsaturated or saturated monocyclic carbocyclic ring, a bicyclic fused ring formed of a monocyclic aromatic carbocyclic ring and an unsaturated or saturated monocyclic heterocyclic ring, or a bicyclic fused ring formed of a monocyclic aromatic heterocyclic ring and an unsaturated or saturated monocyclic heterocyclic ring. For example, pyrrole, imidazole, triazole, pyrazole, pyridine, pyrazine, pyrimidine, pyridazine, furan, thiophene, oxazole, isooxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chroman, isochroman, tetrahydroquinoline, dihydroquinoline, tetrahydroisoquinoline, dihydroisoquinoline, tetrahydroquinoxaline, dihydroquinoxaline, tetrahydroquinazoline, dihydroquinazoline, and dioxaindan rings are given. However, in the case of the indole, isoindole, benzofuran, isobenzofuran, benzothiophene, isobenzothiophene, indazole, phthalazine, quinoxaline, quinazoline, cinnoline, benzoxazole, benzothiazole, benzimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chroman, isochroman, and dioxaindan rings, a benzene ring among those rings, or in the case of tetrahydroquinoline, dihydroquinoline, tetrahydroisoquinoline, dihydroisoquinoline, tetrahydroquinoxaline, dihydroquinoxaline, tetrahydroquinazoline, and dihydroquinazoline rings, a pyridine, pyrimidine or pyrazine ring among those rings binds to pyrrolo[2,1-f][1,2,4]triazin-4(3H)-one.

In the present invention, "a cyclic group which has planarity, binds to pyrrolo[2,1-f][1,2,4]triazin-4(3H)-one ring through the carbon atom and may have a substituent group" represented by ring $1^X$ means a 5-12 membered monocyclic or bicyclic aromatic cyclic group to be binded to pyrrolo[2,1-f][1,2,4]triazin-4(3H)-one ring through the carbon atom, being unsubstituted or having 1-3 substituent(s), which may contain 1-4 heteroatom(s) selected from a nitrogen atom, an oxygen atom and/or a sulfur atom which may be oxidized. As the aromatic cyclic group, an aromatic carbocyclic group or an aromatic heterocyclic group containing 1-4 heteroatom(s) selected from a nitrogen atom, an oxygen atom and/or a sulfur atom which may be oxidized, is included.

The "aromatic carbocyclic group" in ring $1^X$ represents a 5-12 membered monocyclic or bicyclic aromatic carbocyclic group to be binded to pyrrolo[2,1-f][1,2,4]triazin-4(3H)-one ring through the carbon atom, and includes a monocyclic aromatic carbocyclic ring, a bicyclic aromatic carbocyclic ring, a bicyclic fused ring formed of a monocyclic aromatic carbocyclic ring and an unsaturated or saturated monocyclic carbocyclic ring. For example, benzene, indene, indan, naphthalene, dihydronaphthalene, tetrahydronaphthalene and azulene rings are given. However, in the case of an indene, indan, dihydronaphthalene, and tetrahydronaphthalene rings, a benzene ring among those rings binds to pyrrolo[2,1-f][1,2,4]triazin-4(3H)-one.

The "aromatic heterocyclic group containing 1-4 heteroatom(s) selected from a nitrogen atom, an oxygen atom and/or a sulfur atom which may be oxidized" in ring $1^X$ represents a 5-12 membered monocyclic or bicyclic aromatic heterocyclic group to be binded to pyrrolo[2,1-f][1,2,4]triazin-4(3H)-one ring through the carbon atom, which is containing 1-4 heteroatom(s) selected from a nitrogen atom, an oxygen atom and/or a sulfur atom which may be oxidized, and includes a monocyclic aromatic heterocyclic ring, a bicyclic aromatic heterocyclic ring, a bicyclic fused ring formed of a monocyclic aromatic heterocyclic ring and an unsaturated or saturated monocyclic carbocyclic ring, a bicyclic fused ring formed of a monocyclic aromatic carbocyclic ring and an unsaturated or saturated monocyclic heterocyclic ring, or a bicyclic fused ring formed of a monocyclic aromatic heterocyclic ring and an unsaturated or saturated monocyclic heterocyclic ring. For example, pyrrole, imidazole, triazole, pyrazole, pyridine, pyrazine, pyrimidine, pyridazine, furan, thiophene, oxazole, isooxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chroman, isochroman, tetrahydroquinoline, dihydroquinoline, tetrahydroisoquinoline, dihydroisoquinoline, tetrahydroquinoxaline, dihydroquinoxaline, tetrahydroquinazoline, dihydroquinazoline, and dioxaindan rings are given. However, in the case of the indole, isoindole, benzofuran, isobenzofuran, benzothiophene, isobenzothiophene, indazole, phthalazine, quinoxaline, quinazoline, cinnoline, benzoxazole, benzothiazole, benzimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chroman, isochroman, and dioxaindan rings, a benzene ring among those rings, or in the case of tetrahydroquinoline, dihydroquinoline, tetrahydroisoquinoline, dihydroisoquinoline, tetrahydroquinoxaline, dihydroquinoxaline, tetrahydroquinazoline, and dihydroquinazoline rings, a pyridine, pyrimidine or pyrazine ring among those rings binds to pyrrolo[2,1-f][1,2,4]triazin-4(3H)-one.

In the present invention, as the "substituents" in the aromatic cyclic group represented by the "a cyclic group which has planarity and may have a substituent group", (1) C1-15 alkyl which may be substituted, (2) C2-15 alkenyl which may be substituted, (3) C2-15 alkynyl which may be substituted, (4) hydroxy which may be protected, (5) mercapto which may be protected, (6) amino which may be protected, (7) carbamoyl which may be protected, (8) sulfamoyl which may be protected, (9) carboxyl which may be protected, (10) sulfo (—$SO_3H$) which may be protected, (11) sulfino (—$SO_2H$) which may be protected, (12) nitro, (13) cyano, (14) amidino, (15) imino, (16) a halogen atom, (17) a cyclic group which may be substituted, (18) C1-7 acyl, (19) oxo, and (20) thioxo are given. Those substituents may be arbitrary substituted at 1-3 substitutable positions.

In the present invention, C1-15 alkyl which may be substituted represents straight or branched C1-15 alkyl which may be substituted, and for example, methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, or pentadecyl which may be substituted is given.

In the present invention, C2-15 alkenyl which may be substituted represents straight or branched C2-15 alkenyl having 1-3 double bonds and which may be substituted, and for example, vinyl, propenyl, butenyl, pentenyl, hexenyl, hexadienyl, heptenyl, heptadienyl, octenyl, octadienyl, nonenyl, nonadienyl, decenyl, decadienyl, undecenyl, dodecenyl, tridecenyl, tetradecenyl, and pentadecenyl which may be substituted are given.

In the present invention, C2-15 alkynyl which may be substituted represents straight or branched C2-15 alkynyl having 1-3 triple bonds and which may be substituted, and for example, ethynyl, propynyl, butynyl, pentynyl, hexynyl, hexadynyl, heptynyl, heptadynyl, octynyl, octadynyl, nonynyl, decynyl, undecynyl, dodecynyl, tridecynyl, tetradecynyl, and pentadecynyl which may be substituted are given.

In the present invention, "C1-15 alkyl which may be substituted", "C2-15 alkenyl which may be substituted", and "C2-15 alkynyl which may be substituted" each represent "C1-15 alkyl which is substituted by a substituent(s) or unsubstituted", "C2-15 alkenyl which is substituted by a substituent(s) or unsubstituted", and "C2-15 alkynyl which is substituted by a substituent(s) or unsubstituted", and as the "substituent(s)", a group selected from the following substituent group A is given. Those substituents may be substituted at 1-4 substitutable positions.

The substituent group A represents (1) a halogen atom, (2) $CF_3$, (3) $OCF_3$, (4) cyano, (5) nitro, (6) hydroxy which may be protected by C1-6 alkyl, C2-6 alkenyl, C2-6 alkynyl, a cyclic group or a protective group having desorption property, (7) C1-7 acyl, (8) carboxyl which may be protected by C1-6 alkyl, C2-6 alkenyl, C2-6 alkynyl, or a cyclic group, (9) carbamoyl which may be protected by C1-6 alkyl, C2-6 alkenyl, C2-6 alkynyl, or a cyclic group, (10) mercapto which may be protected by C1-6 alkyl, C2-6 alkenyl, C2-6 alkynyl, or a cyclic group, (11) $NR^{10}R^{11}$, in which $R^{10}$ represents (a) a hydrogen atom, (b) C1-6 alkyl, (c) C2-6 alkenyl, (d) C2-6 alkynyl, or (e) a cyclic group; $R^{11}$ represents (a) a hydrogen atom, (b) C1-6 alkyl, (c) C2-6 alkenyl, (d) C2-6 alkynyl, (e) —$COR^{12}$ in which $R^{12}$ represents a hydrogen atom, C1-6 alkyl, C2-6 alkenyl, C2-6 alkynyl, or a cyclic group; (f) —$COOR^{12}$ in which $R^{12}$ represent the same meaning described above; or (g) —$CON(R^{10})_2$ in which two $R^{10}$'s each independently represent the same meaning described above, (12) —$S(O)_nR^{13}$ in which n represents 1 or 2; $R^{13}$ represents a hydrogen atom, C1-6 alkyl, C2-6 alkenyl, or C2-6 alkynyl, or a cyclic group, (13) —$COR^{12}$ in which $R^{12}$ represents the same meaning described above, and (14) a cyclic group which may be substituted.

Further, C1-6 alkyl, C2-6 alkenyl, and C2-6 alkynyl in the substituent group A may be substituted by a group selected from a substituent group B, the cyclic group described in (14) of the substituent group A may be substituted by a group selected from a substituent group C. Those substituents may be substituted at 1-5 substitutable positions.

The substituent group B represents (1) C1-6 alkoxy, (2) C1-6 alkylthio, (3) a halogen atom, (4) hydroxy which may be protected by C1-6 alkyl, C2-6 alkenyl, C2-6 alkynyl, a cyclic group, a cyclic group-C1-6 alkyl or a protective group having desorption property, (5) $CF_3$, (6) $OCF_3$, (7) nitro, (8) cyano, (9) carboxyl, (10) (C1-6 alkoxy)carbonyl, (11) benzyloxycarbonyl, (12) mercapto, (13) amino, (14) C1-6 alkylamino, (15) di(C1-6 alkyl)amino, (16) carbamoyl, (17) N—(C1-6 alkyl)carbamoyl, (18) N,N-di(C1-6 alkyl)carbamoyl, (19) sulfamoyl, (20) N—(C1-6 alkyl)sulfamoyl, (21) N,N-di(C1-6 alkyl)sulfamoyl, (22) C1-7 acyl, and (23) a cyclic group which may be substituted by a group selected from a substituent group D.

As the substituent group C, (1) C1-6 alkyl, (2) C2-6 alkenyl, (3) C2-6 alkynyl, (4) hydroxy which may be protected by C1-6 alkyl, C2-6 alkenyl, C2-6 alkynyl, a cyclic group, or a protective group having desorption property, (5) mercapto which may be protected by C1-6 alkyl, C2-6 alkenyl, C2-6 alkynyl, or the cyclic group, (6) amino which each may be protected by 1-2 groups selected from C1-6 alkyl, C2-6 alkenyl, C2-6 alkynyl, and the cyclic group, (7) carbamoyl which each may be protected by 1-2 groups selected from C1-6 alkyl, C2-6 alkenyl, C2-6 alkynyl, or the cyclic group, (8) sulfamoyl which each may be protected by 1-2 groups selected from C1-6 alkyl, C2-6 alkenyl, C2-6 alkynyl, or the cyclic group, (9) carboxyl which may be protected by C1-6 alkyl, C2-6 alkenyl, C2-6 alkynyl or the cyclic group, (10) nitro, (11) cyano, (12) amidino, (13) a halogen atom, (14) $CF_3$, (15) $OCF_3$, (16) C1-7 acyl, (17) oxo, and (18) thioxo are given.

Further, C1-6 alkyl, C2-6 alkenyl, and C2-6 alkynyl in the substituent group C may be substituted by a group selected from the substituent group B, and a cyclic group included in the substituent group C may be substituted by a group selected from the substituent group D.

The substituent group D represents (1) C1-6 alkyl, (2) C2-6 alkenyl, (3) C2-6 alkynyl, (4) C1-6 alkoxy, (5) C1-6 alkylthio, (6) a halogen atom, (7) $CF_3$, (8) $OCF_3$, (9) nitro, (10) cyano,

(11) hydroxy which may be protected by C1-6 alkyl, C2-6 alkenyl, C2-6 alkynyl, the cyclic group, the cyclic group-C1-6 alkyl, or a protective group having desorption property, (12) carboxyl, (13) (C1-6 alkoxy)carbonyl, (14) benzyloxycarbonyl, (15) mercapto, (16) amino, (17) C1-6 alkylamino, (18) di(C1-6 alkyl)amino, (19) carbamoyl, (20) N—(C1-6 alkyl)carbamoyl, (21) N,N-di(C1-6 alkyl)carbamoyl, (22) sulfamoyl, (23) N—(C1-6 alkyl)sulfamoyl, (24) N,N-di (C1-6 alkyl)sulfamoyl, (25) C1-7 acyl, (26) oxo, and (27) thioxo.

In the present invention, as the hydroxy which may be protected, for example, (a) C1-15 alkyl which may be substituted, (b) C2-15 alkenyl which may be substituted, (c) C2-15 alkynyl which may be substituted, (d) a cyclic group which may be substituted, or (e) hydroxy protected by a protective group having desorption property or hydroxy which is not protected is given. In this case, as the protective group having desorption property, for example, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxy carbonyl (Alloc), 2,2,2-trichloroethoxycarbonyl (Troc) are given. Further, hydroxy protected by C1-15 alkyl which may be substituted means C1-15 alkoxy which may be substituted.

In the present invention, mercapto which may be protected represents (a) C1-15 alkyl which may be substituted, (b) C2-15 alkenyl which may be substituted, (c) C2-15 alkynyl which may be substituted, or (d) mercapto protected by a cyclic group which may be substituted or unprotected mercapto.

In the present invention, amino which may be protected represents amino protected by the following 1-2 protective groups or unprotected amino. As the protective groups for the amino, (a) C1-15 alkyl which may be substituted, (b) C2-15 alkenyl which may be substituted, (c) C2-15 alkynyl which may be substituted, (d) a cyclic group which may be substituted, (e) —$COR^{14}$ in which $R^{14}$ represents a hydrogen atom, C1-15 alkyl which may be substituted, C2-15 alkenyl which may be substituted, C2-15 alkynyl which may be substituted, or a cyclic group which may be substituted, (f) —$COOR^{14}$ in which $R^{14}$ represents the same meaning described above, (g) —$CON(R^{15})_2$ in which two $R^{15}$'s each independently represent, a hydrogen atom, C1-15 alkyl which may be substituted, C2-15 alkenyl which may be substituted, or C2-15 alkynyl which may be substituted, and (h) —$SO_2R^{16}$ in which $R^{16}$ represents a hydrogen atom, C1-15 alkyl which may be substituted, C2-15 alkenyl which may be substituted, C2-15 alkynyl which may be substituted, or a cyclic group which may be substituted are given.

In the present invention, as the "protective group" in the "carbamoyl which may be protected", "sulfamoyl which may be protected", "carboxyl which may be protected", "sulfo which may be protected", and "sulfino which may be protected", (a) C1-15 alkyl which may be substituted, (b) C2-15 alkenyl which may be substituted, (c) C2-15 alkynyl which may be substituted, or (d) a cyclic group which may be substituted are given.

In the present invention, C1-7 acyl represents, for example, formyl, acetyl, propanoyl, pivaloyl, or benzoyl.

In the present invention, the "cyclic group" which is shown as "substituent" in the aromatic cyclic group represented by the "a cyclic group which has planarity and may have a substituent group" represents a carbocyclic group or a heterocyclic group.

The carbocyclic group represents a C3-12 totally saturated, a partially saturated, or a totally unsaturated monocyclic or bicyclic carbocyclic group, and, for example, cyclopropane, cyclobutane, cyclopentane, cyclohexane, cycloheptane, cyclopentene, cyclohexene, cycloheptene, cyalopentadiene, cyclohexadiene, cycloheptadiene, benzene, pentalene, perhydropentalene, azulene, perhydroazulene, indene, perhydroindene, indan, naphthalene, dihydronaphthalene, tetrahydronaphthalene, perhydronaphthalene, heptalene, and perhydroheptalene rings are given.

The heterocyclic group represents a 3-12 membered totally saturated, partially saturated, or totally unsaturated monocyclic or bicyclic heterocyclic group containing 1-4 heteroatom(s) selected from a nitrogen atom, an oxygen atom and/or a sulfur atom which may be oxidized, and, for example, oxirane, thiirane, aziridine, oxetane, thietane, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydroxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepine, benzodiazepine, benzofurazan, benzothiadiazole, and benzotriazole rings are given.

In the present invention, the cyclic group which may be substituted represents a carbocyclic group or a heterocyclic group which each may be arbitrary substituted with 1-5 groups selected from a substituent group C. As the carbocyclic group and the heterocyclic group, the cyclic groups described above are given.

In the present invention, C1-6 alkyl represents, for example, methyl, ethyl, n-propyl, isopropyl, n-butyl, isobutyl, sec-butyl, tert-butyl, pentyl, hexyl, and isomers thereof.

In the present invention, C2-6 alkenyl represents, for example, vinyl, propenyl, butenyl, pentenyl, hexenyl, hexadienyl, and isomers thereof.

In the present invention, C2-6 alkynyl represents, for example, ethynyl, propynyl, butynyl, pentynyl, hexynyl, hexadynyl and isomers thereof.

In the present invention, hydroxy protected with C1-6 alkyl means C1-6 alkoxy.

In the present invention, C1-6 alkoxy represents, for example, methoxy, ethoxy, propoxy, isopropoxy, butoxy, isobutoxy, sec-butoxy, tert-butoxy, pentyloxy, or hexyloxy.

In the present invention, C1-15 alkoxy represents straight or branched C1-15 alkoxy, and, for example, methoxy, ethoxy, propoxy, isopropoxy, butoxy, isobutoxy, sec-butoxy, tert-butoxy, pentyloxy, hexyloxy, heptyloxy, octyloxy, nonyloxy, decyloxy, undecyloxy, dodecyloxy, tridecyloxy, tetradecyloxy, or pentadecyloxy is given.

In the present invention, C1-6 alkylthio represents, for example, methylthio, ethylthio, propylthio, isopropylthio, n-butylthio, isobutylthio, sec-butylthio, tert-butylthio, pentylthio, or hexylthio.

In the present invention, C1-5 acyl represents, for example, formyl, acetyl, propanoyl, butanoyl, 2-methylpropanoyl, and pivaloyl.

In the present invention, (C1-6 alkoxy)carbonyl represents, for example, methoxycarbonyl, ethoxycarbonyl, propylcarbonyl, isopropylcarbonyl, butoxycarbonyl, isobutoxycarbonyl, sec-butoxycarbonyl, tert-butoxycarbonyl, pentyloxycarbonyl, or hexyloxycarbonyl.

In the present invention, C1-6 alkylamino represents, for example, methylamino, ethylamino, propylamino, isopropylamino, n-butylamino, isobutylamino, sec-butylamino, tert-butylamino, pentylamino, or hexylamino.

In the present invention, di(C1-6 alkyl)amino represents, for example, dimethylamino, diethylamino, dipropylamino, diisopropylamino, dibutylamino, dipentylamino, dihexylamino, or N-methyl-N-ethylamino.

In the present invention, N—(C1-6 alkyl)carbamoyl represents, for example, N-methylcarbamoyl, N-ethylcarbamoyl, N-propylcarbamoyl, N-isopropylcarbamoyl, N-butylcarbamoyl, N-isobutylcarbamoyl, N-(sec-butyl)carbamoyl, N-(tert-butyl)carbamoyl, N-pentylcarbamoyl, or N-hexylcarbamoyl.

In the present invention, N,N-di(C1-6 alkyl)carbamoyl represents, for example, N,N-dimethylcarbamoyl, N,N-diethylcarbamoyl, N,N-dipropylcarbamoyl, N,N-diisopropylcarbamoyl, N,N-dibutylcarbamoyl, N,N-dipentylcarbamoyl, N,N-dihexylcarbamoyl, or N-methyl-N-ethylcarbamoyl.

In the present invention, N—(C1-6 alkyl)sulfamoyl represents, for example, N-methylsulfamoyl, N-ethylsulfamoyl, N-propylsulfamoyl, N-isopropylsulfamoyl, N-butylsulfamoyl, N-isobutylsulfamoyl, N-(sec-butyl)sulfamoyl, N-(tert-butyl)sulfamoyl, N-pentylsulfamoyl, or N-hexylsulfamoyl.

In the present invention, N,N-di(C1-6 alkyl)sulfamoyl represents, for example, N,N-dimethylsulfamoyl, N,N-diethylsulfamoyl, N,N-dipropylsulfamoyl, N,N-diisopropylsulfamoyl, N,N-dibutylsulfamoyl, N,N-dipentylsulfamoyl, N,N-dihexylsulfamoyl, or N-methyl-N-ethylsulfamoyl.

In the present invention, the cyclic group-C1-6 alkyl represents a carbocyclic group (C1-6) alkyl or a heterocyclic group (C1-6) alkyl, each representing (C1-6) alkyl substituted with one carbocyclic group or (C1-6) alkyl substituted with one heterocyclic group. The carbocyclic group, heterocyclic group and C1-6 alkyl each represent the same meanings described above.

In the present invention, $R^{40}$ described afterward represents the same meanings as the "substituent" in the aromatic cyclic group represented by the "a cyclic group which has planarity and may have a substituent group" described above.

In the present invention, $R^{50}, R^{51}, R^{52}, R^{53}, R^{54}, R^{55}, R^{56}, R^{57}, R^{58}, R^{59}, R^{60}$ and $R^{61}$ each independently represent the same meanings as the "substituent" in the aromatic cyclic group represented by the "a cyclic group which has planarity and may have a substituent group" described above.

In the present invention, it is preferred that $R^1$ has a branched chain. $R^1$ preferably includes (1) C3-10 branched alkyl which may be substituted, or (2) —$NR^5R^6$ in which all symbols represent the same meanings described above.

In the present invention, in (1) C3-10 branched alkyl which may be substituted, or (2) —$NR^5R^6$ in which all symbols represent the same meanings described above, being a preferred group as $R^1$, (1) C3-10 unsubstituted branched alkyl, or C3-10 branched alkyl substituted with 1-2 substituent(s), and (2) —$NR^5R^6$ in which $R^5$ and $R^6$ each independently represent, C1-6 unsubstituted alkyl, C1-6 alkyl substituted with 1-2 substituent(s), or $R^5$ represents a hydrogen atom, and $R^6$ represents unsubstituted C3-6 branched alkyl, or C3-6 branched alkyl substituted with 1-2 substituent(s) are more preferred.

In the case of C3-10 branched alkyl which may be substituted, C3-10 branched alkyl whose branch source is a carbon atom at position 1, is more preferred. Particularly preferred is C3-8 branched alkyl which may be substituted, and C3-8 branched alkyl whose branch source is a carbon atom at position 1, is further preferred. Specifically, isopropyl, sec-butyl, tert-butyl, 1-methylbutyl, 1-ethylpropyl, 1,1-dimethylpropyl, 1,2-dimethylpropyl, 1-methylpentyl, 1-ethylbutyl, 1-ethyl-1-methylpropyl, 1-ethyl-2-methylpropyl, 1,1-dimethylbutyl, 1,2-dimethylbutyl, 1,3-dimethylbutyl, 1-methylhexyl, 1-ethylpentyl, 1-propylbutyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 1-methylheptyl, 1-ethylhexyl, 1-propylpentyl, 1,5-dimethylhexyl, 1-ethyl-4-methylpentyl, 1-propyl-3-methylbutyl, 1,1-dimethylhexyl, 1-ethyl-1-methylpentyl, 1,1-diethylbutyl, (1S)-1-methylbutyl, (1R)-1-methylbutyl, (1S)-1-methypropyl, and (1R)-1-methypropyl are given. Particularly preferably, isopropyl, 1-methylbutyl, 1-ethylpropyl, 1-methylpentyl, 1-ethylbutyl, 1-methylhexyl, 1-ethylpentyl, 1-propylbutyl, 1-methylheptyl, 1-ethylhexyl, 1-propylpentyl, (1S)-1-methylbutyl, and (1R)-1-methylbutyl. Besides, it is also preferred that in the C3-10 alkyl, the number of carbon atoms of two alkyl groups branched from the carbon at position 1 be the same.

As the preferred substituents in "C3-10 branched alkyl substituted", "C1-6 alkyl substituted", and "C3-6 branched alkyl substituted", C1-4 alkoxy, —CF$_3$, —OCF$_3$, cyclopropyl, and cyclobutyl are given, and those substituents may be substituted at 1-2 substitutable positions.

In the present invention, m preferably is 0.

In the present invention, R$^2$ preferably is hydrogen.

In the present invention, R$^3$ preferably represents C1-4 alkyl which may be substituted, and methyl is more preferred.

In the present invention, R$^4$ preferably represents C1-4 alkyl which may be substituted or C3-6 cycloalkyl which may be substituted, and methyl, ethyl, cyclopropyl, cyclopropylmethyl, or 1-hydroxyethyl is more preferred.

In the present invention, ring 1 preferably includes, each having 1-3 substituent(s), a 5-12 membered monocyclic aromatic carbocyclic ring, a bicyclic aromatic carbocyclic ring, or a bicyclic fused ring formed of a monocyclic aromatic carbocyclic ring and an unsaturated or saturated monocyclic carbocyclic ring, or, each containing 1-4 heteroatom(s) selected from a nitrogen atom, an oxygen atom and/or a sulfur atom which may be oxidized, a 5-12 membered monocyclic aromatic heterocyclic ring, a bicyclic aromatic heterocyclic ring, or a bicyclic fused ring formed of a monocyclic aromatic heterocyclic ring and an unsaturated or saturated monocyclic carbocyclic ring, a bicyclic fused ring formed of a monocyclic aromatic carbocyclic ring and an unsaturated or a saturated monocyclic heterocyclic ring, or a bicyclic fused ring formed of monocyclic aromatic heterocyclic ring and an unsaturated or saturated monocyclic heterocyclic ring, and more preferably, ring 1 includes, each having 1-3 substituent(s), a 5-12 membered monocyclic aromatic carbocyclic ring, a bicyclic aromatic carbocyclic ring, or, each containing 1-4 heteroatom(s) selected from a nitrogen atom, an oxygen atom and/or a sulfur atom which may be oxidized, a 5-12 membered monocyclic aromatic heterocyclic ring, a bicyclic aromatic heterocyclic ring, and further preferably, ring 1 includes, a monocyclic aromatic carbocyclic ring having 1-3 substituent(s), a 5-6 membered monocyclic aromatic heterocyclic ring containing 1-4 heteroatom(s) selected from a nitrogen atom, an oxygen atom and/or a sulfur atom which may be oxidized, having 1-3 substituent(s). Ring 1 includes, each having 1-3 substituent(s), benzene, indan, imidazole, pyrazole, pyrazine, pyridine, pyrimidine, pyridazine, thiophene, oxazole, thiazole, isothiazole, indole, benzothiophene, benzooxazole, benzothiazole, benzimidazole, benzofurazan, benzothiadiazole, or benzotriazole ring, particularly preferably. Ring 1 includes, each having 1-3 substituent(s), benzene, pyridine, pyrimidine, or thiazole ring, preferably among other things.

In the present invention, ring 1$^x$ preferably includes, each having 1-3 substituent(s), a 5-12 membered monocyclic aromatic carbocyclic ring, a bicyclic aromatic carbocyclic ring, or a bicyclic fused ring formed of a monocyclic aromatic carbocyclic ring and an unsaturated or saturated monocyclic carbocyclic ring, which has binded to pyrrolo[2,1-f][1,2,4]triazin-4(3H)-one ring through the carbon atom, or, each containing 1-4 heteroatom(s) selected from a nitrogen atom, an oxygen atom and/or a sulfur atom which may be oxidized, a 5-12 membered monocyclic aromatic heterocyclic ring, a bicyclic aromatic heterocyclic ring, or a bicyclic fused ring formed of a monocyclic aromatic heterocyclic ring and an unsaturated or saturated monocyclic carbocyclic ring, a bicyclic fused ring formed of a monocyclic aromatic carbocyclic ring and an unsaturated or a saturated monocyclic heterocyclic ring, or a bicyclic fused ring formed of monocyclic aromatic heterocyclic ring and an unsaturated or saturated monocyclic heterocyclic ring, which has binded to pyrrolo[2,1-f][1,2,4]triazin-4(3H)-one ring through the carbon atom, and more preferably, ring 1$^x$ includes, each having 1-3 substituent(s), a 5-12 membered monocyclic aromatic carbocyclic ring, a bicyclic aromatic carbocyclic ring, or, each containing 1-4 heteroatom(s) selected from a nitrogen atom, an oxygen atom and/or a sulfur atom which may be oxidized, a 5-12 membered monocyclic aromatic heterocyclic ring, a bicyclic aromatic heterocyclic ring, which has binded to pyrrolo[2,1-f][1,2,4]triazin-4(3H)-one ring through the carbon atom, and further preferably, ring 1 includes, a monocyclic aromatic carbocyclic ring having 1-3 substituent(s), which has binded to pyrrolo[2,1-f][1,2,4]triazin-4(3H)-one ring through the carbon atom, a 5-6 membered monocyclic aromatic heterocyclic ring containing 1-4 heteroatom(s) selected from a nitrogen atom, an oxygen atom and/or a sulfur atom which may be oxidized, which has binded to pyrrolo[2,1-f][1,2,4]triazin-4(3H)-one ring through the carbon atom, having 1-3 substituent(s). Ring 1$^x$ includes, each having 1-3 substituent(s), benzene, indan, imidazole, pyrazole, pyrazine, pyridine, pyrimidine, pyridazine, thiophene, oxazole, thiazole, isothiazole, indole, benzothiophene, benzooxazole, benzothiazole, benzimidazole, benzofurazan, benzothiadiazole, or benzotriazole ring, which has binded to pyrrolo[2,1-f][1,2,4]triazin-4(3H)-one ring through the carbon atom, particularly preferably. Ring 1$^x$ includes, each having 1-3 substituent(s), benzene, pyridine, pyrimidine, or thiazole ring, which has binded to pyrrolo[2,1-f][1,2,4]triazin-4(3H)-one ring through the carbon atom, preferably among other things.

As the preferred substituents for ring 1 or ring 1$^x$ described above, (1) C1-15 alkyl which may be substituted, (2) C1-15 alkenyl which may be substituted, (3) hydroxy which may be protected, (4) mercapto which may be protected, (5) amino which may be protected, (6) carbamoyl which may be protected, (7) carboxyl which may be protected, (8) sulfo which may be protected, (9) sulfino which may be protected, (10) cyano, (11) a halogen atom, and (12) a cyclic group which may be substituted are given. Particularly preferred are (1) C1-6 alkyl, (2) C2-6 alkenyl, (3) unsubstituted hydroxy, or hydroxy protected by C1-6 alkyl which may be substituted, or a protective group having desorption property, in which C1-6 alkoxy, difluoromethoxy, and trifluoromethoxy are particularly preferred, (4) unsubstituted mercapto, or mercapto protected by C1-6 alkyl which may be substituted, or a protective group having desorption property, in which particularly C1-6 alkylthio is preferred, (5) carboxyl, or carboxyl protected by C1-6 alkyl, or benzyl, (6) cyano, (7) a halogen atom, and (8) a cyclic group which may be substituted, in which particularly a 5 membered monocyclic aromatic heterocyclic ring is preferred. Further, it is preferred that those substituents may be substituted at 1, 2 or 3 substitutable positions of the ring represented by ring 1 or ring 1$^x$. In particular, in the case where ring 1 or ring 1$^x$ is a 6 membered monocyclic ring, specifically, a benzene or pyridine ring, in the following ring:

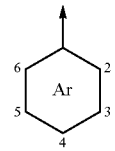

wherein the above ring;

represents a benzene ring or a pyridine ring, and an arrow binds to pyrrolo[2,1-f][1,2,4]triazin-4(3H)-one ring, the substitution is preferably carried out at (1) position 2, (2) position 3, (3) position 4, (4) positions 2 and 4, (5) positions 2, 4, and 5, or (5) positions 2, 4, and 6.

In the present invention, $R^{50}$, $R^{52}$, $R^{54}$, $R^{55}$, $R^{57}$, $R^{58}$, and $R^{60}$ preferably include, each independently, C1-4 alkyl which may be substituted or a halogen atom, and more preferably, methyl, ethyl, a halogen atom.

In the present invention, $R^{51}$ preferably includes (1) C1-6 alkyl which may be substituted, or hydroxy protected by a protective group having desorption property, (2) unsubstituted mercapto, or mercapto protected by C1-6 alkyl which may be substituted, or a protective group having desorption property, (3) a halogen atom, and (4) a cyclic group which may be substituted, and more preferably, C1-6 alkoxy, difluoromethoxy, trifluoromethoxy, C1-6 alkylthio, a halogen atom, pyrazole, and imidazole.

In the present invention, $R^{53}$, $R^{56}$, $R^{59}$, and $R^{61}$ preferably include, each independently, C1-6 alkyl which may be substituted, or hydroxy protected by a protective group having desorption property, more preferably, C1-6 alkoxy, difluoromethoxy.

In the present invention, a compound represented by formula (I) preferably includes a compound represented by formula (I-1):

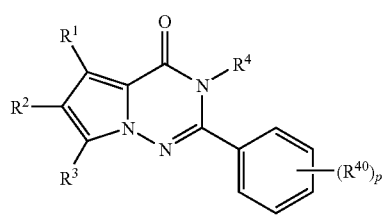

(I-1)

wherein $R^{40}$ represents the same meanings as the "substituent" in the aromatic cyclic group represented by the "a cyclic group which has planarity and may have a substituent group" described above;

p represents an integer of 1 to 3; and all other symbols have the same meanings as described above, or a compound represented by formula (I-2):

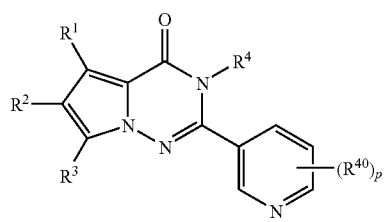

(I-2)

in which all symbols have the same meanings as described above.

In the present invention, a compound preferably includes a compound which illustrated in an example. More preferable compound includes 2-[6-(difluoromethoxy)-4-methyl-3-pyridinyl]-5-(1-ethylpropyl)-3,7-dimethylpyrrolo[2,1-f][1,2,4]triazin-4(3H)-one,
2-[2-chloro-4-(trifluoromethoxy)phenyl]-5-isopropyl-3,7-dimethylpyrrolo[2,1-f][1,2,4]triazin-4(3H)-one,
2-[2-chloro-4-(methylthio)phenyl]-3-ethyl-5-isopropyl-7-methylpyrrolo[2,1-f][1,2,4]triazin-4(3H)-one,
2-[2-chloro-4-(trifluoromethoxy)phenyl]-5-(1-ethylpropyl)-3,7-dimethylpyrrolo[2,1-f][1,2,4]triazin-4(3H)-one,
3-ethyl-5-isopropyl-7-methyl-2-[2-methyl-4-(methylthio) phenyl]pyrrolo[2,1-f][1,2,4]triazin-4(3H)-one,
2-[2-chloro-4-(methylthio)phenyl]-3,7-dimethyl-5-(1-methylbutyl)pyrrolo[2,1-f][1,2,4]triazin-4(3H)-one,
5-(1-ethylpropyl)-2-(5-fluoro-4-methoxy-2-methylphenyl)-3,7-dimethylpyrrolo[2,1-f][1,2,4]triazin-4(3H)-one,
2-(4-chloro-2-methylphenyl)-5-(1-ethylpropyl)-3,7-dimethylpyrrolo[2,1-f][1,2,4]triazin-4(3H)-one,
2-[2-chloro-4-(difluoromethoxy)phenyl]-5-(1-ethylpropyl)-3,7-dimethylpyrrolo[2,1-f][1,2,4]triazin-4(3H)-one,
2-(2-ethyl-4-methoxyphenyl)-5-(1-ethylpropyl)-3,7-dimethylpyrrolo[2,1-f][1,2,4]triazin-4(3H)-one,
5-(1-ethylpropyl)-3,7-dimethyl-2-[2-methyl-4-(1H-pyrazol-1-yl)phenyl]pyrrolo[2,1-f][1,2,4]triazin-4(3H)-one,
2-[2-chloro-4-(methylthio)phenyl]-5-(1-ethylpropyl)-3,7-dimethylpyrrolo[2,1-f][1,2,4]triazin-4(3H)-one,
2-(2-chloro-4-methoxyphenyl)-3-cyclopropyl-5-(1-ethylpropyl)-7-methylpyrrolo[2,1-f][1,2,4]triazin-4(3H)-one,
2-(2-chloro-4-methoxy-6-methylphenyl)-5-(1-ethylpropyl)-3,7-dimethylpyrrolo[2,1-f][1,2,4]triazin-4(3H)-one,
5-(1-ethylpropyl)-2-[4-(1H-imidazol-1-yl)-2-methylphenyl]-3,7-dimethylpyrrolo[2,1-f][1,2,4]triazin-4(3H)-one,
2-(3-chloro-5-methoxy-2-pyridinyl)-5-(1-ethylpropyl)-3,7-dimethylpyrrolo[2,1-f][1,2,4]triazin-4(3H)-one,
2-(2-chloro-5-fluoro-4-methoxyphenyl)-5-(1-ethylpropyl)-3,7-dimethylpyrrolo[2,1-f][1,2,4]triazin-4(3H)-one,
3-ethyl-5-(1-ethylpropyl)-2-(2-fluoro-4-methoxyphenyl)-7-methylpyrrolo[2,1-f][1,2,4]triazin-4(3H)-one,
5-sec-butyl-2-(2-chloro-5-fluoro-4-methoxyphenyl)-3,7-dimethylpyrrolo[2,1-f][1,2,4]triazin-4(3H)-one,
5-sec-butyl-2-[2-chloro-4-(difluoromethoxy)phenyl]-3,7-dimethylpyrrolo[2,1-f][1,2,4]triazin-4(3H)-one,
2-[4-(difluoromethoxy)-5-fluoro-2-methylphenyl]-3-ethyl-5-isopropyl-7-methylpyrrolo[2,1-f][1,2,4]triazin-4(3H)-one,
2-[4-(difluoromethoxy)-2-methylphenyl]-3-ethyl-5-isopropyl-7-methylpyrrolo[2,1-f][1,2,4]triazin-4(3H)-one,
2-[2-chloro-4-(difluoromethoxy)-6-fluorophenyl]-3-ethyl-5-isopropyl-7-methylpyrrolo[2,1-f][1,2,4]triazin-4(3H)-one,
2-[2-chloro-4-(difluoromethoxy)phenyl]-3,7-dimethyl-5-(1-methylbutyl)pyrrolo[2,1-f][1,2,4]triazin-4(3H)-one,
2-(2-chloro-5-fluoro-4-methoxyphenyl)-3,7-dimethyl-5-(1-methylbutyl)pyrrolo[2,1-f][1,2,4]triazin-4(3H)-one,
2-[6-(difluoromethoxy)-4-methyl-3-pyridinyl]-3,7-dimethyl-5-(1-methylbutyl)pyrrolo[2,1-f][1,2,4]triazin-4(3H)-one,
2-[5-chloro-4-(difluoromethoxy)-2-methylphenyl]-3-ethyl-5-isopropyl-7-methylpyrrolo[2,1-f][1,2,4]triazin-4(3H)-one,
2-[2-chloro-4-(methylthio)phenyl]-3,7-dimethyl-5-[(1S)-1-methylbutyl]pyrrolo[2,1-f][1,2,4]triazin-4(3H)-one, or
2-[2-chloro-4-(methylthio)phenyl]-3,7-dimethyl-5-[(1R)-1-methylbutyl]pyrrolo[2,1-f][1,2,4]triazin-4(3H)-one, a salt thereof, an N-oxide thereof, or a solvate thereof.

Unless otherwise specified, all isomers are included in the present invention. For example, alkyl, alkenyl, alkynyl, alkoxy, alkylthio, alkylene, alkenylene and alkynylene include straight and branched isomers. In addition, isomers based on double bond, ring, fused ring (E, Z, cis, trans), isomers resulting from the presence of asymmetric carbon(s) (R,S-configuration, α,β-configuration, enantiomers, diastereomers), optically active compounds having optical rotation (D, L, d, l-configuration), polar compounds obtained by chromatographic separations (more polar compound, less polar compound), equilibrium compounds, rotational isomers, the mixtures thereof at any ratio, racemic mixtures are included in the present invention.

In the present invention, as is apparent to the one skilled in the art, unless otherwise indicated, ⸽⸽⸽⸽
the mark shows that the bond is on the other side of paper (α-configuration), ◢
the mark shows that the bond is in front of paper (β-configuration), ⁓
the mark shows that the bond is α-configuration or β-configuration, and ╱
the mark shows that the bond is a mixture of α-configuration and β-configuration.

[Salts]

The compound represented by the formula (I) may be converted into a salt by known methods. As the salt, pharmaceutically acceptable salts are preferred.

As the salt, alkali metal salt, alkaline earth metal salt, ammonium salt, amine salt, acid addition salt, etc. are given.

Aqueous salt is preferred as the salt. As appropriate salts thereof, salts of alkali metals such as potassium, and sodium; salts of alkaline-earth metals such as calcium and magnesium; ammonium salts such as tetramethylammonium; and salts of pharmaceutically acceptable organic amines such as triethylamine, methylamine, dimethylamine, cyclopentylamine, benzylamine, phenethylamine, piperidine, monoethanolamine, diethanolamine, tris(hydroxymethyl)aminomethane, lysine, arginine, and N-methyl-D-glucamine are given.

Aqueous salts are preferred as the acid addition salts. As appropriate salts thereof, for example, salts of inorganic acids such as hydrochloride, hydrobromide, hydroiodide, sulfate, phosphate, nitrate, or salts of organic acid such as acetate, lactate, tartrate, benzoate, citrate, methanesulfonate, ethanesulfonate, trifluoroacetate, benzenesulfonate, toluenesulfonate, isethionate, glucuronate, or gluconate are given.

Further, N-oxide is included in the salts. The compound of the present invention may be converted into an N-oxide compound by any methods. The N-oxide is the compound in which a nitrogen atom of the compound represented by the formula (I) is oxidized.

The compound represented by the formula (I) and its salt may be replaced with a solvate.

The solvate is preferably nontoxic and aqueous. As appropriate solvates, for example, water or alcohol-based solvents such as ethanol are given.

[Prodrug]

The prodrug of a compound represented by the formula (I) refers to a compound which is converted into the compound represented by the formula (I) through reaction with an enzyme, a gastric acid, or the like, in the living body. The prodrug of a compound represented by the formula (I) may be exemplified by the compounds represented by the formula (I) where an amino group is contained, in which the amino group has been allowed to undergo acylation, alkylation or phosphorylation (for example, the compounds represented by the formula (I) in which the amino group has been allowed to undergo eicosanoylation, alanylation, pentylaminocarbonylation, (5-methyl-2-oxo-1,3-dioxolen-4-yl)methoxycarbonylation, tetrahydrofuranylation, pyrrolizylmethylation, pivaloyloxymethylation, acetoxymethylation, sec-butylation, etc.); the compounds represented by the formula (I) where a hydroxy group is contained, in which the hydroxy group has been allowed to undergo acylation, alkylation, phosphorylation or boration (for example, the compounds represented by the formula (I) in which the hydroxy group has been allowed to undergo acetylation, palmitoylation, propanoylation, pivaloylation, succinylation, fumarylation, alanylation, dimethylaminomethylcarbonylation, etc.); the compounds represented by the formula (I) where a carboxyl group is contained, in which the carboxyl group has been allowed to undergo esterification or amidation (for example, the compounds represented by the formula (I) in which the carboxyl group has been allowed to undergo ethyl-esterification, isopropyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification, methyl-amidation, etc.); the compounds represented by the formula (I) where a carboxyl group is contained, in which the carboxyl group has been allowed to undergo replacement with a hydroxymethyl group, and the like. Those compounds can be produced in accordance with the per se known processes. Besides, the prodrug of the compound represented by the formula (I) may be any of the forms of hydrated or non-hydrated products.

[Process for Preparation of the Compounds of the Present Invention]

The compounds of the present invention represented by formula (I) can be prepared by the known method, for example, the method shown below, similar methods thereof, the method as described in Examples. The starting material in each preparation method shown below may be used in the form of a salt. Such salt used is the pharmaceutically acceptable salt of the compounds represented by formula (I).

The compound represented by the formula (I) can be produced by subjecting a compound represented by formula (II):

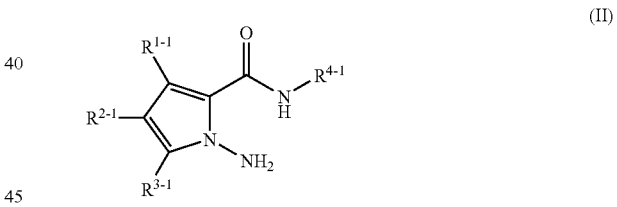

wherein $R^{1-1}$, $R^{2-1}$, $R^{3-1}$ and $R^{4-1}$ respectively have the same meanings of $R^1$, $R^2$, $R^3$ and $R^4$, with the proviso that the hydroxyl group and the amino group contained in the groups represented by $R^{1-1}$, $R^{2-1}$, $R^{3-1}$ and $R^{4-1}$ are protected as occasion demands, and a compound represented by a formula (III):

wherein ring $1^1$ has the same meaning as ring 1, with the proviso that the a carboxy group, a hydroxyl group, an amino group and a mercapto group contained in the groups represented by ring $1^1$ are protected as occasion demands, to a cyclization reaction and further to a deprotection reaction as occasion demands.

Cyclization reaction of the compound represented by formula (II) with the compound represented by formula (III) is carried out, for example, by allowing them to undergo the reaction at from room temperature to about 250° C. in the presence of an oxidizing agent (e.g., oxygen, air, DDQ, Mn(OAc)$_3$, PhI(OAc)$_2$, NiO$_2$, BaMnO$_4$, Pb(OAc)$_4$ and the like) in an organic solvent (e.g., xylene, dichloromethane, tetrahydrofuran, acetic acid and the like) or without solvent and in the presence or absence of a catalyst (e.g., activated carbon, palladium carbon, Yb(OTf)$_3$, Cu(OAc)$_2$ and the like).

The deprotection method for the protecting group of carboxy, hydroxy, amino, and mercapto group is well known. Examples of such deprotection are
(1) alkali hydrolysis,
(2) deprotection under acidic conditions,
(3) deprotection by hydrogenolysis,
(4) deprotection of silyl groups,
(5) deprotection using a metal,
(6) deprotection using a metal complex.

Details of these deprotection methods are hereinafter illustrated.

(1) The deprotection by alkali hydrolysis is carried out at about 0° C. to about 40° C., using an alkali hydroxide (e.g., sodium hydroxide, potassium hydroxide, lithium hydroxide, etc.), an alkaline earth metal hydroxide (e.g., barium hydroxide, calcium hydroxide, etc.) or a carbonate (e.g., sodium carbonate, potassium carbonate, etc.) or an aqueous solution thereof or a mixture thereof, in an organic solvent (e.g., methanol, tetrahydrofuran, 1,4-dioxane, etc.).

(2) The deprotection under acidic conditions is carried out at about 0° C. to about 100° C. with an organic acid (e.g., acetic acid, trifluoroacetic acid, methanesulfonic acid, p-toluenesulfonic acid, etc.) or an inorganic acid (e.g., hydrochloric acid, sulfuric acid, etc.) or a mixture thereof (e.g., hydrogen bromide/acetic acid) in an organic solvent (e.g., dichloromethane, chloroform, dioxane, ethyl acetate, anisole, etc.) in the presence or absence of 2,2,2-trifluoroethanol.

(3) The deprotection by hydrogenolysis is carried out at about 0° C. to about 200° C. in a solvent [ethers (e.g., tetrahydrofuran, dioxane, dimethoxyethane, diethyl ether, etc.), alcohols (e.g., methanol, ethanol, etc.), benzenes (e.g., benzene, toluene, etc.), ketones (e.g., acetone, methyl ethyl ketone, etc.), nitriles (e.g., acetonitrile, etc.), amides (e.g., dimethylformamide, etc.), water, ethyl acetate, acetic acid or a mixture of two or more solvents thereof] in the presence of a catalyst (e.g., palladium-carbon, palladium black, palladium hydroxide-carbon, platinum oxide, Raney-Ni, etc.) under a normal pressure or an increased pressure in a hydrogen stream or in the presence of ammonium formate.

(4) The deprotection of the silyl group is carried out in a water-miscible organic solvent (e.g., tetrahydrofuran, acetonitrile, etc.) using tetrabutylammonium fluoride at about 0° C. to about 40° C.

(5) The deprotection using a metal is carried out in an acidic solvent (e.g., acetic acid, a buffer of pH 4.2 to 7.2, or a mixture of a solvent thereof and an organic solvent such as tetrahydrofuran) in the presence of a zinc dust at about 0° C. to about 40° C. while applying ultrasonic waves, if required.

(6) The deprotection using a metal complex is carried out at about 0° C. to about 40° C. in an organic solvent (e.g., dichloromethane, dimethylformamide, tetrahydrofuran, ethyl acetate, acetonitrile, dioxane, ethanol, etc.), water or a mixture thereof in the presence of a trapping reagent (e.g., tributyltin hydride, triethylsilane, dimedone, morpholine, diethylamine, pyrrolidine, etc.), an organic acid (e.g., acetic acid, formic acid, 2-ethylhexanoic acid, etc.) and/or an organic acid salt (e.g., sodium 2-ethylhexanoate, potassium 2-ethylhexanoate, etc.) and in the presence or absence of a phosphine reagent (e.g., triphenylphosphine, etc.), using a metal complex [e.g., tetrakistriphenylphosphine palladium(0), bis(triphenylphosphine)palladium(II) dichloride, palladium(II) acetate, tris(triphenylphosphine)rhodium(I) chloride].

For example, as well as above, the deprotection reaction can be done by means of a method described by T. W. Greene, Protective Groups in Organic Synthesis, Wiley, New York, 1999.

As the carboxyl-protecting group, there are exemplified methyl group, ethyl group, allyl group, tert-butyl group, trichloroethyl group, benzyl (Bn) group, phenacyl group, p-methoxybenzyl group, trityl group, 2-chlorotrityl group, or a solid-phase carrier are coupled by those structures, and so forth.

As the hydroxy-protecting group, there are exemplified methyl group, trityl group, methoxymethyl (MOM) group, 1-ethoxyethyl (EE) group, methoxyethoxymethyl (MEM) group, 2-tetrahydropyranyl (THP) group, trimethylsilyl (TMS) group, triethylsilyl (TES) group, tert-butyldimethylsilyl (TBDMS) group, tert-butyldiphenylsilyl (TBDPS) group, acetyl (Ac) group, pivaloyl group, benzoyl group, benzyl (Bn) group, p-methoxybenzyl group, allyloxycarbonyl (Alloc) group, and 2,2,2-trichloroethoxycarbonyl (Troc) group, and so forth.

As the amino-protecting group, there are exemplified benzyloxycarbonyl group, tert-butoxycarbonyl (Boc) group, allyloxycarbonyl (Alloc) group, 1-methyl-1-(4-biphenypethoxycarbonyl (Bpoc) group, trifluoroacetyl group, 9-fluorenylmethoxycarbonyl (Fmoc) group, benzyl (Bn) group, p-methoxybenzyl group, benzyloxymethyl (BOM) group, 2-(trimethylsilyl)ethoxymethyl (SEM) group, and so forth.

As the mercapto-protecting group, there are exemplified benzyl group, methoxybenzyl group, methoxymethyl (MOM) group, 2-tetrahydropyranyl (THP) group, diphenylmethyl group, acetyl (Ac) group, and so forth.

In addition to the above protecting groups for carboxyl, hydroxy, amino, or mercapto groups, there is no particular limitation so long as it can be easily and selectively removed. For example, protecting groups described in T. W. Greene, Protective Groups in Organic Synthesis, Wiley, New York, 1999 can be used.

Those skilled in the art can easily understand that the desired compounds of the present invention can be easily produced by selectively employing these deprotection methods.

In addition, the compound represented by formula (I) can be prepared by subjecting a compound represented by formula (XI):

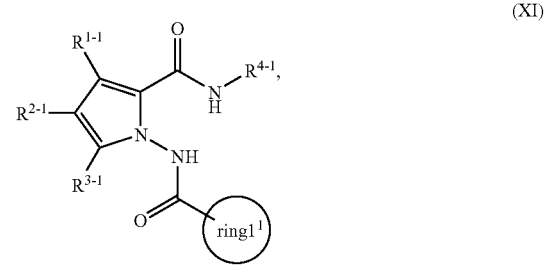

to the cyclization reaction under acid condition. The compound represented by formula (XI) can be prepared by subjecting the compound represented by formula (II) and a compound represented by formula (X):

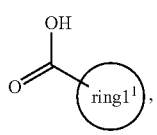

(X)

wherein ring¹ have the same meanings as described above, to amidation reaction. If required, it can be produced by referring to deprotection reaction of protecting group.

The amidation reaction of the compound represented by formula (II) and the compound represented by formula (X) is known and examples thereof include:

(1) a method using an acyl halide,
(2) a method using a mixed acid anhydride, and
(3) a method using a condensing agent.

These methods are described in detail below.

(1) The method using an acyl halide is carried out, for example, by reacting carboxylic acid with an acid halogenating agent (for example, oxalyl chloride, thionyl chloride, phosphorus pentachloride and phosphorus trichloride, etc.) in an organic solvent (for example, halogenated hydrocarbon such as chloroform and dichloromethane, etc., for example, ether such as diethyl ether, tetrahydrofuran and dioxane, etc., for example, acid amide such as dimethylformamide, etc., is used. These solvents can be used alone, and if necessary, mixed at the suitable rate, for example, at ratio of about 1:1~1:10, of two or more, and it may be used) or in the absence of the solvent at a temperature of about −20° C. to a refluxing temperature. Then the obtained acyl halide derivative may be reacted with amine in the presence of a base (for example, alkyl amine such as triethylamine, tributylamine and diisopropyl ethylamine, for example, aromatic amine such as N,N-dimethylaniline, pyridine and 4-(dimethylamino)pyridine) about 0 to 40° C. Alternatively, the obtained acyl halide can be reacted with amine in an organic solvent (for example, diethyl ether, dioxane, tetrahydrofuran, etc., is used. These solvents can be used alone, and if necessary, mixed at the suitable rate, for example, at ratio of about 1:1~1:10, of two or more, and it may be used) about 0 to 40° C. using an aqueous alkali solution (sodium bicarbonate solution or sodium hydroxide solution, etc.).

(2) The method using a mixed acid anhydride is carried out, for example, by reacting carboxylic acid with an acyl halide (for example, pivaloyl chloride, tosyl chloride, mesyl chloride, etc.) or an acid derivative (for example, ethyl chloroformate, isobutyl chloroformate, etc.) in the presence of a base (for example, pyridine, triethylamine, dimethylaniline, dimethylaminopyridine, diisopropylethylamine, etc.) in an organic solvent (for example, halogenated hydrocarbon such as chloroform and dichloromethane, etc., for example, ether such as diethyl ether, tetrahydrofuran and dioxane, etc., for example, acid amide such as dimethylformamide, etc., is used. These solvents can be used alone, and if necessary, mixed at the suitable rate, for example, at ratio of about 1:1~1:10, of two or more, and it may be used) or in the absence of the solvent about 0 to 40° C., and reacting the resulting mixed acid anhydride with amine in an organic solvent (for example, halogenated hydrocarbon such as chloroform and dichloromethane, etc., for example, ether such as diethyl ether, tetrahydrofuran and dioxane, etc., for example, acid amide such as dimethylformamide, etc., is used. These solvents can be used alone, and if necessary, mixed at the suitable rate, for example, at ratio of about 1:1~1:10, of two or more, and it may be used) about 0 to 40° C.

(3) The method using a condensing agent is carried out, for example, by reacting carboxylic acid with amine in an organic solvent (for example, halogenated hydrocarbon such as chloroform and dichloromethane, etc., for example, ether such as diethyl ether, tetrahydrofuran and dioxane, etc., for example, acid amide such as dimethylformamide, etc., is used. These solvents can be used alone, and if necessary, mixed at the suitable rate, for example, at ratio of about 1:1~1:10, of two or more, and it may be used) or in the absence of the solvent about 0 to 40° C. in the presence or absence of a base (for example, alkyl amine such as triethylamine, tributylamine and diisopropyl ethylamine, for example, aromatic amine such as N,N-dimethylaniline, pyridine and 4-(dimethylamino)pyridine), using a condensing agent (for example, 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, 1-propylphosphonic acid cyclic anhydride (PPA), etc.) and using, or not using, 1-hydroxybenztriazole (HOBt).

The cyclization reaction under acid condition of the compound represented by formula (XI) is carried out at room temperature to 160° C. with an organic acid (e.g., acetic acid, trifluoroacetic acid, methanesulfonic acid, p-toluenesulfonic acid, etc.) or an inorganic acid (e.g., hydrochloric acid, sulfuric acid, etc.) or a mixture thereof (e.g., hydrogen bromide/acetic acid) in a solvent (e.g., dichloromethane, chloroform, dioxane, ethyl acetate, anisole, toluene, etc.), or in the absence of the solvent.

The deprotection reaction of protecting group of carboxyl group, hydroxyl group, amino group, or mercapto group is done by means of the same methods as described above.

The compound represented by formula (II) can be produced by the method by represented by the reaction process (I). All symbols have the same meanings as described above in the reaction process (I).

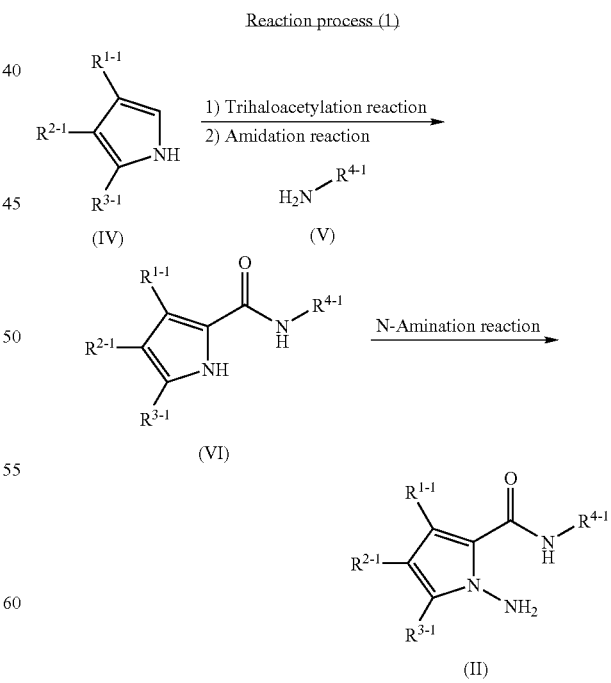

Among the compounds represented by formula (IV), a compound in which $R^{1-1}$ is a branched alkyl group having 3, 5, 7 or 9 carbon atoms (e.g., isopropyl, 1-ethylpropyl, 1-propylbutyl and the like), wherein the beginning of branching is the 1-position carbon atom and the two alkyl groups branched from the 1-position carbon have the same number of carbon atoms, namely, the compound represented by formula (IV-a), can be produced by the method shown by the reaction process 2. In the reaction process 2, $R^{20}$ and $R^{30}$ each independently represent a C1-4 alkyl group, X represents a chlorine atom, a bromine atom or an iodine atom, $R^{1-1a}$ represents a branched alkyl group having 3, 5, 7 or 9 carbon atoms, wherein the beginning of branching is the 1-position carbon atom and the two alkyl groups branched from the 1-position carbon have the same number of carbon atoms, and all other symbols have the same meanings as described above.

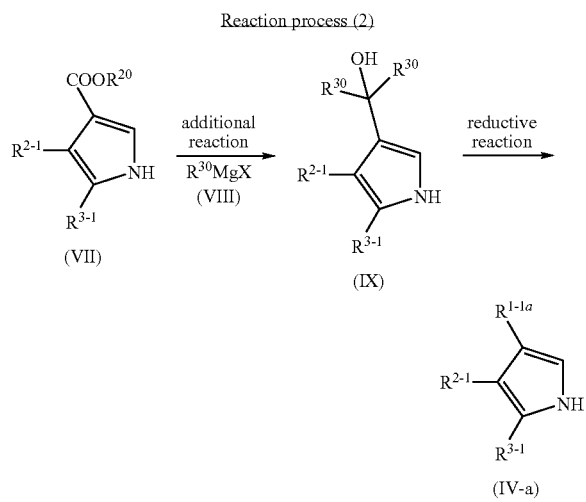

Trihaloacetylation reaction-amidation reaction, N-amination reaction, additional reaction and reductive reaction shown with reaction process 1 and 2 can be done with the condition of an example described in the present specification or a known condition.

The compounds represented by a formula (III) and (X) to use as a starting material are well known, or can be produced easily by using a known method, for example, the method described in "Comprehensive Organic Transformations: A Guide to Functional Group Preparations 2nd Edition (Richard C. Larock, John Wiley & Sons Inc, 1999)".

The compounds represented by a formula (IV), (V), (VII) and (VIII) to use as a starting material in reaction process 1 and 2 are well known, or can be produced easily by using a known method, for example, the method described in "Comprehensive Organic Transformations: A Guide to Functional Group Preparations 2nd Edition (Richard C. Larock, John Wiley & Sons Inc, 1999)".

Besides compounds shown as above of the compounds of the present invention described by formula (I), they can be produced by an example described in the present specification, the known method, for example, the method described in "Comprehensive Organic Transformations: A Guide to Functional Group Preparations, 2nd Edition (Richard C. Larock, John Wiley & Sons Inc, 1999)", or a combination method thereof.

The heating reaction in each reaction of the present specification may be performed using a water bath, an oil bath, a sand bath or a microwave, though it is apparent to those skilled in the art.

In each reaction of the present specification, a reagent appropriately carried on a solid carrier of polymers (e.g., polystyrene, polyacrylamide, polypropylene, polyethylene glycol, etc.) may be used.

In each reaction in the present specification, reaction products may be purified by general purification techniques, for example, by distillation under atmospheric or reduced pressure, by high performance liquid chromatography, by thin layer chromatography, by ion exchange resin, by scavenger resin, or by column chromatography using silica gel or magnesium silicate; or by washing or by recrystallization. Purification may be carried out after each reaction or after a series of reactions.

[Toxicity]

The toxicity of the compound represented by the formula (I), a salt thereof, an N-oxide thereof, a solvate thereof, or a prodrug thereof (hereinafter, all these are abbreviated to "the compound(s) of the present invention represented by formula (I)", "the compound(s) of the present invention" and "the compound(s) represented by formula (I)") is very low, and therefore it was confirmed that the compound is sufficiently safe for use as medicine.

[Application to Pharmaceuticals]

The compound of the present invention represented by the formula (I) binds to a CRF receptor, and exhibits antagonist action, and therefore is useful for preventing and/or treating CRF mediated diseases, for example, neuropsychiatric diseases, digestive diseases, respiratory diseases, endocrine diseases, metabolic diseases, cardiovascular diseases, dermatologic diseases, genitourinary diseases, ophthalmologic diseases, or musculoskeletal diseases.

More specifically, as neuropsychiatric diseases, for example, mood disorders (e.g., depression (major depressive disorder (MDD), minor depressive disorder, single episode depression, postpartum depression, child abuse induced depression, elderly depression, masked depression, seasonal depression, recurrent depression), bipolar disorder, indefinite complaint, premenstrual dysphoric disorder, postpartum mood disorder, dysphoric disorder in around the time of climacteric, and perimenopausal dysphoric disorder); anxiety disorders (e.g. generalized anxiety disorder, panic disorder, posttraumatic stress disorder (PTSD), obsessive compulsive disorder, social anxiety disorders, phobic anxiety disorders (e.g. acrophobia, claustrophobia, agoraphobia, social phobia, etc.)); adjustment disorders (e.g. emotional injury, conduct disorder or disorder with both, physical complaint, isolating oneself from society, occupational stagnant, and stagnant academic achievement); stress-related disorders (e.g. stress induced immunosuppression, stress induced headache, stress induced fever, stress induced pain, post operative stress, stress induced gastrointestinal disorder (e.g. gastritis, gastric ulcer, and duodenal ulcer, etc.), irritable bowel syndrome, hyposexuality, and erectile dysfunction)); eating disorders (e.g. anorexia nervosa, binge eating disorder, and nervous vomiting); symptom caused by psychotropic substance or dependency thereon (e.g. alcoholic withdrawal symptoms, alcohol dependence, drug addiction, and drug dependency); organic mental disorder (e.g. senile dementia of Alzheimer's type, and multi-infarct dementia); schizophrenic disorder; attention-deficit hyperactivity disorder; neurodegenerative diseases (e.g. Alzheimer's disease, Parkinson's disease, Huntington's disease, and amyotrophic lateral sclerosis); pain; convulsive disorders (e.g. convulsion and muscle spasm); episodic diseases (e.g. epilepsy, attack and migraine); restless legs syndrome, or sleep disorders (e.g. nonorganic sleep disorder and fiber myalgic sleep disorder) are given. As digestive diseases, for example, peptic ulcer (e.g. gastric ulcer and duodenal ulcer); inflammatory bowel disease (e.g. ulcerative colitis and Crohn's disease); irritable bowel syndrome; stress induced gastrointestinal disorder (e.g. gastritis, gastric ulcer, and duodenal ulcer, etc.); diarrhea; or constipation is given. As respiratory diseases, for example, asthma, bronchitis, chronic obstructive pulmonary disease, or allergic rhinitis is given. As endocrine diseases, for example, disturbed thyroid function, Cushing's disease, or syndrome of inappropriate antidiuretic hormone secretion is given. As metabolic diseases, for example, obesity or hypoglycemia is given. As cardiovascular diseases, for example, hypertension, ischemic heart disease, tachycardia, congestive heart failure, or cerebral vascular disease is given. As dermatologic diseases, for example, atopic dermatitis, allergic contact dermatitis or psoriasis is given. As genitourinary diseases, for example, urinary disturbance, pollakiuria or urinary incontinence is given. As ophthalmologic diseases, for example, uveitis is given. As musculoskeletal diseases, for example, chronic rheumatoid arthritis, osteoarthrosis, or osteoporosis is given.

The compound represented by the formula (I) shown by the present invention is very useful since it has a strong CRF receptor antagonistic activity and also is excellent in solubility, chemical stability, biological stability and the like properties which are important as pharmaceutical preparations. Particularly, regarding the solubility, since $R^4$ in the compound represented by the formula (I) shown by the present invention is a C1-4 alkyl which may be substituted or a C3-6 cycloalkyl which may be substituted, it is a compound in which its solubility in water was sharply improved in comparison with a compound in which $R^4$ is a hydrogen atom. Regarding evaluation of the solubility, it can be measured, for example, by the method described in The Pharmacopoeia of Japan, $15^{th}$ revision.

Also, the compound represented by the formula (I) shown by the present invention is stable, for example, under acidic condition and under light irradiation. The fact that the compound represented by the formula (I) shown by the present invention is stable is shown by a stability test which is described later.

Additionally, since its ratio of forming a covalent bond with protein is very low, the compound represented by the formula (I) shown by the present invention is a compound having a low possibility of causing side effects such as hepatotoxicity and the like. Amount of its covalent bond with protein can be measured, for example, by the method described in the following.

i) Reaction Operation and Preparation of Microsome Residue Solution

A human liver microsome (final concentration: 1 mg protein/mL), a magnesium chloride solution (final concentration: 3.3 mmol/L) and a radioisotope-labeled evaluation compound (final concentration: 10 won) are added to a test tube whose tare mass was measured in advance and pre-incubated at 37° C. for 5 minutes. Then a (3-NADPH solution (final concentration: 2 mmol/L) is added thereto to start the reaction (n=2, total volume of reaction liquid: 500 μL). To the control sample (n=2), 100 mmol/L potassium phosphate buffer (pH 7.4) is added instead of (3-NADPH solution. One hour after commencement of the reaction, 2 mL of ice-cooled acetone is added thereto and mixed therewith to stop the reaction. After centrifugation (about 1800×g, 4° C., 20 minutes), the supernatant is collected in a vial and 14 mL of a scintillator ACSH is added thereto, followed by measurement of amount of the radioactivity by a liquid scintillation counter (to be referred to as LSC hereinafter, 2500TR manufactured by Perkin-Elmer). To the residue in the test tube, 2 mL of a water/methanol mixed liquid (20/80, v/v) is added and stirred. The residue is dispersed by an ultrasonic treatment so that the residue becomes uniform and then centrifuged (about 1800×g, 4° C., 20 minutes) to collect the supernatant in a vial. By adding 10 mL of a scintillator HIONIC-FLUOR thereto, amount of the radioactivity is measured. When amount of the radioactivity in the supernatant became 100 dpm or reached steady state by repeating washing with 2 mL of the water/methanol mixed liquid (20/80, v/v), the solvent in the test tube is removed by carrying out evaporation to dryness under a reduced pressure using an evaporator. The residue is dissolved by adding 1 mL of 2% sodium dodecyl sulfate (to be referred to as SDS hereinafter) thereto and then allowed to stand overnight at 37° C. to prepare a microsome residue solution (to be referred to as residue solution hereinafter).

ii) Measurement of the Amount of Radioactivity in the Residue

After measuring mass of the test tube which contains the residue solution, 500 μL of the residue solution is added to a vial whose tare mass was measured in advance and mass of the vial which contains the residue solution is measured. To the vial which contains the residue solution, 10 mL of a scintillator HIONIC-FLUOR is added, and amount of the radioactivity is measured by LSC and the amount of radioactivity in the residue is calculated using the following formula.

Amount of radioactivity in the residue (dpm)=amount of radioactivity in vial which contains residue solution×(mass of test tube which contains residue solution−tare mass of test tube)/(mass of vial which contains residue solution−tare mass of vial)

iii) Determination of Total Protein in Residue

Protein concentration of the residue solution is measured using BCA-Protein assay kit manufactured by PIERCE. A bovine serum albumin standard solution having a concentration of 0.05, 0.1, 0.2, 0.5, 0.75 or 1 mg/ml containing 2% SDS and the residue solution are added in 25 pit portions to a 96 well plate. A mixed liquid prepared by mixing the Reagent A and Reagent B of the BCA-Protein assay kit at a ratio of 50:1 (v/v) were added in 200 μL, portions to respective wells, incubated at 37° C. for 30 minutes and then allowed to stand at room temperature for 10 minutes. Protein concentration in the residue solution is calculated by measuring absorbance of each well at a wavelength of 562 nm using a plate reader (HT, manufactured by Biotech). Additionally, 25 μL of the residue solution is added to a vial whose tare mass was measured in advance, and mass of the vial which contains 25 μL of the residue solution is measured. Amount of total protein in the residue is calculated using the following calculation formula.

Amount of total protein in residue (mg)=protein concentration in residue solution (mg/mL)×0.025 (mL)×(mass of test tube which contains residue solution−tare mass of the test tube)/(mass of vial which contains 25 μL of residue solution−tare mass of the vial)

iv) Binding Amount Per 1 mg Protein

Binding amount per 1 mg protein is calculated from the amount of radioactivity in the residue, specific radioactivity of the evaluation compound solution and amount of total protein in the residue, using the following formula.

Binding amount per 1 mg protein (pmol/mg)=amount of radioactivity in the residue/specific radioactivity of the evaluation compound solution (dpm/pmol)/amount of total protein in the residue (mg)

v) Judgment

It is judged that hepatopathy risk is low when the value, obtained by subtracting average value of the binding amount per 1 mg protein in a control sample (β-NADPH was not added) from average value of the binding amount per 1 mg protein in a reaction sample (β-NADPH added), is less than 50 pmol/mg.

The compound of the present invention represented by the formula (I) may be administered as a concomitant drug with other medicaments to accomplish the following purposes:
(1) to supplement and/or enhance the preventive and/or therapeutic effect of the present compound;
(2) to improve the kinetics and/or absorption and reduce the dose of the present compound; and/or
(3) to reduce the side effects of the present compound.

A combination of the compound represented by the formula (I) and other medicaments may be administered in the form of the formulations having those components incorporated in one preparation, or may be administered in separate preparations. In the case where those medicaments are administered in separate preparations, they may be administered simultaneously or at different times. Further, in the latter case, the compound of the present invention represented by the formula (I) may be administered before the other medicaments. Alternatively, the other medicaments may be administered before the compound of the present invention represented by the formula (I). The method for the administration of those medicaments are the same or different.

The diseases on which the preventive and/or therapeutic effect of the above combination preparations works are not specifically limited but may be those for which the preventive and/or therapeutic effect of the compound of the present invention represented by the formula (I) is supplemented and/or enhanced.

Examples of other medicaments for supplementing and/or enhancing the preventive and/or therapeutic effect of the compound of the present invention represented by the formula (I) on mood disorders include an antidepressant, a psychoanaleptic, an antianxiety agent, an antipsychotic agent, a mitochondrial benzodiazepine receptor (MBR) ligand, a neurokinin-1 (NK1) antagonist, and the like.

Examples of other medicaments for supplementing and/or enhancing the preventive and/or therapeutic effect of the compound of the present invention represented by the formula (I) on anxiety disorders include an antianxiety agent and a MBR ligand.

Examples of other medicaments for supplementing and/or enhancing the preventive and/or therapeutic effect of the compound of the present invention represented by the formula (I) on irritable bowel syndrome include a gastrointestinal promotility agent, a histamine $H_2$ receptor antagonist, a proton pump inhibitor, a 5-$HT_3$ antagonist, a 5-$HT_4$ agonist, an anticholinergic agent, an antidiarrheal drug, a laxative agent, an autonomic modulating agent, an antidepressant, an antianxiety agent, an MBR ligand, and the like.

As an antidepressant, for example, a tricyclic antidepressant (e.g. amitriptyline hydrochloride, imipramine hydrochloride, clomipramine hydrochloride, dosulepin hydrochloride, nortriptyline hydrochloride, lofepramine hydrochloride, trimipramine maleate, amoxapine); a tetracyclic antidepressant (e.g. maprotiline hydrochloride, mianserin hydrochloride, setiptiline maleate); a monoamine oxidase (MAO) inhibitor (safrazine hydrochloride); serotonin and noradrenaline reuptake inhibitors (SNRI) (e.g. milnacipran hydrochloride, venlafaxine hydrochloride); a selective serotonin reuptake inhibitor (SSRI) (e.g. fluvoxamine maleate, paroxetine hydrochloride, fluoxetine hydrochloride, citalopram hydrochloride); and a serotonin reuptake inhibitor (e.g. trazodone hydrochloride) are given.

As an antianxiety agent, for example, a benzodiazepine anxiolytic (e.g. alprazolam, oxazepam, oxazolam, cloxazolam, clorazepate dipotassium, chlordiazepoxide, diazepam, tofisopam, triazolam, prazepam, fludiazepam, flutazolam, flutoprazepam, bromazepam, mexazolam, medazepam, ethyl loflazepate, lorazepam); a thienodiazepine anxiolytic (e.g. etizolam and clotiazepam); and a non-benzodiazepine anxiolytic (e.g. tandospirone citrate and hydroxylzine hydrochloride) are given.

As a psychoanaleptic, for example, methylphenidate hydrochloride and pemoline are given.

As an antipsychotic agent, for example, sulpiride, trazodone hydrochloride, and serotonin-dopamine antagonist (e.g. risperidone, perospirone hydrochloride hydrate, quetiapine fumarate, and olanzapine) are given.

As a gastrointestinal promotility agent, for example, trimebutine maleate and polycarbophil calcium are given.

As a proton pump inhibitor, for example, omeprazole, lansoprazole, rabeprazole are given.

As a histamine $H_2$ receptor antagonist, for example, cimetidine, ranitidine, famotidine, nizatidine, lafutidine are given.

As a 5-$HT_3$ antagonist, for example, alosetron is given.

As a 5-$HT_4$ agonist, for example, tegaserod, cisapride and mosapride citrate are given.

The mass ratio of the compound represented by the formula (I) and the other medicaments is not specifically limited.

Any combination of two or more kinds of other medicaments may be administered.

Further, the other medicaments for supplementing and/or enhancing the preventive and/or therapeutic effect of the compound represented by the formula (I) include not only those found so far but also those which will be found on the basis of the above-mentioned mechanism.

For the purpose described above, the compounds of the present invention represented by the formula (I), a non-toxic salt thereof, or a combination of the compounds represented by the formula (I) and other medicaments may be normally administered systemically or locally, usually by oral or parenteral administration.

The doses to be administered are determined depending upon, for example, ages, body weights, symptoms, the desired therapeutic effects, the route of administration, and the duration of the treatment. For the human adult, the dose per person is generally from 1 mg to 1,000 mg, by oral administration, from one to several times per day, and from 0.1 mg to 100 mg, by parenteral administration (preferably, nasal drops, eye drops, or ointments), from one to several times per day, or continuous administration for 1 to 24 hours per day from vein.

As described above, of course, the doses to be used depend upon various conditions. Therefore, there are cases in which doses lower than or greater than the ranges specified above may be used.

In the case where the compound of the present invention represented by the formula (I), or the combination agent of the compound represented by the formula (I) and the other medicaments is administrated, those are used as solid preparations for internal use and liquid preparations for internal use for oral administration as well as preparations for injections, external preparations, suppositories, eye drops, inhalations and the like for parenteral administration.

Examples of the solid preparations for internal use for oral administration include tablets, pills, capsules, powders, granules and the like. The capsules include hard capsules and soft capsules. Further, the tablets include sublingual tablet, oral patch and orally disintegrating tablet.

Such solid preparations for internal use is prepared by a formulation method commonly employed by using one or more active substances without modification, or a mixture of one or more active substances with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer, a solubilizing agent (glutamic acid, aspartic acid, etc.). Further, if necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The liquid preparations for internal use for oral administration include pharmaceutically acceptable aqueous solutions, suspensions, emulsions, syrups, elixirs and the like. Such liquid preparations are prepared by dissolving, suspending or emulsifying one or more active substances in a diluent commonly employed (purified water, ethanol or a mixture liquid thereof, etc.). Such liquid forms may also further contain humectants, suspending agents, emulsifying agents, sweetening agents, flavoring agents, aroma, preservatives, buffers, and the like.

The dose forms of the external preparations for parenteral administration include ointments, gels, creams, fomentations, patches, liniments, atomized agents, inhalations, sprays, aerosols, eye drops, nasal drops, and the like. Such preparations contain one or more active substances and are prepared by a known method or a commonly employed formulation.

Atomized agents, inhalations, and sprays may contain, in addition to a diluent commonly employed, a stabilizer such as sodium bisulfite, and a buffer for imparting isotonicity such as an isotonic agent such as sodium chloride, sodium citrate or citric acid. Methods for producing a spray are described in detail in, for example, U.S. Pat. No. 2,868,691 and U.S. Pat. No. 3,095,355.

The injections for parenteral administration include solutions, suspensions, emulsions and solid injections to be dissolved or suspended before use. The injection is used by dissolving, suspending or emulsifying one or more active substances in a solvent. The solvent includes, for example, distilled water for injection, physiological saline, vegetable oils, alcohols such as propylene glycol, polyethylene glycol and ethanol, and the combinations thereof. The injection may further contain a stabilizer, a dissolution aid (glutamic acid, aspartic acid, Polysorbate 80 (registered trademark), etc.), a suspending agent, an emulsifier, a soothing agent, a buffer, a preservative, and the like. The injection may be produced by sterilizing at the final step or employing an aseptic process. Alternatively, it is also possible that an aseptic solid product such as a freeze-dried product is produced and sterilized or dissolved in aseptic distilled water for injection or another solvent before use.

Other compositions for parenteral administration include suppositories for colorectal administration, pessaries for vaginal administration, and the like, which contain one or more active substances, and are formulated in accordance with common method.

EFFECT OF THE INVENTION

The compound of the present invention binds strongly to the CRF receptor, shows a strong antagonistic activity, has strong activity in an in vivo model (elevated plus maze or the like), also has all of the properties important as a pharmaceutical preparation (e.g., solubility, chemical stability and the like) and further alleviates side effects (e.g., hepatotoxicity and the like). Accordingly, the compound of the present invention is an easily usable medicine which is very effective for a CRF mediated disease such as a neuropsychiatric disease or a digestive disease.

BEST MODE FOR CARRYING OUT THE INVENTION

Hereinafter, the present invention is described in detail by way of examples, but not limited thereto.

Solvents given in parentheses concerning chromatographic separation and TLC each indicate the elution solvent or the developing solvent employed, and the ratio is expressed in ratio by volume.

Solvents given in parentheses concerning NMR each indicate the solvent employed in measurement.

The nomenclature used in the description of the present invention is based on ACD/Name (registered trademark) (version 6.00, manufactured by Advanced Chemistry Development Inc).

EXAMPLE 1

Ethyl 5-methyl-1H-pyrrole-3-carboxylate

10% palladium carbon (anhydrous) (2.5 g) was suspended with ethanol (500 mL) under argon gas atmosphere. Ethyl 2-chloro-5-methyl-1H-pyrrole-3-carboxylate (50 g; see, Tetrahedron Letters, Vol. 35, No. 33, 5989-5992 (1994)) and ammonium formate (51 g) were added to the reaction mixture at room temperature, and it was stirred at room temperature for 8 hours. The reaction mixture was subjected to filtration with Celite (trade name), the filtrate was concentrated under reduced pressure. Water and ethyl acetate were added to the obtained residue, and the mixture was extracted with ethyl acetate. The organic layer was washed by water and a saturated aqueous solution of sodium chloride, and concentrated under reduced pressure after drying with anhydrous magnesium sulfate, to thereby obtain a title compound (40 g) having the following physical properties.

TLC: Rf 0.32 (n-hexane/ethyl acetate=2/1);

$^1$H-NMR (CDCl$_3$): δ 8.10 (brs, 1H), 7.27 (m, 1H), 6.30 (m, 1H), 4.26 (q, J=7.2 Hz, 2H), 2.26 (d, J=0.9 Hz, 3H), 1.33 (t, J=7.2 Hz, 3H).

EXAMPLE 2

3-(5-methyl-1H-pyrrol-3-yl)-3-pentanol

The compound prepared in Example 1 (4.60 g) was dissolved with tetrahydrofuran (60 mL). Ethyl magnesium bromide (3.0M diethylether solution, 40 mL) was added to the reaction mixture on ice bath, and the reaction mixture was stirred at 50° C. overnight. The reaction mixture was cooled, poured into the mixture of ice and a saturated aqueous solution of ammonium chloride, and extracted with ethyl acetate. The organic layer was washed by water and a saturated aqueous solution of sodium chloride, and concentrated under reduced pressure after drying with anhydrous sodium sulfate, to thereby obtain a title compound (4.98 g) having the following physical properties.

TLC: Rf 0.29 (n-hexane/ethyl acetate=2/1);

$^1$H-NMR (CDCl$_3$): δ 0.85 (t, J=7.4 Hz, 6 H), 1.74 (q, J=7.4 Hz, 4 H), 2.25 (d, J=0.7 Hz, 3 H), 5.62-5.94 (m, 1 H), 6.39-6.70 (m, 1 H), 7.71 (s, 1 H).

EXAMPLE 3

4-(1-ethylpropyl)-2-methyl-1H-pyrrole

Lithium aluminum hydride (3.00 g) was suspended with tetrahydrofuran (150 mL). The tetrahydrofuran solution (50 mL) of the compound prepared in Example 2 (3.31 g) was dropped to the mixture under reflux for 30 minutes, and the reaction mixture was stirred overnight. The reaction mixture was cooled, and a saturated aqueous solution of sodium sulfate was added to the reaction mixture on ice bath. The reaction mixture was stirred at room temperature for 1.5 hours, and dried with anhydrous sodium sulfate. The reaction mixture was subjected to filtration with Celite (trade name), the filtrate was concentrated under reduced pressure. A title compound (3.38 g) having the following physical properties was obtained.

TLC: Rf 0.46 (n-hexane/ethyl acetate=9/1);

$^1$H-NMR (CDCl$_3$): δ 0.84 (t, J=7.4 Hz, 6 H), 1.36-1.66 (m, 4 H), 2.13-2.34 (m, 4 H), 5.68-5.78 (m, 1 H), 6.33-6.42 (m, 1 H), 7.61 (s, 1 H).

EXAMPLE 4

3-(1-ethylpropyl)-N,5-dimethyl-1H-pyrrole-2-carboxamide

Trichloroacetyl chloride (2.03 mL) was added to the tetrahydrofuran solution (36 mL) of the compound prepared in Example 3 (2.76 g), and the reaction mixture was stirred at 0° C. for an hour. The reaction mixture was dropped to an aqueous solution of 40% methylamine (36 mL) on ice bath, and stirred at room temperature for 30 minutes. Water was added to the reaction mixture, and the reaction mixture was extracted with ethyl acetate. The organic layer was washed by a saturated aqueous solution of sodium chloride, and dried with anhydrous sodium sulfate. The organic layer was concentrated under reduced pressure. The obtained residue was purified by column chromatography on silica gel (high flash-SI, size 3 L (made in Yamazen corporation), n-hexane/ethyl acetate=60/40→35/65) to obtain a title compound (1.55 g) having the following physical data.

TLC: Rf 0.30 (n-hexane/ethyl acetate=1/1);

$^1$H-NMR (CDCl$_3$): δ 0.84 (t, J=7.3 Hz, 6 H), 1.38-1.81 (m, 4 H), 2.24 (s, 3 H), 2.38-2.62 (m, 1 H), 2.97 (d, J=4.9 Hz, 3 H), 5.67 (s, 1 H), 5.75 (d, J=3.1 Hz, 1 H), 8.90 (s, 1 H).

EXAMPLE 5

1-amino-3-(1-ethylpropyl)-N,5-dimethyl-1H-pyrrole-2-carboxamide

Sodium hydride (60% oil suspended solids, 200 mg) was added to the N,N-dimethylformamide solution (25 mL) of the compound prepared in Example 4 (1.04 g) on ice bath, and the reaction mixture was stirred at 0° C. for an hour. Monochloroamine diethylether solution (about 0.15 M, 50 mL) (The reagent was prepared in accordance with a method described in Journal of Organic Chemistry, 69, 1368-1371 (2004)) was dropped to the reaction mixture, and the reaction mixture was stirred 0° C. for 15 mixtures. A saturated aqueous solution of sodium thiosulfate was added to the reaction mixture on ice bath, and the reaction mixture was extracted twice with ethyl acetate. The organic layer was washed by water and a saturated aqueous solution of sodium chloride, and dried with anhydrous sodium sulfate. The organic layer was concentrated under reduced pressure. The obtained residue was purified by column chromatography on silica gel (high flash-SI, size 3 L (made in Yamazen corporation), n-hexane/ethyl acetate=55/45→30/70) to obtain a title compound (491 mg) having the following physical data.

TLC: Rf 0.28 (n-hexane/ethyl acetate=1/1);

$^1$H-NMR (CDCl$_3$): δ 0.82 (t, J=7.3 Hz, 6 H), 1.38-1.78 (m, 4 H), 2.23 (d, J=0.7 Hz, 3 H), 2.77-2.92 (m, 1 H), 2.95 (d, J=4.8 Hz, 3 H), 5.14 (s, 2 H), 5.65 (s, 1 H), 6.65 (s, 1 H).

EXAMPLE 6

2-chloro-4-(trifluoromethoxy)benzonitrile

An aqueous solution of 2-chloro-4-(trifluoromethoxy)phenylamine (9.0 g) was cooled at 0° C., and concentrated hydrochloric acid (75 mL) was dropped slowly to its solution. The reaction mixture was stirred for 30 minutes, and sodium nitrite (3.73 g) was added to the reaction mixture. The reaction mixture was stirred for 40 minutes. An aqueous mixture solution of copper cyanide (4.65 g) and sodium cyanide (7.08 g) which been cooled off in 0° C. was added to the reaction mixture, and the reaction mixture stirred at room temperature for an hour. The reaction mixture was poured into 5N aqueous solution of sodium hydroxide which been cooled with ice, and extracted twice with ethyl acetate. The organic layer was washed by a saturated aqueous solution of sodium chloride, and dried with anhydrous sodium sulfate. The organic layer was concentrated under reduced pressure. The obtained residue was purified by column chromatography on silica gel (high flash-SI, size 4 L (made in Yamazen corporation), n-hexane→ethyl acetate/n-hexane=1/8) to obtain a title compound (7.36 g) having the following physical data.

TLC: Rf 0.50 (n-hexane/ethyl acetate=20/1);

$^1$H-NMR (CDCl$_3$): δ 7.18 (m, 1 H), 7.37 (m, 1 H), 7.72 (d, J=8.6 Hz, 1 H).

EXAMPLE 7

2-chloro-4-(trifluoromethoxy)benzaldehyde

The toluene solution (50 mL) of the compound prepared in Example 6 (7.36 g) was cooled to −78° C., and diisobutylaluminum hydride (1.0 M toluene solution, 33 mL) was added to the reaction mixture and the reaction mixture was stirred for 2 hours 40 minutes. The reaction mixture was poured into an aqueous solution of L-tartaric acid which been cooled with ice, and extracted twice with ethyl acetate after stirring for an hour. The organic layer was washed by a saturated aqueous solution of sodium chloride, and dried with anhydrous sodium sulfate. The organic layer was concentrated under reduced pressure. The obtained residue was purified by column chromatography on silica gel (high flash-SI, size 4 L (made in Yamazen corporation), n-hexane→ethyl acetate/n-hexane=1/19) and distilled under reduced pressure (25 mmHg, 160° C.) to obtain a title compound (2.96 g) having the following physical data.

TLC: Rf 0.55 (n-hexane/ethyl acetate=15/1);

$^1$H-NMR (CDCl$_3$): δ 7.25 (m, 1 H), 7.33 (m, 1 H), 8.00 (d, J=8.6 Hz, 1 H), 10.44 (m, 1 H).

EXAMPLE 8

2-[2-chloro-4-(trifluoromethoxy)phenyl]-5-(1-ethyl-propyl)-3,7-dimethylpyrrolo[2,1-f][1,2,4]triazin-4(3H)-one

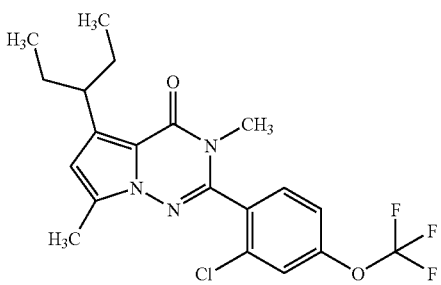 [SMILES: CCC(CC)c1cc(C)n2nc(-c3ccc(OC(F)(F)F)cc3Cl)n(C)c(=O)c12]

The compound prepared in Example 5 (72 mg) and an activated carbon (trade name Darco KB, and it is made in Aldrich company, catalog number 278,092, a CAS number: 7440-44-0) were added to a xylene solution (0.8 mL) of the compound prepared in Example 7 (76 mg), and the reaction mixture was stirred at 130° C. for 27 hours. The reaction mixture was subjected to filtration with Celite (trade name), the filtrate was concentrated. The obtained residue was purified by column chromatography on silica gel (high flash-SI, size L (made in Yamazen corporation), n-hexane→ethyl acetate/n-hexane=15/85) to obtain the compound of the present invention (66 mg) having the following physical data.

TLC: Rf 0.63 (ethyl acetate/n-hexane=1/6);
$^1$H-NMR (CDCl$_3$): δ 0.80-0.92 (m, 6 H), 1.46-1.86 (m, 4 H), 2.39 (s, 3 H), 3.21 (s, 3 H), 3.32-3.48 (m, 1 H), 6.20 (s, 1 H), 7.27-7.35 (m, 1 H), 7.38-7.45 (m, 1 H), 7.54 (d, J=8.42 Hz, 1 H).

EXAMPLES 8(1)~(52)

By the same procedure as a series of reactions of Example 5→Example 8, using the compound provided by using the corresponding amines instead of methylamine instead of the compound prepared in Example 4, and using the corresponding aldehydes instead of the compound prepared in Example 7, the compounds of the present invention having the following physical data were obtained.

EXAMPLE 8(1)

5-(1-ethylpropyl)-2-(4-methoxy-2-methylphenyl)-3,7-dimethylpyrrolo[2,1-f][1,2,4]triazin-4(3H)-one TLC: Rf 0.54 (n-hexane/ethyl acetate=2/1);
$^1$H-NMR (CDCl$_3$): δ 0.79-0.95 (m, 6 H), 1.52-1.82 (m, 4 H), 2.29 (s, 3 H), 2.39 (s, 3 H), 3.14 (s, 3 H), 3.33-3.47 (m, 1 H), 3.85 (s, 3 H), 6.17 (s, 1 H), 6.80-6.90 (m, 2 H), 7.26 (d, J=8.97 Hz, 1 H).

EXAMPLE 8(2)

2-(2-chloro-4-methoxyphenyl)-5-(1-ethylpropyl)-3,7-dimethylpyrrolo[2,1-f][1,2,4]triazin-4(3H)-one TLC: Rf 0.46 (n-hexane/ethyl acetate=2/1);
$^1$H-NMR (CDCl$_3$): δ 7.38 (d, J=8.4 Hz, 1 H), 7.04 (d, J=2.4 Hz, 1 H), 6.94 (dd, J=8.4, 2.4 Hz, 1 H), 6.18 (s, 1 H), 3.87 (s, 3 H), 3.31-3.50 (m, 1 H), 3.21 (s, 3 H), 2.40 (s, 3 H), 1.47-1.87 (m, 4 H), 0.87 (m, 6 H).

EXAMPLE 8(3)

5-(1-ethylpropyl)-3-(2-methoxyethyl)-2-(4-methoxy-2-methylphenyl)-7-methylpyrrolo[2,1-f][1,2,4]triazin-4(3H)-one TLC: Rf 0.30 (n-hexane/ethyl acetate=4/1);
$^1$H-NMR (CDCl$_3$): δ 0.79-0.96 (m, 6 H), 1.48-1.85 (m, 4 H), 2.28 (s, 3 H), 2.39 (s, 3 H), 3.15 (s, 3 H), 3.31-3.49 (m, 3 H), 3.58-3.73 (m, 1 H), 3.85 (s, 3 H), 4.05-4.25 (m, 1 H), 6.16 (s, 1 H), 6.76-6.89 (m, 2 H), 7.27-7.33 (m, 1 H).

EXAMPLE 8(4)

Methyl [5-(1-ethylpropyl)-2-(4-methoxy-2-methylphenyl)-7-methyl-4-oxopyrrolo[2,1-f][1,2,4]triazin-3(4H)-yl]acetate TLC: Rf 0.36 (n-hexane/ethyl acetate=3/1);
$^1$H-NMR (CDCl$_3$): δ 0.78-0.96 (m, 6 H), 1.45-1.86 (m, 4 H), 2.30 (s, 3 H), 2.40 (s, 3 H), 3.20-3.49 (m, 1 H), 3.66 (s, 3 H), 3.84 (s, 3 H), 4.08 (d, J=17.0 Hz, 1 H), 4.69 (d, J=17.0 Hz, 1 H), 6.18 (s, 1 H), 6.69-6.91 (m, 2 H), 7.11-7.34 (m, 1 H).

EXAMPLE 8(5)

5-(1-ethylpropyl)-3,7-dimethyl-2-[2-methyl-4-(trifluoromethoxy)phenyl]pyrrolo[2,1-f][1,2,4]triazin-4(3H)-one TLC: Rf 0.64 (ethyl acetate/n-hexane=1/6);
$^1$H-NMR (CDCl$_3$): δ 0.79-0.95 (m, 6 H), 1.50-1.83 (m, 4 H), 2.35 (s, 3 H), 2.39 (s, 3 H), 3.14 (s, 3 H), 3.28-3.47 (m, 1 H), 6.19 (s, 1 H), 7.15-7.24 (m, 2 H), 7.34-7.44 (m, 1 H).

EXAMPLE 8(6)

2-[6-(dimethylamino)-4-methyl-3-pyridinyl]-5-(1-ethylpropyl)-3,7-dimethylpyrrolo[2,1-f][1,2,4]triazin-4(3H)-one TLC: Rf 0.57 (n-hexane/ethyl acetate=1/1);
$^1$H-NMR (CDCl$_3$): δ 0.87 (t, J=7.4 Hz, 6 H), 1.49-1.87 (m, 4 H), 2.24 (s, 3 H), 2.39 (s, 3 H), 3.14 (s, 6 H), 3.21 (s, 3 H), 3.39 (m, 1 H), 6.17 (s, 1 H), 6.41 (s, 1 H), 8.12 (s, 1 H).

EXAMPLE 8(7)

3-ethyl-5-(1-ethylpropyl)-2-(4-methoxy-2-methylphenyl)-7-methylpyrrolo[2,1-f][1,2,4]triazin-4(3H)-one TLC: Rf 0.29 (n-hexane/ethyl acetate=9/1);
$^1$H-NMR (CDCl$_3$): δ 0.80-0.96 (m, 6 H), 1.05 (t, J=7.0 Hz, 3 H), 1.51-1.85 (m, 4 H), 2.28 (s, 3 H), 2.38 (d, J=0.7 Hz, 3 H), 3.30-3.51 (m, 2 H), 3.86 (s, 3 H), 3.98-4.18 (m, 1 H), 6.16 (s, 1 H), 6.80-6.94 (m, 2 H), 7.27-7.38 (m, 1 H).

EXAMPLE 8(8)

5-(1-ethylpropyl)-3-isopropyl-2-(4-methoxy-2-methylphenyl)-7-methylpyrrolo[2,1-f][1,2,4]triazin-4(3H)-one TLC: Rf 0.34 (n-hexane/ethyl acetate=9/1);
$^1$H-NMR (CDCl$_3$): δ 0.79-0.98 (m, 6 H), 1.44 (d, J=6.8 Hz, 3 H), 1.50-1.85 (m, 7 H), 2.33 (s, 3 H), 2.36 (d, J=0.5 Hz, 3 H), 3.35-3.52 (m, 1 H), 3.75-3.99 (m, 4 H), 6.13 (s, 1 H), 6.78-6.92 (m, 2 H), 7.17-7.34 (m, 1 H).

EXAMPLE 8(9)

5-(1-ethylpropyl)-3-(methoxymethyl)-2-(4-methoxy-2-methylphenyl)-7-methylpyrrolo[2,1-f][1,2,4]triazin-4(3H)-one TLC: Rf 0.61 (n-hexane/ethyl acetate=3/1);
$^1$H-NMR (CDCl$_3$): δ 0.76-0.99 (m, 6 H), 1.50-1.89 (m, 4 H), 2.29 (s, 3 H), 2.40 (s, 3 H), 3.27 (s, 3 H), 3.33-3.50 (m, 1 H), 3.84 (s, 3 H), 4.87 (d, J=9.3 Hz, 1 H), 5.20 (d, J=9.3 Hz, 1 H), 6.17 (s, 1 H), 6.70-6.94 (m, 2 H), 7.29-7.41 (m, 1 H).

EXAMPLE 8(10)

2-(2-chloro-4-methoxy-5-methylphenyl)-5-(1-ethylpropyl)-3,7-dimethylpyrrolo[2,1-f][1,2,4]triazin-4(3H)-one TLC: Rf 0.59 (n-hexane/ethyl acetate=1/1);
$^1$H-NMR (CDCl$_3$): δ 0.77-0.95 (m, 6 H), 1.48-1.82 (m, 4 H), 2.23 (s, 3 H), 2.40 (s, 3 H), 3.21 (s, 3 H), 3.33-3.49 (m, 1 H), 3.89 (s, 3 H), 6.17 (s, 1 H), 6.93 (s, 1 H), 7.22 (s, 1 H).

EXAMPLE 8(11)

2-[2,4-bis(trifluoromethyl)phenyl]-5-(1-ethylpropyl)-3,7-dimethylpyrrolo[2,1-f][1,2,4]triazin-4(3H)-one TLC: Rf 0.58 (n-hexane/ethyl acetate=4/1);
$^1$H-NMR (CDCl$_3$): δ 0.85 (t, J=7.50 Hz, 3 H), 0.88 (t, J=7.41 Hz, 3 H), 1.47-1.85 (m, 4 H), 2.35 (s, 3 H), 3.13 (s, 3 H), 3.30-3.47 (m, 1 H), 6.20 (s, 1 H), 7.70 (d, J=8.23 Hz, 1 H), 8.00 (m, 1 H), 8.10 (m, 1 H).

EXAMPLE 8(12)

5-(1-ethylpropyl)-2-(5-fluoro-4-methoxy-2-methylphenyl)-3,7-dimethylpyrrolo[2,1-f][1,2,4]triazin-4(3H)-one TLC: Rf 0.47 (n-hexane/ethyl acetate=1/1);
$^1$H-NMR (CDCl$_3$): δ 0.79-0.94 (m, 6 H), 1.50-1.83 (m, 4 H), 2.27 (s, 3 H), 2.39 (s, 3 H), 3.16 (s, 3 H), 3.31-3.47 (m, 1 H), 3.94 (s, 3 H), 6.18 (s, 1 H), 6.89 (d, J=8.4 Hz, 1 H), 7.08 (d, J=11.0 Hz, 1 H).

EXAMPLE 8(13)

5-(1-ethylpropyl)-2-mesityl-3,7-dimethylpyrrolo[2,1-f][1,2,4]triazin-4(3H)-one

TLC: Rf 0.55 (ethyl acetate/n-hexane=1/6);
$^1$H-NMR (CDCl$_3$): δ 0.88 (t, J=7.4 Hz, 6 H), 1.51-1.86 (m, 4 H), 2.20 (s, 6 H), 2.34 (s, 3 H), 2.39 (s, 3 H), 3.10 (s, 3 H), 3.28-3.52 (m, 1 H), 6.17 (s, 1 H), 6.97 (s, 2 H).

EXAMPLE 8(14)

5-(1-ethylpropyl)-3,7-dimethyl-2-[4-(methylthio)-2-(trifluoromethyl)phenyl]pyrrolo[2,1-f][1,2,4]triazin-4(3H)-one TLC: Rf 0.28 (ethyl acetate/n-hexane=1/6);
$^1$H-NMR (CDCl$_3$): δ 0.80-0.95 (m, 6 H), 1.46-1.85 (m, 4 H), 2.36 (d, J=0.7 Hz, 3 H), 2.58 (s, 3 H), 3.13 (s, 3 H), 3.31-3.47 (m, 1 H), 6.17 (s, 1 H), 7.36-7.43 (m, 1 H), 7.45-7.55 (m, 1 H), 7.60-7.63 (m, 1 H).

EXAMPLE 8(15)

5-(1-ethylpropyl)-2-[4-methoxy-2-(trifluoromethyl)phenyl]-3,7-dimethylpyrrolo[2,1-f][1,2,4]triazin-4(3H)-one TLC: Rf 0.48 (n-hexane/ethyl acetate=1/1);
$^1$H-NMR (CDCl$_3$): δ 0.76-0.96 (m, 6 H), 1.48-1.83 (m, 4 H), 2.36 (s, 3 H), 3.12 (s, 3 H), 3.30-3.47 (m, 1 H), 3.92 (s, 3 H), 6.17 (s, 1 H), 7.19 (dd, J=8.6, 2.7 Hz, 1 H), 7.31 (d, J=2.7 Hz, 1 H), 7.42 (d, J=8.6 Hz, 1 H).

EXAMPLE 8(16)

2-(4-chloro-2-methoxyphenyl)-5-(1-ethylpropyl)-3,7-dimethylpyrrolo[2,1-f][1,2,4]triazin-4(3H)-one TLC: Rf 0.62 (n-hexane/ethyl acetate=1/1);
$^1$H-NMR (CDCl$_3$): δ 0.80-0.94 (m, 6 H), 1.49-1.83 (m, 4 H), 2.39 (s, 3 H), 3.19 (s, 3 H), 3.33-3.48 (m, 1 H), 3.86 (s, 3 H), 6.16 (s, 1 H), 7.00 (d, J=1.9 Hz, 1 H), 7.09 (dd, J=8.1, 1.9 Hz, 1 H), 7.35 (d, J=8.1 Hz, 1 H).

EXAMPLE 8(17)

5-(1-ethylpropyl)-3-isobutyl-2-(4-methoxy-2-methylphenyl)-7-methylpyrrolo[2,1-f][1,2,4]triazin-4(3H)-one TLC: Rf 0.29 (n-hexane/ethyl acetate=9/1);
$^1$H-NMR (CDCl$_3$): δ 0.69 (d, J=6.8 Hz, 3 H), 0.75 (d, J=6.8 Hz, 3 H), 0.80-0.97 (m, 6 H), 1.47-1.99 (m, 5 H), 2.26 (s, 3 H), 2.39 (s, 3 H), 3.10-3.30 (m, 1 H), 3.34-3.56 (m, 1 H), 3.69-4.21 (m, 4 H), 6.16 (s, 1 H), 6.59-7.18 (m, 2 H), 7.16-7.46 (m, 1 H).

EXAMPLE 8(18)

2-(2-chloro-4-ethoxyphenyl)-5-(1-ethylpropyl)-3,7-dimethylpyrrolo[2,1-f][1,2,4]triazin-4(3H)-one TLC: Rf 0.42 (ethyl acetate/n-hexane=1/6);
$^1$H-NMR (CDCl$_3$): δ 0.77-0.95 (m, 6 H), 1.45 (t, J=7.0 Hz, 3 H), 1.51-1.86 (m, 4 H), 2.39 (s, 3 H), 3.20 (s, 3 H), 3.31-3.48 (m, 1 H), 4.08 (q, J=7.0 Hz, 2 H), 6.17 (s, 1 H), 6.92 (dd, J=8.5, 2.5 Hz, 1 H), 7.03 (d, J=2.5 Hz, 1 H), 7.36 (d, J=8.5 Hz, 1 H).

EXAMPLE 8(19)

2-(2,4-dimethylphenyl)-5-(1-ethylpropyl)-3,7-dimethylpyrrolo[2,1-f][1,2,4]triazin-4(3H-one TLC: Rf 0.50 (ethyl acetate/n-hexane=1/6);
$^1$H-NMR (CDCl$_3$): δ 0.76-0.98 (m, 6 H), 1.49-1.83 (m, 4 H), 2.27 (s, 3 H), 2.39 (s, 6 H), 3.14 (s, 3 H), 3.30-3.51 (m, 1 H), 6.17 (s, 1 H), 7.08-7.17 (m, 2 H), 7.18-7.25 (m, 1 H).

EXAMPLE 8(20)

2-(4-chloro-2-methylphenyl)-5-(1-ethylpropyl)-3,7-dimethylpyrrolo[2,1-f][1,2,4]triazin-4(3 H)-one TLC: Rf 0.61 (n-hexane/ethyl acetate=2/1);
$^1$H-NMR (CDCl$_3$): δ 0.73-0.97 (m, 6 H), 1.47-1.84 (m, 4 H), 2.30 (s, 3 H), 2.39 (s, 3 H), 3.14 (s, 3 H), 3.31-3.47 (m, 1 H), 6.18 (s, 1 H), 7.22-7.39 (m, 3 H).

EXAMPLE 8(21)

3-(ethoxymethyl)-5-(1-ethylpropyl)-2-(4-methoxy-2-methylphenyl)-7-methylpyrrolo[2,1-f][1,2,4]triazin-4(3H)-one TLC: Rf 0.20 (n-hexane/ethyl acetate=9/1);
$^1$H-NMR (CDCl$_3$): δ 0.71-0.98 (m, 6 H), 1.10 (t, J=7.0 Hz, 3 H), 1.45-1.93 (m, 4 H), 2.30 (s, 3 H), 2.39 (s, 3 H), 3.27-3.56 (m, 3 H), 3.84 (s, 3 H), 4.93 (d, J=11.0 Hz, 1 H), 5.22 (d, J=11.0 Hz, 1 H), 6.17 (s, 1 H), 6.73-6.93 (m, 2 H), 7.29-7.43 (m, 1 H).

EXAMPLE 8(22)

2-[2-chloro-4-(difluoromethoxy)phenyl]-5-(1-ethyl-propyl)-3,7-dimethylpyrrolo[2,1-f][1,2,4]triazin-4(3H)-one TLC: Rf 0.47 (n-hexane/ethyl acetate=2/1);
$^1$H-NMR (CDCl$_3$): δ 0.76-0.97 (m, 6 H), 1.47-1.83 (m, 4 H), 2.39 (d, J=0.7 Hz, 3 H), 3.21 (s, 3 H), 3.32-3.47 (m, 1 H), 6.19 (s, 1 H), 6.59 (t, J=72.5 Hz, 1 H), 7.21 (dd, J=8.6, 2.1 Hz, 1 H), 7.33 (d, J=2.0 Hz, 1 H), 7.50 (d, J=8.6 Hz, 1 H).

EXAMPLE 8(23)

2-[6-(dimethylamino)-2-methyl-3-pyridinyl]-5-(1-ethylpropyl)-3,7-dimethylpyrrolo[2,1-f][1,2,4]triazin-4(3H)-one TLC: Rf 0.44 (ethyl acetate/n-hexane=1/3);
$^1$H-NMR (CDCl$_3$): δ 0.86 (t, J=7.3 Hz, 6 H), 1.47-1.85 (m, 4 H), 2.38 (s, 3 H), 2.39 (s, 3 H), 3.14 (s, 6 H), 3.21 (s, 3 H), 3.30-3.49 (m, 1 H), 6.16 (s, 1 H), 6.43 (d, J=8.6 Hz, 1 H), 7.37 (d, J=8.6 Hz, 1 H).

EXAMPLE 8(24)

2-[6-(dimethylamino)-2,4-dimethyl-3-pyridinyl]-5-(1-ethylpropyl)-3,7-dimethylpyrrolo[2,1-f][1,2,4]triazin-4(3H)-one TLC: Rf 0.44 (ethyl acetate/n-hexane=1/3);
$^1$H-NMR (CDCl$_3$): δ 0.88 (t, J=7.3 Hz, 6 H), 1.49-1.83 (m, 4 H), 2.15 (s, 3 H), 2.31 (s, 3 H), 2.39 (s, 3 H), 3.12 (s, 6 H), 3.16 (s, 3 H), 3.30-3.49 (m, 1 H), 6.17 (s, 1 H), 6.27 (s, 1H).

EXAMPLE 8(25)

2-(2-ethyl-4-methoxyphenyl)-5-(1-ethylpropyl)-3,7-dimethylpyrrolo[2,1-f][1,2,4]triazin-4(3H)-one TLC: Rf 0.43 (ethyl acetate/n-hexane=1/6);
$^1$H-NMR (CDCl$_3$): δ 0.78-0.98 (m, 6 H), 1.23 (t, J=7.6 Hz, 3 H), 1.49-1.89 (m, 4 H), 2.39 (s, 3 H), 2.47-2.70 (m, 2 H), 3.14 (s, 3 H), 3.33-3.49 (m, 1 H), 3.86 (s, 3 H), 6.17 (s, 1 H), 6.82-6.88 (m, 1 H), 6.90 (d, J=2.2 Hz, 1 H), 7.24 (d, J=8.2 Hz, 1 H).

EXAMPLE 8(26)

2-(4-ethoxy-2-methylphenyl)-5-(1-ethylpropyl)-3,7-dimethylpyrrolo[2,1-f][1,2,4]triazin-4(3H)-one TLC: Rf 0.44 (ethyl acetate/n-hexane=1/6);
$^1$H-NMR (CDCl$_3$): δ 0.76-0.96 (m, 6 H), 1.44 (t, J=7.0 Hz, 3 H), 1.52-1.84 (m, 4 H), 2.27 (s, 3 H), 2.39 (s, 3 H), 3.14 (s, 3 H), 3.33-3.47 (m, 1 H), 4.07 (q, J=7.0 Hz, 2 H), 6.17 (s, 1 H), 6.76-6.88 (m, 2 H), 7.20-7.26 (m, 1 H).

EXAMPLE 8(27)

2-[2-(dimethylamino)-4,6-dimethyl-5-pyrimidinyl]-5-(1-ethylpropyl)-3,7-dimethylpyrrolo[2,1-f][1,2,4]triazin-4(3H)-one TLC: Rf 0.49 (ethyl acetate/n-hexane=1/3);
$^1$H-NMR (CDCl$_3$): δ 0.87 (t, J=7.4 Hz, 6 H), 1.50-1.84 (m, 4 H), 2.26 (s, 6 H), 2.38 (s, 3H), 3.19 (s, 3 H), 3.21-3.25 (s, 6 H), 3.33-3.47 (m, 1 H), 6.18 (s, 1 H).

EXAMPLE 8(28)

3-(cyclopropylmethyl)-5-(1-ethylpropyl)-2-(4-methoxy-2-methylphenyl)-7-methylpyrrolo[2,1-f][1,2,4]triazin-4(3H)-one TLC: Rf 0.32 (n-hexane/ethyl acetate=9/1);
$^1$H-NMR (CDCl$_3$): δ −0.08-0.22 (m, 2 H), 0.24-0.46 (m, 2 H), 0.74-1.08 (m, 7 H), 1.47-1.88 (m, 4 H), 2.28 (s, 3 H), 2.40 (s, 3 H), 3.18-3.56 (m, 2 H), 3.76-4.04 (m, 4 H), 6.17 (s, 1 H), 6.73-6.95 (m, 2 H), 7.29-7.40 (m, 1 H).

EXAMPLE 8(29)

5-(1-ethylpropyl)-2-(2-isopropyl-4-methoxyphenyl)-3,7-dimethylpyrrolo[2,1-f][1,2,4]triazin-4(3H)-one TLC: Rf 0.45 (ethyl acetate/n-hexane=1/6);
$^1$H-NMR (CDCl$_3$): δ 0.82-0.95 (m, 6 H), 1.21-1.28 (m, 6 H), 1.46-1.83 (m, 4 H), 2.38 (s, 3 H), 2.76-2.95 (m, 1 H), 3.14 (s, 3 H), 3.28-3.52 (m, 1 H), 3.87 (s, 3 H), 6.17 (s, 1 H), 6.85 (dd, J=8.4, 2.6 Hz, 1 H), 6.96 (d, J=2.6 Hz, 1 H), 7.22 (d, J=8.4 Hz, 1 H).

EXAMPLE 8(30)

N-{4-[5-(1-ethylpropyl)-3,7-dimethyl-4-oxo-3,4-dihydropyrrolo[2,1-f][1,2,4]triazin-2-yl]-3-methylphenyl}-N-methylmethanesulfonamide TLC: Rf 0.45 (n-hexane/ethyl acetate=1/1);
$^1$H-NMR (CDCl$_3$): δ 0.83-0.90 (m, 6 H), 1.59-1.80 (m, 4 H), 2.33 (s, 3 H), 2.39 (s, 3 H), 2.91 (s, 3 H), 3.14 (s, 3 H), 3.34-3.43 (m, 1 H), 3.37 (s, 3 H), 6.17 (s, 1 H), 7.32-7.39 (m, 3 H).

EXAMPLE 8(31)

2-[4-(dimethylamino)-2-methylphenyl]-5-(1-ethylpropyl)-3,7-dimethylpyrrolo[2,1-f][1,2,4]triazin-4(3H)-one TLC: Rf 0.50 (n-hexane/ethyl acetate=3/1);
$^1$H-NMR (CDCl$_3$): δ 0.87 (t, J=7.1 Hz, 6 H), 1.60-1.79 (m, 4 H), 2.26 (s, 3 H), 2.39 (s, 3 H), 3.00 (s, 6 H), 3.16 (s, 3 H), 3.35-3.44 (m, 1 H), 6.14 (s, 1 H), 6.59-6.64 (m, 2 H), 7.16 (d, J=8.2 Hz, 1 H).

EXAMPLE 8(32)

5-(1-ethylpropyl)-3,7-dimethyl-2-[2-methyl-4-(1H-pyrazol-1-yl)phenyl]pyrrolo[2,1-f][1,2,4]triazin-4(3H)-one TLC: Rf 0.38 (n-hexane/ethyl acetate=3/1);
$^1$H-NMR (CDCl$_3$): δ 0.82-0.94 (m, 6 H), 1.55-1.80 (m, 4 H), 2.39 (s, 3 H), 2.40 (s, 3 H), 3.16 (s, 3 H), 3.35-3.45 (m, 1 H), 6.18 (s, 1 H), 6.50 (dd, J=2.6, 1.8 Hz, 1 H), 7.42 (d, J=8.2 Hz, 1 H), 7.63 (dd, J=8.2, 2.4 Hz, 1 H), 7.73 (d, J=2.4 Hz, 1 H), 7.75 (dd, J=1.8, 0.5 Hz, 1 H), 7.97 (dd, J=2.6, 0.5 Hz, 1 H).

EXAMPLE 8(33)

2-(2-chloro-6-fluoro-4-methoxyphenyl)-5-(1-ethylpropyl)-3,7-dimethylpyrrolo[2,1-f][1,2,4]triazin-4(3H)-one TLC: Rf 0.37 (ethyl acetate/n-hexane=1/6);
$^1$H-NMR (CDCl$_3$): δ 0.80-0.95 (m, 6 H), 1.46-1.86 (m, 4 H), 2.40 (s, 3 H), 3.22 (s, 3 H), 3.32-3.47 (m, 1 H), 3.87 (s, 3 H), 6.18 (s, 1 H), 6.70 (dd, J=10.6, 2.4 Hz, 1 H), 6.89 (dd, J=2.4, 1.5 Hz, 1 H).

EXAMPLE 8(34)

2-[4-chloro-2-(4-morpholinyl)-1,3-thiazol-5-yl]-5-(1-ethylpropyl)-3,7-dimethylpyrrolo[2,1-f][1,2,4]triazin-4(3H)-one TLC: Rf 0.65 (ethyl acetate/n-hexane=1/1);
$^1$H-NMR (CDCl$_3$): δ 0.84 (t, J=7.4 Hz, 6 H), 1.46-1.83 (m, 4 H), 2.40 (s, 3 H), 3.30-3.46 (m, 4 H), 3.48-3.57 (m, 4 H), 3.75-3.91 (m, 4 H), 6.18 (s, 1 H).

EXAMPLE 8(35)

2-[4-chloro-2-(1-pyrrolidinyl)-1,3-thiazol-5-yl]-5-(1-ethylpropyl)-3,7-dimethylpyrrolo[2,1-f][1,2,4]triazin-4(3H)-one TLC: Rf 0.38 (ethyl acetate/n-hexane=1/2);
$^1$H-NMR (CDCl$_3$): δ 0.84 (t, J=7.3 Hz, 6 H), 1.46-1.80 (m, 4 H), 2.02-2.15 (m, 4 H), 2.40 (d, J=0.7 Hz, 3 H), 3.31-3.44 (m, 4 H), 3.45-3.58 (m, 4 H), 6.17 (s, 1 H).

EXAMPLE 8(36)

2-[4-chloro-2-(1-piperidinyl)-1,3-thiazol-5-yl]-5-(1-ethylpropyl)-3,7-dimethylpyrrolo[2,1-f][1,2,4]triazin-4(3H)-one TLC: Rf 0.62 (ethyl acetate/n-hexane=1/2);
$^1$H-NMR (CDCl$_3$): δ 0.84 (t, J=7.4 Hz, 6 H), 1.46-1.83 (m, 10 H), 2.40 (s, 3 H), 3.29-3.45 (m, 4 H), 3.45-3.57 (m, 4 H), 6.17 (s, 1 H).

EXAMPLE 8(37)

2-[4-chloro-2-(4-methyl-1-piperazinyl)-1,3-thiazol-5-yl]-5-(1-ethylpropyl)-3,7-dimethylpyrrolo[2,1-f][1,2,4]triazin-4(3H)-one TLC: Rf 0.32 (ethyl acetate/methanol=4/1);
$^1$H-NMR (CDCl$_3$): δ 0.84 (t, J=7.4 Hz, 6 H), 1.47-1.82 (m, 4 H), 2.37 (s, 3 H), 2.40 (s, 3 H), 2.47-2.57 (m, 4 H), 3.30-3.45 (m, 4 H), 3.51-3.61 (m, 4 H), 6.18 (s, 1 H).

EXAMPLE 8(38)

2-[5-(1-ethylpropyl)-2-(4-methoxy-2-methylphenyl)-7-methyl-4-oxopyrrolo[2,1-f][1,2,4]triazin-3(4H)-yl]acetamide TLC: Rf 0.20 (n-hexane/ethyl acetate=1/1);
$^1$H-NMR (CDCl$_3$): δ 0.59-1.02 (m, 6 H), 1.43-1.88 (m, 4 H), 2.29 (s, 3 H), 2.39 (s, 3 H), 3.20-3.43 (m, 1 H), 3.83 (s, 3 H), 4.03 (d, J=15.9 Hz, 1 H), 4.57 (d, J=15.9 Hz, 1 H), 5.55 (s, 1 H), 5.94 (s, 1 H), 6.18 (s, 1 H), 6.72-6.97 (m, 2 H), 7.28-7.46 (m, 1 H).

EXAMPLE 8(39)

2-[2-chloro-4-(methylthio)phenyl]-5-(1-ethylpropyl)-3,7-dimethylpyrrolo[2,1-f][1,2,4]triazin-4(3H)-one TLC: Rf 0.69 (n-hexane/ethyl acetate=2/1);
$^1$H-NMR (CDCl$_3$): δ 0.79-0.93 (m, 6 H), 1.53-1.82 (m, 4 H), 2.39 (s, 3 H), 2.54 (s, 3 H), 3.21 (s, 3 H), 3.40 (m, 1 H), 6.18 (s, 1 H), 7.24 (dd, J=7.80, 1.65 Hz, 1 H), 7.33 (d, J=1.65 Hz, 1 H), 7.36 (d, J=7.80 Hz, 1 H).

EXAMPLE 8(40)

2-(2-chloro-4-methoxyphenyl)-3-ethyl-5-(1-ethylpropyl)-7-methylpyrrolo[2,1-f][1,2,4]triazin-4(3H)-one TLC: Rf 0.47 (n-hexane/ethyl acetate=4/1);
$^1$H-NMR (CDCl$_3$): δ 0.76-0.97 (m, 6 H), 1.07 (t, J=7.0 Hz, 3 H), 1.41-1.86 (m, 4 H), 2.39 (s, 3 H), 3.24-3.52 (m, 2 H), 3.88 (s, 3 H), 4.03-4.29 (m, 1 H), 6.17 (s, 1 H), 6.94 (dd, J=8.6, 2.6 Hz, 1 H), 7.04 (d, J=2.6 Hz, 1 H), 7.41 (d, J=8.6 Hz, 1 H).

EXAMPLE 8(41)

2-[2-chloro-4-(trifluoromethoxy)phenyl]-3-cyclopropyl-5-(1-ethylpropyl)-7-methylpyrrolo[2,1-f][1,2,4]triazin-4(3H)-one TLC: Rf 0.54 (n-hexane/ethyl acetate=4/1);
$^1$H-NMR (CDCl$_3$): δ 0.29-0.50 (m, 1 H), 0.54-1.05 (m, 9 H), 1.49-1.89 (m, 4 H), 2.38 (s, 3 H), 2.70-2.96 (m, 1 H), 3.17-3.54 (m, 1 H), 6.17 (s, 1 H), 7.25-7.34 (m, 1 H), 7.36-7.43 (m, 1 H), 7.54 (d, J=8.6 Hz, 1 H).

EXAMPLE 8(42)

2-(2-chloro-4-methoxyphenyl)-3-cyclopropyl-5-(1-ethylpropyl)-7-methypyrrolo[2,1-f][1,2,4]triazin-4(3H)-one TLC: Rf 0.37 (n-hexane/ethyl acetate=4/1);
$^1$H-NMR (CDCl$_3$): δ 0.34-0.51 (m, 1 H), 0.57-0.98 (m, 9 H), 1.47-1.82 (m, 4 H), 2.39 (s, 3 H), 2.76-3.00 (m, 1 H), 3.31-3.50 (m, 1 H), 3.87 (s, 3 H), 6.15 (s, 1 H), 6.93 (dd, J=8.6, 2.6 Hz, 1 H), 7.02 (d, J=2.6 Hz, 1 H), 7.38 (d, J=8.6 Hz, 1 H).

EXAMPLE 8(43)

3-[2-(dimethylamino)ethyl]-5-(1-ethylpropyl)-2-(4-methoxy-2-methylphenyl)-7-methylpyrrolo[2,1-f][1,2,4]triazin-4(3H)-one TLC: Rf 0.52 (methylene chloride/methanol=9/1);
$^1$H-NMR (CDCl$_3$): δ 0.79-0.98 (m, 6 H), 1.51-1.85 (m, 4 H), 1.98-2.13 (m, 6 H), 2.20-2.57 (m, 8 H), 3.32-3.59 (m, 2 H), 3.84 (s, 3 H), 4.01-4.23 (m, 1 H), 6.16 (s, 1 H), 6.73-6.98 (m, 2 H), 7.27-7.35 (m, 1 H).

EXAMPLE 8(44)

5-(1-ethylpropyl)-3-(2-hydroxyethyl)-2-(4-methoxy-2-methylphenyl)-7-methylpyrrolo[2,1-f][1,2,4]triazin-4(3H)-one TLC: Rf 0.51 (n-hexane/ethyl acetate=1/1);
$^1$H-NMR (CDCl$_3$): δ 0.69-1.05 (m, 6 H), 1.43-1.86 (m, 4 H), 2.28 (s, 3 H), 2.39 (s, 3 H), 2.88 (t, J=5.2 Hz, 1 H), 3.24-3.47 (m, 1 H), 3.52-3.73 (m, 3 H), 3.84 (s, 3 H), 4.07-4.34 (m, 1 H), 6.19 (s, 1 H), 6.71-6.94 (m, 2 H), 7.20-7.38 (m, 1 H).

EXAMPLE 8(45)

2-[5-(1-ethylpropyl)-2-(4-methoxy-2-methylphenyl)-7-methyl-4-oxopyrrolo[2,1-f][1,2,4]triazin-3(4H)-yl] ethyl dimethylcarbamate TLC: Rf 0.47 (n-hexane/ethyl acetate=1/1);
$^1$H-NMR (CDCl$_3$): δ 0.79-0.96 (m, 6 H), 1.49-1.80 (m, 4 H), 2.27 (s, 3 H), 2.39 (s, 3 H), 2.72-2.88 (m, 6 H), 3.28-3.46 (m, 1 H), 3.60-3.73 (m, 1 H), 3.85 (s, 3 H), 3.93-4.18 (m, 2 H), 4.29-4.47 (m, 1 H), 6.16 (s, 1 H), 6.75-6.93 (m, 2 H), 7.29-7.39 (m, 1 H).

EXAMPLE 8(46)

2-(2-ethyl-4-methoxy-6-methylphenyl)-5-(1-ethylpropyl)-3,7-dimethylpyrrolo[2,1-f][1,2,4]triazin-4(3H)-one TLC: Rf 0.38 (ethyl acetate/n-hexane=1/6);
$^1$H-NMR (CDCl$_3$): δ 0.82-0.96 (m, 6 H), 1.21 (t, J=7.6 Hz, 3 H), 1.54-1.82 (m, 4 H), 2.20 (s, 3 H), 2.39 (s, 3 H), 2.44-2.55 (m, 2 H), 3.09 (s, 3 H), 3.34-3.49 (m, 1 H), 3.84 (s, 3 H), 6.18 (s, 1 H), 6.69 (d, J=2.6 Hz, 1 H), 6.73 (d, J=2.6 Hz, 1 H).

EXAMPLE 8(47)

2-(2-chloro-4-phenoxyphenyl)-5-(1-ethylpropyl)-3,7-dimethylpyrrolo[2,1-f][1,2,4]triazin-4(3H)-one TLC: Rf 0.61 (ethyl acetate/n-hexane=1/6);
$^1$H-NMR (CDCl$_3$): δ 0.79-0.97 (m, 6 H), 1.47-1.83 (m, 4 H), 2.40 (s, 3 H), 3.23 (s, 3 H), 3.33-3.51 (m, 1 H), 6.18 (s, 1 H), 7.00 (dd, J=8.5, 2.5 Hz, 1 H), 7.06-7.15 (m, 3 H), 7.18-7.29 (m, 1 H), 7.33-7.49 (m, 3 H).

EXAMPLE 8(48)

2-[4-chloro-2-(dimethylamino)-1,3-thiazol-5-yl]-5-(1-ethylpropyl)-3,7-dimethylpyrrolo[2,1-f][1,2,4]triazin-4(3H)-one TLC: Rf 0.59 (ethyl acetate/n-hexane=1/1);
$^1$H-NMR (CDCl$_3$): δ 0.84 (t, J=7.4 Hz, 6 H), 1.46-1.86 (m, 4 H), 2.40 (d, J=0.5 Hz, 3 H), 3.15 (s, 6 H), 3.33-3.45 (m, 4 H), 6.18 (s, 1 H).

EXAMPLE 8(49)

5-(1-ethylpropyl)-3,7-dimethyl-2-[4-methyl-2-(4-morpholinyl)-1,3-thiazol-5-yl]pyrrolo[2,1-f][1,2,4]triazin-4(3H)-one TLC: Rf 0.36 (ethyl acetate/n-hexane=1/1);
$^1$H-NMR (CDCl$_3$): δ 0.84 (t, J=7.4 Hz, 6 H), 1.43-1.88 (m, 4 H), 2.28 (s, 3 H), 2.40 (s, 3 H), 3.22-3.44 (m, 4 H), 3.46-3.57 (m, 4 H), 3.74-3.94 (m, 4 H), 6.17 (s, 1 H).

EXAMPLE 8(50)

5-(1-ethylpropyl)-3,7-dimethyl-2-[2-methyl-4-(1-pyrrolidinyl)phenyl]pyrrolo[2,1-f][1,2,4]triazin-4(3H)-one TLC: Rf 0.31 (n-hexane/ethyl acetate=5/1);
$^1$H-NMR (CDCl$_3$): δ 0.78-0.99 (m, 6 H), 1.51-1.85 (m, 4 H), 1.94-2.09 (m, 4 H), 2.25 (s, 3 H), 2.39 (d, J=0.7 Hz, 3 H), 3.18 (s, 3 H), 3.24-3.56 (m, 5 H), 6.15 (s, 1 H), 6.38-6.52 (m, 2 H), 7.15 (d, J=8.2 Hz, 1 H).

EXAMPLE 8(51)

5-(1-ethylpropyl)-3,7-dimethyl-2-[2-methyl-4-(1-piperidinyl)phenyl]pyrrolo[2,1-f][1,2,4]triazin-4(3H)-one TLC: Rf 0.31 (n-hexane/ethyl acetate=5/1);
$^1$H-NMR (CDCl$_3$): δ 0.87 (t, J=7.1 Hz, 6 H), 1.47-1.84 (m, 10 H), 2.25 (s, 3 H), 2.39 (s, 3 H), 3.15 (s, 3 H), 3.20-3.30 (m, 4 H), 3.32-3.49 (m, 1 H), 6.15 (s, 1 H), 6.75-6.89 (m, 2 H), 7.11-7.22 (m, 1 H).

EXAMPLE 8(52)

2-[2-chloro-4-(trifluoromethoxy)phenyl]-3-ethyl-5-(1-ethylpropyl)-7-methylpyrrolo[2,1-f][1,2,4]triazin-4(3H)-one TLC: Rf 0.63 (n-hexane/ethyl acetate=4/1);
$^1$H-NMR (CDCl$_3$): δ 0.79-0.94 (m, 6 H), 1.08 (t, J=7.0 Hz, 3 H), 1.54-1.84 (m, 4 H), 2.38 (s, 3 H), 3.22-3.50 (m, 2 H), 3.98-4.32 (m, 1 H), 6.19 (s, 1 H), 7.28-7.35 (m, 1 H), 7.36-7.47 (m, 1 H), 7.57 (d, J=8.4 Hz, 1 H).

EXAMPLE 9

2-(4-methoxy-2-methylphenyl)-3,7-dimethyl-5-(1-propylbutyl)pyrrolo[2,1-f][1,2,4]triazin-4(3H)-one By the same procedure as a series of reactions of Example 3→Example 4→Example 5→Example 8, using the compound provided by using propylmagnesium bromide instead of ethylmagnesium bromide instead of the compound prepared in Example 2, and using the corresponding aldehydes instead of the compound prepared in Example 7, the compound of the present invention having the following physical data was obtained.

TLC: Rf 0.77 (n-hexane/ethyl acetate=2/1);
$^1$H-NMR (CDCl$_3$): δ 0.88 (t, J=7.3 Hz, 6 H), 1.17-1.39 (m, 4 H), 1.48-1.73 (m, 4 H), 2.29 (s, 3 H), 2.38 (s, 3 H), 3.14 (s, 3 H), 3.48-3.69 (m, 1 H), 3.85 (s, 3 H), 6.17 (s, 1 H), 6.81-6.90 (m, 2 H), 7.17-7.32 (m, 1 H).

EXAMPLE 10

5-bromo-2-(difluoromethoxy)-4-methylpyridine 5N aqueous solution of sodium hydroxide (5.70 mL) was added to the tetrahydrofuran solution (28 mL) of 5-bromo-2-hydroxy-4-methylpyridine (1.07 g). The reaction mixture was stirred at 70° C. under chlorodifluoromethane gas atmosphere. The reaction mixture was cooled to room temperature after the disappearance of raw material, diluted with tert-butyl methyl ether, and extracted. The organic layer was washed by water and a saturated aqueous solution of sodium chloride, and dried with magnesium sulfate. The organic layer was concentrated under reduced pressure. The obtained residue was purified by column chromatography on silica gel (high flash-SI, size L (made in Yamazen corporation)) to obtain a title compound (751 mg) having the following physical data.

TLC: Rf 0.58 (ethyl acetate/n-hexane=5/95);
$^1$H-NMR (CDCl$_3$): δ 2.40 (d, J=0.7 Hz, 3 H), 6.80 (s, 1 H), 7.39 (t, J=72.9 Hz, 1 H), 8.22 (s, 1 H).

EXAMPLE 11

Ethyl 6-(difluoromethoxy)-4-methylnicotinate

A mixed solution of dimethyl sulfoxide (11 mL)/ethanol (7.7 mL) of the compound prepared in Example 10 (835 mg) and diisopropylethylamine (1.53 mL) was deaerated, and it was substituted in argon. After having added bis(diphenylphosphino)ferrocene (195 mg) and palladium acetate (79 mg) to the reaction mixture, the reaction mixture was deaerated. The reaction mixture was substituted in carbon monoxide, and stirred at 90° C. overnight. The reaction mixture was subjected to filtration with Celite (trade name) after having been cooled to room temperature. The obtained filtrate was extracted with ethyl acetate. The organic layer was washed by a saturated aqueous solution of sodium chloride, and dried with magnesium sulfate. The organic layer was concentrated under reduced pressure. The obtained residue was purified by column chromatography on silica gel (high flash-SI, size L (made in Yamazen corporation)) to obtain a title compound (618 mg) having the following physical data.

TLC: Rf 0.52 (ethyl acetate/n-hexane=1/5);
$^1$H-NMR (CDCl$_3$): δ 1.40 (t, J=7.2 Hz, 3 H), 2.63 (s, 3 H), 4.38 (q, J=7.2 Hz, 2 H), 6.76 (s, 1 H), 7.24-7.78 (m, 1 H), 8.74 (s, 1 H).

EXAMPLE 12

6-(difluoromethoxy)-4-methylnicotinaldehyde

Lithium aluminium hydride (122 mg) was added to the anhydrous tetrahydrofuran solution (10 mL) of the compound prepared in Example 11 (618 mg) on ice bath, and the reaction mixture was stirred. Water (0.12 mL), 5N aqueous solution of sodium hydroxide (0.12 mL) and water (0.36 mL) were dropped sequentially to the reaction mixture after the disappearance of raw material. The reaction mixture was subjected to filtration with Celite (trade name) after having been stirred for a while. The obtained filtrate was concentrated under reduced pressure. The obtained residue was dissolved with dimethyl sulfoxide (7.5 mL). Triethylamine (1.9 mL) and sulfur trioxide/pyridine complex (1.08 g) were added to the reaction mixture, and the reaction mixture was stirred. The reaction mixture was diluted with ethyl acetate and extracted after having been stirred at room temperature for 15 minutes. The organic layer was washed by water and a saturated aqueous solution of sodium chloride, and dried with magnesium sulfate. The organic layer was concentrated under reduced pressure. The obtained residue was purified by column chromatography on silica gel (high flash-SI, size L (made in Yamazen corporation)) to obtain a title compound (403 mg) having the following physical data.

TLC: Rf 0.59 (ethyl acetate/n-hexane=1/3);
$^1$H-NMR (CDCl$_3$): δ 2.68 (s, 3 H), 6.79 (s, 1 H), 7.54 (t, J=72.3 Hz, 1 H), 8.55 (s, 1 H), 10.17 (s, 1 H).

EXAMPLE 13

2-[6-(difluoromethoxy)-4-methyl-3pyridinyl]-5-(1-ethylpropyl)-3,7-dimethylpyrrolo[2,1-f][1,2,4]triazin-4(3H)-one By the same procedure as a reaction of Example 8, using the compound prepared in Example 12 instead of the compound prepared in Example 7, the compound of the present invention (194 mg) having the following physical data was obtained.

TLC: Rf 0.67 (ethyl acetate/n-hexane=1/3);
$^1$H-NMR (CDCl$_3$): δ 0.86 (t, J=7.32 Hz, 6 H), 1.51-1.85 (m, 4 H), 2.37 (dd, J=8.60, 0.73 Hz, 6 H), 3.18 (s, 3 H), 3.30-3.49 (m, 1 H), 6.20 (s, 1 H), 6.89 (d, J=0.73 Hz, 1 H), 7.51 (t, J=72.73 Hz, 1 H), 8.20 (s, 1 H).

EXAMPLES 14(1)~(2)

By the same procedure as a series of reactions of Example 2→Example 3→Example 4→Example 5→Example 8, using methylmagnesium bromide (3.0M in diethyl ether solution) instead of ethylmagnesium bromide (3.0M in diethyl ether solution), using ethylamine instead of methylamine or methylamine, and using 2-chloro-4-methylthiobenzaldehyde (Sodium thiomethoxide (2.91 g) was added to the N,N-dimethylformamide solution (76 mL) of 2-chloro-4-fluorobenzaldehyde (6.00 g) at room temperature. The reaction mixture was stirred at 80° C. for 3 hours. The reaction mixture was cooled, and water was added to the reaction mixture. The reaction mixture was extracted with ethyl acetate. The organic layer was washed by water and a saturated aqueous solution of sodium chloride. The organic layer was dried with anhydrous magnesium sulfate and concentrated under reduced pressure. The obtained residue was purified by column chromatography on silica gel (high flash-3 L (made in Yamazen corporation), n-hexane/ethyl acetate, 100/0→92/8) to obtain 2-chloro-4-methylthiobenzaldehyde (3.45 g)) instead of the compound prepared in Example 7 or the compound prepared in Example 7, the compounds of the present invention having the following physical data were obtained.

EXAMPLE 14(1)

2-[2-chloro-4-(trifluoromethoxy)phenyl]-5-isopropyl-3,7-dimethylpyrrolo[2,1-f][1,2,4]triazin-4(3H)-one TLC: Rf 0.60 (ethyl acetate/n-hexane=1/4);
$^1$H-NMR (CDCl$_3$): δ 1.23-1.36 (m, 6 H), 2.32-2.43 (m, 3 H), 3.21 (s, 3 H), 3.67-3.82 (m, 1 H), 6.27 (s, 1 H), 7.27-7.34 (m, 1 H), 7.38-7.45 (m, 1 H), 7.52 (d, J=8.4 Hz, 1 H).

EXAMPLE 14(2)

2-[2-chloro-4-(methylthio)phenyl]-3-ethyl-5-isopropyl-7-methylpyrrolo[2,1-f][1,2,4]triazin-4(3H)-one TLC: Rf 0.33 (ethyl acetate/n-hexane=1/9);
$^1$H-NMR (CDCl$_3$): δ 1.08 (t, J=7.1 Hz, 3 H), 1.27-1.35 (m, 6 H), 2.33-2.42 (m, 3 H), 2.54 (s, 3 H), 3.28-3.46 (m, 1 H), 3.63-3.90 (m, 1 H), 4.06-4.25 (m, 1 H), 6.24 (s, 1 H), 7.23 (dd, J=8.1, 1.8 Hz, 1 H), 7.31 (d, J=1.8 Hz, 1 H), 7.35 (d, J=8.1 Hz, 1 H).

EXAMPLE 15

Ethyl 4-methyl-2-nitro-3-(2-oxopropyl)hexanoate

Triethylamine (165 mL) was added to the acetonitrile solution (500 mL) of 5-methyl-3-hepten-2-one (149 g) and ethyl nitroacetate (157 g) under argon gas atmosphere, and the reaction mixture was stirred at 65° C. overnight. 2N hydrochloric acid was added to the reaction mixture, and the reaction mixture was extracted with ethyl acetate. The organic layer was washed by 0.2N aqueous solution of sodium hydroxide, water and a saturated aqueous solution of sodium chloride. The organic layer was dried with anhydrous magnesium sulfate and concentrated under reduced pressure. The title compound (205 g) having the following physical data was obtained.
TLC: Rf 0.32 and 0.38 (ethyl acetate/n-hexane=1/3);
$^1$H-NMR (CDCl$_3$): δ 0.81-0.94 (m, 6 H), 1.13-1.53 (m, 6 H), 2.16-2.18 (m, 3 H), 2.42-3.29 (m, 3 H), 4.15-4.30 (m, 2 H), 5.12-5.40 (m, 1 H).

EXAMPLE 16

Ethyl 2-(hydroxyimino)-4-methyl-3-(2-oxopropyl)hexanoate

Amidinosulfinic acid (93.4 g) and triethylamine (60 mL) were added to the N,N-dimethylformamide solution (860 mL) of the compound prepared in Example 15 (112 g) under argon gas atmosphere. The reaction mixture was stirred at 80° C. for 2.5 hours. Water was added to the reaction mixture, and the reaction mixture was extracted with ethyl acetate/hexane (50/50). The organic layer was washed by water and a saturated aqueous solution of sodium chloride. The organic layer was dried with anhydrous magnesium sulfate and concentrated under reduced pressure. The title compound (70 g) having the following physical data was obtained.
TLC: Rf 0.29 (ethyl acetate/n-hexane=1/2).

EXAMPLE 17

Ethyl 3-sec-butyl-5-methyl-1H-pyrrole-2-carboxylate

Ammonium acetate (92.5 g) was added to the acetic acid solution (430 mL) of the compound prepared in Example 16 under argon gas atmosphere. The reaction mixture was stirred at 100° C. for an hour. Water was added to the reaction mixture, and the reaction mixture was stirred for an hour. A precipitate was filtrated. The precipitate which was filtrated was dissolved in methylene chloride again, and the solution was purified by column chromatography on silica gel (ethyl acetate:n-hexane=1:3) to obtain a title compound (44.1 g) having the following physical data.
TLC: Rf 0.54 (ethyl acetate/n-hexane=1/3);
$^1$H-NMR (CDCl$_3$): δ 0.86 (t, J=7.4 Hz, 3 H), 1.17 (d, J=7.0 Hz, 3 H), 1.34 (t, J=7.1 Hz, 3 H), 1.45-1.61 (m, 2 H), 2.26 (s, 3 H), 3.24-3.36 (m, 1 H), 4.25-4.33 (m, 2 H), 5.86 (d, J=2.9 Hz, 1 H), 8.52-8.61 (m, 1 H).

EXAMPLE 18

4-sec-butyl-2-methyl-1H-pyrrole 5N aqueous solution of sodium hydroxide (130 mL) was added to the ethanol solution (210 mL) of the compound prepared in Example 17 (44.1 g), and the reaction mixture was stirred at 100° C. for 6 hours. The reaction mixture was cooled to 0° C. 5N hydrochloric acid (200 mL) was added to the reaction mixture, and the reaction mixture was stirred at room temperature for an hour. The reaction mixture was extracted with tert-butyl methyl ether. The organic layer was washed by water and a saturated aqueous solution of sodium chloride. The organic layer was dried with anhydrous magnesium sulfate and concentrated under reduced pressure. The title compound (33 g) having the following physical data was obtained.
TLC: Rf 0.57 (ethyl acetate/n-hexane=14/86);
$^1$H-NMR (CDCl$_3$): δ 0.88 (t, J=7.4 Hz, 3 H), 1.17 (d, J=6.8 Hz, 3 H), 1.39-1.65 (m, 2 H), 2.22-2.27 (m, 3 H), 2.45-2.57 (m, 1 H), 5.78 (s, 1 H), 6.41 (s, 1 H), 7.54-7.68 (m, 1 H).

EXAMPLE 19

5-sec-butyl-2-(2-chloro-4-methoxyphenyl)-3,7-dimethylpyrrolo[2,1-f][1,2,4]triazin-4(3H)-one By the same procedure as a series of reactions of Example 4→Example 5→Example 8, using the compound prepared in Example 18 instead of the compound prepared in Example 3, and using the corresponding aldehydes instead of the compound prepared in Example 7, the compound of the present invention (108 mg) having the following physical data was obtained.
TLC: Rf 0.50 (ethyl acetate/n-hexane=1/3);
$^1$H-NMR (CDCl$_3$): δ 0.90 (t, J=7.3 Hz, 1.5H), 0.93 (t, J=7.3 Hz, 1.5H), 1.27 (d, J=7.0 Hz, 1.5H), 1.28 (d, J=7.0 Hz, 1.5H), 1.57-1.76 (m, 2 H), 2.39 (s, 3 H), 3.21 (s, 3 H), 3.49-3.63 (m, 1 H), 3.87 (s, 3 H), 6.21 (s, 1 H), 6.94 (dd, J=8.5, 2.5 Hz, 1 H), 7.04 (d, J=2.5 Hz, 1 H), 7.36 (d, J=8.5 Hz, 0.5H), 7.37 (d, J=8.5 Hz, 0.5H).

EXAMPLE 20

2-(2-chloro-4-methoxy-6-methylphenyl)-5-isobutyl-3,7-dimethylpyrrolo[2,1-f][1,2,4]triazin-4(3H)-one By the same procedure as a series of reactions of Example 15→Example 16→Example 17→Example 18→Example 4→Example 5→Example 8, using 6-methyl-3-hepten-2-one instead of 5-methyl-3-hepten-2-one, and using the corresponding aldehydes instead of the compound prepared in Example 7, the compound of the present invention (108 mg) having the following physical data was obtained.

TLC: Rf 0.39 (ethyl acetate/n-hexane=1/6);

¹H-NMR (CDCl₃): δ 0.98 (d, J=6.8 Hz, 6H) 1.92-2.05 (m, 1H) 2.25 (s, 3H) 2.39 (s, 3H) 2.85 (d, J=7.0 Hz, 2H) 3.15 (s, 3H) 3.84 (s, 3H) 6.16 (s, 1H) 6.77 (d, J=2.3 Hz, 1H) 6.89 (d, J=2.3 Hz, 1 H).

EXAMPLE 21

5-methyl-3-octen-2-one 2-methylpentaldehyde (25 mL) was dissolved with dichloromethane (240 mL) under argon gas atmosphere. 1-(triphenylphosphoranylidene)-2-propanone (75 g) was added to the reaction mixture, and the reaction mixture was stirred at room temperature for 2 weeks. The reaction mixture was concentrated under reduced pressure. Hexane was added to the obtained residue, and a precipitate was filtrated. The obtained filtrate was concentrated to obtain the title compound (26 g) having the following physical data.

TLC: Rf 0.53 (ethyl acetate/n-hexane=1/3);

¹H-NMR (CDCl₃): δ 0.87-0.92 (m, 3 H), 1.06 (d, J=6.6 Hz, 3 H), 1.26-1.43 (m, 4 H), 2.25 (s, 3 H), 2.28-2.37 (m, 1 H), 6.03 (dd, J=−15.9, 1.1 Hz, 1 H), 6.68 (dd, J=15.9, 7.9 Hz, 1H).

EXAMPLE 22

2-[2-chloro-4-(methylthio)phenyl]-3,7-dimethyl-5-(1-methylbutyl)pyrrolo[2,1-f][1,2,4]triazin-4(3H)-one By the same procedure as a series of reactions of Example 15→Example 16→Example 17→Example 18→Example 4→Example 5→Example 8, using the compound prepared in Example 21 instead of 6-methyl-3-penten-2-one, and using 2-chloro-4-methylthiobenzaldehyde instead of the compound prepared in Example 7, the compound of the present invention (383 mg) having the following physical data was obtained.

TLC: Rf 0.54 (ethyl acetate/n-hexane=1/4);

¹H-NMR (CDCl₃): δ 0.83-0.97 (m, 3 H), 1.19-1.45 (m, 5 H), 1.45-1.86 (m, 2 H), 2.38 (s, 3 H), 2.54 (s, 3 H), 3.21 (s, 3 H), 3.55-3.77 (m, 1 H), 6.22 (s, 1 H), 7.16-7.28 (m, 1 H), 7.31-7.45 (m, 2 H).

EXAMPLE 23

3-ethyl-5-isopropyl-7-methyl-2-[2-methyl-4-(methylthio)phenyl]pyrrolo[2,1-f][1,2,4]triazin-4(3H)-one By the same procedure as a series of reactions of Example 2→Example 3→Example 4→Example 5→Example 8, using 2-methyl-4-methylthiobenzaldehyde (4-fluoro-2-methylbenzaldehyde (8.72 g) was dissolved with dimethylformamide (65 mL). Sodium thiomethoxide (4.87 g) was added to the reaction mixture, and the reaction mixture was stirred at 70° C. for 2 hours. Water was added to the reaction mixture after the reaction mixture was cooled, and the reaction mixture was stopped and extracted with ethyl acetate. The organic layer was washed by water, dried with anhydrous magnesium sulfate and concentrated under reduced pressure. The obtained residue was purified by column chromatography on silica gel (Yamazen corporation, high flash 3 L, n-hexane/ethyl acetate=85/15~70/30) to obtain 2-methyl-4-methylthiobenzaldehyde (7.39 g)) instead of the compound prepared in Example 7, using methylmagnesium bromide instead of ethylmagnesium bromide, and using ethylamine instead of methylamine, the compound of the present invention (8.61 g) having the following physical data was obtained.

TLC: Rf 0.46 (ethyl acetate/n-hexane=1/6);

¹H-NMR (CDCl₃): δ 1.06 (t, J=7.0 Hz, 3 H), 1.30 (d, J=6.8 Hz, 6 H), 2.26 (s, 3 H), 2.37 (s, 3 H), 2.52 (s, 3 H), 3.30-3.48 (m, 1 H), 3.66-3.84 (m, 1 H), 3.98-4.16 (m, 1 H), 6.23 (s, 1 H), 7.11-7.20 (m, 2 H), 7.21-7.32 (m, 1 H).

EXAMPLES 24(1)~(101)

By the same procedure as a reaction of Example 8, using the corresponding aldehydes instead of the compound prepared in Example 7, the compounds of the present invention having the following physical data were obtained.

EXAMPLE 24(1)

5-(1-ethylpropyl)-3,7-dimethyl-2-[4-methyl-2-(1-piperidinyl)-1,3-thiazol-5-yl]pyrrolo[2,1-f][1,2,4]triazin-4(3H)-one

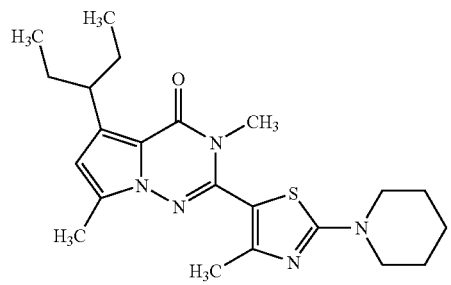 [SMILES: CCC(CC)c1cc(C)n2nc(-c3sc(N4CCCCC4)nc3C)n(C)c(=O)c12]

TLC: Rf 0.70 (ethyl acetate/n-hexane=1/1);

¹H-NMR (CDCl₃): δ 0.85 (t, J=7.4 Hz, 6 H), 1.50-1.81 (m, 10 H), 2.27 (s, 3 H), 2.40 (d, J=0.7 Hz, 3 H), 3.31-3.44 (m, 4 H), 3.44-3.54 (m, 4 H), 6.16 (s, 1 H).

EXAMPLE 24(2)

5-(1-ethylpropyl)-3,7-dimethyl-2-[2-methyl-6-(1-pyrrolidinyl)-3-pyridinyl]pyrrolo[2,1-f][1,2,4]triazin-4(3H)-one TLC: Rf 0.38 (ethyl acetate/n-hexane=1/4);

¹H-NMR (CDCl₃): δ 0.87 (t, J=7.4 Hz, 6 H), 1.50-1.85 (m, 4 H), 1.95-2.10 (m, 4 H), 2.38 (s, 3 H), 2.39 (d, J=0.5 Hz, 3 H), 3.21 (s, 3 H), 3.33-3.47 (m, 1 H), 3.46-3.56 (m, 4 H), 6.16 (s, 1 H), 6.28 (d, J=8.6 Hz, 1 H), 7.35 (d, J=8.6 Hz, 1 H).

EXAMPLE 24(3)

5-(1-ethylpropyl)-3,7-dimethyl-2-[2-methyl-4-(1H-1,2,4-triazol-1-yl)phenyl]pyrrolo[2,1-f][1,2,4]triazin-4(3H)-one TLC: Rf 0.27 (n-hexane/ethyl acetate=1/1);

¹H-NMR (CDCl₃): δ 0.79-0.96 (m, 6 H), 1.47-1.86 (m, 4 H), 2.40 (s, 3 H), 2.42 (s, 3 H), 3.17 (s, 3 H), 3.33-3.47 (m, 1

H), 6.20 (s, 1 H), 7.51 (d, J=8.1 Hz, 1 H), 7.62-7.70 (m, 1 H), 7.72 (d, J=2.4 Hz, 1 H), 8.15 (s, 1 H), 8.62 (s, 1 H).

EXAMPLE 24(4)

5-(1-ethylpropyl)-3,7-dimethyl-2-[2-methyl-4-(4-morpholinyl)phenyl]pyrrolo[2,1-f][1,2,4]triazin-4(3H)-one TLC: Rf 0.60 (n-hexane/ethyl acetate=1/1);
$^1$H-NMR (CDCl$_3$): δ 0.87 (t, J=6.1 Hz, 6 H), 1.51-1.83 (m, 4 H), 2.27 (s, 3 H), 2.39 (s, 3 H), 3.15 (s, 3 H), 3.19-3.27 (m, 4 H), 3.28-3.49 (m, 1 H), 3.81-3.94 (m, 4 H), 6.16 (s, 1 H), 6.77-6.87 (m, 2 H), 7.23 (d, J=9.0 Hz, 1 H).

EXAMPLE 24(5)

2-(2-chloro-4-methoxy-6-methylphenyl)-5-(1-ethylpropyl)-3,7-dimethylpyrrolo[2,1-f][1,2,4]triazin-4(3H)-one TLC: Rf 0.73 (n-hexane/ethyl acetate=2/1);
$^1$H-NMR (CDCl$_3$): δ 0.88 (t, J=7.4 Hz, 6 H), 1.48-1.88 (m, 4 H), 2.26 (s, 3 H), 2.40 (d, J=0.7 Hz, 3 H), 3.16 (s, 3 H), 3.30-3.51 (m, 1 H), 3.84 (s, 3 H), 6.18 (s, 1 H), 6.78 (dd, J=2.4, 0.7 Hz, 1 H), 6.89 (d, J=2.4 Hz, 1 H).

EXAMPLE 24(6)

2-[4-(1,1-dioxido-2-isothiazolidinyl)-2-methylphenyl]-5-(1-ethylpropyl)-3,7-dimethylpyrrolo[2,1-f][1,2,4]triazin-4(3H)-one TLC: Rf 0.40 (n-hexane/ethyl acetate=1/9);
$^1$H-NMR (CDCl$_3$): δ 0.73-0.96 (m, 6 H), 1.51-1.82 (m, 4 H), 2.32 (s, 3 H), 2.38 (s, 3 H), 2.49-2.69 (m, 2 H), 3.14 (s, 3 H), 3.33-3.43 (m, 1 H), 3.43 (t, J=7.5 Hz, 2 H), 3.83 (t, J=6.5 Hz, 2 H), 6.17 (s, 1 H), 7.18 (dd, J=8.2, 1.8 Hz, 1 H), 7.23 (d, J=1.8 Hz, 1 H), 7.34 (d, J=8.2 Hz, 1 H).

EXAMPLE 24(7)

2-(2,4-dichlorophenyl)-5-(1-ethylpropyl)-3,7-dimethylpyrrolo[2,1-f][1,2,4]triazin-4(3H)-one TLC: Rf 0.58 (ethyl acetate/n-hexane=1/6);
$^1$H-NMR (CDCl$_3$): δ 0.81-0.93 (m, 6 H), 1.42-1.89 (m, 4 H), 2.39 (s, 3 H), 3.20 (s, 3 H), 3.31-3.49 (m, 1 H), 6.19 (s, 1 H), 7.43 (d, J=1.1 Hz, 2 H), 7.55 (t, J=1.2 Hz, 1 H).

EXAMPLE 24(8)

5-(1-ethylpropyl)-2-[4-(4-hydroxy-1-piperidinyl)-2-methylphenyl]-3,7-dimethylpyrrolo[2,1-f][1,2,4]triazin-4(3H)-one TLC: Rf 0.53 (methylene chloride/methanol=9/1);
$^1$H-NMR (CDCl$_3$): δ 0.74-1.00 (m, 6 H), 1.43-1.82 (m, 7 H), 1.94-2.12 (m, 2 H), 2.25 (s, 3 H), 2.39 (s, 3 H), 2.90-3.10 (m, 2 H), 3.15 (s, 3 H), 3.27-3.48 (m, 1 H), 3.56-3.73 (m, 2 H), 3.80-3.99 (m, 1 H), 6.15 (s, 1 H), 6.75-6.89 (m, 2 H), 7.11-7.22 (m, 1 H).

EXAMPLE 24(9)

2-[4-chloro-2-(diethylamino)-1,3-thiazol-5-yl]-5-(1-ethylpropyl)-3,7-dimethylpyrrolo[2,1-f][1,2,4]triazin-4(3H)-one TLC: Rf 0.54 (n-hexane/ethyl acetate=1/1);
$^1$H-NMR (CDCl$_3$): δ 0.84 (t, J=7.32 Hz, 6 H), 1.27 (t, J=7.14 Hz, 6 H), 1.46-1.81 (m, 4 H), 2.41 (s, 3 H), 3.29-3.42 (m, 1 H), 3.43 (s, 3 H), 3.50 (q, J=7.14 Hz, 4 H), 6.16 (s, 1 H).

EXAMPLE 24(10)

5-(1-ethylpropyl)-2-[4-(1H-imidazol-1-yl)-2-methylphenyl]-3,7-dimethylpyrrolo[2,1-f][1,2,4]triazin-4(3H)-one TLC: Rf 0.67 (ethyl acetate/methanol=95/5);
$^1$H-NMR (CDCl$_3$): δ 0.79-1.00 (m, 6 H), 1.50-1.90 (m, 4 H), 2.40 (s, 3 H), 2.41 (s, 3 H), 3.19 (s, 3 H), 3.32-3.52 (m, 1 H), 6.20 (s, 1 H), 7.25 (s, 1 H), 7.31-7.34 (t, J=1.3 Hz, 1 H), 7.35-7.42 (m, 2 H), 7.43-7.53 (m, 1 H), 7.92 (s, 1 H).

EXAMPLE 24(11)

2-[4-(diethylamino)-2-methylphenyl]-5-(1-ethylpropyl)-3,7-dimethylpyrrolo[2,1-f][1,2,4]triazin-4(3H)-one TLC: Rf 0.74 (n-hexane/ethyl acetate=2/1);
$^1$H-NMR (CDCl$_3$): δ 0.87 (t, J=7.2 Hz, 6 H), 1.19 (t, J=7.0 Hz, 6 H), 1.51-1.83 (m, 4 H), 2.25 (s, 3 H), 2.39 (s, 3 H), 3.19 (s, 3 H), 3.28-3.49 (m, 5 H), 6.15 (s, 1 H), 6.51-6.62 (m, 2 H), 7.13 (d, J=8.4 Hz, 1 H).

EXAMPLE 24(12)

5-(1-ethylpropyl)-2-(4-methoxy-2,6-dimethylphenyl)-3,7-dimethylpyrrolo[2,1-f][1,2,4]triazin-4(3H)-one TLC: Rf 0.48 (n-hexane/ethyl acetate=4/1);
$^1$H-NMR (CDCl$_3$): δ 0.88 (t, J=7.4 Hz, 6 H), 1.53-1.90 (m, 4 H), 2.21 (s, 6 H), 2.39 (s, 3 H), 3.10 (s, 3 H), 3.40 (m, 1 H), 3.83 (s, 3 H), 6.17 (s, 1 H), 6.69 (s, 2 H).

EXAMPLE 24(13)

2-[4-(difluoromethoxy)-2-methylphenyl]-5-(1-ethylpropyl)-3,7-dimethylpyrrolo[2,1-f][1,2,4]triazin-4(3H)-one TLC: Rf 0.59 (n-hexane/ethyl acetate=3/1);
$^1$H-NMR (CDCl$_3$): δ 0.87 (q, J=7.0 Hz, 6 H), 1.47-1.85 (m, 4 H), 2.33 (s, 3 H), 2.39 (s, 3H), 3.14 (s, 3 H), 3.31-3.47 (m, 1 H), 6.18 (s, 1 H), 6.57 (t, J=73.6 Hz, 1 H), 6.98-7.21 (m, 2 H), 7.31-7.43 (m, 1 H).

EXAMPLE 24(14)

2-[2-chloro-4-(methylsulfinyl)phenyl]-5-(1-ethylpropyl)-3,7-dimethylpyrrolo[2,1-f][1,2,4]triazin-4(3H)-one TLC: Rf 0.17 (n-hexane/ethyl acetate=1/3);
$^1$H-NMR (CDCl$_3$): δ 0.76-0.96 (m, 6 H), 1.48-1.83 (m, 4 H), 2.39 (s, 3 H), 2.82 (s, 3 H), 3.17-3.25 (m, 3 H), 3.31-3.47 (m, 1 H), 6.19 (s, 1 H), 7.54-7.95 (m, 3 H).

EXAMPLE 24(15)

2-[4-chloro-2-(difluoromethoxy)phenyl]-5-(1-ethylpropyl)-3,7-dimethylpyrrolo[2,1-f][1,2,4]triazin-4(3H)-one TLC: Rf 0.29 (n-hexane/ethyl acetate=9/1);
$^1$H-NMR (CDCl$_3$): δ 0.72-1.01 (m, 6 H), 1.56-1.84 (m, 4 H), 2.33-2.42 (m, 3 H), 3.21 (s, 3 H), 3.39 (m, 1 H), 6.18 (s, 1 H), 6.30-6.84 (m, 1 H), 7.33-7.40 (m, 2 H), 7.42-7.49 (m, 1H).

EXAMPLE 24(16)

5-(1-ethylpropyl)-3,7-dimethyl-2-[2-methyl-4-(4-methyl-1-piperazinyl)phenyl]pyrrolo[2,1-f][1,2,4]triazin-4(3H)-one TLC: Rf 0.15 (ethyl acetate/methanol=8/2);
$^1$H-NMR (CDCl$_3$): δ 0.87 (t, J=7.0 Hz, 6 H), 1.49-1.82 (m, 4 H), 2.26 (s, 3 H), 2.37 (s, 3 H), 2.39 (s, 3 H), 2.51-2.67 (m, 4 H), 3.15 (s, 3 H), 3.22-3.34 (m, 4 H), 3.33-3.48 (m, 1 H), 6.16 (s, 1 H), 6.79-6.88 (m, 2 H), 7.16-7.25 (m, 1 H).

EXAMPLE 24(17)

2-[2-chloro-4-(methylsulfonyl)phenyl]-5-(1-ethylpropyl)-3,7-dimethylpyrrolo[2,1-f][1,2,4]triazin-4(3H)-one TLC: Rf 0.58 (n-hexane/ethyl acetate=1/3);
$^1$H-NMR (CDCl$_3$): δ 0.77-0.94 (m, 6 H), 1.50-1.81 (m, 4 H), 2.38 (d, J=0.7 Hz, 3 H), 3.14 (s, 3 H), 3.20 (s, 3 H), 3.30-3.49 (m, 1 H), 6.20 (s, 1 H), 7.72 (d, J=8.1 Hz, 1 H), 8.00 (dd, J=8.1, 1.8 Hz, 1 H), 8.11 (d, J=1.8 Hz, 1 H).

EXAMPLE 24(18)

5-(1-ethylpropyl)-3,7-dimethyl-2-[2-methyl-6-(1H-1,2,4-triazol-1-yl)-3-pyridinyl]pyrrolo[2,1-f][1,2,4]triazin-4(3H)-one TLC: Rf 0.55 (ethyl acetate/n-hexane=2/1);
$^1$H-NMR (CDCl$_3$): δ 0.87 (t, J=7.3 Hz, 6 H), 1.49-1.84 (m, 4 H), 2.40 (s, 3 H), 2.60 (s, 3 H), 3.21 (s, 3 H), 3.31-3.48 (m, 1 H), 6.21 (s, 1 H), 7.82-7.96 (m, 2 H), 8.14 (s, 1 H), 9.24 (s, 1 H).

EXAMPLE 24(19)

2-(2,6-dimethylphenyl)-5-(1-ethylpropyl)-3,7-dimethylpyrrolo[2,1-f][1,2,4]triazin-4(3H)-one TLC: Rf 0.49 (ethyl acetate/n-hexane=1/6);
$^1$H-NMR (CDCl$_3$): δ 0.89 (t, J=7.4 Hz, 6 H), 1.52-1.83 (m, 4 H), 2.24 (s, 6 H), 2.39 (s, 3 H), 3.09 (s, 3 H), 3.34-3.47 (m, 1 H), 6.18 (s, 1 H), 7.12-7.19 (m, 2 H), 7.26-7.33 (m, 1H).

EXAMPLE 24(20)

2-(2,5-dichlorophenyl)-5-(1-ethylpropyl)-3,7-dimethylpyrrolo[2,1-f][1,2,4]triazin-4(3H)-one TLC: Rf 0.48 (ethyl acetate/n-hexane=1/6);
$^1$H-NMR (CDCl$_3$): δ 0.72-1.00 (m, 6 H), 1.44-1.86 (m, 4 H), 2.40 (s, 3 H), 3.22 (s, 3 H), 3.31-3.52 (m, 1 H), 6.19 (s, 1 H), 7.40-7.57 (m, 3 H).

EXAMPLE 24(21)

2-(3-chloro-5-methoxy-2-pyridinyl)-5-(1-ethylpropyl)-3,7-dimethylpyrrolo[2,1-f][1,2,4]triazin-4(3H)-one TLC: Rf 0.42 (n-hexane/ethyl acetate=1/1);
$^1$H-NMR (CDCl$_3$): δ 0.77-0.92 (m, 6 H), 1.48-1.84 (m, 4 H), 2.39 (s, 3 H), 3.19 (s, 3 H), 3.31-3.50 (m, 1 H), 3.95 (s, 3 H), 6.17 (s, 1 H), 7.37 (d, J=2.7 Hz, 1 H), 8.34 (d, J=2.6 Hz, 1 H).

EXAMPLE 24(22)

5-(1-ethylpropyl)-3,7-dimethyl-2-[2-methyl-6-(1H-pyrazol-1-yl)-3-pyridinyl]pyrrolo[2,1-f][1,2,4]triazin-4(3H)-one TLC: Rf 0.46 (ethyl acetate/n-hexane=1/4);
$^1$H-NMR (CDCl$_3$): δ 0.87 (t, J=7.2 Hz, 6 H), 1.47-1.91 (m, 4 H), 2.40 (s, 3 H), 2.56 (s, 3 H), 3.21 (s, 3 H), 3.30-3.52 (m, 1 H), 6.20 (s, 1 H), 6.50 (dd, J=2.6, 1.6 Hz, 1 H), 7.79 (d, J=8.2 Hz, 2 H), 7.96 (d, J=8.2 Hz, 1 H), 8.63 (d, J=2.6 Hz, 1 H).

EXAMPLE 24(23)

5-(1-ethylpropyl)-2-[6-(1H-imidazol-1-yl)-2-methyl-3-pyridinyl]-3,7-dimethylpyrrolo[2,1-f][1,2,4]triazin-4(3H)-one TLC: Rf 0.44 (ethyl acetate);
$^1$H-NMR (CDCl$_3$): δ 0.87 (t, J=7.4 Hz, 6 H), 1.50-1.85 (m, 4 H), 2.40 (s, 3 H), 2.59 (s, 3 H), 3.21 (s, 3 H), 3.31-3.47 (m, 1 H), 6.21 (s, 1 H), 7.25 (s, 1 H), 7.36 (d, J=7.9 Hz, 1 H), 7.71 (s, 1 H), 7.82 (d, J=7.9 Hz, 1 H), 8.48 (s, 1 H).

EXAMPLE 24(24)

4-[5-(1-ethylpropyl)-3,7-dimethyl-4-oxo-3,4-dihydropyrrolo[2,1-f][1,2,4]triazin-2-yl]-3-methylphenyl methanesulfonate TLC: Rf 0.64 (ethyl acetate/n-hexane=1/1);
$^1$H-NMR (CDCl$_3$): δ 0.80-0.98 (m, 6 H), 1.47-1.87 (m, 4 H), 2.35 (s, 3 H), 2.38 (s, 3 H), 3.14 (s, 3 H), 3.22 (s, 3 H), 3.30-3.54 (m, 1 H), 6.18 (s, 1 H), 7.18-7.33 (m, 2 H), 7.37-7.50 (m, 1 H).

EXAMPLE 24(25)

2-(2,6-dichlorophenyl)-5-(1-ethylpropyl)-3,7-dimethylpyrrolo[2,1-f][1,2,4]triazin-4(3H)-one TLC: Rf 0.38 (ethyl acetate/n-hexane=1/6);
$^1$H-NMR (CDCl$_3$): δ 0.88 (t, J=7.4 Hz, 6 H), 1.48-1.89 (m, 4 H), 2.40 (d, J=0.7 Hz, 3 H), 3.18 (s, 3 H), 3.33-3.55 (m, 1 H), 6.19 (s, 1 H), 7.33-7.51 (m, 3 H).

EXAMPLE 24(26)

2-(2,6-dimethoxyphenyl)-5-(1-ethylpropyl)-3,7-dimethylpyrrolo[2,1-f][1,2,4]triazin-4(3H)-one TLC: Rf 0.51 (ethyl acetate/n-hexane=1/2);
$^1$H-NMR (CDCl$_3$): δ 0.88 (t, J=7.4 Hz, 6 H), 1.51-1.84 (m, 4 H), 2.40 (s, 3 H), 3.12 (s, 3 H), 3.32-3.51 (m, 1 H), 3.80 (s, 6 H), 6.13 (s, 1 H), 6.63 (d, J=8.4 Hz, 2 H), 7.39 (t, J=8.4 Hz, 1 H).

EXAMPLE 24(27)

2-(2-chloro-6-fluorophenyl)-5-(1-ethylpropyl)-3,7-dimethylpyrrolo[2,1-f][1,2,4]triazin-4(3H)-one TLC: Rf 0.36 (ethyl acetate/n-hexane=1/6);
$^1$H-NMR (CDCl$_3$): δ 0.83-0.94 (m, 6 H), 1.50-1.86 (m, 4 H), 2.40 (d, J=0.7 Hz, 3 H), 3.21 (s, 3 H), 3.34-3.50 (m, 1 H), 6.19 (s, 1 H), 7.13-7.22 (m, 1 H), 7.32-7.37 (m, 1 H), 7.41-7.52 (m, 1 H).

EXAMPLE 24(28)

5-(1-ethylpropyl)-2-[2-fluoro-6-(trifluoromethyl) phenyl]-3,7-dimethylpyrrolo[2,1-f][1,2,4]triazin-4 (3H)-one TLC: Rf 0.53 (ethyl acetate/n-hexane=1/4);
$^1$H-NMR (CDCl$_3$): δ 0.78-0.99 (m, 6 H), 1.41-1.89 (m, 4 H), 2.37 (d, J=0.7 Hz, 3 H), 3.18 (s, 3 H), 3.30-3.53 (m, 1 H), 6.19 (s, 1 H), 7.39-7.53 (m, 1 H), 7.59-7.78 (m, 2 H).

EXAMPLE 24(29)

5-(1-ethylpropyl)-2-(2-fluoro-6-methoxyphenyl)-3,7-dimethylpyrrolo[2,1-f][1,2,4]triazin-4(3H)-one TLC: Rf 0.61 (ethyl acetate/n-hexane=1/2);
$^1$H-NMR (CDCl$_3$): δ 0.71-1.00 (m, 6 H), 1.44-1.91 (m, 4 H), 2.40 (s, 3 H), 3.19 (s, 3 H), 3.30-3.51 (m, 1 H), 3.86 (s, 3 H), 6.16 (s, 1 H), 6.70-6.94 (m, 2 H), 7.33-7.56 (m, 1 H).

EXAMPLE 24(30)

5-(1-ethylpropyl)-2-(2-fluoro-6-phenoxyphenyl)-3,7-dimethylpyrrolo[2,1-f][1,2,4]triazin-4(3H)-one TLC: Rf 0.52 (ethyl acetate/n-hexane=1/4);
$^1$H-NMR (CDCl$_3$): δ 0.80-0.91 (m, 6 H), 1.46-1.83 (m, 4 H), 2.35 (s, 3 H), 3.33 (s, 3 H), 3.34-3.45 (m, 1 H), 6.14 (s, 1 H), 6.74 (dd, J=8.4, 0.9 Hz, 1 H), 6.91-7.00 (m, 1 H), 7.01-7.09 (m, 2 H), 7.10-7.19 (m, 1 H), 7.28-7.44 (m, 3 H).

EXAMPLE 24(31)

2-[2-(dimethylamino)-4-(trifluoromethyl)-1,3-thiazol-5-yl]-5-(1-ethylpropyl)-3,7-dimethylpyrrolo[2,1-f][1,2,4]triazin-4(3H)-one TLC: Rf 0.61 (n-hexane/ethyl acetate=1/1);
$^1$H-NMR (CDCl$_3$): δ 0.84 (t, J=7.4 Hz, 6 H), 1.45-1.82 (m, 4 H), 2.38 (s, 3 H), 3.18 (s, 6 H), 3.28-3.44 (m, 4 H), 6.18 (s, 1 H).

EXAMPLE 24(32)

2-(2-chloro-6-methylphenyl)-5-(1-ethylpropyl)-3,7-dimethylpyrrolo[2,1-f][1,2,4]triazin-4(3H)-one TLC: Rf 0.66 (ethyl acetate/n-hexane=1/6);
$^1$H-NMR (CDCl$_3$): δ 0.88 (t, J=7.4 Hz, 6 H), 1.53-1.81 (m, 4 H), 2.30 (s, 3 H), 2.40 (s, 3 H), 3.15 (s, 3 H), 3.33-3.48 (m, 1 H), 6.19 (s, 1 H), 7.21-7.29 (m, 1 H), 7.30-7.39 (m, 2H).

EXAMPLE 24(33)

5-(1-ethylpropyl)-2-[4-fluoro-2-(trifluoromethyl) phenyl]-3,7-dimethylpyrrolo[2,1-f][1,2,4]triazin-4 (3H)-one TLC: Rf 0.55 (ethyl acetate/n-hexane=1/6);
$^1$H-NMR (CDCl$_3$): δ 0.79-0.94 (m, 6 H), 1.48-1.86 (m, 4 H), 2.36 (s, 3 H), 3.12 (s, 3 H), 3.31-3.46 (m, 1 H), 6.18 (s, 1 H), 7.37-7.47 (m, 1 H), 7.48-7.63 (m, 2 H).

EXAMPLE 24(34)

5-(1-ethylpropyl)-2-(2-methoxyphenyl)-3,7-dimethylpyrrolo[2,1-f][1,2,4]triazin-4(3H)-one TLC: Rf 0.63 (ethyl acetate/n-hexane=1/6);
$^1$H-NMR (CDCl$_3$): δ 0.77-0.92 (m, 6 H), 1.46-1.84 (m, 4 H), 2.40 (s, 3 H), 3.19 (s, 3 H), 3.33-3.47 (m, 1 H), 3.85 (s, 3 H), 6.14 (s, 1 H), 6.99 (d, J=8.2 Hz, 1 H), 7.04-7.12 (m, 1 H), 7.39 (dd, J=7.3, 1.6 Hz, 1 H), 7.44-7.52 (m, 1 H).

EXAMPLE 24(35)

2-(4-ethoxy-5-fluoro-2-methylphenyl)-5-(1-ethylpropyl)-3,7-dimethylpyrrolo[2,1-f][1,2,4]triazin-4(3H)-one TLC: Rf 0.30 (ethyl acetate/n-hexane=1/6);
$^1$H-NMR (CDCl$_3$): δ 0.75-0.97 (m, 6 H), 1.49 (t, J=7.0 Hz, 3 H), 1.54-1.81 (m, 4 H), 2.25 (s, 3 H), 2.39 (s, 3 H), 3.15 (s, 3 H), 3.32-3.45 (m, 1 H), 4.15 (q, J=7.0 Hz, 2 H), 6.16 (s, 1 H), 6.87 (d, J=8.2 Hz, 1 H), 7.06 (d, J=11.0 Hz, 1 H).

EXAMPLE 24(36)

5-(1-ethylpropyl)-2-(2-methoxy-6-methylphenyl)-3,7-dimethylpyrrolo[2,1-f][1,2,4]triazin-4(3H)-one TLC: Rf 0.39 (ethyl acetate/n-hexane=1/6);
$^1$H-NMR (CDCl$_3$): δ 0.88 (t, J=7.3 Hz, 6 H), 1.52-1.84 (m, 4 H), 2.26 (s, 3 H), 2.39 (s, 3 H), 3.12 (s, 3 H), 3.33-3.48 (m, 1 H), 3.81 (s, 3 H), 6.16 (s, 1 H), 6.83 (d, J=8.4 Hz, 1 H), 6.93 (d, J=7.5 Hz, 1 H), 7.31-7.39 (m, 1 H).

EXAMPLE 24(37)

5-(1-ethylpropyl)-3,7-dimethyl-2-(2-methylphenyl) pyrrolo[2,1-f][1,2,4]triazin-4(3H)-one TLC: Rf 0.59 (ethyl acetate/n-hexane=1/6);
$^1$H-NMR (CDCl$_3$): δ 0.78-0.99 (m, 6 H), 1.48-1.85 (m, 4 H), 2.31 (s, 3 H), 2.39 (s, 3 H), 3.13 (s, 3 H), 3.31-3.47 (m, 1 H), 6.17 (s, 1 H), 7.21-7.53 (m, 4 H).

EXAMPLE 24(38)

2-[5-(1-ethylpropyl)-3,7-dimethyl-4-oxo-3,4-dihydropyrrolo[2,1-f][1,2,4]triazin-2-yl]benzonitrile TLC: Rf 0.67 (ethyl acetate/n-hexane=1/2);
$^1$H-NMR (CDCl$_3$): δ 0.86 (t, J=7.4 Hz, 6 H), 1.50-1.83 (m, 4 H), 2.41 (s, 3 H), 3.25 (s, 3 H), 3.32-3.45 (m, 1 H), 6.19 (s, 1 H), 7.56-7.70 (m, 2 H), 7.70-7.80 (m, 1 H), 7.80-7.92 (m, 1 H).

EXAMPLE 24(39)

2-(2-ethoxyphenyl)-5-(1-ethylpropyl)-3,7-dimethylpyrrolo[2,1-f][1,2,4]triazin-4(3H)-one TLC: Rf 0.52 (ethyl acetate/n-hexane=1/2);
$^1$H-NMR (CDCl$_3$): δ 0.77-0.95 (m, 6 H), 1.36 (t, J=7.0 Hz, 3 H), 1.50-1.89 (m, 4 H), 2.40 (s, 3 H), 3.22 (s, 3 H), 3.34-3.49 (m, 1 H), 4.11 (q, J=7.0 Hz, 2 H), 6.15 (s, 1 H), 6.97 (d, J=8.4 Hz, 1 H), 7.05 (t, J=7.3 Hz, 1 H), 7.39 (dd, J=7.3, 1.8 Hz, 1 H), 7.41-7.50 (m, 1 H).

EXAMPLE 24(40)

5-(1-ethylpropyl)-2-(2-isopropylphenyl)-3,7-dimethylpyrrolo[2,1-f][1,2,4]triazin-4(3H)-one TLC: Rf 0.68 (ethyl acetate/n-hexane=1/2);
$^1$H-NMR (CDCl$_3$): δ 0.82-0.96 (m, 6 H), 1.25 (t, J=7.0 Hz, 6 H), 1.51-1.85 (m, 4 H), 2.38 (s, 3 H), 2.78-2.98 (m, 1 H), 3.13 (s, 3 H), 3.33-3.49 (m, 1 H), 6.18 (s, 1 H), 7.22-7.38 (m, 2 H), 7.41-7.54 (m, 2 H).

EXAMPLE 24(41)

2-(2-ethylphenyl)-5-(1-ethylpropyl)-3,7-dimethylpyrrolo[2,1-f][1,2,4]triazin-4(3H)-one TLC: Rf 0.60 (ethyl acetate/n-hexane=1/2);
$^1$H-NMR (CDCl$_3$): δ 0.79-0.99 (m, 6 H), 1.24 (t, J=7.6 Hz, 3 H), 1.50-1.84 (m, 4 H), 2.39 (s, 3 H), 2.51-2.74 (m, 2 H), 3.12 (s, 3 H), 3.33-3.48 (m, 1 H), 6.18 (s, 1 H), 7.28-7.52 (m, 4 H).

EXAMPLE 24(42)

5-(1-ethylpropyl)-3,7-dimethyl-2-{2-[(trifluoromethyl)thio]phenyl}pyrrolo[2,1-f][1,2,4]triazin-4(3H)-one TLC: Rf 0.47 (ethyl acetate/n-hexane=1/6);
$^1$H-NMR (CDCl$_3$): δ 0.76-0.99 (m, 6 H), 1.45-1.89 (m, 4 H), 2.37 (s, 3 H), 3.16 (s, 3 H), 3.30-3.50 (m, 1 H), 6.19 (s, 1 H), 7.44-7.72 (m, 3 H), 7.76-8.01 (m, 1 H).

EXAMPLE 24(43)

2-[4-chloro-2-(trifluoromethyl)phenyl]-5-(1-ethylpropyl)-3,7-dimethylpyrrolo[2,1-f][1,2,4]triazin-4(3H)-one TLC: Rf 0.38 (ethyl acetate/n-hexane=1/6);
$^1$H-NMR (CDCl$_3$): δ 0.78-0.97 (m, 6 H), 1.47-1.86 (m, 4 H), 2.35 (d, J=0.7 Hz, 3 H), 3.12 (s, 3 H), 3.30-3.45 (m, 1 H), 6.18 (s, 1 H), 7.47 (d, J=8.2 Hz, 1 H), 7.70 (dd, J=8.2, 1.6 Hz, 1 H), 7.83 (d, J=1.6 Hz, 1 H).

EXAMPLE 24(44)

5-(1-ethylpropyl)-3,7-dimethyl-2-[2-(trifluoromethoxy)phenyl]pyrrolo[2,1-f][1,2,4]triazin-4(3H)-one TLC: Rf 0.62 (ethyl acetate/n-hexane=1/6);
$^1$H-NMR (CDCl$_3$): δ 0.78-1.01 (m, 6 H), 1.48-1.87 (m, 4 H), 2.39 (s, 3 H), 3.20 (s, 3 H), 3.33-3.49 (m, 1 H), 6.19 (s, 1 H), 7.38-7.50 (m, 2 H), 7.50-7.66 (m, 2 H).

EXAMPLE 24(45)

2-[2-(difluoromethoxy)phenyl]-5-(1-ethylpropyl)-3,7-dimethylpyrrolo[2,1-f][1,2,4]triazin-4(3H)-one TLC: Rf 0.40 (ethyl acetate/n-hexane=1/6);
$^1$H-NMR (CDCl$_3$): δ 0.77-0.95 (m, 6 H), 1.49-1.82 (m, 4 H), 2.38 (s, 3 H), 3.20 (s, 3 H), 3.31-3.47 (m, 1 H), 6.17 (s, 1 H), 6.30-6.84 (m, 1 H), 7.28-7.40 (m, 2 H), 7.46-7.60 (m, 2H).

EXAMPLE 24(46)

2-[2-chloro-6-(trifluoromethyl)phenyl]-5-(1-ethylpropyl)-3,7-dimethylpyrrolo[2,1-f][1,2,4]triazin-4(3H)-one TLC: Rf 0.38 (ethyl acetate/n-hexane=1/6);
$^1$H-NMR (CDCl$_3$): δ 0.88 (t, J=7.4 Hz, 6 H), 1.49-1.84 (m, 4 H), 2.36 (s, 3 H), 3.14 (s, 3 H), 3.31-3.46 (m, 1 H), 6.18 (s, 1 H), 7.56-7.67 (m, 1 H), 7.69-7.80 (m, 2 H).

EXAMPLE 24(47)

5-(1-ethylpropyl)-2-(4-fluoro-2-methylphenyl)-3,7-dimethylpyrrolo[2,1-f][1,2,4]triazin-4(3H)-one TLC: Rf 0.57 (n-hexane/ethyl acetate=9/1);
$^1$H-NMR (CDCl$_3$): δ 0.81-0.93 (m, 6 H), 1.54-1.79 (m, 4 H), 2.32 (s, 3 H), 2.39 (d, J=0.73 Hz, 3 H), 3.13 (s, 3 H), 3.34-3.45 (m, 1 H), 6.18 (s, 1 H), 6.98-7.09 (m, 2 H), 7.29-7.37 (m, 1 H).

EXAMPLE 24(48)

5-(1-ethylpropyl)-2-(4-fluoro-2-methoxyphenyl)-3,7-dimethylpyrrolo[2,1-f][1,2,4]triazin-4(3H)-one TLC: Rf 0.36 (n-hexane/ethyl acetate=9/1);
$^1$H-NMR (CDCl$_3$): δ 0.80-0.93 (m, 6 H), 1.51-1.81 (m, 4 H), 2.39 (s, 3 H), 3.19 (s, 3 H), 3.34-3.46 (m, 1 H), 3.85 (s, 3 H), 6.16 (s, 1 H), 6.69-6.86 (m, 2 H), 7.38 (dd, J=8.42, 6.40 Hz, 1 H).

EXAMPLE 24(49)

2-(2,6-difluorophenyl)-5-(1-ethylpropyl)-3,7-dimethylpyrrolo[2,1-f][1,2,4]triazin-4(3H)-one TLC: Rf 0.48 (ethyl acetate/n-hexane=1/6);
$^1$H-NMR (CDCl$_3$): δ 0.87 (t, J=7.4 Hz, 6 H), 1.49-1.83 (m, 4 H), 2.40 (d, J=0.7 Hz, 3 H), 3.26 (s, 3 H), 3.33-3.46 (m, 1 H), 6.19 (s, 1 H), 6.94-7.18 (m, 2 H), 7.37-7.63 (m, 1 H).

EXAMPLE 24(50)

2-[3-chloro-5-(trifluoromethyl)-2-pyridinyl]-5-(1-ethylpropyl)-3,7-dimethylpyrrolo[2,1-f][1,2,4]triazin-4(3H)-one TLC: Rf 0.50 (n-hexane/ethyl acetate=6/1);
$^1$H-NMR (CDCl$_3$): δ 0.85 (t, J=7.4 Hz, 6 H), 1.58-1.78 (m, 4 H), 2.39 (s, 3 H), 3.20 (s, 3 H), 3.35-3.45 (m, 1 H), 6.21 (s, 1 H), 8.15-8.16 (m, 1 H), 8.92-8.93 (m, 1 H).

EXAMPLE 24(51)

2-[5-(1-ethylpropyl)-3,7-dimethyl-4-oxo-3,4-dihydropyrrolo[2,1-f][1,2,4]triazin-2-yl]phenyl methanesulfonate TLC: Rf 0.50 (ethyl acetate/n-hexane=1/2);
$^1$H-NMR (CDCl$_3$): δ 0.79-0.93 (m, 6 H), 1.48-1.83 (m, 4 H), 2.36 (d, J=0.7 Hz, 3 H), 3.02 (s, 3 H), 3.19 (s, 3 H), 3.32-3.46 (m, 1 H), 6.18 (s, 1 H), 7.43-7.54 (m, 2 H), 7.55-7.64 (m, 2 H).

EXAMPLE 24(52)

4-[5-(1-ethylpropyl)-3,7-dimethyl-4-oxo-3,4-dihydropyrrolo[2,1-f][1,2,4]triazin-2-yl]-3,5-dimethylphenyl methanesulfonate TLC: Rf 0.44 (ethyl acetate/n-hexane=1/2);
$^1$H-NMR (CDCl$_3$): δ 0.88 (t, J=7.4 Hz, 6 H), 1.50-1.87 (m, 4 H), 2.27 (s, 6 H), 2.39 (s, 3 H), 3.10 (s, 3 H), 3.17-3.26 (m, 3 H), 3.29-3.52 (m, 1 H), 6.19 (s, 1 H), 7.11 (s, 2 H).

EXAMPLE 24(53)

5-(1-ethylpropyl)-2-[2-methoxy-4-(trifluoromethyl)phenyl]-3,7-dimethylpyrrolo[2,1-f][1,2,4]triazin-4(3H)-one TLC: Rf 0.57 (ethyl acetate/n-hexane=1/6);
$^1$H-NMR (CDCl$_3$): δ 0.81-0.94 (m, 6 H), 1.50-1.83 (m, 4 H), 2.39 (s, 3 H), 3.20 (s, 3 H), 3.33-3.47 (m, 1 H), 3.93 (s, 3 H), 6.18 (s, 1 H), 7.22 (s, 1 H), 7.38 (dd, J=7.9, 0.7 Hz, 1 H), 7.55 (d, J=7.9 Hz, 1 H).

EXAMPLE 24(54)

5-(1-ethylpropyl)-3,7-dimethyl-2-[2-(trifluoromethyl)phenyl]pyrrolo[2,1-f][1,2,4]triazin-4(3H)-one TLC: Rf 0.41 (ethyl acetate/n-hexane=1/6);
$^1$H-NMR (CDCl$_3$): δ 0.80-0.95 (m, 6 H), 1.48-1.85 (m, 4 H), 2.37 (s, 3 H), 3.12 (s, 3 H), 3.33-3.47 (m, 1 H), 6.18 (s, 1 H), 7.48-7.55 (m, 1 H), 7.62-7.76 (m, 2 H), 7.84 (dd, J=7.6, 1.7 Hz, 1 H).

EXAMPLE 24(55)

5-(1-ethylpropyl)-3,7-dimethyl-2-[2-(methylthio)phenyl]pyrrolo[2,1-f][1,2,4]triazin-4(3H)-one TLC: Rf 0.45 (ethyl acetate/n-hexane=1/6);
$^1$H-NMR (CDCl$_3$): δ 0.87 (t, J=7.2 Hz, 6 H), 1.48-1.84 (m, 4 H), 2.39 (d, J=0.7 Hz, 3 H), 2.48 (s, 3 H), 3.17 (s, 3 H), 3.32-3.50 (m, 1 H), 6.16 (s, 1 H), 7.22-7.39 (m, 3 H), 7.43-7.51 (m, 1 H).

EXAMPLE 24(56)

2-(2,5-dimethyl-1,3-oxazol-4-yl)-5-(1-ethylpropyl)-3,7-dimethylpyrrolo[2,1-f][1,2,4]triazin-4(3H)-one TLC: Rf 0.28 (n-hexane/ethyl acetate=4/1);
$^1$H-NMR (CDCl$_3$): δ 0.84 (t, J=7.32 Hz, 6 H), 1.49-1.79 (m, 4 H), 2.40 (d, J=0.73 Hz, 3 H), 2.47 (s, 3 H), 2.49 (s, 3 H), 3.33-3.44 (m, 1 H), 3.49 (s, 3 H), 6.16 (s, 1 H).

EXAMPLE 24(57)

3-chloro-4-[5-(1-ethylpropyl)-3,7-dimethyl-4-oxo-3,4-dihydropyrrolo[2,1-f][1,2,4]triazin-2-yl]phenyl methanesulfonate TLC: Rf 0.38 (n-hexane/ethyl acetate=2/1);
$^1$H-NMR (CDCl$_3$): δ 0.82-0.91 (m, 6 H), 1.58-1.78 (m, 4 H), 2.39 (s, 3 H), 3.21 (s, 3 H), 3.27 (s, 3 H), 3.35-3.44 (m, 1 H), 6.20 (s, 1 H), 7.39 (dd, J=8.4, 2.4 Hz, 1 H), 7.50 (d, J=2.4 Hz, 1 H), 7.56 (d, J=8.4 Hz, 1 H).

EXAMPLE 24(58)

5-(1-ethylpropyl)-2-(4-methoxy-2,5-dimethylphenyl)-3,7-dimethylpyrrolo[2,1-f][1,2,4]triazin-4(3H)-one TLC: Rf 0.60 (n-hexane/ethyl acetate=3/1);
$^1$H-NMR (CDCl$_3$): δ 0.83-0.91 (m, 6 H), 1.59-1.77 (m, 4 H), 2.22 (s, 3 H), 2.27 (s, 3 H), 2.39 (s, 3 H), 3.15 (s, 3 H), 3.35-3.45 (m, 1 H), 3.87 (s, 3 H), 6.16 (s, 1 H), 6.74 (s, 1 H), 7.09 (s, 1 H).

EXAMPLE 24(59)

2-[4-(difluoromethoxy)-2,6-dimethylphenyl]-5-(1-ethylpropyl)-3,7-dimethylpyrrolo[2,1-f][1,2,4]triazin-4(3H)-one TLC: Rf 0.77 (n-hexane/ethyl acetate=5/1);
$^1$H-NMR (CDCl$_3$): δ 0.88 (t, J=7.41 Hz, 6 H), 1.51-1.83 (m, 4 H), 2.25 (s, 6 H), 2.39 (s, 3H) 3.10 (s, 3H) 3.29-3.52 (m, 1H) 6.19 (s, 1H) 6.55 (t, J=73.64 Hz, 1H) 6.93 (s, 2 H).

EXAMPLE 24(60)

2-{4-[(dimethylamino)methyl]-2-methylphenyl}-5-(1-ethylpropyl)-3,7-dimethylpyrrolo[2,1-f][1,2,4]triazin-4(3H)-one TLC: Rf 0.25 (methylene chloride/methanol=9/1);
$^1$H-NMR (CDCl$_3$): δ 0.81-0.93 (m, 6 H), 1.54-1.82 (m, 4 H), 2.28-2.31 (m, 9 H), 2.40 (s, 3 H), 3.12 (s, 3 H), 3.34-3.45 (m, 1 H), 3.46 (s, 2 H), 6.17 (s, 1 H), 7.22-7.34 (m, 3 H).

EXAMPLE 24(61)

5-(1-ethylpropyl)-3,7-dimethyl-2-(3-methyl-4-pyridinyl)pyrrolo[2,1-f][1,2,4]triazin-4(3H)-one TLC: Rf 0.23 (ethyl acetate/n-hexane=1/2);
$^1$H-NMR (CDCl$_3$): δ 0.87 (t, J=7.4 Hz, 6 H), 1.52-1.81 (m, 4 H), 2.34 (s, 3 H), 2.38 (s, 3 H), 3.14 (s, 3 H), 3.32-3.44 (m, 1 H), 6.19 (s, 1 H), 7.27 (d, J=4.9 Hz, 1 H), 8.61 (d, J=4.9 Hz, 1 H), 8.63 (s, 1 H).

EXAMPLE 24(62)

2-[4-chloro-2-(trifluoromethoxy)phenyl]-5-(1-ethylpropyl)-3,7-dimethylpyrrolo[2,1-f][1,2,4]triazin-4(3H)-one TLC: Rf 0.53 (ethyl acetate/n-hexane=1/6);
$^1$H-NMR (CDCl$_3$): δ 0.77-0.96 (m, 6 H), 1.45-1.84 (m, 4 H), 2.37 (s, 3 H), 3.19 (s, 3 H), 3.31-3.48 (m, 1 H), 6.18 (s, 1 H), 7.37-7.55 (m, 3 H).

EXAMPLE 24(63)

2-[2-chloro-4-(difluoromethoxy)-3,5-difluorophenyl]-5-(1-ethylpropyl)-3,7-dimethylpyrrolo[2,1-f][1,2,4]triazin-4(3H)-one TLC: Rf 0.50 (ethyl acetate/n-hexane=1/6);
$^1$H-NMR (CDCl$_3$): δ 0.80-0.92 (m, 6 H), 1.49-1.82 (m, 4 H), 2.39 (s, 3 H), 3.23 (s, 3 H), 3.32-3.44 (m, 1 H), 6.21 (s, 1 H), 6.69 (t, J=72.2 Hz, 1 H), 7.22 (dd, J=9.1, 2.3 Hz, 1 H).

EXAMPLE 24(64)

2-(2-chloro-3,5-difluoro-4-methoxyphenyl)-5-(1-ethylpropyl)-3,7-dimethylpyrrolo[2,1-f][1,2,4]triazin-4(3H)-one TLC: Rf 0.46 (ethyl acetate/n-hexane=1/6);
$^1$H-NMR (CDCl$_3$): δ 0.79-0.93 (m, 6 H), 1.50-1.80 (m, 4 H), 2.38 (s, 3 H), 3.22 (s, 3 H), 3.32-3.46 (m, 1 H), 4.12 (t, J=1.4 Hz, 3 H), 6.19 (s, 1 H), 7.10 (dd, J=10.2, 2.2 Hz, 1 H).

EXAMPLE 24(65)

2-(2-chloro-4-ethoxy-3,5-difluorophenyl)-5-(1-ethylpropyl)-3,7-dimethylpyrrolo[2,1-f][1,2,4]triazin-4(3H)-one TLC: Rf 0.61 (ethyl acetate/n-hexane=1/6);
$^1$H-NMR (CDCl$_3$): δ 0.79-0.91 (m, 6 H), 1.45 (t, J=7.0 Hz, 3 H), 1.49-1.89 (m, 4 H), 2.39 (s, 3 H), 3.21 (s, 3 H), 3.29-3.51 (m, 1 H), 4.33 (q, J=7.0 Hz, 2 H), 6.19 (s, 1 H), 7.09 (dd, J=10.1, 2.2 Hz, 1 H).

EXAMPLE 24(66)

5-(1-ethylpropyl)-3,7-dimethyl-2-{2-methyl-4-[(methylamino)methyl]phenyl}pyrrolo[2,1-f][1,2,4]triazin-4(3H)-one hydrochloride TLC: Rf 0.12 (methylene chloride/methanol=9/1);
$^1$H-NMR (CDCl$_3$): δ 0.79-0.93 (m, 6 H), 1.53-1.81 (m, 4 H), 2.35 (s, 6 H), 2.60 (s, 3 H), 3.11 (s, 3 H), 3.32-3.45 (m, 1 H), 4.15 (s, 2 H), 6.18 (s, 1 H), 7.42 (d, J=8.4 Hz, 1 H), 7.56-7.63 (m, 2 H), 9.81-10.22 (m, 2 H).

EXAMPLE 24(67)

5-(1-ethylpropyl)-2-[4-(1H-imidazol-1-ylmethyl)-2-methylphenyl]-3,7-dimethylpyrrolo[2,1-f][1,2,4]triazin-4(3H)-one hydrochloride TLC: Rf 0.31 (methylene chloride/methanol=9/1);
$^1$H-NMR (CDCl$_3$): δ 0.78-0.96 (m, 6 H), 1.47-1.86 (m, 5 H), 2.35 (s, 3 H), 2.38 (s, 3 H), 3.13 (s, 3 H), 3.32-3.46 (m, 1 H), 5.57 (s, 2 H), 6.19 (s, 1 H), 7.14 (s, 1 H), 7.32-7.50 (m, 4 H), 9.69-9.86 (m, 1 H).

EXAMPLE 24(68)

2-(2,4-dimethyl-1,3-thiazol-5-yl)-5-(1-ethylpropyl)-3,7-dimethylpyrrolo[2,1-f][1,2,4]triazin-4(3H)-one TLC: Rf 0.55 (n-hexane/ethyl acetate=1/1);
$^1$H-NMR (CDCl$_3$): δ 0.85 (t, J=7.4 Hz, 6 H), 1.47-1.87 (m, 4 H), 2.40 (s, 3 H), 2.43 (s, 3 H), 2.74 (s, 3 H), 3.31 (s, 3 H), 3.33-3.47 (m, 1 H), 6.19 (s, 1 H).

EXAMPLE 24(69)

2-(3,5-dimethyl-4-isoxazolyl)-5-(1-ethylpropyl)-3,7-dimethylpyrrolo[2,1-f][1,2,4]triazin-4(3H)-one TLC: Rf 0.48 (n-hexane/ethyl acetate=3/1);
$^1$H-NMR (CDCl$_3$): δ 0.86 (t, J=7.4 Hz, 6 H), 1.51-1.85 (m, 4 H), 2.31 (s, 3 H), 2.40 (s, 3 H), 2.48 (s, 3 H), 3.29 (s, 3 H), 3.31-3.45 (m, 1 H), 6.20 (s, 1 H).

EXAMPLE 24(70)

2-(2-chloro-5-fluoro-4-methoxyphenyl)-5-(1-ethylpropyl)-3,7-dimethylpyrrolo[2,1-f][1,2,4]triazin-4(3H)-one TLC: Rf 0.43 (n-hexane/ethyl acetate=2/1);
$^1$H-NMR (CDCl$_3$): δ 0.80-0.92 (m, 6 H), 1.51-1.84 (m, 4 H), 2.39 (s, 3 H), 3.22 (s, 3 H), 3.32-3.47 (m, 1 H), 3.96 (s, 3 H), 6.18 (s, 1 H), 7.09 (d, J=7.5 Hz, 1 H), 7.22 (d, J=10.6 Hz, 1 H).

EXAMPLE 24(71)

2-(2-chloro-4-ethoxy-5-fluorophenyl)-5-(1-ethylpropyl)-3,7-dimethylpyrrolo[2,1-f][1,2,4]triazin-4(3H)-one TLC: Rf 0.41 (n-hexane/ethyl acetate=5/1);
$^1$H-NMR (CDCl$_3$): δ 0.76-0.95 (m, 6 H), 1.51 (t, J=7.01 Hz, 3 H), 1.55-2.00 (m, 4 H), 2.39 (s, 3 H), 3.22 (s, 3 H), 3.31-3.56 (m, 1 H), 4.17 (q, J=7.01 Hz, 2 H), 6.18 (s, 1 H), 7.07 (d, J=7.50 Hz, 1 H), 7.21 (d, J=10.61 Hz, 1 H).

EXAMPLE 24(72)

2-[2-chloro-4-(difluoromethoxy)-5-fluorophenyl]-5-(1-ethylpropyl)-3,7-dimethylpyrrolo[2,1-f][1,2,4]triazin-4(3H)-one TLC: Rf 0.58 (n-hexane/ethyl acetate=3/1);
$^1$H-NMR (CDCl$_3$): δ 0.75-0.94 (m, 6 H), 1.46-1.86 (m, 4 H), 2.39 (s, 3 H), 3.23 (s, 3 H), 3.30-3.50 (m, 1 H), 6.20 (s, 1 H), 6.65 (t, J=72.18 Hz, 1 H), 7.36 (d, J=9.51 Hz, 1 H), 7.45 (d, J=6.95 Hz, 1 H).

EXAMPLE 24(73)

2-(2-chloro-4-isopropoxyphenyl)-5-(1-ethylpropyl)-3,7-dimethylpyrrolo[2,1-f][1,2,4]triazin-4(3H)-one TLC: Rf 0.62 (n-hexane/ethyl acetate=3/1);
$^1$H-NMR (CDCl$_3$): δ 0.75-0.95 (m, 6 H), 1.38 (d, J=6.04 Hz, 6 H), 1.49-1.89 (m, 4 H), 2.40 (s, 3 H), 3.21 (s, 3 H), 3.33-3.51 (m, 1 H), 4.50-4.69 (m, 1 H), 6.17 (s, 1 H), 6.90 (dd, J=8.42, 2.38 Hz, 1 H), 7.01 (d, J=2.38 Hz, 1 H), 7.35 (d, J=8.42 Hz, 1 H).

EXAMPLE 24(74)

5-(1-ethylpropyl)-2-(4-isopropoxy-2-methylphenyl)-3,7-dimethylpyrrolo[2,1-f][1,2,4]triazin-4(3H)-one TLC: Rf 0.56 (n-hexane/ethyl acetate=3/1);
$^1$H-NMR (CDCl$_3$): δ 0.78-1.00 (m, 6 H), 1.37 (d, J=6.04 Hz, 6 H), 1.47-1.84 (m, 4 H), 2.27 (s, 3 H), 2.40 (s, 3 H), 3.15 (s, 3 H), 3.31-3.50 (m, 1 H), 4.50-4.70 (m, 1 H), 6.16 (s, 1 H), 6.75-6.92 (m, 2 H), 7.16-7.25 (m, 1 H).

EXAMPLE 24(75)

4-[5-(1-ethylpropyl)-3,7-dimethyl-4-oxo-3,4-dihydropyrrolo[2,1-f][1,2,4]triazin-2-yl]-3-methylbenzonitrile TLC: Rf 0.56 (n-hexane/ethyl acetate=3/1);
$^1$H-NMR (CDCl$_3$): δ 0.83-0.90 (m, 6 H), 1.57-1.80 (m, 4 H), 2.38 (s, 6 H), 3.12 (s, 3 H), 3.34-3.43 (m, 1 H), 6.20 (s, 1 H), 7.48 (d, J=8.4 Hz, 1 H), 7.63-7.66 (m, 2 H).

EXAMPLE 24(76)

5-(1-ethylpropyl)-2-(2-fluoro-4-methoxyphenyl)-3,7-dimethylpyrrolo[2,1-f][1,2,4]triazin-4(3H)-one TLC: Rf 0.56 (n-hexane/ethyl acetate=3/1);
$^1$H-NMR (CDCl$_3$): δ 0.85 (t, J=7.3 Hz, 6 H), 1.58-1.78 (m, 4 H), 2.40 (d, J=0.7 Hz, 3 H), 3.28 (d, J=1.5 Hz, 3 H), 3.34-3.44 (m, 1 H), 3.87 (s, 3 H), 6.17 (s, 1 H), 6.74 (dd, J=11.6, 2.5 Hz, 1 H), 6.84 (dd, J=8.4, 2.5 Hz, 1 H), 7.41 (t, J=8.4 Hz, 1 H).

EXAMPLE 24(77)

5-(1-ethylpropyl)-2-(6-methoxy-2-methyl-3-pyridinyl)-3,7-dimethylpyrrolo[2,1-f][1,2,4]triazin-4(3H)-one TLC: Rf 0.53 (n-hexane/ethyl acetate=3/1);
$^1$H-NMR (CDCl$_3$): δ 0.87 (t, J=7.23 Hz, 6 H), 1.49-1.84 (m, 4 H), 2.39 (s, 3 H), 2.45 (s, 3 H), 3.18 (s, 3 H), 3.31-3.48 (m, 1 H), 3.98 (s, 3 H), 6.18 (s, 1 H), 6.70 (dd, J=8.42, 0.55 Hz, 1 H), 7.52 (d, J=8.42 Hz, 1 H).

EXAMPLE 24(78)

5-(1-ethylpropyl)-2-(6-methoxy-4-methyl-3-pyridinyl)-3,7-dimethylpyrrolo[2,1-f][1,2,4]triazin-4(3H)-one TLC: Rf 0.60 (n-hexane/ethyl acetate=3/1);
$^1$H-NMR (CDCl$_3$): δ 0.87 (t, J=7.41 Hz, 6 H), 1.50-1.84 (m, 4 H), 2.28 (d, J=0.55 Hz, 3 H), 2.39 (d, J=0.73 Hz, 3 H), 3.18 (s, 3 H), 3.30-3.48 (m, 1 H), 3.98 (s, 3 H), 6.19 (s, 1 H), 6.68-6.74 (m, 1 H), 8.16 (s, 1 H).

EXAMPLE 24(79)

2-[2-chloro-4-(trifluoromethyl)phenyl]-5-(1-ethylpropyl)-3,7-dimethylpyrrolo[2,1-f][1,2,4]triazin-4(3H)-one TLC: Rf 0.60 (n-hexane/ethyl acetate=1/1);
$^1$H-NMR (CDCl$_3$): δ 0.76-0.97 (m, 6 H), 1.49-1.83 (m, 4 H), 2.39 (s, 3 H), 3.21 (s, 3 H), 3.32-3.48 (m, 1 H), 6.20 (s, 1 H), 7.58-7.76 (m, 2 H), 7.81 (s, 1 H).

EXAMPLE 24(80)

2-(4,5-difluoro-2-methoxyphenyl)-5-(1-ethylpropyl)-3,7-dimethylpyrrolo[2,1-f][1,2,4]triazin-4(3H)-one TLC: Rf 0.28 (ethyl acetate/n-hexane=1/6);
$^1$H-NMR (CDCl$_3$): δ 0.85 (t, J=7.4 Hz, 6 H), 1.47-1.82 (m, 4 H), 2.40 (s, 3 H), 3.29 (d, J=1.6 Hz, 3 H), 3.32-3.46 (m, 1 H), 3.95 (s, 3 H), 6.18 (s, 1 H), 6.82 (dd, J=10.6, 7.0 Hz, 1 H), 7.19-7.29 (m, 1 H).

EXAMPLE 24(81)

5-(1-ethylpropyl)-3,7-dimethyl-2-(2,4,5-trifluorophenyl)pyrrolo[2,1-f][1,2,4]triazin-4(3H)-one TLC: Rf 0.47 (ethyl acetate/n-hexane=1/6);
$^1$H-NMR (CDCl$_3$): δ 0.85 (t, J=7.3 Hz, 6 H), 1.50-1.83 (m, 4 H), 2.39 (d, J=0.7 Hz, 3 H), 3.28 (d, J=1.6 Hz, 3 H), 3.32-3.45 (m, 1 H), 6.19 (s, 1 H), 7.05-7.17 (m, 1 H), 7.39 (ddd, J=9.5, 8.4, 6.4 Hz, 1 H).

EXAMPLE 24(82)

2-[6-(difluoromethoxy)-2-methyl-3-pyridinyl]-5-(1-ethylpropyl)-3,7-dimethylpyrrolo[2,1-f][1,2,4]triazin-4(3H)-one TLC: Rf 0.50 (n-hexane/ethyl acetate=5/1);
$^1$H-NMR (CDCl$_3$): δ 0.86 (t, J=7.23 Hz, 6 H), 1.47-1.86 (m, 4 H), 2.38 (s, 3 H), 2.48 (s, 3 H), 3.18 (s, 3 H), 3.31-3.49 (m, 1 H), 6.19 (s, 1 H), 6.88 (d, J=8.42 Hz, 1 H), 7.30-7.88 (m, 2 H).

EXAMPLE 24(83)

2-[4-(difluoromethoxy)-5-fluoro-2-methylphenyl]-5-(1-ethylpropyl)-3,7-dimethylpyrrolo[2,1-f][1,2,4]triazin-4(3H)-one TLC: Rf 0.42 (ethyl acetate/n-hexane=1/6);
$^1$H-NMR (CDCl$_3$): δ 0.72-0.97 (m, 6 H), 1.49-1.83 (m, 4 H), 2.29 (s, 3 H), 2.39 (d, J=0.7 Hz, 3 H), 3.16 (s, 3 H), 3.31-3.47 (m, 1 H), 6.19 (s, 1 H), 6.62 (t, J=73.0 Hz, 1 H), 7.15-7.25 (m, 2 H).

EXAMPLE 24(84)

N-{4-[5-(1-ethylpropyl)-3,7-dimethyl-4-oxo-3,4-dihydropyrrolo[2,1-f][1,2,4]triazin-2-yl]-3-methylphenyl}methanesulfonamide TLC: Rf 0.50 (n-hexane/ethyl acetate=1/1);
$^1$H-NMR (CDCl$_3$): δ 0.77-0.95 (m, 6 H), 1.44-1.91 (m, 4 H), 2.32 (s, 3 H), 2.39 (s, 3 H), 3.11 (s, 3 H), 3.15 (s, 3 H), 3.31-3.48 (m, 1 H), 6.19 (s, 1 H), 7.05 (s, 1 H), 7.15-7.24 (m, 2 H), 7.30-7.40 (m, 1 H).

EXAMPLE 24(85)

2-[2-chloro-4-(difluoromethoxy)-5-methylphenyl]-5-(1-ethylpropyl)-3,7-dimethylpyrrolo[2,1-f][1,2,4]triazin-4(3H)-one TLC: Rf 0.35 (n-hexane/ethyl acetate=9/1);
$^1$H-NMR (CDCl$_3$): δ 0.77-0.96 (m, 6 H), 1.47-1.84 (m, 4 H), 2.33 (s, 3 H), 2.40 (s, 3 H), 3.21 (s, 3 H), 3.30-3.47 (m, 1 H), 6.18 (s, 1 H), 6.59 (t, J=72.8 Hz, 1 H), 7.27 (s, 1 H), 7.36 (s, 1 H).

EXAMPLE 24(86)

5-(1-ethylpropyl)-2-(4-isopropyl-2-methylphenyl)-3,7-dimethylpyrrolo[2,1-f][1,2,4]triazin-4(3H)-one TLC: Rf 0.66 (n-hexane/ethyl acetate=5/1);
$^1$H-NMR (CDCl$_3$): δ 0.78-0.95 (m, 6 H), 1.28 (d, J=6.95 Hz, 6 H), 1.51-1.85 (m, 4 H), 2.29 (s, 3 H), 2.39 (s, 3 H), 2.83-3.02 (m, 1 H), 3.14 (s, 3 H), 3.31-3.48 (m, 1 H), 6.17 (s, 1 H), 7.12-7.22 (m, 2 H), 7.22-7.32 (m, 1 H).

EXAMPLE 24(87)

2-[4-(difluoromethoxy)-2-ethylphenyl]-5-(1-ethylpropyl)-3,7-dimethylpyrrolo[2,1-f][1,2,4]triazin-4(3H)-one TLC: Rf 0.52 (ethyl acetate/n-hexane=1/6);
$^1$H-NMR (CDCl$_3$): δ 0.81-0.94 (m, 6 H), 1.24 (t, J=7.5 Hz, 3 H), 1.50-1.83 (m, 4 H), 2.38 (d, J=0.7 Hz, 3 H), 2.55-2.70 (m, 2 H), 3.12 (s, 3 H), 3.31-3.45 (m, 1 H), 6.17 (s, 1 H), 6.57 (t, J=73.3 Hz, 1 H), 7.05-7.11 (m, 1 H), 7.13 (d, J=2.0 Hz, 1 H), 7.32 (d, J=8.2 Hz, 1H).

EXAMPLE 24(88)

4-[5-(1-ethylpropyl)-3,7-dimethyl-4-oxo-3,4-dihydropyrrolo[2,1-f][1,2,4]triazin-2-yl]-3-methylbenzenesulfonamide TLC: Rf 0.66 (n-hexane/ethyl acetate=1/2);
$^1$H-NMR (CDCl$_3$): δ 0.74-0.99 (m, 6 H), 1.46-1.84 (m, 4 H), 2.38 (d, J=0.73 Hz, 3 H), 2.41 (s, 3 H), 3.13 (s, 3 H), 3.30-3.48 (m, 1 H), 4.88 (s, 2 H), 6.20 (s, 1 H), 7.53 (d, J=8.05 Hz, 1 H), 7.85-7.99 (m, 2 H).

EXAMPLE 24(89)

2-[2-chloro-5-(difluoromethoxy)-3-methylphenyl]-5-(1-ethylpropyl)-3,7-dimethylpyrrolo[2,1-f][1,2,4]triazin-4(3H)-one TLC: Rf 0.55 (ethyl acetate/n-hexane=1/6);
$^1$H-NMR (CDCl$_3$): δ 0.77-0.97 (m, 6 H), 1.50-1.84 (m, 4 H), 2.39 (s, 3 H), 2.47 (s, 3 H), 3.20 (s, 3 H), 3.33-3.47 (m, 1 H), 6.19 (s, 1 H), 6.54 (t, J=72.9 Hz, 1 H), 7.12 (d, J=2.4 Hz, 1 H), 7.20 (d, J=2.4 Hz, 1 H).

EXAMPLE 24(90)

4-[5-(1-ethylpropyl)-3,7-dimethyl-4-oxo-3,4-dihydropyrrolo[2,1-f][1,2,4]triazin-2-yl]-N,3-dimethylbenzenesulfonamide TLC: Rf 0.22 (n-hexane/ethyl acetate=2/1);
$^1$H-NMR (CDCl$_3$): δ 0.74-0.98 (m, 6 H), 1.48-1.87 (m, 4 H), 2.39 (d, J=0.73 Hz, 3 H), 2.41 (s, 3 H), 2.76 (d, J=5.24 Hz, 3 H), 3.13 (s, 3 H), 3.30-3.49 (m, 1 H), 4.38 (q, J=5.24 Hz, 1 H), 6.20 (s, 1 H), 7.53 (d, J=7.68 Hz, 1 H), 7.76-7.92 (m, 2 H).

EXAMPLE 24(91)

4-[5-(1-ethylpropyl)-3,7-dimethyl-4-oxo-3,4-dihydropyrrolo[2,1-f][1,2,4]triazin-2-yl]-N,N,3-trimethylbenzenesulfonamide TLC: Rf 0.56 (n-hexane/ethyl acetate=2/1);
$^1$H-NMR (CDCl$_3$): δ 0.77-0.99 (m, 6 H), 1.50-1.86 (m, 4 H), 2.40 (d, J=0.55 Hz, 3 H), 2.42 (s, 3 H), 2.80 (s, 6 H), 3.12 (s, 3 H), 3.31-3.48 (m, 1 H), 6.20 (s, 1 H), 7.51-7.58 (m, 1 H), 7.70-7.81 (m, 2 H).

EXAMPLE 24(92)

2-(5-chloro-2-methoxy-4-methylphenyl)-5-(1-ethylpropyl)-3,7-dimethylpyrrolo[2,1-f][1,2,4]triazin-4(3H)-one TLC: Rf 0.50 (n-hexane/ethyl acetate=3/1);
$^1$H-NMR (CDCl$_3$): δ 0.82-0.89 (m, 6 H), 1.54-1.79 (m, 4 H), 2.40 (s, 3 H), 2.44 (s, 3 H), 3.21 (s, 3 H), 3.34-3.44 (m, 1 H), 3.84 (s, 3 H), 6.15 (s, 1 H), 6.86 (s, 1 H), 7.39 (s, 1 H).

EXAMPLE 24(93)

3-chloro-4-[5-(1-ethylpropyl)-3,7-dimethyl-4-oxo-3,4-dihydropyrrolo[2,1-f][1,2,4]triazin-2-yl]benzonitrile TLC: Rf 0.56 (n-hexane/ethyl acetate=3/1);
$^1$H-NMR (CDCl$_3$): δ 0.82-0.90 (m, 6 H), 1.56-1.77 (m, 4 H), 2.38 (s, 3 H), 3.19 (s, 3 H), 3.33-3.43 (m, 1 H), 6.20 (s, 1 H), 7.62 (d, J=7.9 Hz, 1 H), 7.73 (dd, J=7.9, 1.5 Hz, 1 H), 7.83 (d, J=1.5 Hz, 1 H).

EXAMPLE 24(94)

2-[4-(difluoromethoxy)-2,5-dimethylphenyl]-5-(1-ethylpropyl)-3,7-dimethylpyrrolo[2,1-f][1,2,4]triazin-4(3H)-one TLC: Rf 0.57 (ethyl acetate/n-hexane=1/6);
$^1$H-NMR (CDCl$_3$): δ 0.78-0.96 (m, 6 H), 1.47-1.85 (m, 4 H), 2.28 (s, 3 H), 2.30 (s, 3 H), 2.39 (s, 3 H), 3.14 (s, 3 H), 3.29-3.49 (m, 1 H), 6.17 (s, 1 H), 6.54 (t, J=73.6 Hz, 1 H), 7.02 (s, 1 H), 7.21 (s, 1 H).

EXAMPLE 24(95)

5-chloro-2-[5-(1-ethylpropyl)-3,7-dimethyl-4-oxo-3,4-dihydropyrrolo[2,1-f][1,2,4]triazin-2-yl]benzonitrile TLC: Rf 0.50 (n-hexane/ethyl acetate=3/1);

$^1$H-NMR (CDCl$_3$): δ 0.85 (t, J=7.4 Hz, 6 H), 1.54-1.79 (m, 4 H), 2.39 (d, J=0.7 Hz, 3 H), 3.26 (s, 3 H), 3.32-3.42 (m, 1 H), 6.19-6.19 (m, 1 H), 7.54 (d, J=8.3 Hz, 1 H), 7.72 (dd, J=8.3, 2.1 Hz, 1 H), 7.82 (d, J=2.1 Hz, 1 H).

EXAMPLE 24(96)

2-[5-(1-ethylpropyl)-3,7-dimethyl-4-oxo-3,4-dihydropyrrolo[2,1-f][1,2,4]triazin-2-yl]-5-methylbenzonitrile TLC: Rf 0.43 (n-hexane/ethyl acetate=3/1);

$^1$H-NMR (CDCl$_3$): δ 0.86 (t, J=7.4 Hz, 6 H), 1.57-1.77 (m, 4 H), 2.40 (s, 3 H), 2.49 (s, 3 H), 3.24 (s, 3 H), 3.33-3.42 (m, 1 H), 6.18 (s, 1 H), 7.46 (d, J=8.1 Hz, 1 H), 7.52-7.56 (m, 1 H), 7.63-7.64 (m, 1 H).

EXAMPLE 24(97)

2-(2-chloro-4-isopropylphenyl)-5-(1-ethylpropyl)-3,7-dimethylpyrrolo[2,1-f][1,2,4]triazin-4(3H)-one TLC: Rf 0.47 (n-hexane/ethyl acetate=7/1);

$^1$H-NMR (CDCl$_3$): δ 0.81-0.93 (m, 6 H), 1.29 (d, J=7.0 Hz, 6 H), 1.49-1.84 (m, 4 H), 2.40 (s, 3 H), 2.86-3.08 (m, 1 H), 3.21 (s, 3 H), 3.31-3.50 (m, 1 H), 6.18 (s, 1 H), 7.25-7.30 (m, 1 H), 7.36 (d, J=1.5 Hz, 1 H), 7.39 (d, J=7.9 Hz, 1 H).

EXAMPLE 24(98)

2-[4-(difluoromethoxy)-2-fluorophenyl]-5-(1-ethylpropyl)-3,7-dimethylpyrrolo[2,1-f][1,2,4]triazin-4(3H)-one TLC: Rf 0.56 (ethyl acetate/n-hexane=1/6);

$^1$H-NMR (CDCl$_3$): δ 0.85 (t, J=7.4 Hz, 6 H), 1.48-1.81 (m, 4 H), 2.39 (d, J=0.7 Hz, 3 H), 3.27 (d, J=1.5 Hz, 3 H), 3.31-3.46 (m, 1 H), 6.17 (s, 1 H), 6.59 (t, J=72.4 Hz, 1 H), 7.02 (dd, J=10.2, 2.2 Hz, 1 H), 7.05-7.12 (m, 1 H), 7.52 (t, J=8.1 Hz, 1 H).

EXAMPLE 24(99)

2-(2,6-difluoro-4-methoxyphenyl)-5-(1-ethylpropyl)-3,7-dimethylpyrrolo[2,1-f][1,2,4]triazin-4(3H)-one TLC: Rf 0.44 (ethyl acetate/n-hexane=1/6);

$^1$H-NMR (CDCl$_3$): δ 0.86 (t, J=7.4 Hz, 6 H), 1.46-1.88 (m, 4 H), 2.39 (d, J=0.7 Hz, 3 H), 3.26 (s, 3 H), 3.31-3.49 (m, 1 H), 3.86 (s, 3 H), 6.18 (s, 1 H), 6.52-6.70 (m, 2 H).

EXAMPLE 24(100)

2-[2-chloro-4-(dimethylamino)-5-fluorophenyl]-5-(1-ethylpropyl)-3,7-dimethylpyrrolo[2,1-f][1,2,4]triazin-4(3H)-one TLC: Rf 0.45 (n-hexane/ethyl acetate=3/1);

$^1$H-NMR (CDCl$_3$): δ 0.78-0.94 (m, 6 H), 1.49-1.80 (m, 4 H), 2.39 (s, 3 H), 2.96 (d, J=1.3 Hz, 6 H), 3.24 (s, 3 H), 3.32-3.46 (m, 1 H), 6.17 (s, 1 H), 6.88 (d, J=8.1 Hz, 1 H), 7.10 (d, J=13.0 Hz, 1 H).

EXAMPLE 24(101)

2-[2-chloro-4-(difluoromethoxy)-6-methylphenyl]-5-(1-ethylpropyl)-3,7-dimethylpyrrolo[2,1-f][1,2,4]triazin-4(3H)-one TLC: Rf 0.41 (ethyl acetate/n-hexane=1/6);

$^1$H-NMR (CDCl$_3$): δ 0.88 (t, J=7.4 Hz, 6 H), 1.49-1.90 (m, 4 H), 2.31 (s, 3 H), 2.35-2.43 (m, 3 H), 3.16 (s, 3 H), 3.29-3.48 (m, 1 H), 6.19 (s, 1 H), 6.27-6.86 (t, J=72.7 Hz, 1 H), 6.98-7.11 (m, 1 H), 7.16 (d, J=1.8 Hz, 1 H).

EXAMPLES 25(1)~(50)

By the same procedure as a series of reactions of Example 3→Example 4→Example 5→Example 8, using the compound provided by using methylmagnesium bromide instead of ethylmagnesium bromide instead of the compound prepared in Example 2, and using the corresponding aldehydes instead of the compound prepared in Example 7, the compounds of the present invention having the following physical data were obtained.

EXAMPLE 25(1)

2-(2-chloro-4-methoxyphenyl)-5-isopropyl-3,7-dimethylpyrrolo[2,1-f][1,2,4]triazin-4(3H)-one

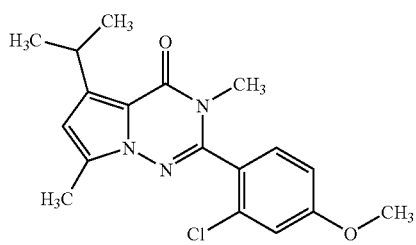 [SMILES: COc1ccc(-c2nn3c(C)cc(C(C)C)c3c(=O)n2C)c(Cl)c1]

TLC: Rf 0.57 (n-hexane/ethyl acetate=2/1);

$^1$H-NMR (CDCl$_3$): δ 1.26-1.40 (m, 6 H), 2.37-2.41 (m, 3 H), 3.21 (s, 3 H), 3.76 (m, 1 H), 3.87 (s, 3 H), 6.25 (s, 1 H), 6.94 (dd, J=8.4, 2.6 Hz, 1 H), 7.04 (d, J=2.6 Hz, 1 H), 7.36 (d, J=8.4 Hz, 1 H).

EXAMPLE 25(2)

5-isopropyl-3,7-dimethyl-2-[2-methyl-4-(trifluoromethoxy)phenyl]pyrrolo[2,1-f][1,2,4]triazin-4(3H)-one TLC: Rf 0.58 (n-hexane/ethyl acetate=4/1);
$^1$H-NMR (CDCl$_3$): δ 1.31 (d, J=7.0 Hz, 6 H), 2.33 (s, 3 H), 2.39 (s, 3 H), 3.14 (s, 3 H), 3.68-3.82 (m, 1 H), 6.26 (s, 1 H), 7.13-7.24 (m, 2 H), 7.32-7.41 (m, 1 H).

EXAMPLE 25(3)

2-[4-chloro-2-(dimethylamino)-1,3-thiazol-5-yl]-5-isopropyl-3,7-dimethylpyrrolo[2,1-f][1,2,4]triazin-4(3H)-one TLC: Rf 0.15 (n-hexane/ethyl acetate=4/1);
$^1$H-NMR (CDCl$_3$): δ 1.28 (d, J=6.8 Hz, 6 H), 2.29-2.50 (m, 3 H), 3.15 (s, 6 H), 3.43 (s, 3 H), 3.65-3.84 (m, 1 H), 6.25 (s, 1 H).

EXAMPLE 25(4)

2-(2-chloro-4-ethoxyphenyl)-5-isopropyl-3,7-dimethylpyrrolo[2,1-f][1,2,4]triazin-4(3H)-one TLC: Rf 0.48 (n-hexane/ethyl acetate=4/1);
$^1$H-NMR (CDCl$_3$): δ 1.24-1.37 (m, 6 H), 1.45 (t, J=7.0 Hz, 3 H), 2.39 (s, 3 H), 3.20 (s, 3 H), 3.65-3.86 (m, 1 H), 4.08 (q, J=7.0 Hz, 2 H), 6.24 (s, 1 H), 6.91 (dd, J=8.4, 2.4 Hz, 1 H), 7.01 (d, J=2.4 Hz, 1 H), 7.32 (d, J=8.4 Hz, 1 H).

EXAMPLE 25(5)

5-isopropyl-2-(2-isopropyl-4-methoxyphenyl)-3,7-dimethylpyrrolo[2,1-f][1,2,4]triazin-4(3H)-one TLC: Rf 0.48 (n-hexane/ethyl acetate=4/1);
$^1$H-NMR (CDCl$_3$): δ 1.15-1.27 (m, 6 H), 1.28-1.37 (m, 6 H), 2.37 (s, 3 H), 2.67-2.93 (m, 1 H), 3.14 (s, 3 H), 3.68-3.81 (m, 1 H), 3.86 (s, 3 H), 6.24 (s, 1 H), 6.83 (dd, J=8.4, 2.6 Hz, 1 H), 6.94 (d, J=2.6 Hz, 1 H), 7.18 (d, J=8.4 Hz, 1 H).

EXAMPLE 25(6)

2-[2-chloro-4-(methylthio)phenyl]-5-isopropyl-3,7-dimethylpyrrolo[2,1-f][1,2,4]triazin-4(3H)-one TLC: Rf 0.40 (n-hexane/ethyl acetate=4/1);
$^1$H-NMR (CDCl$_3$): δ 1.17-1.36 (m, 6 H), 2.39 (s, 3 H), 2.54 (s, 3 H), 3.21 (s, 3 H), 3.75 (m, 1 H), 6.26 (s, 1 H), 7.19-7.30 (m, 1 H), 7.31-7.39 (m, 2 H).

EXAMPLE 25(7)

2-(2-chloro-4-methoxy-5-methylphenyl)-5-isopropyl-3,7-dimethylpyrrolo[2,1-f][1,2,4]triazin-4(3H)-one TLC: Rf 0.45 (ethyl acetate/n-hexane=1/6);
$^1$H-NMR (CDCl$_3$): δ 1.30 (dd, J=6.8, 3.1 Hz, 6 H), 2.23 (s, 3 H), 2.39 (s, 3 H), 3.21 (s, 3H), 3.68-3.83 (m, 1 H), 3.89 (s, 3 H), 6.25 (s, 1 H), 6.92 (s, 1 H), 7.18 (s, 1 H).

EXAMPLE 25(8)

5-isopropyl-2-[4-methoxy-2-(trifluoromethyl)phenyl]-3,7-dimethylpyrrolo[2,1-f][1,2,4]triazin-4(3H)-one TLC: Rf 0.36 (ethyl acetate/n-hexane=1/3);
$^1$H-NMR (CDCl$_3$): δ 1.26-1.34 (m, 6 H), 2.36 (s, 3 H), 3.13 (s, 3 H), 3.65-3.83 (m, 1 H), 3.92 (s, 3 H), 6.25 (s, 1 H), 7.18 (dd, J=8.4, 2.5 Hz, 1 H), 7.30 (d, J=2.5 Hz, 1 H), 7.39 (d, J=8.4 Hz, 1 H).

EXAMPLE 25(9)

2-(4-chloro-2-methoxyphenyl)-5-isopropyl-3,7-dimethylpyrrolo[2,1-f][1,2,4]triazin-4(3H)-one TLC: Rf 0.35 (ethyl acetate/n-hexane=1/6);
$^1$H-NMR (CDCl$_3$): δ 1.25-1.34 (m, 6 H), 2.38 (d, J=0.7 Hz, 3 H), 3.19 (s, 3 H), 3.68-3.81 (m, 1 H), 3.85 (s, 3 H), 6.23 (s, 1 H), 7.00 (d, J=1.8 Hz, 1 H), 7.08 (dd, J=8.1, 1.8 Hz, 1 H), 7.32 (d, J=8.1 Hz, 1 H).

EXAMPLE 25(10)

2-(2,4-dimethylphenyl)-5-isopropyl-3,7-dimethylpyrrolo[2,1-f][1,2,4]triazin-4(3H)-one TLC: Rf 0.51 (ethyl acetate/n-hexane=1/6);
$^1$H-NMR (CDCl$_3$): δ 1.27-1.37 (m, 6 H), 2.25 (s, 3 H), 2.39 (s, 6 H), 3.14 (s, 3 H), 3.67-3.84 (m, 1 H), 6.24 (s, 1 H), 7.09-7.16 (m, 2 H), 7.17-7.22 (m, 1 H).

EXAMPLE 25(11)

2-(4-chloro-2-methylphenyl)-5-isopropyl-3,7-dimethylpyrrolo[2,1-f][1,2,4]triazin-4(3H)-one TLC: Rf 0.35 (n-hexane/ethyl acetate=9/1);
$^1$H-NMR (CDCl$_3$): δ 1.30 (d, J=6.8 Hz, 6 H), 2.29 (s, 3 H), 2.38 (s, 3 H), 3.14 (s, 3 H), 3.62-3.85 (m, 1 H), 6.26 (s, 1 H), 7.23-7.28 (m, 1 H), 7.30-7.32 (m, 1 H), 7.32-7.36 (m, 1H).

EXAMPLE 25(12)

5-isopropyl-2-(4-methoxy-2,6-dimethylphenyl)-3,7-dimethylpyrrolo[2,1-f][1,2,4]triazin-4(3H)-one TLC: Rf 0.25 (n-hexane/ethyl acetate=9/1);
$^1$H-NMR (CDCl$_3$): δ 1.31 (d, J=7.0 Hz, 6 H), 2.20 (s, 6 H), 2.39 (s, 3 H), 3.10 (s, 3 H), 3.70-3.80 (m, 1 H), 3.83 (s, 3 H), 6.25 (s, 1 H), 6.69 (s, 2 H).

EXAMPLE 25(13)

2-(2-chloro-4-methoxy-6-methylphenyl)-5-isopropyl-3,7-dimethylpyrrolo[2,1-f][1,2,4]triazin-4(3H)-one TLC: Rf 0.53 (n-hexane/ethyl acetate=3/1);
$^1$H-NMR (CDCl$_3$): δ 1.31 (d, J=7.0 Hz, 6 H), 2.25 (s, 3 H), 2.32-2.47 (m, 3 H), 3.16 (s, 3H), 3.66-3.82 (m, 1 H), 3.84 (s, 3 H), 6.26 (s, 1 H), 6.73-6.82 (m, 1 H), 6.85-6.95 (m, 1H).

EXAMPLE 25(14)

2-[2-chloro-4-(difluoromethoxy)phenyl]-5-isopropyl-3,7-dimethylpyrrolo[2,1-f][1,2,4]triazin-4(3H)-one TLC: Rf 0.27 (n-hexane/ethyl acetate=9/1);
$^1$H-NMR (CDCl$_3$): δ 1.20-1.44 (m, 6 H), 2.27-2.53 (m, 3 H), 3.21 (s, 3 H), 3.66-3.82 (m, 1 H), 6.26 (s, 1 H), 6.59 (t, J=72.5 Hz, 1 H), 7.20 (dd, J=8.6, 2.4 Hz, 1 H), 7.32 (d, J=2.4 Hz, 1 H), 7.47 (d, J=8.6 Hz, 1 H).

EXAMPLE 25(15)

2-(2-ethyl-4-methoxyphenyl)-5-isopropyl-3,7-dimethylpyrrolo[2,1-f][1,2,4]triazin-4(3H)-one TLC: Rf 0.25 (n-hexane/ethyl acetate=9/1);
$^1$H-NMR (CDCl$_3$): δ 1.22 (t, J=7.6 Hz, 3 H), 1.28-1.36 (m, 6 H), 2.39 (s, 3 H), 2.45-2.72 (m, 2 H), 3.14 (s, 3 H), 3.66-3.83 (m, 1 H), 3.86 (s, 3 H), 6.25 (s, 1 H), 6.85 (dd, J=8.4, 2.4 Hz, 1 H), 6.89 (d, J=2.4 Hz, 1 H), 7.21 (d, J=8.4 Hz, 1 H).

EXAMPLE 25(16)

2-(5-fluoro-4-methoxy-2-methylphenyl)-5-isopropyl-3,7-dimethylpyrrolo[2,1-f][1,2,4]triazin-4(3H)-one TLC: Rf 0.16 (n-hexane/ethyl acetate=9/1);
$^1$H-NMR (CDCl$_3$): δ 1.30 (d, J=7.0 Hz, 6 H), 2.26 (s, 3 H), 2.39 (s, 3 H), 3.16 (s, 3 H), 3.62-3.84 (m, 1 H), 3.94 (s, 3 H), 6.25 (s, 1 H), 6.89 (d, J=8.2 Hz, 1 H), 7.06 (d, J=11.0 Hz, 1 H).

EXAMPLE 25(17)

2-[4-(difluoromethoxy)-2,6-dimethylphenyl]-5-isopropyl-3,7-dimethylpyrrolo[2,1-f][1,2,4]triazin-4(3H)-one TLC: Rf 0.53 (ethyl acetate/n-hexane=1/6);
$^1$H-NMR (CDCl$_3$): δ 1.31 (d, J=6.8 Hz, 6 H), 2.23 (s, 6 H), 2.38 (s, 3 H), 3.10 (s, 3 H), 3.66-3.84 (m, 1 H), 6.25 (s, 1 H), 6.54 (t, J=73.5 Hz, 1 H), 6.91 (s, 2 H).

EXAMPLE 25(18)

5-isopropyl-2-(4-methoxy-2,5-dimethylphenyl)-3,7-dimethylpyrrolo[2,1-f][1,2,4]triazin-4(3H)-one TLC: Rf 0.51 (ethyl acetate/n-hexane=1/6);
$^1$H-NMR (CDCl$_3$): δ 1.31 (d, J=6.8 Hz, 6 H), 2.22 (s, 3 H), 2.25 (s, 3 H), 2.39 (s, 3 H), 3.15 (s, 3 H), 3.67-3.83 (m, 1 H), 3.87 (s, 3 H), 6.24 (s, 1 H), 6.74 (s, 1 H), 7.06 (s, 1 H).

EXAMPLE 25(19)

2-[4-(difluoromethoxy)-2-methylphenyl]-5-isopropyl-3,7-dimethylpyrrolo[2,1-f][1,2,4]triazin-4(3H)-one TLC: Rf 0.56 (n-hexane/ethyl acetate=3/1);
$^1$H-NMR (CDCl$_3$): δ 1.31 (d, J=6.95 Hz, 6 H), 2.31 (s, 3 H), 2.39 (s, 3 H), 3.14 (s, 3 H), 3.67-3.83 (m, 1 H), 6.26 (s, 1 H), 6.57 (t, J=73.37 Hz, 1 H), 7.04-7.16 (m, 2 H), 7.29-7.39 (m, 1 H).

EXAMPLE 25(20)

2-(2-chloro-3,5-difluoro-4-methoxyphenyl)-5-isopropyl-3,7-dimethylpyrrolo[2,1-f][1,2,4]triazin-4(3H)-one TLC: Rf 0.46 (ethyl acetate/n-hexane=1/6);
$^1$H-NMR (CDCl$_3$): δ 1.26-1.34 (m, 6 H), 2.38 (s, 3 H), 3.22 (s, 3 H), 3.65-3.84 (m, 1 H), 4.11 (t, J=1.3 Hz, 3 H), 6.27 (s, 1 H), 7.08 (dd, J=10.2, 2.2 Hz, 1 H).

EXAMPLE 25(21)

2-(2-chloro-4-ethoxy-3,5-difluorophenyl)-5-isopropyl-3,7-dimethylpyrrolo[2,1-f][1,2,4]triazin-4(3H)-one TLC: Rf 0.53 (ethyl acetate/n-hexane=1/6);
$^1$H-NMR (CDCl$_3$): δ 1.26-1.33 (m, 6 H), 1.46 (t, J=7.0 Hz, 3 H), 2.39 (s, 3 H), 3.22 (s, 3 H), 3.63-3.85 (m, 1 H), 4.33 (q, J=7.0 Hz, 2 H), 6.27 (s, 1 H), 7.07 (dd, J=10.2, 2.1 Hz, 1H).

EXAMPLE 25(22)

2-[2-chloro-4-(difluoromethoxy)-3,5-difluorophenyl]-5-isopropyl-3,7-dimethylpyrrolo[2,1-f][1,2,4]triazin-4(3H)-one TLC: Rf 0.46 (ethyl acetate/n-hexane=1/6);
$^1$H-NMR (CDCl$_3$): δ 1.24-1.33 (m, 6 H), 2.38 (d, J=0.7 Hz, 3 H), 3.23 (s, 3 H), 3.65-3.81 (m, 1 H), 6.27 (s, 1 H), 6.68 (t, J=72.1 Hz, 1 H), 7.18 (dd, J=9.1, 2.3 Hz, 1 H).

EXAMPLE 25(23)

2-(3-chloro-5-methoxy-2-pyridinyl)-5-isopropyl-3,7-dimethylpyrrolo[2,1-f][1,2,4]triazin-4(3H)-one TLC: Rf 0.69 (n-hexane/ethyl acetate=1/1);
$^1$H-NMR (CDCl$_3$): δ 1.29 (d, J=7.0 Hz, 6 H), 2.39 (s, 3 H), 3.18 (s, 3 H), 3.62-3.86 (m, 1 H), 3.94 (s, 3 H), 6.24 (s, 1 H), 7.35 (d, J=2.6 Hz, 1 H), 8.32 (d, J=2.6 Hz, 1 H).

EXAMPLE 25(24)

2-[4-(dimethylamino)-2-methylphenyl]-5-isopropyl-3,7-dimethylpyrrolo[2,1-f][1,2,4]triazin-4(3H)-one TLC: Rf 0.26 (n-hexane/ethyl acetate=9/1);
$^1$H-NMR (CDCl$_3$): δ 1.30 (d, J=7.0 Hz, 6 H), 2.25 (s, 3 H), 2.39 (s, 3 H), 3.00 (s, 6 H), 3.17 (s, 3 H), 3.66-3.87 (m, 1 H), 6.23 (s, 1 H), 6.55-6.67 (m, 2 H), 7.15 (d, J=8.4 Hz, 1 H).

EXAMPLE 25(25)

5-isopropyl-3,7-dimethyl-2-[2-methyl-4-(1H-pyrazol-1-yl)phenyl]pyrrolo[2,1-f][1,2,4]triazin-4(3H)-one TLC: Rf 0.45 (n-hexane/ethyl acetate=3/1);
$^1$H-NMR (CDCl$_3$): δ 1.31 (d, J=7.0 Hz, 6 H), 2.37 (s, 3 H), 2.40 (d, J=0.6 Hz, 3 H), 3.17 (s, 3 H), 3.70-3.82 (m, 1 H), 6.26 (d, J=0.6 Hz, 1 H), 6.52 (dd, J=2.5, 1.8 Hz, 1 H), 7.41 (d, J=8.2 Hz, 1 H), 7.62-7.67 (m, 1 H), 7.74 (d, J=1.3 Hz, 1 H), 7.77 (dd, J=1.8, 0.6 Hz, 1 H), 7.98 (dd, J=2.5, 0.6 Hz, 1 H).

EXAMPLE 25(26)

2-[2-chloro-4-(difluoromethoxy)-5-fluorophenyl]-5-isopropyl-3,7-dimethylpyrrolo[2,1-f][1,2,4]triazin-4(3H)-one TLC: Rf 0.66 (n-hexane/ethyl acetate=3/1);
$^1$H-NMR (CDCl$_3$): δ 1.27-1.35 (m, 6 H), 2.39 (s, 3 H), 3.23 (s, 3 H), 3.66-3.83 (m, 1 H), 6.27 (s, 1 H), 6.65 (t, J=72.2 Hz, 1 H), 7.33 (d, J=9.5 Hz, 1 H), 7.45 (d, J=7.0 Hz, 1 H).

EXAMPLE 25(27)

2-[6-(dimethylamino)-2-methyl-3-pyridinyl]-5-isopropyl-3,7-dimethylpyrrolo[2,1-f][1,2,4]triazin-4(3H)-one TLC: Rf 0.5 (n-hexane/ethyl acetate=3/1);
$^1$H-NMR (CDCl$_3$): δ 1.30 (d, J=7.0 Hz, 6 H), 2.36 (s, 3 H), 2.39 (s, 3 H), 3.13 (s, 6 H), 3.21 (s, 3 H), 3.68-3.83 (m, 1 H), 6.24 (s, 1 H), 6.43 (d, J=8.8 Hz, 1 H), 7.35 (d, J=8.8 Hz, 1H).

EXAMPLE 25(28)

5-isopropyl-2-(6-methoxy-2-methyl-3-pyridinyl)-3,7-dimethylpyrrolo[2,1-f][1,2,4]triazin-4(3H)-one TLC: Rf 0.35 (n-hexane/ethyl acetate=9/1);
$^1$H-NMR (CDCl$_3$): δ 1.30 (d, J=7.0 Hz, 6 H), 2.39 (s, 3 H), 2.43 (s, 3 H), 3.18 (s, 3 H), 3.66-3.85 (m, 1 H), 3.98 (s, 3 H), 6.26 (s, 1 H), 6.69 (d, J=8.4 Hz, 1 H), 7.50 (d, J=8.4 Hz, 1 H).

EXAMPLE 25(29)

2-(2-fluoro-4-methoxyphenyl)-5-isopropyl-3,7-dimethylpyrrolo[2,1-f][1,2,4]triazin-4(3H)-one TLC: Rf 0.25 (n-hexane/ethyl acetate=9/1);
$^1$H-NMR (CDCl$_3$): δ 1.29 (d, J=7.0 Hz, 6 H), 2.39 (s, 3 H), 3.28 (d, J=1.5 Hz, 3 H), 3.69-3.82 (m, 1 H), 3.87 (s, 3 H), 6.24 (s, 1 H), 6.74 (dd, J=11.5, 2.5 Hz, 1 H), 6.83 (dd, J=8.4, 2.5 Hz, 1 H), 7.39 (t, J=8.4 Hz, 1 H).

EXAMPLE 25(30)

2-(2-chloro-4-isopropoxyphenyl)-5-isopropyl-3,7-dimethylpyrrolo[2,1-f][1,2,4]triazin-4(3H)-one TLC: Rf 0.64 (n-hexane/ethyl acetate=3/1);
$^1$H-NMR (CDCl$_3$): δ 1.22-1.33 (m, 6 H), 1.38 (d, J=6.0 Hz, 6 H), 2.39 (s, 3 H), 3.21 (s, 3 H), 3.68-3.81 (m, 1 H), 4.51-4.65 (m, 1 H), 6.24 (s, 1 H), 6.88 (dd, J=8.4, 2.4 Hz, 1 H), 7.00 (d, J=2.4 Hz, 1 H), 7.31 (d, J=8.4 Hz, 1 H).

EXAMPLE 25(31)

2-(4-fluoro-2-methoxyphenyl)-5-isopropyl-3,7-dimethylpyrrolo[2,1-f][1,2,4]triazin-4(3H)-one TLC: Rf 0.55 (n-hexane/ethyl acetate=3/1);
$^1$H-NMR (CDCl$_3$): δ 1.20-1.34 (m, 6 H), 2.39 (s, 3 H), 3.19 (s, 3 H), 3.68-3.82 (m, 1 H), 3.84 (s, 3 H), 6.23 (s, 1 H), 6.67-6.86 (m, 2 H), 7.36 (dd, J=8.4, 6.6 Hz, 1 H).

EXAMPLE 25(32)

2-[2-chloro-4-(trifluoromethyl)phenyl]-5-isopropyl-3,7-dimethylpyrrolo[2,1-f][1,2,4]triazin-4(3H)-one TLC: Rf 0.59 (n-hexane/ethyl acetate=3/1);
$^1$H-NMR (CDCl$_3$): δ 1.24-1.37 (m, 6 H), 2.38 (s, 3 H), 3.21 (s, 3 H), 3.66-3.83 (m, 1 H), 6.28 (s, 1 H), 7.59-7.65 (m, 1 H), 7.67-7.74 (m, 1 H), 7.80 (s, 1 H).

EXAMPLE 25(33)

2-[4-chloro-2-(trifluoromethoxy)phenyl]-5-isopropyl-3,7-dimethylpyrrolo[2,1-f][1,2,4]triazin-4(3H)-one TLC: Rf 0.45 (n-hexane/ethyl acetate=9/1);
$^1$H-NMR (CDCl$_3$): δ 1.23-1.37 (m, 6 H), 2.30-2.43 (m, 3 H), 3.20 (s, 3 H), 3.68-3.83 (m, 1 H), 6.27 (s, 1 H), 7.40-7.48 (m, 3 H).

EXAMPLE 25(34)

2-[4-chloro-2-(trifluoromethyl)phenyl]-5-isopropyl-3,7-dimethylpyrrolo[2,1-f][1,2,4]triazin-4(3H)-one TLC: Rf 0.35 (n-hexane/ethyl acetate=9/1);
$^1$H-NMR (CDCl$_3$): δ 1.27-1.34 (m, 6 H), 2.30-2.40 (m, 3 H), 3.13 (s, 3 H), 3.67-3.82 (m, 1 H), 6.26 (s, 1 H), 7.44 (d, J=8.2 Hz, 1 H), 7.69 (dd, J=8.2, 2.0 Hz, 1 H), 7.83 (d, J=2.0 Hz, 1 H).

EXAMPLE 25(35)

2-(4,5-difluoro-2-methoxyphenyl)-5-isopropyl-3,7-dimethylpyrrolo[2,1-f][1,2,4]triazin-4(3H)-one TLC: Rf 0.46 (n-hexane/ethyl acetate=3/1);
$^1$H-NMR (CDCl$_3$): δ 1.29 (d, J=6.77 Hz, 6 H), 2.39 (s, 3 H), 3.29 (d, J=1.65 Hz, 3 H), 3.67-3.80 (m, 1 H), 3.95 (s, 3 H), 6.25 (s, 1 H), 6.82 (dd, J=10.5, 6.9 Hz, 1 H), 7.22 (dd, J=10.5, 6.5 Hz, 1 H).

EXAMPLE 25(36)

5-isopropyl-3,7-dimethyl-2-(2,4,5-trifluorophenyl)pyrrolo[2,1-f][1,2,4]triazin-4(3H)-one TLC: Rf 0.56 (n-hexane/ethyl acetate=4/1);
$^1$H-NMR (CDCl$_3$): δ 1.29 (d, J=6.95 Hz, 6 H), 2.39 (d, J=0.73 Hz, 3 H), 3.28 (d, J=1.65 Hz, 3 H), 3.67-3.80 (m, 1 H), 6.22-6.29 (m, 1 H), 7.04-7.16 (m, 1 H), 7.31-7.42 (m, 1 H).

EXAMPLE 25(37)

2-(2,4-dichlorophenyl)-5-isopropyl-3,7-dimethylpyrrolo[2,1-f][1,2,4]triazin-4(3H)-one TLC: Rf 0.42 (n-hexane/ethyl acetate=9/1);
$^1$H-NMR (CDCl$_3$): δ 1.27-1.36 (m, 6 H), 2.38 (s, 3 H), 3.20 (s, 3 H), 3.64-3.84 (m, 1 H), 6.26 (s, 1 H), 7.35-7.49 (m, 2 H), 7.48-7.60 (m, 1 H).

EXAMPLE 25(38)

2-(2-chloro-5-fluoro-4-methoxyphenyl)-5-isopropyl-3,7-dimethylpyrrolo[2,1-f][1,2,4]triazin-4(3H)-one TLC: Rf 0.27 (n-hexane/ethyl acetate=9/1);
$^1$H-NMR (CDCl$_3$): δ 1.17-1.37 (m, 6 H), 2.26-2.49 (m, 3 H), 3.23 (s, 3 H), 3.63-3.88 (m, 1 H), 3.96 (s, 3 H), 6.26 (s, 1 H), 7.08 (d, J=7.5 Hz, 1 H), 7.19 (d, J=10.4 Hz, 1 H).

EXAMPLE 25(39)

2-[2-chloro-4-(dimethylamino)-5-fluorophenyl]-5-isopropyl-3,7-dimethylpyrrolo[2,1-f][1,2,4]triazin-4(3H)-one TLC: Rf 0.38 (n-hexane/ethyl acetate=5/1);
$^1$H-NMR (CDCl$_3$): δ 1.26-1.32 (m, 6 H), 2.39 (s, 3 H), 2.95 (d, J=1.3 Hz, 6 H), 3.24 (s, 3 H), 3.66-3.82 (m, 1 H), 6.24 (s, 1 H), 6.87 (d, J=8.1 Hz, 1 H), 7.06 (d, J=12.8 Hz, 1 H).

EXAMPLE 25(40)

2-(2-chloro-4-isopropylphenyl)-5-isopropyl-3,7-dimethylpyrrolo[2,1-f][1,2,4]triazin-4(3H)-one TLC: Rf 0.48 (n-hexane/ethyl acetate=5/1);
$^1$H-NMR (CDCl$_3$): δ 1.25-1.33 (m, 12 H), 2.39 (s, 3 H), 2.89-3.03 (m, 1 H), 3.20 (s, 3 H), 3.69-3.81 (m, 1 H), 6.24 (s, 1 H), 7.22-7.28 (m, 1 H), 7.32-7.38 (m, 2 H).

EXAMPLE 25(41)

2-[2-chloro-4-(difluoromethoxy)-5-methylphenyl]-5-isopropyl-3,7-dimethylpyrrolo[2,1-f][1,2,4]triazin-4(3H)-one TLC: Rf 0.50 (n-hexane/ethyl acetate=4/1);
$^1$H-NMR (CDCl$_3$): δ 1.30 (dd, J=6.9, 3.2 Hz, 6 H), 2.32 (s, 3 H), 2.37-2.41 (m, 3 H), 3.21 (s, 3 H), 3.67-3.82 (m, 1 H), 6.23-6.26 (m, 1 H), 6.57 (t, J=72.6 Hz, 1 H), 7.25-7.27 (m, 1 H), 7.30-7.34 (m, 1 H).

EXAMPLE 25(42)

2-[4-(difluoromethoxy)-2-ethylphenyl]-5-isopropyl-3,7-dimethylpyrrolo[2,1-f][1,2,4]triazin-4(3H)-one TLC: Rf 0.29 (n-hexane/ethyl acetate=9/1);
$^1$H-NMR (CDCl$_3$): δ 1.23 (t, J=7.6 Hz, 3 H), 1.28-1.37 (m, 6 H), 2.38 (s, 3 H), 2.49-2.72 (m, 2 H), 3.13 (s, 3 H), 3.66-3.84 (m, 1 H), 6.26 (s, 1 H), 6.58 (t, J=73.4 Hz, 1 H), 7.05-7.12 (m, 1 H), 7.11-7.15 (m, 1 H), 7.31 (d, J=8.4 Hz, 1 H).

EXAMPLE 25(43)

2-[6-(difluoromethoxy)-2-methyl-3-pyridinyl]-5-isopropyl-3,7-dimethylpyrrolo[2,1-f][1,2,4]triazin-4(3H)-one TLC: Rf 0.27 (n-hexane/ethyl acetate=9/1);
$^1$H-NMR (CDCl$_3$): δ 1.30 (d, J=6.8 Hz, 6 H), 2.38 (s, 3 H), 2.46 (s, 3 H), 3.18 (s, 3 H), 3.59-3.88 (m, 1 H), 6.27 (s, 1 H), 6.88 (d, J=8.4 Hz, 1 H), 7.29-7.89 (m, 2 H).

EXAMPLE 25(44)

2-[4-chloro-2-(difluoromethoxy)phenyl]-5-isopropyl-3,7-dimethylpyrrolo[2,1-f][1,2,4]triazin-4(3H)-one TLC: Rf 0.38 (n-hexane/ethyl acetate=9/1);
$^1$H-NMR (CDCl$_3$): δ 1.27-1.36 (m, 6 H), 2.39 (s, 3 H), 3.21 (s, 3 H), 3.67-3.85 (m, 1 H), 6.27 (s, 1 H), 6.59 (t, J=72.5 Hz, 1 H), 7.21 (dd, J=8.6, 2.0 Hz, 1 H), 7.32 (d, J=2.0 Hz, 1 H), 7.47 (d, J=8.6 Hz, 1 H).

EXAMPLE 25(45)

2-[4-(dimethylamino)-5-fluoro-2-methylphenyl]-5-isopropyl-3,7-dimethylpyrrolo[2,1-f][1,2,4]triazin-4(3H)-one TLC: Rf 0.41 (n-hexane/ethyl acetate=4/1);
$^1$H-NMR (CDCl$_3$): δ 1.30 (d, J=7.0 Hz, 6 H), 2.21 (s, 3 H), 2.39 (s, 3 H), 2.91 (s, 6 H), 3.17 (s, 3 H), 3.68-3.81 (m, 1 H), 6.23 (s, 1 H), 6.73 (d, J=9.0 Hz, 1 H), 6.95 (d, J=13.0 Hz, 1H).

EXAMPLE 25(46)

5-isopropyl-2-[2-methoxy-4-(trifluoromethyl)phenyl]-3,7-dimethylpyrrolo[2,1-f][1,2,4]triazin-4(3H)-one TLC: Rf 0.40 (n-hexane/ethyl acetate=5/1);
$^1$H-NMR (CDCl$_3$): δ 1.30 (dd, J=6.9, 2.8 Hz, 6 H), 2.38 (s, 3 H), 3.19 (s, 3 H), 3.67-3.82 (m, 1 H), 3.91 (s, 3 H), 6.24 (s, 1 H), 7.20 (s, 1 H), 7.36 (dd, J=7.9, 0.7 Hz, 1 H), 7.51 (d, J=7.9 Hz, 1 H).

EXAMPLE 25(47)

5-isopropyl-3,7-dimethyl-2-[4-methyl-2-(methylthio)phenyl]pyrrolo[2,1-f][1,2,4]triazin-4(3H)-one TLC: Rf 0.44 (n-hexane/ethyl acetate=5/1);
$^1$H-NMR (CDCl$_3$): δ 1.30 (d, J=7.0 Hz, 6 H), 2.38 (s, 3 H), 2.42 (s, 3 H), 2.46 (s, 3 H), 3.17 (s, 3 H), 3.67-3.82 (m, 1 H), 6.23 (s, 1 H), 7.04-7.11 (m, 1 H), 7.16 (s, 1 H), 7.17-7.22 (m, 1 H).

EXAMPLE 25(48)

2-[4-(difluoromethoxy)-2-isopropylphenyl]-5-isopropyl-3,7-dimethylpyrrolo[2,1-f][1,2,4]triazin-4(3H)-one TLC: Rf 0.41 (n-hexane/ethyl acetate=4/1);
$^1$H-NMR (CDCl$_3$): δ 1.24 (dd, J=7.9, 7.0 Hz, 6 H), 1.31 (dd, J=7.0, 3.5 Hz, 6 H), 2.37 (s, 3 H), 2.80-2.97 (m, 1 H), 3.14 (s, 3 H), 3.68-3.84 (m, 1 H), 6.26 (s, 1 H), 6.58 (t, J=73.5 Hz, 1 H), 7.08 (dd, J=8.4, 2.6 Hz, 1 H), 7.18 (d, J=2.6 Hz, 1 H), 7.29 (d, J=8.4 Hz, 1 H).

EXAMPLE 25(49)

2-[4-(difluoromethoxy)-2-ethyl-6-methylphenyl]-5-isopropyl-3,7-dimethylpyrrolo[2,1-f][1,2,4]triazin-4(3H)-one TLC: Rf 0.37 (n-hexane/ethyl acetate=5/1);
$^1$H-NMR (CDCl$_3$): δ 1.21 (t, J=7.5 Hz, 3 H), 1.32 (d, J=7.0 Hz, 6 H), 2.23 (s, 3 H), 2.39 (s, 3 H), 2.44-2.58 (m, 2 H), 3.10 (s, 3 H), 3.67-3.84 (m, 1 H), 6.27 (s, 1 H), 6.56 (t, J=73.6 Hz, 1 H), 6.95 (dd, J=10.0, 2.1 Hz, 2 H).

EXAMPLE 25(50)

5-isopropyl-2-[4-isopropyl-2-(methylthio)phenyl]-3,7-dimethylpyrrolo[2,1-f][1,2,4]triazin-4(3H)-one TLC: Rf 0.61 (n-hexane/ethyl acetate=3/1);
$^1$H-NMR (CDCl$_3$): δ 1.30 (dd, J=7.0, 1.8 Hz, 12 H), 2.39 (s, 3 H), 2.48 (s, 3 H), 2.91-3.04 (m, 1 H), 3.18 (s, 3 H), 3.70-3.83 (m, 1 H), 6.24 (s, 1 H), 7.13-7.18 (m, 1 H), 7.20-7.25 (m, 2 H).

EXAMPLES 26(1)~(36)

By the same procedure as a series of reactions of Example 4→Example 5→Example 8, using the compound prepared in Example 18 instead of the compound prepared in Example 3, and using the corresponding aldehydes instead of the compound prepared in Example 7, the compounds of the present invention having the following physical data were obtained.

EXAMPLE 26(1)

5-sec-butyl-3,7-dimethyl-2-[2-methyl-4-(1H-pyrazol-1-yl)phenyl]pyrrolo[2,1-f][1,2,4]triazin-4(3H)-one

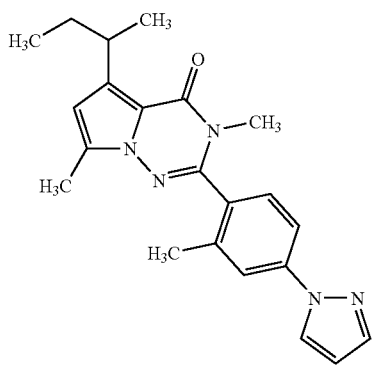 [SMILES: CCC(C)c1cc(C)n2nc(-c3ccc(-n4cccn4)cc3C)n(C)c(=O)c12]

TLC: Rf 0.56 (n-hexane/ethyl acetate=3/1);
$^1$H-NMR (CDCl$_3$): δ 0.86-0.99 (m, 3 H), 1.23-1.32 (m, 3 H), 1.59-1.75 (m, 2 H), 2.38 (s, 3 H), 2.40 (s, 3 H), 3.17 (s, 3 H), 3.51-3.61 (m, 1 H), 6.21-6.25 (m, 1 H), 6.52 (dd, J=2.6, 1.6 Hz, 1 H), 7.43 (d, J=8.6 Hz, 1 H), 7.62-7.68 (m, 1 H), 7.74 (d, J=1.6 Hz, 1 H), 7.77 (d, J=1.8 Hz, 1 H), 7.98 (d, J=2.6 Hz, 1 H).

EXAMPLE 26(2)

5-sec-butyl-2-(2-fluoro-4-methoxyphenyl)-3,7-dimethylpyrrolo[2,1-f][1,2,4]triazin-4(3H)-one TLC: Rf 0.49 (n-hexane/ethyl acetate=3/1);
$^1$H-NMR (CDCl$_3$): δ 0.85-0.98 (m, 3 H), 1.26 (d, J=6.95 Hz, 3 H), 1.59-1.77 (m, 2 H), 2.39 (s, 3 H), 3.28 (s, 3 H), 3.47-3.65 (m, 1 H), 3.87 (s, 3 H), 6.20 (s, 1 H), 6.69-6.79 (m, 1 H), 6.83 (dd, J=9.33, 2.01 Hz, 1 H), 7.34-7.46 (m, 1 H).

EXAMPLE 26(3)

5-sec-butyl-2-[6-(dimethylamino)-2-methyl-3-pyridinyl]-3,7-dimethylpyrrolo[2,1-f][1,2,4]triazin-4(3H)-one TLC: Rf 0.48 (n-hexane/ethyl acetate=3/1);
$^1$H-NMR (CDCl$_3$): δ 0.91 (t, J=7.41 Hz, 3 H), 1.27 (d, J=6.95 Hz, 3 H), 1.57-1.76 (m, 2 H), 2.36 (s, 3 H), 2.38 (s, 3 H), 3.13 (s, 6 H), 3.20 (s, 3 H), 3.47-3.62 (m, 1 H), 6.19 (s, 1 H), 6.41 (d, J=8.50 Hz, 1 H), 7.34 (d, J=8.60 Hz, 1 H).

EXAMPLE 26(4)

5-sec-butyl-2-(4-chloro-2-methylphenyl)-3,7-dimethylpyrrolo[2,1-f][1,2,4]triazin-4(3H)-one TLC: Rf 0.53 (n-hexane/ethyl acetate=9/1);
$^1$H-NMR (CDCl$_3$): δ 0.76-1.11 (m, 3 H), 1.27 (d, J=7.0 Hz, 3 H), 1.55-1.84 (m, 2 H), 2.29 (s, 3 H), 2.38 (s, 3 H), 3.13 (s, 3 H), 3.36-3.68 (m, 1 H), 6.22 (s, 1 H), 7.22-7.39 (m, 3 H).

EXAMPLE 26(5)

5-sec-butyl-2-(2-chloro-5-fluoro-4-methoxyphenyl)-3,7-dimethylpyrrolo[2,1-f][1,2,4]triazin-4(3H)-one TLC: Rf 0.29 (n-hexane/ethyl acetate=9/1);
$^1$H-NMR (CDCl$_3$): δ 0.81-1.00 (m, 3 H), 1.20-1.33 (m, 3 H), 1.58-1.77 (m, 2 H), 2.39 (s, 3 H), 3.22 (s, 3 H), 3.45-3.63 (m, 1 H), 3.96 (s, 3 H), 6.22 (s, 1 H), 7.09 (d, J=7.5 Hz, 1 H), 7.20 (dd, J=10.5, 4.7 Hz, 1 H).

EXAMPLE 26(6)

5-sec-butyl-2-(2-ethyl-4-methoxyphenyl)-3,7-dimethylpyrrolo[2,1-f][1,2,4]triazin-4(3H)-one TLC: Rf 0.53 (n-hexane/ethyl acetate=2/1);
$^1$H-NMR (CDCl$_3$): δ 0.87-0.98 (m, 3 H), 1.18-1.30 (m, 6 H), 1.58-1.79 (m, 2 H), 2.38 (s, 3 H), 2.49-2.67 (m, 2 H), 3.13 (s, 3 H), 3.48-3.64 (m, 1 H), 3.86 (s, 3 H), 6.21 (s, 1 H), 6.85 (dd, J=8.4, 2.4 Hz, 1 H), 6.89 (d, J=2.4 Hz, 1 H), 7.22 (dd, J=8.3, 4.7 Hz, 1 H).

EXAMPLE 26(7)

5-sec-butyl-2-(4-methoxy-2,5-dimethylphenyl)-3,7-dimethylpyrrolo[2,1-f][1,2,4]triazin-4(3H)-one TLC: Rf 0.51 (n-hexane/ethyl acetate=2/1);
$^1$H-NMR (CDCl$_3$): δ 0.86-0.97 (m, 3 H), 1.27 (d, J=7.0 Hz, 3 H), 1.58-1.76 (m, 2 H), 2.21 (s, 3 H), 2.26 (s, 3 H), 2.39 (s, 3 H), 3.15 (s, 3 H), 3.47-3.64 (m, 1 H), 3.87 (s, 3 H), 6.20 (s, 1 H), 6.74 (s, 1 H), 7.07 (d, J=3.7 Hz, 1 H).

EXAMPLE 26(8)

5-sec-butyl-2-(5-fluoro-4-methoxy-2-methylphenyl)-3,7-dimethylpyrrolo[2,1-f][1,2,4]triazin-4(3H)-one TLC: Rf 0.46 (n-hexane/ethyl acetate=3/1);
$^1$H-NMR (CDCl$_3$): δ 0.91 (t, J=7.3 Hz, 3 H), 1.27 (d, J=7.0 Hz, 3 H), 1.58-1.72 (m, 2 H), 2.26 (s, 3 H), 2.38 (s, 3 H), 3.15 (s, 3 H), 3.49-3.58 (m, 1 H), 3.93 (s, 3 H), 6.20 (s, 1 H), 6.87 (d, J=8.2 Hz, 1 H), 7.05 (d, J=11.0 Hz, 1 H).

EXAMPLE 26(9)

5-sec-butyl-2-(2-chloro-4-methoxy-6-methylphenyl)-3,7-dimethylpyrrolo[2,1-f][1,2,4]triazin-4(3H)-one TLC: Rf 0.52 (n-hexane/ethyl acetate=3/1);
$^1$H-NMR (CDCl$_3$): δ 0.93 (t, J=7.4 Hz, 3 H), 1.28 (d, J=7.0 Hz, 3 H), 1.57-1.76 (m, 2 H), 2.24 (s, 1.5H), 2.25 (s, 1.5H), 2.39 (s, 3 H), 3.15 (s, 3 H), 3.49-3.61 (m, 1 H), 3.83 (s, 3 H), 6.21 (s, 1 H), 6.76 (d, J=2.6 Hz, 1 H), 6.88 (d, J=2.6 Hz, 1 H).

EXAMPLE 26(10)

5-sec-butyl-2-[2-chloro-4-(trifluoromethoxy)phenyl]-3,7-dimethylpyrrolo[2,1-f][1,2,4]triazin-4(3H)-one TLC: Rf 0.61 (n-hexane/ethyl acetate=5/1);
$^1$H-NMR (CDCl$_3$): δ 0.86-0.97 (m, 3 H), 1.22-1.33 (m, 3 H), 1.54-1.78 (m, 2 H), 2.39 (d, J=0.74 Hz, 3 H), 3.21 (s, 3 H), 3.46-3.68 (m, 1 H), 6.23 (s, 1 H), 7.28-7.35 (m, 1 H), 7.38-7.44 (m, 1 H), 7.48-7.60 (m, 1 H).

EXAMPLE 26(11)

5-sec-butyl-2-[2-chloro-4-(methylthio)phenyl]-3,7-dimethylpyrrolo[2,1-f][1,2,4]triazin-4(3H)-one TLC: Rf 0.39 (n-hexane/ethyl acetate=5/1);
$^1$H-NMR (CDCl$_3$): δ 0.86-0.97 (m, 3 H), 1.22-1.34 (m, 3 H), 1.52-1.79 (m, 2 H), 2.39 (s, 3 H), 2.53 (s, 3 H), 3.21 (s, 3 H), 3.42-3.65 (m, 1 H), 6.22 (s, 1 H), 7.19-7.29 (m, 1 H), 7.30-7.40 (m, 2 H).

EXAMPLE 26(12)

5-sec-butyl-2-(4-chloro-2-methoxyphenyl)-3,7-dimethylpyrrolo[2,1-f][1,2,4]triazin-4(3H)-one TLC: Rf 0.50 (n-hexane/ethyl acetate=5/1);
$^1$H-NMR (CDCl$_3$): δ 0.83-1.01 (m, 3 H), 1.21-1.32 (m, 3 H), 1.51-1.78 (m, 2 H), 2.39 (s, 3 H), 3.19 (s, 3 H), 3.41-3.70 (m, 1 H), 3.79-3.94 (m, 3 H), 6.20 (s, 1 H), 7.00 (d, J=1.83 Hz, 1 H), 7.09 (dd, J=8.05, 1.83 Hz, 1 H), 7.30-7.42 (m, 1 H).

EXAMPLE 26(13)

5-sec-butyl-2-[2-chloro-4-(difluoromethoxy)-5-fluorophenyl]-3,7-dimethylpyrrolo[2,1-f][1,2,4]triazin-4(3H)-one TLC: Rf 0.43 (n-hexane/ethyl acetate=5/1);
$^1$H-NMR (CDCl$_3$): δ 0.80-1.00 (m, 3 H), 1.18-1.35 (m, 3 H), 1.53-1.78 (m, 2 H), 2.39 (s, 3 H), 3.23 (s, 3 H), 3.42-3.65 (m, 1 H), 6.24 (s, 1 H), 6.64 (t, J=72.18 Hz, 1 H), 7.29-7.38 (m, 1 H), 7.45 (d, J=6.95 Hz, 1 H).

EXAMPLE 26(14)

5-sec-butyl-2-[2-chloro-4-(difluoromethoxy)phenyl]-3,7-dimethylpyrrolo[2,1-f][1,2,4]triazin-4(3H)-one TLC: Rf 0.60 (n-hexane/ethyl acetate=3/1);
$^1$H-NMR (CDCl$_3$): δ 0.92 (q, J=7.26 Hz, 3 H), 1.27 (dd, J=6.86, 3.20 Hz, 3 H), 1.58-1.75 (m, 2 H), 2.39 (s, 3 H), 3.21 (s, 3 H), 3.47-3.63 (m, 1 H), 6.23 (s, 1 H), 6.59 (t, J=72.55 Hz, 1 H), 7.21 (dd, J=8.42, 2.38 Hz, 1 H), 7.32 (d, J=2.38 Hz, 1 H), 7.48 (dd, J=8.51, 4.48 Hz, 1 H).

EXAMPLE 26(15)

5-sec-butyl-2-(6-methoxy-2-methyl-3-pyridinyl)-3,7-dimethylpyrrolo[2,1-f][1,2,4]triazin-4(3H)-one TLC: Rf 0.57 (n-hexane/ethyl acetate=3/1);
$^1$H-NMR (CDCl$_3$): δ 0.92 (t, J=7.32 Hz, 3 H), 1.27 (d, J=6.95 Hz, 3 H), 1.59-1.75 (m, 2 H), 2.38 (s, 3 H), 2.43 (s, 3 H), 3.18 (s, 3 H), 3.42-3.64 (m, 1 H), 3.98 (s, 3 H), 6.22 (s, 1 H), 6.64-6.75 (m, 1 H), 7.50 (d, J=8.42 Hz, 1 H).

EXAMPLE 26(16)

5-sec-butyl-2-(2,4-dimethylphenyl)-3,7-dimethylpyrrolo[2,1-f][1,2,4]triazin-4(3H)-one TLC: Rf 0.63 (n-hexane/ethyl acetate=2/1);
$^1$H-NMR (CDCl$_3$): δ 0.75-1.02 (m, 3 H), 1.28 (d, J=7.0 Hz, 3 H), 1.51-1.81 (m, 2 H), 2.26 (s, 3 H), 2.39 (s, 3 H), 2.38 (s, 3 H), 3.14 (s, 3 H), 3.47-3.64 (m, 1 H), 6.20 (s, 1 H), 7.08-7.25 (m, 3 H).

EXAMPLE 26(17)

5-sec-butyl-2-[4-(difluoromethoxy)-2-methylphenyl]-3,7-dimethylpyrrolo[2,1-f][1,2,4]triazin-4(3H)-one TLC: Rf 0.40 (ethyl acetate/n-hexane=1/6);
$^1$H-NMR (CDCl$_3$): δ 0.85-1.02 (m, 3 H), 1.28 (d, J=7.0 Hz, 3 H), 1.54-1.79 (m, 2 H), 2.32 (s, 3 H), 2.39 (d, J=0.7 Hz, 3 H), 3.14 (s, 3 H), 3.45-3.66 (m, 1 H), 6.22 (s, 1 H), 6.57 (t, J=73.4 Hz, 1 H), 7.04-7.13 (m, 2 H), 7.29-7.42 (m, 1 H).

EXAMPLE 26(18)

5-sec-butyl-2-[4-(dimethylamino)-2-methylphenyl]-3,7-dimethylpyrrolo[2,1-f][1,2,4]triazin-4(3H)-one TLC: Rf 0.31 (ethyl acetate/n-hexane=1/6);
$^1$H-NMR (CDCl$_3$): δ 0.92 (t, J=7.3 Hz, 3 H), 1.27 (d, J=6.8 Hz, 3 H), 1.54-1.79 (m, 2 H), 2.25 (s, 3 H), 2.39 (d, J=0.7 Hz, 3 H), 3.00 (s, 6 H), 3.17 (s, 3 H), 3.45-3.65 (m, 1 H), 6.19 (s, 1 H), 6.55-6.67 (m, 2 H), 7.16 (d, J=8.4 Hz, 1 H).

EXAMPLE 26(19)

5-sec-butyl-2-(4-methoxy-2,6-dimethylphenyl)-3,7-dimethylpyrrolo[2,1-f][1,2,4]triazin-4(3H)-one TLC: Rf 0.33 (n-hexane/ethyl acetate=9/1);
$^1$H-NMR (CDCl$_3$): δ 0.93 (t, J=7.4 Hz, 3 H), 1.28 (d, J=7.0 Hz, 3 H), 1.57-1.81 (m, 2 H), 2.09-2.28 (m, 6 H), 2.39 (s, 3 H), 3.10 (s, 3 H), 3.44-3.63 (m, 1 H), 3.82 (s, 3 H), 6.20 (s, 1 H), 6.67 (s, 2 H).

EXAMPLE 26(20)

5-sec-butyl-2-(2-chloro-4-methoxy-5-methylphenyl)-3,7-dimethylpyrrolo[2,1-f][1,2,4]triazin-4(3H)-one TLC: Rf 0.38 (n-hexane/ethyl acetate=9/1);
$^1$H-NMR (CDCl$_3$): δ 0.81-0.99 (m, 3 H), 1.19-1.33 (m, 3 H), 1.56-1.78 (m, 2 H), 2.22 (s, 3 H), 2.39 (s, 3 H), 3.10-3.25 (m, 3 H), 3.39-3.68 (m, 1 H), 3.88 (s, 3 H), 6.20 (s, 1 H), 6.91 (s, 1 H), 7.18 (dd, J=5.2, 0.8 Hz, 1 H).

EXAMPLE 26(21)

5-sec-butyl-2-[4-(difluoromethoxy)-2,6-dimethylphenyl]-3,7-dimethylpyrrolo[2,1-f][1,2,4]triazin-4(3H)-one TLC: Rf 0.75 (n-hexane/ethyl acetate=3/1);
$^1$H-NMR (CDCl$_3$): δ 0.93 (t, J=7.41 Hz, 3 H), 1.28 (d, J=6.95 Hz, 3 H), 1.56-1.77 (m, 2 H), 2.23 (s, 3 H), 2.24 (s, 3 H), 2.38 (s, 3 H), 3.10 (s, 3 H), 3.46-3.62 (m, 1 H), 6.22 (s, 1 H), 6.54 (t, J=73.46 Hz, 1 H), 6.91 (s, 2 H).

EXAMPLE 26(22)

5-sec-butyl-2-(2,4-dichlorophenyl)-3,7-dimethylpyrrolo[2,1-f][1,2,4]triazin-4(3H)-one TLC: Rf 0.70 (n-hexane/ethyl acetate=3/1);
$^1$H-NMR (CDCl$_3$): δ 0.91 (q, J=7.32 Hz, 3 H), 1.27 (dd, J=6.95, 3.11 Hz, 3 H), 1.57-1.77 (m, 2 H), 2.38 (s, 3 H), 3.19 (s, 3 H), 3.47-3.61 (m, 1 H), 6.21 (s, 1 H), 7.40 (t, J=1.56 Hz, 2 H), 7.51-7.56 (m, 1 H).

EXAMPLE 26(23)

5-sec-butyl-2-(4-methoxy-2-methylphenyl)-3,7-dimethylpyrrolo[2,1-f][1,2,4]triazin-4(3H)-one TLC: Rf 0.33 (n-hexane/ethyl acetate=9/1);
$^1$H-NMR (CDCl$_3$): δ 0.77-1.01 (m, 3 H), 1.27 (d, J=7.0 Hz, 3 H), 1.57-1.79 (m, 2 H), 2.27 (s, 3 H), 2.39 (s, 3 H), 3.14 (s, 3 H), 3.40-3.73 (m, 1 H), 3.84 (s, 3 H), 6.19 (s, 1 H), 6.77-6.88 (m, 2 H), 7.17-7.25 (m, 1 H).

EXAMPLE 26(24)

5-sec-butyl-3,7-dimethyl-2-[2-methyl-4-(trifluoromethoxy)phenyl]pyrrolo[2,1-f][1,2,4]triazin-4(3H)-one TLC: Rf 0.44 (n-hexane/ethyl acetate=9/1);
$^1$H-NMR (CDCl$_3$): δ 0.81-1.02 (m, 3 H), 1.27 (d, J=7.0 Hz, 3 H), 1.57-1.79 (m, 2 H), 2.33 (s, 3 H), 2.39 (s, 3 H), 3.13 (s, 3 H), 3.38-3.73 (m, 1 H), 6.22 (s, 1 H), 7.04-7.22 (m, 2 H), 7.31-7.46 (m, 1 H).

EXAMPLE 26(25)

5-sec-butyl-2-[2-chloro-4-(trifluoromethyl)phenyl]-3,7-dimethylpyrrolo[2,1-f][1,2,4]triazin-4(3H)-one TLC: Rf 0.37 (n-hexane/ethyl acetate=9/1);
$^1$H-NMR (CDCl$_3$): δ 0.73-1.08 (m, 3 H), 1.11-1.40 (m, 3 H), 1.58-1.81 (m, 2 H), 2.38 (s, 3 H), 3.20 (s, 3 H), 3.43-3.64 (m, 1 H), 6.23 (s, 1 H), 7.53-7.65 (m, 1 H), 7.67-7.75 (m, 1 H), 7.75-7.83 (m, 1 H).

EXAMPLE 26(26)

5-sec-butyl-2-[4-(difluoromethoxy)-2-ethylphenyl]-3,7-dimethylpyrrolo[2,1-f][1,2,4]triazin-4(3H)-one TLC: Rf 0.49 (n-hexane/ethyl acetate=4/1);
$^1$H-NMR (CDCl$_3$): δ 0.92 (q, J=7.6 Hz, 3 H), 1.18-1.32 (m, 6 H), 1.57-1.80 (m, 2 H), 2.38 (s, 3 H), 2.52-2.70 (m, 2 H), 3.13 (s, 3 H), 3.46-3.62 (m, 1 H), 6.22 (s, 1 H), 6.58 (t, J=73.4 Hz, 1 H), 7.05-7.16 (m, 2 H), 7.32 (dd, J=8.2, 4.9 Hz, 1 H).

EXAMPLE 26(27)

5-sec-butyl-2-[4-(difluoromethoxy)-2,5-dimethylphenyl]-3,7-dimethylpyrrolo[2,1-f][1,2,4]triazin-4(3H)-one TLC: Rf 0.53 (ethyl acetate/n-hexane=1/6);
$^1$H-NMR (CDCl$_3$): δ 0.85-0.99 (m, 3 H), 1.27 (d, J=6.8 Hz, 3 H), 1.51-1.79 (m, 2 H), 2.26 (s, 3 H), 2.30 (s, 3 H), 2.39 (s, 3 H), 3.14 (s, 3 H), 3.44-3.64 (m, 1 H), 6.20 (s, 1 H), 6.54 (t, J=73.6 Hz, 1 H), 7.02 (s, 1 H), 7.19 (d, J=4.8 Hz, 1 H).

EXAMPLE 26(28)

5-sec-butyl-2-[4-chloro-2-(trifluoromethyl)phenyl]-3,7-dimethylpyrrolo[2,1-f][1,2,4]triazin-4(3H)-one TLC: Rf 0.60 (ethyl acetate/n-hexane=1/6);
$^1$H-NMR (CDCl$_3$): δ 0.85-0.99 (m, 3 H), 1.22-1.32 (m, 3 H), 1.51-1.81 (m, 2 H), 2.35 (s, 3 H), 3.12 (s, 3 H), 3.43-3.65 (m, 1 H), 6.21 (s, 1 H), 7.40-7.48 (m, 1 H), 7.68 (dd, J=8.2, 2.0 Hz, 1 H), 7.81 (d, J=2.0 Hz, 1 H).

EXAMPLE 26(29)

5-sec-butyl-2-(2-isopropyl-4-methoxyphenyl)-3,7-dimethylpyrrolo[2,1-f][1,2,4]triazin-4(3H)-one TLC: Rf 0.57 (n-hexane/ethyl acetate=4/1);
$^1$H-NMR (DMSO-D$_6$): δ 0.85-1.00 (m, 2 H), 1.16-1.34 (m, 8 H), 1.58-1.83 (m, 4 H), 2.38 (s, 3 H), 2.76-2.94 (m, 1 H), 3.14 (s, 3 H), 3.46-3.67 (m, 1 H), 3.87 (s, 3 H), 6.21 (s, 1 H), 6.81-6.88 (m, 1 H), 6.95 (d, J=2.6 Hz, 1 H), 7.20 (dd, J=8.6, 2.6 Hz, 1 H).

EXAMPLE 26(30)

5-sec-butyl-2-(2-chloro-4-ethoxyphenyl)-3,7-dimethylpyrrolo[2,1-f][1,2,4]triazin-4(3H)-one TLC: Rf 0.46 (n-hexane/ethyl acetate=4/1);
$^1$H-NMR (CDCl$_3$): δ 0.82-1.02 (m, 3 H), 1.20-1.34 (m, 3 H), 1.45 (t, J=7.0 Hz, 3 H), 1.57-1.79 (m, 2 H), 2.39 (s, 3 H), 3.21 (s, 3 H), 3.49-3.62 (m, 1 H), 4.02-4.18 (m, 2 H), 6.21 (s, 1 H), 6.92 (dd, J=8.6, 2.4 Hz, 1 H), 7.03 (d, J=2.4 Hz, 1 H), 7.25-7.37 (m, 1 H).

EXAMPLE 26(31)

5-sec-butyl-2-(4-ethoxy-5-fluoro-2-methylphenyl)-3,7-dimethylpyrrolo[2,1-f][1,2,4]triazin-4(3H)-one TLC: Rf 0.48 (n-hexane/ethyl acetate=4/1);
$^1$H-NMR (CDCl$_3$): δ 0.85-1.00 (m, 3 H), 1.27 (d, J=7.0 Hz, 3 H), 1.49 (t, J=7.0 Hz, 3 H), 1.57-1.79 (m, 2 H), 2.25 (s, 3 H), 2.39 (s, 3 H), 3.16 (s, 3 H), 3.48-3.64 (m, 1 H), 4.16 (q, J=7.0 Hz, 2 H), 6.21 (s, 1 H), 6.88 (d, J=8.1 Hz, 1 H), 7.06 (d, J=10.8 Hz, 1 H).

EXAMPLE 26(32)

5-sec-butyl-2-(2-chloro-4-ethoxy-5-fluorophenyl)-3,7-dimethylpyrrolo[2,1-f][1,2,4]triazin-4(3H)-one TLC: Rf 0.50 (n-hexane/ethyl acetate=4/1);
$^1$H-NMR (CDCl$_3$): δ 0.91 (q, J=7.1 Hz, 3 H), 1.27 (d, J=6.2 Hz, 3 H), 1.43-1.81 (m, 6 H), 2.39 (s, 3 H), 3.22 (s, 3 H), 3.44-3.63 (m, 1 H), 4.16 (q, J=6.5 Hz, 2 H), 6.21 (s, 1 H), 7.06 (d, J=7.1 Hz, 1 H), 7.13-7.23 (m, 1 H).

EXAMPLE 26(33)

5-sec-butyl-2-(2-chloro-3,5-difluoro-4-methoxyphenyl)-3,7-dimethylpyrrolo[2,1-f][1,2,4]triazin-4(3H)-one TLC: Rf 0.45 (n-hexane/ethyl acetate=9/1);
$^1$H-NMR (CDCl$_3$): δ 0.75-1.06 (m, 3 H), 1.17-1.38 (m, 3 H), 1.55-1.82 (m, 2 H), 2.38 (s, 3 H), 3.22 (s, 3 H), 3.34-3.68 (m, 1 H), 4.02-4.24 (m, 3 H), 6.23 (s, 1 H), 6.99-7.16 (m, 1H).

EXAMPLE 26(34)

5-sec-butyl-2-[4-methoxy-2-(trifluoromethyl)phenyl]-3,7-dimethylpyrrolo[2,1-f][1,2,4]triazin-4(3H)-one TLC: Rf 0.43 (ethyl acetate/n-hexane=2/1);
$^1$H-NMR (CDCl$_3$): δ 0.84-0.99 (m, 3 H), 1.23-1.31 (m, 3 H), 1.52-1.82 (m, 2 H), 2.36 (d, J=0.7 Hz, 3 H), 3.12 (s, 3 H), 3.44-3.62 (m, 1 H), 3.92 (s, 3 H), 6.21 (s, 1 H), 7.19 (dd, J=8.4, 2.6 Hz, 1 H), 7.30 (d, J=2.6 Hz, 1 H), 7.40 (dd, J=8.4, 5.4 Hz, 1 H).

EXAMPLE 26(35)

5-sec-butyl-2-[3-chloro-5-(trifluoromethyl)-2-pyridinyl]-3,7-dimethylpyrrolo[2,1-f][1,2,4]triazin-4(3H)-one TLC: Rf 0.48 (n-hexane/ethyl acetate=6/1);
$^1$H-NMR (CDCl$_3$): δ 0.90 (t, J=7.3 Hz, 3 H), 1.27 (d, J=7.0 Hz, 3 H), 1.59-1.73 (m, 2 H), 2.38 (s, 3 H), 3.20 (s, 3 H), 3.48-3.61 (m, 1 H), 6.23 (s, 1 H), 8.13-8.14 (m, 1 H), 8.90-8.91 (m, 1 H).

EXAMPLE 26(36)

5-sec-butyl-2-(2-chloro-4-isopropylphenyl)-3,7-dimethylpyrrolo[2,1-f][1,2,4]triazin-4(3H)-one TLC: Rf 0.44 (n-hexane/ethyl acetate=7/1);
$^1$H-NMR (CDCl$_3$): δ 0.85-0.97 (m, 3 H), 1.24-1.34 (m, 9 H), 1.52-1.81 (m, 2 H), 2.33-2.47 (m, 3 H), 2.88-3.04 (m, 1 H), 3.21 (s, 3 H), 3.48-3.63 (m, 1 H), 6.22 (s, 1 H), 7.24-7.30 (m, 1 H), 7.34-7.41 (m, 2 H).

EXAMPLES 27(1)~(19)

By the same procedure as a series of reactions of Example 3→Example 4→Example 5→Example 8, using the compound provided by using propylmagnesium bromide instead of ethylmagnesium bromide instead of the compound prepared in Example 2, and using the corresponding aldehydes instead of the compound prepared in Example 7, the compounds of the present invention having the following physical data were obtained.

EXAMPLE 27(1)

2-(2-chloro-4-methoxyphenyl)-3,7-dimethyl-5-(1-propylbutyl)pyrrolo[2,1-f][1,2,4]triazin-4(3H)-one

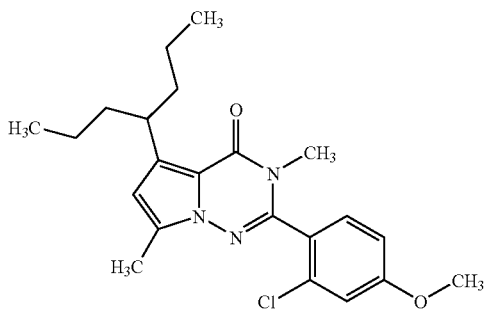 [SMILES: CCCC(CCC)c1cc(C)n2nc(-c3ccc(OC)cc3Cl)n(C)c(=O)c12]

TLC: Rf 0.53 (ethyl acetate/n-hexane=1/4);
$^1$H-NMR (CDCl$_3$): δ 0.76-0.98 (m, 6 H), 1.14-1.41 (m, 4 H), 1.44-1.76 (m, 4 H), 2.39 (s, 3 H), 3.20 (s, 3 H), 3.47-3.69 (m, 1 H), 3.87 (s, 3 H), 6.17 (s, 1 H), 6.94 (dd, J=8.6, 2.4 Hz, 1 H), 7.04 (d, J=2.4 Hz, 1 H), 7.38 (d, J=8.6 Hz, 1 H).

EXAMPLE 27(2)

2-[2-chloro-4-(trifluoromethoxy)phenyl]-3,7-dimethyl-5-(1-propylbutyl)pyrrolo[2,1-f][1,2,4]triazin-4(3H)-one TLC: Rf 0.63 (ethyl acetate/n-hexane=1/6);
$^1$H-NMR (CDCl$_3$): δ 0.77-1.00 (m, 6 H), 1.13-1.43 (m, 4 H), 1.44-1.79 (m, 4 H), 2.38 (s, 3 H), 3.21 (s, 3 H), 3.49-3.70 (m, 1 H), 6.20 (s, 1 H), 7.31 (dd, J=8.4, 1.2 Hz, 1 H), 7.42 (d, J=1.2 Hz, 1 H), 7.54 (d, J=8.4 Hz, 1 H).

EXAMPLE 27(3)

2-(4-methoxy-2,6-dimethylphenyl)-3,7-dimethyl-5-(1-propylbutyl)pyrrolo[2,1-f][1,2,4]triazin-4(3H)-one TLC: Rf 0.49 (n-hexane/ethyl acetate=3/1);
$^1$H-NMR (CDCl$_3$): δ 0.88 (t, J=7.3 Hz, 6 H), 1.18-1.42 (m, 4 H), 1.49-1.74 (m, 4 H), 2.21 (s, 6 H), 2.38 (s, 3 H), 3.09 (s, 3 H), 3.50-3.65 (m, 1 H), 3.82 (s, 3 H), 6.16 (s, 1 H), 6.67 (s, 2 H).

EXAMPLE 27(4)

2-[4-methoxy-2-(trifluoromethyl)phenyl]-3,7-dimethyl-5-(1-propylbutyl)pyrrolo[2,1-f][1,2,4]triazin-4(3H)-one TLC: Rf 0.48 (n-hexane/ethyl acetate=3/1);
$^1$H-NMR (CDCl$_3$): δ 0.76-0.99 (m, 6 H), 1.15-1.40 (m, 4 H), 1.45-1.77 (m, 4 H), 2.35 (s, 3 H), 3.12 (s, 3 H), 3.47-3.67

(m, 1 H), 3.92 (s, 3 H), 6.16 (s, 1 H), 7.17 (dd, J=8.6, 2.6 Hz, 1 H), 7.29 (d, J=2.6 Hz, 1 H), 7.40 (d, J=8.4 Hz, 1 H).

EXAMPLE 27(5)

2-[2-chloro-4-(difluoromethoxy)phenyl]-3,7-dimethyl-5-(1-propylbutyl)pyrrolo[2,1-f][1,2,4]triazin-4(3H)-one TLC: Rf 0.49 (n-hexane/ethyl acetate=3/1);
$^1$H-NMR (CDCl$_3$): δ 0.81-0.95 (m, 6 H), 1.16-1.38 (m, 4 H), 1.51-1.72 (m, 4 H), 2.38 (s, 3 H), 3.20 (s, 3 H), 3.50-3.65 (m, 1 H), 6.18 (s, 1 H), 6.58 (t, J=72.4 Hz, 1 H), 7.19 (dd, J=8.4, 2.4 Hz, 1 H), 7.31 (d, J=2.4 Hz, 1 H), 7.48 (d, J=8.4 Hz, 1 H).

EXAMPLE 27(6)

2-(5-fluoro-4-methoxy-2-methylphenyl)-3,7-dimethyl-5-(1-propylbutyl)pyrrolo[2,1-f][1,2,4]triazin-4(3H)-one TLC: Rf 0.36 (n-hexane/ethyl acetate=5/1);
$^1$H-NMR (CDCl$_3$): δ 0.88 (t, J=7.32 Hz, 6 H), 1.14-1.42 (m, 4 H), 1.47-1.77 (m, 4 H), 2.27 (s, 3 H), 2.38 (s, 3 H), 3.15 (s, 3 H), 3.48-3.66 (m, 1 H), 3.94 (s, 3 H), 6.18 (s, 1 H), 6.89 (d, J=8.42 Hz, 1 H), 7.08 (d, J=10.98 Hz, 1 H).

EXAMPLE 27(7)

2-[4-chloro-2-(difluoromethoxy)phenyl]-3,7-dimethyl-5-(1-propylbutyl)pyrrolo[2,1-f][1,2,4]triazin-4(3H)-one TLC: Rf 0.63 (n-hexane/ethyl acetate=5/1);
$^1$H-NMR (CDCl$_3$): δ 0.80-0.97 (m, 6 H), 1.14-1.41 (m, 4 H), 1.44-1.72 (m, 4 H), 2.37 (d, J=0.73 Hz, 3 H), 3.20 (s, 3 H), 3.47-3.67 (m, 1 H), 6.18 (s, 1 H), 6.30-6.86 (m, 1 H), 7.33-7.39 (m, 2 H), 7.45 (d, J=8.79 Hz, 1 H).

EXAMPLE 27(8)

2-(2-chloro-4-methoxy-5-methylphenyl)-3,7-dimethyl-5-(1-propylbutyl)pyrrolo[2,1-f][1,2,4]triazin-4(3H)-one TLC: Rf 0.63 (n-hexane/ethyl acetate=5/1);
$^1$H-NMR (CDCl$_3$): δ 0.78-0.94 (m, 6 H), 1.15-1.37 (m, 4 H), 1.50-1.70 (m, 4 H), 2.23 (s, 3 H), 2.39 (s, 3 H), 3.21 (s, 3 H), 3.50-3.64 (m, 1 H), 3.89 (s, 3 H), 6.17 (s, 1 H), 6.92 (s, 1 H), 7.21 (d, J=0.73 Hz, 1 H).

EXAMPLE 27(9)

2-(2-chloro-6-fluoro-4-methoxyphenyl)-3,7-dimethyl-5-(1-propylbutyl)pyrrolo[2,1-f][1,2,4]triazin-4(3H)-one TLC: Rf 0.43 (n-hexane/ethyl acetate=5/1);
$^1$H-NMR (CDCl$_3$): δ 0.80-0.96 (m, 6 H), 1.14-1.42 (m, 4 H), 1.47-1.73 (m, 4 H), 2.39 (s, 3 H), 3.22 (s, 3 H), 3.49-3.66 (m, 1 H), 3.87 (s, 3 H), 6.18 (s, 1 H), 6.70 (dd, J=10.61, 2.38 Hz, 1 H), 6.89 (dd, J=2.38, 1.46 Hz, 1 H).

EXAMPLE 27(10)

2-(2-ethyl-4-methoxyphenyl)-3,7-dimethyl-5-(1-propylbutyl)pyrrolo[2,1-f][1,2,4]triazin-4(3H)-one TLC: Rf 0.67 (n-hexane/ethyl acetate=3/1);
$^1$H-NMR (CDCl$_3$): δ 0.81-0.95 (m, 6 H), 1.12-1.42 (m, 7 H), 1.45-1.74 (m, 4 H), 2.38 (s, 3 H), 2.50-2.67 (m, 2 H), 3.13 (s, 3 H), 3.49-3.65 (m, 1 H), 3.86 (s, 3 H), 6.16 (s, 1 H), 6.84 (dd, J=8.23, 2.56 Hz, 1 H), 6.88 (d, J=2.56 Hz, 1 H), 7.22 (d, J=8.23 Hz, 1 H).

EXAMPLE 27(11)

2-(2,4-dimethylphenyl)-3,7-dimethyl-5-(1-propylbutyl)pyrrolo[2,1-f][1,2,4]triazin-4(3H)-one TLC: Rf 0.77 (n-hexane/ethyl acetate=3/1);
$^1$H-NMR (CDCl$_3$): δ 0.88 (t, J=7.23 Hz, 6 H), 1.12-1.44 (m, 4 H), 1.45-1.74 (m, 4 H), 2.27 (s, 3 H), 2.38 (s, 3 H), 2.38 (s, 3 H), 3.13 (s, 3 H), 3.50-3.65 (m, 1 H), 6.15 (s, 1 H), 7.08-7.15 (m, 2 H), 7.21 (d, J=8.42 Hz, 1 H).

EXAMPLE 27(12)

2-(4-chloro-2-methoxyphenyl)-3,7-dimethyl-5-(1-propylbutyl)pyrrolo[2,1-f][1,2,4]triazin-4(3H)-one TLC: Rf 0.71 (n-hexane/ethyl acetate=3/1);
$^1$H-NMR (CDCl$_3$): δ 0.79-0.94 (m, 6 H), 1.12-1.42 (m, 4 H), 1.46-1.76 (m, 4 H), 2.38 (s, 3 H), 3.18 (s, 3 H), 3.49-3.66 (m, 1 H), 3.86 (s, 3 H), 6.15 (s, 1 H), 6.99 (d, J=1.83 Hz, 1 H), 7.07 (dd, J=8.05, 1.83 Hz, 1 H), 7.33 (d, J=8.05 Hz, 1 H).

EXAMPLE 27(13)

2-(4-ethoxy-2-methylphenyl)-3,7-dimethyl-5-(1-propylbutyl)pyrrolo[2,1-f][1,2,4]triazin-4(3H)-one TLC: Rf 0.74 (n-hexane/ethyl acetate=3/1);
$^1$H-NMR (CDCl$_3$): δ 0.88 (t, J=7.32 Hz, 6 H), 1.13-1.38 (m, 4 H), 1.44 (t, J=6.95 Hz, 3 H), 1.49-1.75 (m, 4 H), 2.27 (s, 3 H), 2.38 (s, 3 H), 3.13 (s, 3 H), 3.50-3.65 (m, 1 H), 4.07 (q, J=6.95 Hz, 2 H), 6.15 (s, 1 H), 6.77-6.86 (m, 2 H), 7.20-7.24 (m, 1 H).

EXAMPLE 27(14)

2-(4-chloro-2-methylphenyl)-3,7-dimethyl-5-(1-propylbutyl)pyrrolo[2,1-f][1,2,4]triazin-4(3H)-one TLC: Rf 0.55 (n-hexane/ethyl acetate=9/1);
$^1$H-NMR (CDCl$_3$): δ 0.88 (t, J=7.2 Hz, 6 H), 1.18-1.39 (m, 4 H), 1.53-1.71 (m, 4 H), 2.30 (s, 3 H), 2.35-2.40 (m, 3 H), 3.13 (s, 3 H), 3.49-3.64 (m, 1 H), 6.18 (s, 1 H), 7.28-7.30 (m, 1 H), 7.30-7.32 (m, 1 H), 7.32-7.36 (m, 1 H).

EXAMPLE 27(15)

2-(2-chloro-4-ethoxyphenyl)-3,7-dimethyl-5-(1-propylbutyl)pyrrolo[2,1-f][1,2,4]triazin-4(3H)-one TLC: Rf 0.37 (n-hexane/ethyl acetate=9/1);
$^1$H-NMR (CDCl$_3$): δ 0.77-0.98 (m, 6 H), 1.14-1.36 (m, 4 H), 1.45 (t, J=7.0 Hz, 3 H), 1.53-1.71 (m, 4 H), 2.39 (s, 3 H), 3.20 (s, 3 H), 3.48-3.71 (m, 1 H), 3.96-4.21 (m, 2 H), 6.17 (s, 1 H), 6.92 (dd, J=8.6, 2.4 Hz, 1 H), 7.03 (d, J=2.4 Hz, 1 H), 7.36 (d, J=8.6 Hz, 1 H).

EXAMPLE 27(16)

2-[2-chloro-4-(methylthio)phenyl]-3,7-dimethyl-5-(1-propylbutyl)pyrrolo[2,1-f][1,2,4]triazin-4(3H)-one TLC: Rf 0.37 (n-hexane/ethyl acetate=9/1);
$^1$-NMR (CDCl$_3$): δ 0.76-0.98 (m, 6 H), 1.15-1.38 (m, 4 H), 1.47-1.75 (m, 4 H), 2.38 (s, 3H), 2.54 (s, 3 H), 3.21 (s, 3 H), 3.51-3.65 (m, 1 H), 6.18 (s, 1 H), 7.21-7.26 (m, 2 H), 7.33 (d, J=1.8 Hz, 1 H), 7.36 (d, J=8.4 Hz, 1 H).

EXAMPLE 27(17)

2-(2-chloro-4-methoxy-6-methylphenyl)-3,7-dimethyl-5-(1-propylbutyl)pyrrolo[2,1-f][1,2,4]triazin-4(3H)-one TLC: Rf 0.33 (n-hexane/ethyl acetate=9/1);
$^1$H-NMR (CDCl$_3$): δ 0.88 (t, J=7.3 Hz, 6 H), 1.16-1.41 (m, 4 H), 1.51-1.74 (m, 4 H), 2.26 (s, 3 H), 2.39 (s, 3 H), 3.15 (s, 3 H), 3.49-3.67 (m, 1 H), 3.84 (s, 3 H), 6.18 (s, 1 H), 6.67-6.83 (m, 1 H), 6.82-6.94 (m, 1 H).

EXAMPLE 27(18)

2-(2-isopropyl-4-methoxyphenyl)-3,7-dimethyl-5-(1-propylbutyl)pyrrolo[2,1-f][1,2,4]triazin-4(3H)-one TLC: Rf 0.44 (n-hexane/ethyl acetate=9/1);
$^1$H-NMR (CDCl$_3$): δ 0.78-0.99 (m, 6 H), 1.13-1.39 (m, 10 H), 1.46-1.74 (m, 4 H), 2.37 (s, 3H), 2.79-2.96 (m, 1 H), 3.14 (s, 3 H), 3.49-3.68 (m, 1 H), 3.87 (s, 3 H), 6.17 (s, 1 H), 6.84 (dd, J=8.4, 2.6 Hz, 1 H), 6.95 (d, J=2.6 Hz, 1 H), 7.22 (d, J=8.4 Hz, 1 H).

EXAMPLE 27(19)

2-[4-(difluoromethoxy)-2-methylphenyl]-3,7-dimethyl-5-(1-propylbutyl)pyrrolo[2,1-f][1,2,4]triazin-4(3H)-one TLC: Rf 0.60 (n-hexane/ethyl acetate=3/1);
$^1$H-NMR (CDCl$_3$): δ 0.88 (t, J=7.32 Hz, 6 H), 1.14-1.41 (m, 4 H), 1.46-1.74 (m, 4 H), 2.33 (s, 3 H), 2.38 (s, 3 H), 3.14 (s, 3 H), 3.49-3.68 (m, 1 H), 6.18 (s, 1 H), 6.57 (t, J=73.46 Hz, 1 H), 7.04-7.14 (m, 2 H), 7.31-7.41 (m, 1 H).

EXAMPLES 28(1)~(10)

By the same procedure as a series of reactions of Example 15→Example 16→Example 17→Example 18→Example 4→Example 5→Example 8, using the compound prepared in Example 21 instead of 5-methyl-3-hepten-2-one, and using the corresponding aldehydes instead of the compound prepared in Example 7, the compounds of the present invention having the following physical data were obtained.

EXAMPLE 28(1)

2-(2-chloro-4-methoxyphenyl)-3,7-dimethyl-5-(1-methylbutyl)pyrrolo[2,1-f][1,2,4]triazin-4(3H)-one

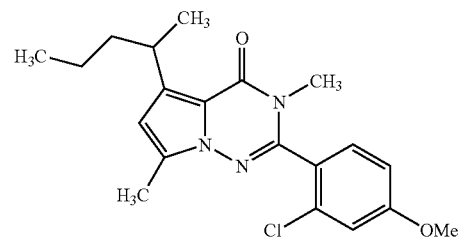 [SMILES: CCCC(C)c1cc(C)n2nc(-c3ccc(OC)cc3Cl)n(C)c(=O)c12]

TLC: Rf 0.36 (n-hexane/ethyl acetate=9/1);
$^1$H-NMR (CDCl$_3$): δ 0.71-1.03 (m, 3 H), 1.15-1.46 (m, 5 H), 1.44-1.79 (m, 2 H), 2.39 (s, 3H), 3.21 (s, 3 H), 3.47-3.77 (m, 1 H), 3.87 (s, 3 H), 6.22 (s, 1 H), 6.94 (dd, J=8.6, 2.4 Hz, 1 H), 7.04 (d, J=2.4 Hz, 1 H), 7.30-7.42 (m, 1 H).

EXAMPLE 28(2)

2-[2-chloro-4-(difluoromethoxy)phenyl]-3,7-dimethyl-5-(1-methylbutyl)pyrrolo[2,1-f][1,2,4]triazin-4(3H)-one TLC: Rf 0.63 (n-hexane/ethyl acetate=4/1);
$^1$H-NMR (CDCl$_3$): δ 0.85-0.97 (m, 3 H), 1.22-1.43 (m, 5 H), 1.48-1.72 (m, 2 H), 2.39 (s, 3H), 3.21 (s, 3 H), 3.53-3.76 (m, 1 H), 6.23 (s, 1 H), 6.59 (t, J=72.45 Hz, 1 H), 7.21 (dd, J=8.14, 2.10 Hz, 1 H), 7.33 (d, J=2.38 Hz, 1 H), 7.48 (dd, J=8.51, 3.75 Hz, 1 H).

EXAMPLE 28(3)

2-(4-chloro-2-methylphenyl)-3,7-dimethyl-5-(1-methylbutyl)pyrrolo[2,1-f][1,2,4]triazin-4(3H)-one TLC: Rf 0.55 (n-hexane/ethyl acetate=5/1);
$^1$H-NMR (CDCl$_3$): δ 0.91 (t, J=7.2 Hz, 3 H), 1.27 (d, J=6.8 Hz, 3 H), 1.29-1.41 (m, 2 H), 1.48-1.69 (m, 2 H), 2.29 (s, 3 H), 2.38 (s, 3 H), 3.13 (s, 3 H), 3.54-3.73 (m, 1 H), 6.21 (s, 1 H), 7.23-7.36 (m, 3 H).

EXAMPLE 28(4)

2-(5-fluoro-4-methoxy-2-methylphenyl)-3,7-dimethyl-5-(1-methylbutyl)pyrrolo[2,1-f][1,2,4]triazin-4(3H)-one TLC: Rf 0.44 (n-hexane/ethyl acetate=4/1);
$^1$H-NMR (CDCl$_3$): δ 0.91 (t, J=7.3 Hz, 3 H), 1.26 (d, J=7.0 Hz, 3 H), 1.29-1.45 (m, 2 H), 1.49-1.64 (m, 2 H), 2.26 (s, 3 H), 2.38 (s, 3 H), 3.16 (s, 3 H), 3.58-3.73 (m, 1 H), 3.94 (s, 3 H), 6.22 (s, 1 H), 6.89 (d, J=8.2 Hz, 1 H), 7.07 (d, J=10.8 Hz, 1 H).

EXAMPLE 28(5)

2-(2-ethyl-4-methoxyphenyl)-3,7-dimethyl-5-(1-methylbutyl)pyrrolo[2,1-f][1,2,4]triazin-4(3H)-one TLC: Rf 0.45 (ethyl acetate/n-hexane=1/6);

$^1$H-NMR (CDCl$_3$): δ 0.83-0.98 (m, 3 H), 1.16-1.47 (m, 8 H), 1.49-1.80 (m, 2 H), 2.38 (s, 3H), 2.46-2.70 (m, 2 H), 3.14 (s, 3 H), 3.56-3.75 (m, 1 H), 3.86 (s, 3 H), 6.21 (s, 1 H), 6.82-6.88 (m, 1 H), 6.90 (d, J=2.6 Hz, 1 H), 7.22 (dd, J=8.4, 4.4 Hz, 1 H).

EXAMPLE 28(6)

2-[4-(difluoromethoxy)-5-fluoro-2-methylphenyl]-3,7-dimethyl-5-(1-methylbutyl)pyrrolo[2,1-f][1,2,4]triazin-4(3H)-one TLC: Rf 0.29 (n-hexane/ethyl acetate=9/1);

$^1$H-NMR (CDCl$_3$): δ 0.91 (t, J=7.3 Hz, 3 H), 1.13-1.47 (m, 5 H), 1.48-1.73 (m, 2 H), 2.28 (s, 3 H), 2.38 (s, 3 H), 3.16 (s, 3 H), 3.47-3.76 (m, 1 H), 6.23 (s, 1 H), 6.62 (t, J=73.0 Hz, 1 H), 7.11-7.25 (m, 2 H).

EXAMPLE 28(7)

2-[4-(difluoromethoxy)-2-methylphenyl]-3,7-dimethyl-5-(1-methylbutyl)pyrrolo[2,1-f][1,2,4]triazin-4(3H)-one TLC: Rf 0.30 (n-hexane/ethyl acetate=9/1);

$^1$H-NMR (CDCl$_3$): δ 0.91 (t, J=7.3 Hz, 3 H), 1.17-1.44 (m, 5 H), 1.48-1.75 (m, 2 H), 2.32 (s, 3 H), 2.38 (s, 3 H), 3.14 (s, 3 H), 3.65 (s, 1 H), 6.22 (s, 1 H), 6.57 (t, J=73.4 Hz, 1 H), 7.02-7.19 (m, 2 H), 7.29-7.40 (m, 1 H).

EXAMPLE 28(8)

2-(2-chloro-5-fluoro-4-methoxyphenyl)-3,7-dimethyl-5-(1-methylbutyl)pyrrolo[2,1-f][1,2,4]triazin-4(3H)-one TLC: Rf 0.40 (n-hexane/ethyl acetate=7/1);

$^1$H-NMR (CDCl$_3$): δ 0.84-0.96 (m, 3 H), 1.17-1.45 (m, 5 H), 1.47-1.73 (m, 2 H), 2.39 (s, 3H), 3.22 (s, 3 H), 3.55-3.78 (m, 1 H), 3.96 (s, 3 H), 6.23 (s, 1 H), 7.08 (d, J=7.5 Hz, 1 H), 7.16-7.25 (m, 1 H).

EXAMPLE 28(9)

3,7-dimethyl-5-(1-methylbutyl)-2-[2-methyl-4-(methylthio)phenyl]pyrrolo[2,1-f][1,2,4]triazin-4(3H)-one TLC: Rf 0.43 (n-hexane/ethyl acetate=4/1);

$^1$H-NMR (CDCl$_3$): δ 0.91 (t, J=6.8 Hz, 3 H), 1.27 (d, J=6.8 Hz, 3 H), 1.29-1.48 (m, 2 H), 1.48-1.72 (m, 2 H), 2.27 (s, 3 H), 2.38 (s, 3 H), 2.51 (s, 3 H), 3.14 (s, 3 H), 3.54-3.74 (m, 1 H), 6.17-6.24 (m, 1 H), 7.13-7.28 (m, 3 H).

EXAMPLE 28(10)

2-[6-(difluoromethoxy)-4-methyl-3-pyridinyl]-3,7-dimethyl-5-(1-methylbutyl)pyrrolo[2,1-f][1,2,4]triazin-4(3H)-one TLC: Rf 0.38 (n-hexane/ethyl acetate=5/1);

$^1$H-NMR (CDCl$_3$): δ 0.91 (t, J=7.2 Hz, 3 H), 1.11-1.46 (m, 5 H), 1.47-1.81 (m, 2 H), 2.34 (s, 3 H), 2.38 (s, 3 H), 3.17 (s, 3 H), 3.54-3.75 (m, 1 H), 6.23 (s, 1 H), 6.88 (s, 1 H), 7.16-7.82 (m, 1 H), 8.17 (s, 1 H).

EXAMPLES 29(1)~(20)

By the same procedure as a series of reactions of Example 5→Example 8, using the compound provided by using an aqueous solution of 70% ethylamine instead of an aqueous solution of 40% methylamine instead of the compound prepared in Example 4, and using the corresponding aldehydes instead of the compound prepared in Example 7, the compounds of the present invention having the following physical data were obtained.

EXAMPLE 29(1)

3-ethyl-2-(2-ethyl-4-methoxyphenyl)-5-(1-ethylpropyl)-7-methylpyrrolo[2,1-f][1,2,4]triazin-4(3H)-one

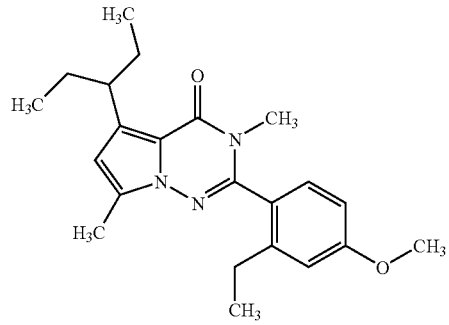 [SMILES: CCc1cc(OC)ccc1-c1nn2c(C)cc(C(CC)CC)c2c(=O)n1C]

TLC: Rf 0.51 (ethyl acetate/n-hexane=1/6);

$^1$H-NMR (CDCl$_3$): δ 0.79-0.97 (m, 6 H), 1.06 (t, J=7.0 Hz, 3 H), 1.24 (t, J=7.5 Hz, 3 H), 1.50-1.84 (m, 4 H), 2.38 (s, 3 H), 2.57 (q, J=7.5 Hz, 2 H), 3.30-3.53 (m, 2 H), 3.87 (s, 3H), 3.92-4.07 (m, 1 H), 6.16 (s, 1 H), 6.81-6.88 (m, 1 H), 6.89 (d, J=2.6 Hz, 1 H), 7.29 (d, J=8.4 Hz, 1 H).

EXAMPLE 29(2)

2-[2-chloro-4-(methylthio)phenyl]-3-ethyl-5-(1-ethylpropyl)-7-methylpyrrolo[2,1-f][1,2,4]triazin-4(3H)-one TLC: Rf 0.56 (ethyl acetate/n-hexane=1/6);

$^1$H-NMR (CDCl$_3$): δ 0.82-0.94 (m, 6 H), 1.07 (t, J=7.0 Hz, 3 H), 1.47-1.87 (m, 4 H), 2.38 (s, 3 H), 2.54 (s, 3 H), 3.25-3.49 (m, 2 H), 4.02-4.30 (m, 1 H), 6.17 (s, 1 H), 7.21-7.29 (m, 1 H), 7.33 (d, J=1.8 Hz, 1 H), 7.39 (d, J=8.1 Hz, 1 H).

EXAMPLE 29(3)

2-[2-chloro-4-(difluoromethoxy)phenyl]-3-ethyl-5-(1-ethylpropyl)-7-methylpyrrolo[2,1-f][1,2,4]triazin-4(3H)-one TLC: Rf 0.51 (ethyl acetate/n-hexane=1/6);
$^1$H-NMR (CDCl$_3$): δ 0.80-0.93 (m, 6 H), 1.08 (t, J=7.0 Hz, 3 H), 1.48-1.83 (m, 4 H), 2.38 (d, J=0.7 Hz, 3 H), 3.27-3.46 (m, 2 H), 4.06-4.27 (m, 1 H), 6.18 (s, 1 H), 6.60 (t, J=72.5 Hz, 1 H), 7.20 (dd, J=8.4, 2.0 Hz, 1 H), 7.32 (d, J=2.0 Hz, 1 H), 7.52 (d, J=8.4 Hz, 1 H).

EXAMPLE 29(4)

2-(2-chloro-4-methoxy-6-methylphenyl)-3-ethyl-5-(1-ethylpropyl)-7-methylpyrrolo[2,1-f][1,2,4]triazin-4(3H)-one TLC: Rf 0.36 (ethyl acetate/n-hexane=1/6);
$^1$H-NMR (CDCl$_3$): δ 0.84-0.93 (m, 6 H), 1.11 (t, J=7.0 Hz, 3 H), 1.50-1.83 (m, 4 H), 2.28 (s, 3 H), 2.39 (d, J=0.7 Hz, 3 H), 3.34-3.47 (m, 1 H), 3.56-3.70 (m, 1 H), 3.73-3.89 (m, 4H), 6.17 (s, 1 H), 6.76-6.79 (m, 1 H), 6.90 (d, J=2.6 Hz, 1 H).

EXAMPLE 29(5)

3-ethyl-5-(1-ethylpropyl)-2-(5-fluoro-4-methoxy-2-methylphenyl)-7-methylpyrrolo[2,1-f][1,2,4]triazin-4(3H)-one TLC: Rf 0.36 (ethyl acetate/n-hexane=1/6);
$^1$H-NMR (CDCl$_3$): δ 0.80-0.93 (m, 6 H), 1.07 (t, J=7.0 Hz, 3 H), 1.47-1.86 (m, 4 H), 2.27 (s, 3 H), 2.38 (s, 3 H), 3.30-3.52 (m, 2 H), 3.94 (s, 3 H), 3.98-4.17 (m, 1 H), 6.17 (s, 1 H), 6.88 (d, J=8.2 Hz, 1 H), 7.12 (d, J=11.0 Hz, 1 H).

EXAMPLE 29(6)

2-(4-chloro-2-methylphenyl)-3-ethyl-5-(1-ethylpropyl)-7-methylpyrrolo[2,1-f][1,2,4]triazin-4(3H)-one TLC: Rf 0.72 (ethyl acetate/n-hexane=1/6);
$^1$H-NMR (CDCl$_3$): δ 0.81-0.94 (m, 6 H), 1.01-1.12 (m, 3 H), 1.50-1.86 (m, 4 H), 2.30 (s, 3H), 2.37 (s, 3 H), 3.26-3.49 (m, 2 H), 3.97-4.14 (m, 1 H), 6.17 (s, 1 H), 7.28-7.37 (m, 3H).

EXAMPLE 29(7)

3-ethyl-5-(1-ethylpropyl)-7-methyl-2-[2-methyl-4-(1H-pyrazol-1-yl)phenyl]pyrrolo[2,1-f][1,2,4]triazin-4(3H)-one TLC: Rf 0.33 (ethyl acetate/n-hexane=1/6);
$^1$H-NMR (CDCl$_3$): δ 0.81-0.95 (m, 6 H), 1.02-1.11 (m, 3 H), 1.52-1.82 (m, 4 H), 2.39 (s, 3H), 2.40 (d, J=0.7 Hz, 3 H), 3.32-3.50 (m, 2 H), 4.01-4.18 (m, 1 H), 6.18 (s, 1 H), 6.52 (dd, J=2.5, 1.7 Hz, 1 H), 7.48 (d, J=8.2 Hz, 1 H), 7.61-7.68 (m, 1 H), 7.73 (dd, J=1.7, 0.5 Hz, 1 H), 7.77 (dd, J=1.7, 0.5 Hz, 1 H), 7.99 (dd, J=2.5, 0.5 Hz, 1 H).

EXAMPLE 29(8)

3-ethyl-5-(1-ethylpropyl)-2-(2-fluoro-4-methoxyphenyl)-7-methylpyrrolo[2,1-f][1,2,4]triazin-4(3H)-one TLC: Rf 0.37 (ethyl acetate/n-hexane=1/6);
$^1$H-NMR (CDCl$_3$): δ 0.86 (t, J=7.3 Hz, 6 H), 1.08 (t, J=7.0 Hz, 3 H), 1.46-1.87 (m, 4 H), 2.38 (s, 3 H), 3.29-3.45 (m, 1 H), 3.46-3.79 (m, 1 H), 3.87 (s, 3 H), 3.90-4.21 (m, 1 H), 6.15 (s, 1 H), 6.74 (dd, J=11.4, 2.4 Hz, 1 H), 6.82 (dd, J=8.3, 2.4 Hz, 1 H), 7.37 (t, J=8.3 Hz, 1 H).

EXAMPLE 29(9)

3-ethyl-5-(1-ethylpropyl)-2-(6-methoxy-2-methyl-3-pyridinyl)-7-methylpyrrolo[2,1-f][1,2,4]triazin-4(3H)-one TLC: Rf 0.52 (ethyl acetate/n-hexane=1/6);
$^1$H-NMR (CDCl$_3$): δ 0.78-0.94 (m, 6 H), 1.06 (t, J=7.0 Hz, 3 H), 1.49-1.83 (m, 4 H), 2.38 (s, 3 H), 2.44 (s, 3 H), 3.31-3.60 (m, 2 H), 3.87-4.12 (m, 4 H), 6.16 (s, 1 H), 6.68 (d, J=8.4 Hz, 1 H), 7.54 (d, J=8.4 Hz, 1 H).

EXAMPLE 29(10)

2-(2-chloro-4-methoxy-5-methylphenyl)-3-ethyl-5-(1-ethylpropyl)-7-methylpyrrolo[2,1-f][1,2,4]triazin-4(3H)-one TLC: Rf 0.51 (ethyl acetate/n-hexane=1/6);
$^1$H-NMR (CDCl$_3$): δ 0.81-0.93 (m, 6 H), 1.07 (t, J=7.0 Hz, 3 H), 1.48-1.84 (m, 4 H), 2.23 (s, 3 H), 2.38 (s, 3 H), 3.33-3.51 (m, 2 H), 3.80-3.95 (m, 3 H), 4.04-4.21 (m, 1 H), 6.15 (s, 1 H), 6.91 (s, 1 H), 7.22 (s, 1 H).

EXAMPLE 29(11)

2-(2-chloro-4-methylphenyl)-3-ethyl-5-(1-ethylpropyl)-7-methylpyrrolo[2,1-f][1,2,4]triazin-4(3H)-one TLC: Rf 0.67 (ethyl acetate/n-hexane=1/6);
$^1$H-NMR (CDCl$_3$): δ 0.82-0.93 (m, 6 H), 1.05 (t, J=7.0 Hz, 3 H), 1.50-1.85 (m, 4 H), 2.29 (s, 3 H), 2.37 (d, J=0.7 Hz, 3 H), 3.24-3.50 (m, 2 H), 3.96-4.14 (m, 1 H), 6.16 (s, 1 H), 7.27-7.36 (m, 3 H).

EXAMPLE 29(12)

2-(4-chloro-2-methoxyphenyl)-3-ethyl-5-(1-ethylpropyl)-7-methylpyrrolo[2,1-f][1,2,4]triazin-4(3H)-one TLC: Rf 0.47 (ethyl acetate/n-hexane=1/6);
$^1$H-NMR (CDCl$_3$): δ 0.81-0.93 (m, 6 H), 1.04 (t, J=7.0 Hz, 3 H), 1.50-1.83 (m, 4 H), 2.38 (d, J=0.7 Hz, 3 H), 3.20-3.49 (m, 2 H), 3.85 (s, 3 H), 4.05-4.21 (m, 1 H), 6.15 (s, 1 H), 7.00 (d, J=1.8 Hz, 1 H), 7.08 (dd, J=8.1, 1.8 Hz, 1 H), 7.34 (d, J=8.1 Hz, 1 H).

EXAMPLE 29(13)

2-(2-chloro-4-ethoxyphenyl)-3-ethyl-5-(1-ethylpropyl)-7-methylpyrrolo[2,1-f][1,2,4]triazin-4(3H)-one TLC: Rf 0.46 (ethyl acetate/n-hexane=1/6);
$^1$H-NMR (CDCl$_3$): δ 0.80-0.94 (m, 6 H), 1.06 (t, J=7.0 Hz, 3 H), 1.46 (t, J=7.0 Hz, 3 H), 1.52-1.87 (m, 4 H), 2.39 (d, J=0.7 Hz, 3 H), 3.25-3.51 (m, 2 H), 3.97-4.30 (m, 3 H), 6.17 (s, 1 H), 6.92 (dd, J=8.4, 2.5 Hz, 1 H), 7.02 (d, J=2.4 Hz, 1 H), 7.39 (d, J=8.4 Hz, 1 H).

EXAMPLE 29(14)

3-ethyl-5-(1-ethylpropyl)-7-methyl-2-[2-methyl-4-(trifluoromethoxy)phenyl]pyrrolo[2,1-f][1,2,4]triazin-4(3H)-one TLC: Rf 0.64 (ethyl acetate/n-hexane=1/6);
$^1$H-NMR (CDCl$_3$): δ 0.82-0.93 (m, 6 H), 1.06 (t, J=7.0 Hz, 3 H), 1.47-1.83 (m, 4 H), 2.34 (s, 3 H), 2.38 (s, 3 H), 3.19-3.51 (m, 2 H), 3.94-4.17 (m, 1 H), 6.17 (s, 1 H), 7.12-7.21 (m, 2 H), 7.35-7.52 (m, 1 H).

EXAMPLE 29(15)

3-ethyl-5-(1-ethylpropyl)-2-(4-methoxy-2,5-dimethylphenyl)-7-methylpyrrolo[2,1-f][1,2,4]triazin-4(3H)-one TLC: Rf 0.31 (n-hexane/ethyl acetate=9/1);
$^1$H-NMR (CDCl$_3$): δ 0.80-0.95 (m, 6 H), 1.05 (t, J=7.0 Hz, 3 H), 1.52-1.83 (m, 4 H), 2.22 (s, 3 H), 2.27 (s, 3 H), 2.38 (s, 3 H), 3.32-3.55 (m, 2 H), 3.88 (s, 3 H), 3.96-4.15 (m, 1 H), 6.15 (s, 1 H), 6.73 (s, 1 H), 7.13 (s, 1 H).

EXAMPLE 29(16)

3-ethyl-5-(1-ethylpropyl)-2-(2-isopropyl-4-methoxyphenyl)-7-methylpyrrolo[2,1-f][1,2,4]triazin-4(3H)-one TLC: Rf 0.33 (n-hexane/ethyl acetate=9/1);
$^1$H-NMR (CDCl$_3$): δ 0.81-0.96 (m, 6 H), 1.07 (t, J=7.0 Hz, 3 H), 1.25 (t, J=7.3 Hz, 6 H), 1.51-1.84 (m, 4 H), 2.37 (s, 3 H), 2.77-2.92 (m, 1 H), 3.32-3.56 (m, 2 H), 3.87 (s, 3 H), 3.91-4.05 (m, 1 H), 6.16 (s, 1 H), 6.84 (dd, J=8.4, 2.6 Hz, 1 H), 6.95 (d, J=2.6 Hz, 1 H), 7.27 (d, J=8.4 Hz, 1 H).

EXAMPLE 29(17)

2-(2-chloro-5-fluoro-4-methoxyphenyl)-3-ethyl-5-(1-ethylpropyl)-7-methylpyrrolo[2,1-f][1,2,4]triazin-4(3H)-one TLC: Rf 0.57 (n-hexane/ethyl acetate=9/1);
$^1$H-NMR (CDCl$_3$): δ 0.74-0.92 (m, 6 H), 1.09 (t, J=7.0 Hz, 3 H), 1.56-1.86 (m, 4 H), 2.38 (s, 3 H), 3.20-3.50 (m, 2 H), 3.96 (s, 3 H), 4.07-4.29 (m, 1 H), 6.18 (s, 1 H), 7.08 (d, J=7.7 Hz, 1 H), 7.24 (d, J=10.6 Hz, 1 H).

EXAMPLE 29(18)

2-[4-(difluoromethoxy)-2-methylphenyl]-3-ethyl-5-(1-ethylpropyl)-7-methylpyrrolo[2,1-f][1,2,4]triazin-4(3H)-one TLC: Rf 0.59 (n-hexane/ethyl acetate=9/1);
$^1$H-NMR (CDCl$_3$): δ 0.79-0.96 (m, 6 H), 1.06 (t, J=6.9 Hz, 3 H), 1.56-1.86 (m, 4 H), 2.32 (s, 3 H), 2.34-2.41 (m, 3 H), 3.24-3.49 (m, 2 H), 3.96-4.17 (m, 1 H), 6.18 (s, 1 H), 6.58 (t, J=73.5 Hz, 1 H), 7.02-7.15 (m, 2 H), 7.31-7.45 (m, 1 H).

EXAMPLE 29(19)

2-[4-(difluoromethoxy)-5-fluoro-2-methylphenyl]-3-ethyl-5-(1-ethylpropyl)-7-methylpyrrolo[2,1-f][1,2,4]triazin-4(3H)-one TLC: Rf 0.40 (n-hexane/ethyl acetate=9/1);
$^1$H-NMR (CDCl$_3$): δ 0.75-0.99 (m, 6 H), 1.09 (t, J=7.0 Hz, 3 H), 1.56-1.89 (m, 4 H), 2.28 (s, 3 H), 2.31-2.43 (m, 3 H), 3.15-3.54 (m, 2 H), 3.93-4.22 (m, 1 H), 6.19 (s, 1 H), 6.62 (t, J=73.1 Hz, 1 H), 7.11-7.28 (m, 2 H).

EXAMPLE 29(20)

2-[4-(difluoromethoxy)-2-fluorophenyl]-3-ethyl-5-(1-ethylpropyl)-7-methylpyrrolo[2,1-f][1,2,4]triazin-4(3H)-one TLC: Rf 0.48 (ethyl acetate/n-hexane=1/6);
$^1$H-NMR (CDCl$_3$): δ 0.86 (t, J=7.4 Hz, 6 H), 1.09 (t, J=7.0 Hz, 3 H), 1.49-1.83 (m, 4 H), 2.38 (d, J=0.7 Hz, 3 H), 3.32-3.46 (m, 1 H), 3.47-3.81 (m, 1 H), 3.83-4.20 (m, 1 H), 6.18 (s, 1 H), 6.61 (t, J=72.5 Hz, 1 H), 7.00-7.06 (m, 1 H), 7.06-7.12 (m, 1 H), 7.51 (t, J=8.1 Hz, 1 H).

EXAMPLES 30(1)~(99)

By the same procedure as a series of reactions of Example 2→Example 3→Example 4→Example 5→Example 8, using methylmagnesium bromide instead of ethylmagnesium bromide, using an aqueous solution of 70% ethylamine instead of an aqueous solution of 40% methylamine, and using the corresponding aldehydes instead of the compound prepared in Example 7, the compounds of the present invention having the following physical data were obtained.

EXAMPLE 30(1)

2-{4-[(difluoromethyl)thio]-2-methylphenyl}-3-ethyl-5-isopropyl-7-methylpyrrolo[2,1-f][1,2,4]triazin-4(3H)-one

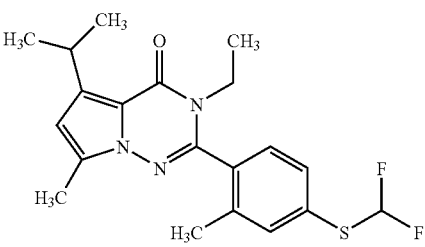 [SMILES: CCn1c(-c2ccc(SC(F)F)cc2C)nn2c(C)cc(C(C)C)c2c1=O]

TLC: Rf 0.56 (n-hexane/ethyl acetate=4/1);
$^1$H-NMR (CDCl$_3$): δ 1.06 (t, J=7.0 Hz, 3 H), 1.31 (d, J=6.8 Hz, 6 H), 2.32 (s, 3 H), 2.37 (s, 3 H), 3.25-3.44 (m, 1 H), 3.63-3.87 (m, 1 H), 3.95-4.17 (m, 1 H), 6.25 (s, 1 H), 6.90 (t, J=56.4 Hz, 1 H), 7.38 (d, J=8.4 Hz, 1 H), 7.49-7.58 (m, 2 H).

EXAMPLE 30(2)

2-[2-chloro-4-(difluoromethoxy)phenyl]-3-ethyl-5-isopropyl-7-methylpyrrolo[2,1-f][1,2,4]triazin-4(3H)-one TLC: Rf 0.64 (n-hexane/ethyl acetate=3/1);
$^1$H-NMR (CDCl$_3$): δ 1.08 (t, J=7.04 Hz, 3 H), 1.22-1.39 (m, 6 H), 2.38 (d, J=0.73 Hz, 3 H), 3.26-3.46 (m, 1 H), 3.65-3.85 (m, 1 H), 4.06-4.28 (m, 1 H), 6.26 (s, 1 H), 6.60 (t, J=72.45 Hz, 1 H), 7.20 (dd, J=8.42, 2.38 Hz, 1 H), 7.32 (d, J=2.38 Hz, 1 H), 7.49 (d, J=8.42 Hz, 1H).

EXAMPLE 30(3)

2-(2-chloro-4-methoxyphenyl)-3-ethyl-5-isopropyl-7-methylpyrrolo[2,1-f][1,2,4]triazin-4(3H)-one TLC: Rf 0.56 (n-hexane/ethyl acetate=3/1);
$^1$H-NMR (CDCl$_3$): δ 1.07 (t, J=7.04 Hz, 3 H), 1.24-1.41 (m, 6 H), 2.38 (s, 3 H), 3.29-3.48 (m, 1 H), 3.69-3.82 (m, 1 H), 3.87 (s, 3 H), 4.01-4.30 (m, 1 H), 6.25 (s, 1 H), 6.94 (dd, J=8.60, 2.56 Hz, 1 H), 7.04 (d, J=2.56 Hz, 1 H), 7.38 (d, J=8.60 Hz, 1 H).

EXAMPLE 30(4)

2-(4-chloro-2-methylphenyl)-3-ethyl-5-isopropyl-7-methylpyrrolo[2,1-f][1,2,4]triazin-4(3H)-one TLC: Rf 0.48 (n-hexane/ethyl acetate=9/1);
$^1$H-NMR (CDCl$_3$): δ 1.06 (t, J=7.0 Hz, 3 H), 1.31 (d, J=7.0 Hz, 6 H), 2.28 (s, 3 H), 2.37 (s, 3 H), 3.21-3.51 (m, 1 H), 3.60-3.84 (m, 1 H), 3.96-4.20 (m, 1 H), 6.25 (s, 1 H), 7.29-7.43 (m, 3 H).

EXAMPLE 30(5)

3-ethyl-5-isopropyl-2-(4-methoxy-2,6-dimethylphenyl)-7-methylpyrrolo[2,1-f][1,2,4]triazin-4(3H)-one TLC: Rf 0.43 (n-hexane/ethyl acetate=9/1);
$^1$H-NMR (CDCl$_3$): δ 1.06 (t, J=7.0 Hz, 3 H), 1.32 (d, J=7.0 Hz, 6 H), 2.23 (s, 6 H), 2.38 (s, 3 H), 3.48-3.84 (m, 3 H), 3.83 (s, 3 H), 6.25 (s, 1 H), 6.68 (s, 2 H).

EXAMPLE 30(6)

2-(2-chloro-4-methoxy-6-methylphenyl)-3-ethyl-5-isopropyl-7-methylpyrrolo[2,1-f][1,2,4]triazin-4(3H)-one TLC: Rf 0.44 (ethyl acetate/n-hexane=1/6);
$^1$H-NMR (CDCl$_3$): δ 1.05-1.18 (m, 3 H), 1.31 (d, J=6.8 Hz, 6 H), 2.27 (s, 3 H), 2.38 (d, J=0.7 Hz, 3 H), 3.47-3.95 (m, 6 H), 6.25 (s, 1 H), 6.72-6.82 (m, 1 H), 6.89 (d, J=2.4 Hz, 1H).

EXAMPLE 30(7)

3-ethyl-2-(2-ethyl-4-methoxyphenyl)-5-isopropyl-7-methylpyrrolo[2,1-f][1,2,4]triazin-4(3H)-one TLC: Rf 0.43 (n-hexane/ethyl acetate=9/1);
$^1$H-NMR (CDCl$_3$): δ 1.06 (t, J=7.0 Hz, 3 H), 1.23 (t, J=7.5 Hz, 3 H), 1.28-1.37 (m, 6 H), 2.37 (s, 3 H), 2.55 (q, J=7.5 Hz, 2 H), 3.30-3.57 (m, 1 H), 3.68-3.84 (m, 1 H), 3.86 (s, 3H), 3.92-4.08 (m, 1 H), 6.23 (s, 1 H), 6.83 (dd, J=8.4, 2.4 Hz, 1 H), 6.88 (d, J=2.4 Hz, 1H), 7.25 (d, J=8.4 Hz, 1 H).

EXAMPLE 30(8)

2-(4-chloro-2-methoxyphenyl)-3-ethyl-5-isopropyl-7-methylpyrrolo[2,1-f][1,2,4]triazin-4(3H)-one TLC: Rf 0.41 (n-hexane/ethyl acetate=9/1);
$^1$H-NMR (CDCl$_3$): δ 1.04 (t, J=7.0 Hz, 3 H), 1.30 (d, J=7.0 Hz, 6 H), 2.37 (s, 3 H), 3.24-3.45 (m, 1 H), 3.67-3.81 (m, 1 H), 3.83 (s, 3 H), 4.03-4.21 (m, 1 H), 6.22 (s, 1 H), 6.98 (d, J=2.0 Hz, 1 H), 7.07 (dd, J=8.1, 2.0 Hz, 1 H), 7.30 (d, J=8.1 Hz, 1 H).

EXAMPLE 30(9)

3-ethyl-5-isopropyl-2-(6-methoxy-2-methyl-3-pyridinyl)-7-methylpyrrolo[2,1-f][1,2,4]triazin-4(3H)-one TLC: Rf 0.33 (ethyl acetate/n-hexane=1/6);
$^1$H-NMR (CDCl$_3$): δ 1.03-1.09 (m, 3 H), 1.31 (d, J=7.0 Hz, 6 H), 2.38 (d, J=0.7 Hz, 3 H), 2.43 (s, 3 H), 3.38-3.57 (m, 1 H), 3.65-3.85 (m, 1 H), 3.88-4.20 (m, 4 H), 6.25 (s, 1 H), 6.69 (dd, J=8.4, 0.7 Hz, 1 H), 7.53 (d, J=8.4 Hz, 1 H).

EXAMPLE 30(10)

2-(2-chloro-4-methoxy-5-methylphenyl)-3-ethyl-5-isopropyl-7-methylpyrrolo[2,1-f][1,2,4]triazin-4(3H)-one TLC: Rf 0.60 (ethyl acetate/n-hexane=1/6);
$^1$H-NMR (CDCl$_3$): δ 1.08 (t, J=7.0 Hz, 3 H), 1.27-1.33 (m, 6 H), 2.23 (s, 3 H), 2.39 (s, 3H), 3.36-3.51 (m, 1 H), 3.70-3.82 (m, 1 H), 3.89 (s, 3 H), 4.06-4.21 (m, 1 H), 6.24 (s, 1H), 6.92 (s, 1 H), 7.20 (s, 1 H).

EXAMPLE 30(11)

3-ethyl-5-isopropyl-2-[4-methoxy-2-(trifluoromethyl)phenyl]-7-methylpyrrolo[2,1-f][1,2,4]triazin-4(3H)-one TLC: Rf 0.32 (ethyl acetate/n-hexane=1/6);
$^1$H-NMR (CDCl$_3$): δ 1.10 (t, J=7.0 Hz, 3 H), 1.27-1.35 (m, 6 H), 2.35 (s, 3 H), 3.29-3.46 (m, 1 H), 3.66-3.81 (m, 1 H), 3.92 (s, 3 H), 3.94-4.07 (m, 1 H), 6.23 (s, 1 H), 7.17 (dd, J=8.4, 2.7 Hz, 1 H), 7.29 (d, J=2.7 Hz, 1 H), 7.43 (d, J=8.4 Hz, 1 H).

EXAMPLE 30(12)

3-ethyl-2-(2-fluoro-4-methoxyphenyl)-5-isopropyl-7-methylpyrrolo[2,1-f][1,2,4]triazin-4(3H)-one TLC: Rf 0.38 (ethyl acetate/n-hexane=1/6);
$^1$H-NMR (CDCl$_3$): δ 1.08 (t, J=7.0 Hz, 3 H), 1.30 (d, J=7.0 Hz, 6 H), 2.38 (d, J=0.7 Hz, 3H), 3.40-3.84 (m, 2 H), 3.87 (s, 3 H), 3.90-4.32 (m, 1 H), 6.24 (s, 1 H), 6.74 (dd, J=11.3, 2.4 Hz, 1 H), 6.83 (dd, J=8.3, 2.4 Hz, 1 H), 7.36 (t, J=8.3 Hz, 1 H).

EXAMPLE 30(13)

3-ethyl-2-(5-fluoro-4-methoxy-2-methylphenyl)-5-isopropyl-7-methylpyrrolo[2,1-f][1,2,4]triazin-4(3H)-one TLC: Rf 0.44 (n-hexane/ethyl acetate=4/1);
$^1$H-NMR (CDCl$_3$): δ 1.07 (t, J=7.0 Hz, 3 H), 1.31 (d, J=7.0 Hz, 6 H), 2.25 (s, 3 H), 2.38 (s, 3 H), 3.32-3.50 (m, 1 H), 3.67-3.82 (m, 1 H), 3.94 (s, 3 H), 4.00-4.16 (m, 1 H), 6.25 (s, 1H), 6.88 (d, J=8.1 Hz, 1 H), 7.09 (d, J=11.0 Hz, 1 H).

EXAMPLE 30(14)

2-[2-chloro-4-(trifluoromethoxy)phenyl]-3-ethyl-5-isopropyl-7-methylpyrrolo[2,1-f][1,2,4]triazin-4(3H)-one TLC: Rf 0.51 (n-hexane/ethyl acetate=9/1);
$^1$H-NMR (CDCl$_3$): δ 1.09 (t, J=7.0 Hz, 3 H), 1.26-1.33 (m, 6 H), 2.38 (s, 3 H), 3.22-3.42 (m, 1 H), 3.67-3.86 (m, 1 H), 4.03-4.27 (m, 1 H), 6.25 (s, 1 H), 7.26-7.33 (m, 1 H), 7.35-7.44 (m, 1 H), 7.52 (d, J=8.4 Hz, 1 H).

EXAMPLE 30(15)

3-ethyl-5-isopropyl-7-methyl-2-[2-methyl-4-(1H-pyrazol-1-yl)phenyl]pyrrolo[2,1-f][1,2,4]triazin-4(3H)-one TLC: Rf 0.58 (n-hexane/ethyl acetate=9/1);
$^1$H-NMR (CDCl$_3$): δ 1.07 (t, J=7.0 Hz, 3 H), 1.31 (d, J=6.8 Hz, 6 H), 2.37 (s, 3 H), 2.39 (s, 3 H), 3.34-3.50 (m, 1 H), 3.68-3.84 (m, 1 H), 4.05-4.20 (m, 1 H), 6.25 (s, 1 H), 6.50 (dd, J=2.6, 1.8 Hz, 1 H), 7.44 (d, J=8.2 Hz, 1 H), 7.63 (dd, J=8.2, 2.2 Hz, 1 H), 7.69-7.74 (m, 1H), 7.74-7.79 (m, 1 H), 7.97 (dd, J=2.6, 0.6 Hz, 1 H).

EXAMPLE 30(16)

2-(2,4-dichlorophenyl)-3-ethyl-5-isopropyl-7-methylpyrrolo[2,1-f][1,2,4]triazin-4(3H)-one TLC: Rf 0.34 (n-hexane/ethyl acetate=9/1);
$^1$H-NMR (CDCl$_3$): δ 1.08 (t, J=7.0 Hz, 3 H), 1.20-1.37 (m, J=7.0, 1.5 Hz, 6 H), 2.37 (s, 3H), 3.26-3.42 (m, 1 H), 3.67-3.83 (m, 1 H), 4.08-4.26 (m, 1 H), 6.26 (s, 1 H), 7.42 (d, J=1.1 Hz, 2 H), 7.55 (t, J=1.2 Hz, 1 H).

EXAMPLE 30(17)

2-(2-chloro-5-fluoro-4-methoxyphenyl)-3-ethyl-5-isopropyl-7-methylpyrrolo[2,1-f][1,2,4]triazin-4(3H)-one TLC: Rf 0.33 (n-hexane/ethyl acetate=5/1);
$^1$H-NMR (CDCl$_3$): δ 1.10 (t, J=7.04 Hz, 3 H), 1.26-1.37 (m, 6 H), 2.38 (s, 3 H), 3.30-3.50 (m, 1 H), 3.68-3.82 (m, 1 H), 3.96 (s, 3 H), 4.05-4.26 (m, 1 H), 6.25 (s, 1 H), 7.08 (d, J=7.68 Hz, 1 H), 7.21 (d, J=10.61 Hz, 1 H).

EXAMPLE 30(18)

2-[4-(dimethylamino)-2-methylphenyl]-3-ethyl-5-isopropyl-7-methylpyrrolo[2,1-f][1,2,4]triazin-4(3H)-one TLC: Rf 0.45 (n-hexane/ethyl acetate=4/1);
$^1$H-NMR (CDCl$_3$): δ 1.06 (t, J=7.0 Hz, 3 H), 1.31 (d, J=7.0 Hz, 6 H), 2.24 (s, 3 H), 2.38 (s, 3 H), 3.01 (s, 6 H), 3.40-3.54 (m, 1 H), 3.71-3.83 (m, 1 H), 4.01-4.17 (m, 1 H), 6.22 (s, 1H), 6.57-6.66 (m, 2 H), 7.19 (d, J=8.2 Hz, 1 H).

EXAMPLE 30(19)

3-ethyl-5-isopropyl-7-methyl-2-[2-methyl-4-(trifluoromethoxy)phenyl]pyrrolo[2,1-f][1,2,4]triazin-4(3H)-one TLC: Rf 0.48 (ethyl acetate/n-hexane=1/6);
$^1$H-NMR (CDCl$_3$): δ 1.07 (t, J=7.0 Hz, 3 H), 1.27-1.35 (m, 6 H), 2.32 (s, 3 H), 2.38 (s, 3H), 3.26-3.44 (m, 1 H), 3.66-3.85 (m, 1 H), 3.99-4.17 (m, 1 H), 6.26 (s, 1 H), 7.13-7.23 (m, 2 H), 7.36-7.45 (m, 1 H).

EXAMPLE 30(20)

2-[4-(difluoromethoxy)-5-fluoro-2-methylphenyl]-3-ethyl-5-isopropyl-7-methylpyrrolo[2,1-f][1,2,4]triazin-4(3H)-one TLC: Rf 0.50 (n-hexane/ethyl acetate=4/1);
$^1$H-NMR (CDCl$_3$): δ 1.09 (t, J=7.0 Hz, 3 H), 1.31 (d, J=7.0 Hz, 6 H), 2.27 (s, 3 H), 2.38 (s, 3 H), 3.29-3.45 (m, 1 H), 3.68-3.82 (m, 1 H), 4.02-4.18 (m, 1 H), 6.24-6.28 (m, 1 H), 6.62 (t, J=73.1 Hz, 1 H), 7.18-7.24 (m, 2 H).

EXAMPLE 30(21)

2-[6-(dimethylamino)-2-methyl-3-pyridinyl]-3-ethyl-5-isopropyl-7-methylpyrrolo[2,1-f][1,2,4]triazin-4(3H)-one TLC: Rf 0.23 (n-hexane/ethyl acetate=9/1);
$^1$H-NMR (CDCl$_3$): δ 1.07 (t, J=7.0 Hz, 3 H), 1.30 (d, J=7.0 Hz, 6 H), 2.32-2.40 (m, 6 H), 3.14 (s, 6 H), 3.46-3.64 (m, 1 H), 3.69-3.84 (m, 1 H), 3.99-4.16 (m, 1 H), 6.23 (s, 1 H), 6.42 (d, J=8.6 Hz, 1 H), 7.39 (d, J=8.6 Hz, 1 H).

EXAMPLE 30(22)

2-[4-(difluoromethoxy)-2-methylphenyl]-3-ethyl-5-isopropyl-7-methylpyrrolo[2,1-f][1,2,4]triazin-4(3H)-one TLC: Rf 0.23 (n-hexane/ethyl acetate=9/1);
$^1$H-NMR (CDCl$_3$): δ 1.06 (t, J=6.9 Hz, 3 H), 1.28-1.36 (m, 6 H), 2.31 (s, 3 H), 2.34-2.43 (m, 3 H), 3.30-3.43 (m, 1 H), 3.63-3.83 (m, 1 H), 3.98-4.18 (m, 1 H), 6.25 (s, 1 H), 6.58 (t, J=73.4 Hz, 1 H), 7.02-7.15 (m, 2 H), 7.33-7.43 (m, 1 H).

EXAMPLE 30(23)

2-(2,4-dimethylphenyl)-3-ethyl-5-isopropyl-7-methylpyrrolo[2,1-f][1,2,4]triazin-4(3H)-one TLC: Rf 0.34 (n-hexane/ethyl acetate=9/1);
$^1$H-NMR (CDCl$_3$): δ 1.05 (t, J=7.0 Hz, 3 H), 1.27-1.38 (m, 6 H), 2.25 (s, 3 H), 2.33-2.45 (m, 6 H), 3.26-3.46 (m, 1 H), 3.66-3.84 (m, 1 H), 3.94-4.23 (m, 1 H), 6.24 (s, 1 H), 7.07-7.17 (m, 2 H), 7.21-7.26 (m, 1 H).

EXAMPLE 30(24)

3-ethyl-5-isopropyl-2-(4-methoxy-2,5-dimethylphenyl)-7-methylpyrrolo[2,1-f][1,2,4]triazin-4(3H)-one TLC: Rf 0.27 (n-hexane/ethyl acetate=9/1);
$^1$H-NMR (CDCl$_3$): δ 1.06 (t, J=7.0 Hz, 3 H), 1.23-1.39 (m, 6 H), 2.22 (s, 3 H), 2.25 (s, 3H), 2.38 (s, 3 H), 3.33-3.59 (m, 1 H), 3.67-3.83 (m, 1 H), 3.87 (s, 3 H), 3.96-4.15 (m, 1H), 6.23 (s, 1 H), 6.73 (s, 1 H), 7.10 (s, 1 H).

EXAMPLE 30(25)

2-(3-chloro-5-methoxy-2-pyridinyl)-3-ethyl-5-isopropyl-7-methylpyrrolo[2,1-f][1,2,4]triazin-4(3H)-one TLC: Rf 0.44 (toluene/ethyl acetate=10/1);
$^1$H-NMR (CDCl$_3$): δ 1.12 (t, J=7.0 Hz, 3 H), 1.23-1.39 (m, 8 H), 2.37-2.39 (m, 3 H), 3.69-3.82 (m, 3 H), 3.94 (s, 3 H), 6.22-6.25 (m, 1 H), 7.35 (d, J=2.6 Hz, 1 H), 8.31 (d, J=2.6 Hz, 1 H).

EXAMPLE 30(26)

2-(2-chloro-4-ethoxy-5-fluorophenyl)-3-ethyl-5-isopropyl-7-methylpyrrolo[2,1-f][1,2,4]triazin-4(3H)-one TLC: Rf 0.36 (n-hexane/ethyl acetate=9/1);
$^1$H-NMR (CDCl$_3$): δ 1.10 (t, J=6.9 Hz, 3 H), 1.27-1.35 (m, 6 H), 1.51 (t, J=7.0 Hz, 3 H), 2.33-2.44 (m, 3 H), 3.30-3.49 (m, 1 H), 3.66-3.83 (m, 1 H), 4.07-4.25 (m, 3 H), 6.25 (s, 1H), 7.06 (d, J=7.5 Hz, 1 H), 7.20 (d, J=10.6 Hz, 1 H).

EXAMPLE 30(27)

2-[4-chloro-2-(trifluoromethyl)phenyl]-3-ethyl-5-isopropyl-7-methylpyrrolo[2,1-f][1,2,4]triazin-4(3H)-one TLC: Rf 0.39 (n-hexane/ethyl acetate=9/1);
$^1$H-NMR (CDCl$_3$): δ 1.12 (t, J=7.0 Hz, 3 H), 1.19-1.37 (m, 6 H), 2.27-2.38 (m, 3 H), 3.23-3.45 (m, 1 H), 3.64-3.82 (m, 1 H), 3.91-4.10 (m, 1 H), 6.25 (s, 1 H), 7.49 (d, J=8.2 Hz, 1H), 7.69 (dd, J=8.2, 1.6 Hz, 1 H), 7.77-7.87 (m, 1 H).

EXAMPLE 30(28)

2-[4-(difluoromethoxy)-2,5-dimethylphenyl]-3-ethyl-5-isopropyl-7-methylpyrrolo[2,1-f][1,2,4]triazin-4(3H)-one TLC: Rf 0.44 (ethyl acetate/n-hexane=1/6);
$^1$H-NMR (CDCl$_3$): δ 1.07 (t, J=6.8 Hz, 3 H), 1.31 (d, J=6.8 Hz, 6 H), 2.26 (s, 3 H), 2.31 (s, 3 H), 2.38 (s, 3 H), 3.40 (dd, J=13.7, 7.0 Hz, 1 H), 3.68-3.82 (m, 1 H), 3.98-4.18 (m, 1 H), 6.25 (s, 1 H), 6.56 (t, J=73.7 Hz, 1 H), 7.03 (s, 1 H), 7.23 (s, 1 H).

EXAMPLE 30(29)

2-[2-chloro-4-(trifluoromethyl)phenyl]-3-ethyl-5-isopropyl-7-methylpyrrolo[2,1-f][1,2,4]triazin-4(3H)-one TLC: Rf 0.38 (n-hexane/ethyl acetate=7/1);
$^1$H-NMR (CDCl$_3$): δ 1.09 (t, J=7.1 Hz, 3 H), 1.22-1.37 (m, 6 H), 2.37 (d, J=0.7 Hz, 3 H), 3.25-3.40 (m, 1 H), 3.67-3.86 (m, 1 H), 4.08-4.27 (m, 1 H), 6.23-6.31 (m, 1 H), 7.61-7.67 (m, 1 H), 7.67-7.73 (m, 1 H), 7.81 (dd, J=1.1, 0.5 Hz, 1 H).

EXAMPLE 30(30)

2-[2-chloro-4-(difluoromethoxy)-5-fluorophenyl]-3-ethyl-5-isopropyl-7-methylpyrrolo[2,1-f][1,2,4]triazin-4(3H)-one TLC: Rf 0.28 (n-hexane/ethyl acetate=7/1);
$^1$H-NMR (CDCl$_3$): δ 1.12 (t, J=7.1 Hz, 3 H), 1.30 (d, J=7.0 Hz, 6 H), 2.38 (s, 3 H), 3.28-3.45 (m, 1 H), 3.66-3.85 (m, 1 H), 4.10-4.30 (m, 1 H), 6.27 (s, 1 H), 6.65 (t, J=72.2 Hz, 1H), 7.34 (d, J=9.7 Hz, 1 H), 7.45 (d, J=6.8 Hz, 1 H).

EXAMPLE 30(31)

2-[6-(difluoromethoxy)-4-methyl-3-pyridinyl]-3-ethyl-5-isopropyl-7-methylpyrrolo[2,1-f][1,2,4]triazin-4(3H)-one TLC: Rf 0.28 (n-hexane/ethyl acetate=9/1);
$^1$H-NMR (CDCl$_3$): δ 1.09 (t, J=6.9 Hz, 3 H), 1.31 (d, J=7.0 Hz, 6 H), 2.33 (s, 3 H), 2.37 (s, 3 H), 3.12-3.45 (m, 1 H), 3.58-3.91 (m, 1 H), 3.99-4.28 (m, 1 H), 6.27 (s, 1 H), 6.78-6.96 (m, 1 H), 7.45 (t, J=72.6 Hz, 1 H), 8.21 (s, 1 H).

EXAMPLE 30(32)

2-[4-chloro-2-(trifluoromethoxy)phenyl]-3-ethyl-5-isopropyl-7-methylpyrrolo[2,1-f][1,2,4]triazin-4(3H)-one TLC: Rf 0.43 (n-hexane/ethyl acetate=9/1);
$^1$H-NMR (CDCl$_3$): δ 1.08 (t, J=7.0 Hz, 3 H), 1.27-1.38 (m, 6 H), 2.36 (s, 3 H), 3.26-3.50 (m, 1 H), 3.62-3.86 (m, 1 H), 3.96-4.17 (m, 1 H), 6.26 (s, 1 H), 7.33-7.53 (m, 3 H).

EXAMPLE 30(33)

2-[2-chloro-4-(dimethylamino)-5-fluorophenyl]-3-ethyl-5-isopropyl-7-methylpyrrolo[2,1-f][1,2,4]triazin-4(3H)-one TLC: Rf 0.44 (n-hexane/ethyl acetate=3/1);
$^1$H-NMR (CDCl$_3$): δ 1.10 (t, J=7.0 Hz, 3 H), 1.27-1.33 (m, 6 H), 2.38 (d, J=0.7 Hz, 3 H), 2.97 (d, J=1.3 Hz, 6 H), 3.35-3.51 (m, 1 H), 3.69-3.82 (m, 1 H), 4.10-4.25 (m, 1 H), 6.25 (s, 1 H), 6.88 (d, J=8.1 Hz, 1 H), 7.09 (d, J=12.8 Hz, 1 H).

EXAMPLE 30(34)

2-(4-ethoxy-5-fluoro-2-methylphenyl)-3-ethyl-5-isopropyl-7-methylpyrrolo[2,1-f][1,2,4]triazin-4(3H)-one TLC: Rf 0.32 (n-hexane/ethyl acetate=7/1);
$^1$H-NMR (CDCl$_3$): δ 1.07 (t, J=7.0 Hz, 3 H), 1.30 (d, J=7.0 Hz, 6 H), 1.49 (t, J=7.0 Hz, 3H), 2.24 (s, 3 H), 2.38 (s, 3 H), 3.32-3.49 (m, 1 H), 3.66-3.86 (m, 1 H), 3.98-4.23 (m, 3H), 6.25 (s, 1 H), 6.87 (d, J=8.2 Hz, 1 H), 7.09 (d, J=11.0 Hz, 1 H).

EXAMPLE 30(35)

2-(2-chloro-4-isopropylphenyl)-3-ethyl-5-isopropyl-7-methylpyrrolo[2,1-f][1,2,4]triazin-4(3H)-one TLC: Rf 0.69 (n-hexane/ethyl acetate=7/1);
$^1$H-NMR (CDCl$_3$): δ 1.08 (t, J=7.0 Hz, 3 H), 1.19-1.40 (m, 12 H), 2.38 (d, J=0.7 Hz, 3 H), 2.89-3.05 (m, 1 H), 3.30-3.45 (m, 1 H), 3.69-3.85 (m, 1 H), 4.09-4.24 (m, 1 H), 6.25 (s, 1H), 7.26 (dd, J=7.9, 1.6 Hz, 1 H), 7.36 (d, J=1.6 Hz, 1 H), 7.39 (d, J=7.9 Hz, 1 H).

EXAMPLE 30(36)

2-[4-(difluoromethoxy)-2-ethylphenyl]-3-ethyl-5-isopropyl-7-methylpyrrolo[2,1-f][1,2,4]triazin-4(3H)-one TLC: Rf 0.54 (ethyl acetate/n-hexane=1/6);
$^1$H-NMR (CDCl$_3$): δ 1.02-1.11 (m, 3 H), 1.24 (t, J=7.6 Hz, 3 H), 1.31 (dd, J=6.9, 2.3 Hz, 6H), 2.37 (d, J=0.7 Hz, 3 H), 2.59 (q, J=7.6 Hz, 2 H), 3.33-3.47 (m, 1 H), 3.66-3.85 (m, 1H), 3.93-4.09 (m, 1 H), 6.25 (s, 1 H), 6.59 (t, J=73.5 Hz, 1 H), 7.05-7.11 (m, 1 H), 7.13 (d, J=2.0 Hz, 1 H), 7.33-7.39 (m, 1 H).

EXAMPLE 30(37)

2-[4-(difluoromethoxy)-2-fluorophenyl]-3-ethyl-5-isopropyl-7-methylpyrrolo[2,1-f][1,2,4]triazin-4(3H)-one TLC: Rf 0.54 (ethyl acetate/n-hexane=1/6);
$^1$H-NMR (CDCl$_3$): δ 1.09 (t, J=7.0 Hz, 3 H), 1.30 (d, J=7.0 Hz, 6 H), 2.38 (d, J=0.7 Hz, 3H), 3.34-3.83 (m, 2 H), 3.87 (s, 1 H), 6.25 (s, 1 H), 6.61 (t, J=72.5 Hz, 1 H), 7.00-7.06 (m, 1 H), 7.06-7.12 (m, 1 H), 7.48 (t, J=8.1 Hz, 1 H).

EXAMPLE 30(38)

2-[4-chloro-2-(difluoromethoxy)phenyl]-3-ethyl-5-isopropyl-7-methylpyrrolo[2,1-f][1,2,4]triazin-4(3H)-one TLC: Rf 0.60 (ethyl acetate/n-hexane=1/6);
$^1$H-NMR (CDCl$_3$): δ 1.08 (t, J=7.0 Hz, 3 H), 1.30 (dd, J=7.0, 1.5 Hz, 6 H), 2.38 (s, 3 H), 3.26-3.44 (m, 1 H), 3.67-3.84 (m, 1 H), 4.05-4.28 (m, 1 H), 6.26 (s, 1 H), 6.60 (t, J=72.5 Hz, 1 H), 7.20 (dd, J=8.4, 2.2 Hz, 1 H), 7.32 (d, J=2.2 Hz, 1 H), 7.49 (d, J=8.4 Hz, 1 H).

EXAMPLE 30(39)

4-(3-ethyl-5-isopropyl-7-methyl-4-oxo-3,4-dihydropyrrolo[2,1-f][1,2,4]triazin-2-yl)-3-methylbenzonitrile TLC: Rf 0.48 (n-hexane/ethyl acetate=4/1);
$^1$H-NMR (CDCl$_3$): δ 1.06 (t, J=7.0 Hz, 3 H), 1.31 (d, J=6.6 Hz, 6 H), 2.36 (s, 6 H), 3.21-3.40 (m, 1 H), 3.65-3.85 (m, 1 H), 3.97-4.18 (m, 1 H), 6.27 (s, 1 H), 7.42-7.56 (m, 1 H), 7.58-7.73 (m, 2 H).

EXAMPLE 30(40)

3-chloro-4-(3-ethyl-5-isopropyl-7-methyl-4-oxo-3,4-dihydropyrrolo[2,1-f][1,2,4]triazin-2-yl)benzonitrile TLC: Rf 0.45 (n-hexane/ethyl acetate=4/1);
$^1$H-NMR (CDCl$_3$): δ 1.08 (t, J=7.0 Hz, 3 H), 1.30 (dd, J=6.9, 1.6 Hz, 6 H), 2.36 (s, 3 H), 3.20-3.38 (m, 1 H), 3.68-3.81 (m, 1 H), 4.09-4.25 (m, 1 H), 6.24-6.31 (m, 1 H), 7.58-7.66 (m, 1 H), 7.71-7.77 (m, 1 H), 7.82-7.86 (m, 1 H).

EXAMPLE 30(41)

3-ethyl-2-(4-fluoro-2-methoxyphenyl)-5-isopropyl-7-methylpyrrolo[2,1-f][1,2,4]triazin-4(3H)-one TLC: Rf 0.31 (ethyl acetate/n-hexane=1/6);
$^1$H-NMR (CDCl$_3$): δ 1.04 (t, J=7.0 Hz, 3 H), 1.30 (d, J=7.0 Hz, 6 H), 2.38 (d, J=0.7 Hz, 3H), 3.27-3.42 (m, 1 H), 3.70-3.82 (m, 1 H), 3.83 (s, 3 H), 4.06-4.20 (m, 1 H), 6.23 (s, 1H), 6.73 (dd, J=10.5, 2.3 Hz, 1 H), 6.79 (dt, J=8.2, 2.3 Hz, 1 H), 7.35 (dd, J=8.2, 6.5 Hz, 1H).

EXAMPLE 30(42)

3-ethyl-5-isopropyl-7-methyl-2-[4-(methylthio)-2-(trifluoromethyl)phenyl]pyrrolo[2,1-f][1,2,4]triazin-4(3H)-one TLC: Rf 0.36 (ethyl acetate/n-hexane=1/6);
$^1$H-NMR (CDCl$_3$): δ 1.11 (t, J=7.0 Hz, 3 H), 1.27-1.33 (m, 6 H), 2.35 (s, 3 H), 2.58 (s, 3H), 3.29-3.50 (m, 1 H), 3.64-3.83 (m, 1 H), 3.92-4.08 (m, 1 H), 6.24 (s, 1 H), 7.38-7.46 (m, 1 H), 7.46-7.54 (m, 1 H), 7.61 (d, J=1.6 Hz, 1 H).

EXAMPLE 30(43)

3-ethyl-2-(4-isopropoxy-2-methylphenyl)-5-isopropyl-7-methylpyrrolo[2,1-f][1,2,4]triazin-4(3H)-one TLC: Rf 0.34 (ethyl acetate/n-hexane=1/6);
$^1$H-NMR (CDCl$_3$): δ 1.05 (t, J=7.0 Hz, 3 H), 1.31 (d, J=7.0 Hz, 6 H), 1.37 (d, J=6.0 Hz, 6H), 2.25 (s, 3 H), 2.38 (s, 3 H), 3.41 (dd, J=13.6, 7.0 Hz, 1 H), 3.67-3.86 (m, 1 H), 3.98-4.22 (m, 1 H), 4.51-4.70 (m, 1 H), 6.24 (s, 1 H), 6.76-6.86 (m, 2 H), 7.20-7.28 (m, 1 H).

EXAMPLE 30(44)

2-[2-chloro-4-(difluoromethoxy)-5-methylphenyl]-3-ethyl-5-isopropyl-7-methylpyrrolo[2,1-f][1,2,4]triazin-4(3H)-one TLC: Rf 0.38 (n-hexane/ethyl acetate=5/1);
$^1$H-NMR (CDCl$_3$): δ 1.09 (t, J=7.1 Hz, 3 H), 1.25-1.36 (m, 6 H), 2.33 (s, 3 H), 2.38 (d, J=0.7 Hz, 3 H), 3.31-3.47 (m, 1 H), 3.72-3.83 (m, 1 H), 4.03-4.26 (m, 1 H), 6.22-6.29 (m, 1 H), 6.60 (t, J=72.8 Hz, 1 H), 7.26 (s, 1 H), 7.35 (d, J=0.5 Hz, 1 H).

EXAMPLE 30(45)

2-(2-chloro-4-isopropoxyphenyl)-3-ethyl-5-isopropyl-7-methylpyrrolo[2,1-f][1,2,4]triazin-4(3H)-one TLC: Rf 0.38 (n-hexane/ethyl acetate=5/1);
$^1$H-NMR (CDCl$_3$): δ 1.07 (t, J=7.0 Hz, 3 H), 1.23-1.34 (m, 6 H), 1.38 (d, J=6.0 Hz, 6 H), 2.39 (d, J=0.7 Hz, 3 H), 3.31-3.47 (m, 1 H), 3.66-3.88 (m, 1 H), 4.08-4.28 (m, 1 H), 4.51-4.69 (m, 1 H), 6.19-6.32 (m, 1 H), 6.89 (dd, J=8.6, 2.6 Hz, 1 H), 7.01 (d, J=2.6 Hz, 1 H), 7.35 (d, J=8.6 Hz, 1 H).

EXAMPLE 30(46)

3-ethyl-5-isopropyl-7-methyl-2-(2,4,5-trifluorophenyl)pyrrolo[2,1-f][1,2,4]triazin-4(3H)-one TLC: Rf 0.50 (n-hexane/ethyl acetate=5/1);
$^1$H-NMR (CDCl$_3$): δ 1.11 (t, J=7.0 Hz, 3 H), 1.30 (d, J=7.0 Hz, 6 H), 2.38 (s, 3 H), 3.32-4.32 (m, 3 H), 6.26 (d, J=0.5 Hz, 1 H), 7.05-7.18 (m, 1 H), 7.29-7.40 (m, 1 H).

EXAMPLE 30(47)

2-(4,5-difluoro-2-methoxyphenyl)-3-ethyl-5-isopropyl-7-methylpyrrolo[2,1-f][1,2,4]triazin-4(3H)-one TLC: Rf 0.25 (n-hexane/ethyl acetate=5/1);
$^1$H-NMR (CDCl$_3$): δ 1.10 (t, J=7.0 Hz, 3 H), 1.29 (d, J=7.0 Hz, 6 H), 2.38 (s, 3 H), 3.30-4.34 (m, 6 H), 6.25 (s, 1 H), 6.82 (dd, J=10.4, 6.8 Hz, 1 H), 7.18 (dd, J=10.4, 6.4 Hz, 1 H).

EXAMPLE 30(48)

3-ethyl-5-isopropyl-2-[2-methoxy-4-(trifluoromethyl)phenyl]-7-methylpyrrolo[2,1-f][1,2,4]triazin-4(3H)-one TLC: Rf 0.59 (n-hexane/ethyl acetate=3/1);
$^1$H-NMR (CDCl$_3$): δ 1.05 (t, J=7.0 Hz, 3 H), 1.31 (d, J=7.0 Hz, 6 H), 2.37 (s, 3 H), 3.26-3.42 (m, 1 H), 3.70-3.82 (m, 1 H), 3.90 (s, 3 H), 4.05-4.21 (m, 1 H), 6.24 (s, 1 H), 7.19-7.24 (m, 1 H), 7.37 (dd, J=8.1, 0.7 Hz, 1 H), 7.52 (d, J=8.1 Hz, 1 H).

EXAMPLE 30(49)

3-ethyl-2-(2-ethyl-4-methoxy-6-methylphenyl)-5-isopropyl-7-methylpyrrolo[2,1-f][1,2,4]triazin-4(3H)-one TLC: Rf 0.53 (n-hexane/ethyl acetate=3/1);
$^1$H-NMR (CDCl$_3$): δ 1.04 (t, J=7.0 Hz, 3 H), 1.22 (t, J=7.5 Hz, 3 H), 1.29-1.36 (m, 6 H), 2.22 (s, 3 H), 2.38 (s, 3 H), 2.49 (q, J=7.5 Hz, 2 H), 3.49-3.64 (m, 1 H), 3.69-3.88 (m, 5H), 6.25 (s, 1 H), 6.69 (d, J=2.6 Hz, 1 H), 6.73 (d, J=2.6 Hz, 1 H).

EXAMPLE 30(50)

2-[2,4-bis(trifluoromethyl)phenyl]-3-ethyl-5-isopropyl-7-methylpyrrolo[2,1-f][1,2,4]triazin-4(3H)-one TLC: Rf 0.49 (n-hexane/ethyl acetate=3/1);
$^1$H-NMR (CDCl$_3$): δ 1.13 (t, J=7.0 Hz, 3 H), 1.27-1.36 (m, 6 H), 2.34 (d, J=0.7 Hz, 3 H), 3.24-3.44 (m, 1 H), 3.66-3.81 (m, 1 H), 3.92-4.09 (m, 1 H), 6.27 (s, 1 H), 7.72 (d, J=8.1 Hz, 1 H), 7.99 (d, J=8.1 Hz, 1 H), 8.10 (s, 1 H).

EXAMPLE 30(51)

3-ethyl-5-isopropyl-2-(2-isopropyl-4-methoxyphenyl)-7-methylpyrrolo[2,1-f][1,2,4]triazin-4(3H)-one TLC: Rf 0.55 (n-hexane/ethyl acetate=4/1);
$^1$H-NMR (CDCl$_3$): δ 1.07 (t, J=7.04 Hz, 3 H), 1.24 (dd, J=9.42, 7.04 Hz, 6 H), 1.31 (dd, J=6.95, 2.56 Hz, 6 H), 2.37 (d, J=0.73 Hz, 3 H), 2.74-2.91 (m, 1 H), 3.41-3.56 (m, 1 H), 3.70-3.85 (m, 1 H), 3.85-3.89 (m, 3 H), 3.91-4.06 (m, 1 H), 6.21-6.27 (m, 1 H), 6.84 (dd, J=8.51, 2.65 Hz, 1 H), 6.95 (d, J=2.65 Hz, 1 H), 7.22-7.28 (m, 1 H).

EXAMPLE 30(52)

2-(2-chloro-4-ethoxyphenyl)-3-ethyl-5-isopropyl-7-methylpyrrolo[2,1-f][1,2,4]triazin-4(3H)-one TLC: Rf 0.51 (n-hexane/ethyl acetate=4/1);
$^1$H-NMR (CDCl$_3$): δ 1.07 (t, J=7.04 Hz, 3 H), 1.28-1.34 (m, 6 H), 1.45 (t, J=6.95 Hz, 3 H), 2.38 (s, 3 H), 3.32-3.47 (m, 1 H), 3.69-3.84 (m, 1 H), 4.03-4.25 (m, 3 H), 6.25 (s, 1 H), 6.91 (dd, J=8.51, 2.38 Hz, 1 H), 7.02 (d, J=2.38 Hz, 1 H), 7.36 (d, J=8.51 Hz, 1 H).

EXAMPLE 30(53)

3-ethyl-5-isopropyl-2-(4-methoxy-2-methylphenyl)-7-methylpyrrolo[2,1-f][1,2,4]triazin-4(3H)-one TLC: Rf 0.47 (n-hexane/ethyl acetate=4/1);
$^1$H-NMR (CDCl$_3$): δ 1.06 (t, J=7.04 Hz, 3 H), 1.21-1.41 (m, 6 H), 2.27 (s, 3 H), 2.38 (s, 3H), 3.32-3.50 (m, 1 H), 3.70-3.82 (m, 1 H), 3.85 (s, 3 H), 4.00-4.17 (m, 1 H), 6.24 (s, 1H), 6.79-6.89 (m, 2 H), 7.23-7.33 (m, 1 H).

EXAMPLE 30(54)

2-[6-(difluoromethoxy)-2-methyl-3-pyridinyl]-3-ethyl-5-isopropyl-7-methylpyrrolo[2,1-f][1,2,4]triazin-4(3H)-one TLC: Rf 0.54 (n-hexane/ethyl acetate=4/1);
$^1$H-NMR (CDCl$_3$): δ 1.07 (t, J=7.04 Hz, 3 H), 1.30 (d, J=7.04 Hz, 6 H), 2.37 (s, 3 H), 2.45 (s, 3 H), 3.35-3.53 (m, 1 H), 3.68-3.81 (m, 1 H), 3.98-4.18 (m, 1 H), 6.26 (s, 1 H), 6.87 (d, J=8.42 Hz, 1 H), 7.31-7.83 (m, 2 H).

EXAMPLE 30(55)

2-(4-ethoxy-2-methylphenyl)-3-ethyl-5-isopropyl-7-methylpyrrolo[2,1-f][1,2,4]triazin-4(3H)-one TLC: Rf 0.50 (n-hexane/ethyl acetate=4/1);
$^1$H-NMR (CDCl$_3$): δ 1.05 (t, J=6.95 Hz, 3 H), 1.27-1.36 (m, 6 H), 1.44 (t, J=6.95 Hz, 3 H), 2.25 (s, 3 H), 2.38 (s, 3 H), 3.33-3.49 (m, 1 H), 3.68-3.84 (m, 1 H), 3.97-4.18 (m, 3 H), 6.24 (s, 1 H), 6.78-6.87 (m, 2 H), 7.20-7.31 (m, 1 H).

EXAMPLE 30(56)

3-ethyl-2-[4-fluoro-2-(trifluoromethyl)phenyl]-5-isopropyl-7-methylpyrrolo[2,1-f][1,2,4]triazin-4(3H)-one TLC: Rf 0.46 (n-hexane/ethyl acetate=4/1);
$^1$H-NMR (CDCl$_3$): δ 1.11 (t, J=7.04 Hz, 3 H), 1.24-1.36 (m, 6 H), 2.35 (s, 3 H), 3.26-3.43 (m, 1 H), 3.66-3.83 (m, 1 H), 3.92-4.17 (m, 1 H), 6.25 (s, 1 H), 7.34-7.47 (m, 1 H), 7.48-7.61 (m, 2 H).

EXAMPLE 30(57)

3-ethyl-2-(4-fluoro-2-methylphenyl)-5-isopropyl-7-methylpyrrolo[2,1-f][1,2,4]triazin-4(3H)-one TLC: Rf 0.50 (n-hexane/ethyl acetate=4/1);
$^1$H-NMR (CDCl$_3$): δ 1.06 (t, J=6.95 Hz, 3 H), 1.31 (d, J=6.95 Hz, 6 H), 2.30 (s, 3 H), 2.38 (s, 3 H), 3.27-3.45 (m, 1 H), 3.68-3.83 (m, 1 H), 3.99-4.16 (m, 1 H), 6.25 (s, 1 H), 6.97-7.08 (m, 2 H), 7.30-7.40 (m, 1 H).

EXAMPLE 30(58)

2-[4-(difluoromethoxy)-2,6-dimethylphenyl]-3-ethyl-5-isopropyl-7-methylpyrrolo[2,1-f][1,2,4]triazin-4(3H)-one TLC: Rf 0.38 (n-hexane/ethyl acetate=9/1);
$^1$H-NMR (CDCl$_3$): δ 1.07 (t, J=6.9 Hz, 3 H), 1.32 (d, J=7.0 Hz, 6 H), 2.27 (s, 6 H), 2.34-2.43 (m, 3 H), 3.56-3.88 (m, 3 H), 6.26 (s, 1 H), 6.56 (t, J=73.6 Hz, 1 H), 6.92 (s, 2 H).

EXAMPLE 30(59)

2-(2,6-difluoro-4-methoxyphenyl)-3-ethyl-5-isopropyl-7-methylpyrrolo[2,1-f][1,2,4]triazin-4(3H)-one TLC: Rf 0.28 (n-hexane/ethyl acetate=9/1);
$^1$H-NMR (CDCl$_3$): δ 1.12 (t, J=7.1 Hz, 3 H), 1.30 (d, J=7.0 Hz, 6 H), 2.38 (s, 3 H), 3.65-3.84 (m, 3 H), 3.87 (s, 3 H), 6.25 (s, 1 H), 6.52-6.64 (m, 2 H).

EXAMPLE 30(60)

2-(2-chloro-3,5-difluoro-4-methoxyphenyl)-3-ethyl-5-isopropyl-7-methylpyrrolo[2,1-f][1,2,4]triazin-4(3H)-one TLC: Rf 0.40 (n-hexane/ethyl acetate=9/1);
$^1$H-NMR (CDCl$_3$): δ 1.11 (t, J=7.0 Hz, 3 H), 1.26-1.38 (m, 6 H), 2.37 (s, 3 H), 3.26-3.47 (m, 1 H), 3.65-3.83 (m, 1 H), 4.03-4.26 (m, 4 H), 6.27 (s, 1 H), 7.01-7.18 (m, 1 H).

EXAMPLE 30(61)

2-[2-chloro-4-(difluoromethoxy)-6-methylphenyl]-3-ethyl-5-isopropyl-7-methylpyrrolo[2,1-f][1,2,4]triazin-4(3H)-one TLC: Rf 0.44 (ethyl acetate/n-hexane=1/6);
$^1$H-NMR (CDCl$_3$): δ 1.07-1.17 (m, 3 H), 1.31 (d, J=7.0 Hz, 6 H), 2.32 (s, 3 H), 2.38 (d, J=0.7 Hz, 3 H), 3.54-3.69 (m, 1 H), 3.69-3.86 (m, 2 H), 6.27 (s, 1 H), 6.58 (t, J=72.7 Hz, 1H), 7.03 (d, J=1.8 Hz, 1 H), 7.16 (d, J=1.8 Hz, 1 H).

EXAMPLE 30(62)

2-(5-chloro-2-methoxy-4-methylphenyl)-3-ethyl-5-isopropyl-7-methylpyrrolo[2,1-f][1,2,4]triazin-4(3H)-one TLC: Rf 0.32 (n-hexane/ethyl acetate=5/1);
$^1$H-NMR (CDCl$_3$): δ 1.06 (t, J=7.0 Hz, 3 H), 1.30 (d, J=7.0 Hz, 6 H), 2.38 (s, 3 H), 2.45 (s, 3 H), 3.31-3.47 (m, 1 H), 3.67-3.86 (m, 4 H), 4.04-4.21 (m, 1 H), 6.23 (s, 1 H), 6.85 (s, 1H), 7.34 (s, 1 H).

EXAMPLE 30(63)

2-[3-chloro-5-(trifluoromethyl)-2-pyridinyl]-3-ethyl-5-isopropyl-7-methylpyrrolo[2,1-f][1,2,4]triazin-4(3H)-one TLC: Rf 0.65 (n-hexane/ethyl acetate=4/1);
$^1$H-NMR (CDCl$_3$): δ 1.15 (t, J=6.95 Hz, 3 H), 1.30 (d, J=6.95 Hz, 6 H), 2.35-2.41 (m, 3 H), 3.69-3.84 (m, 3 H), 6.27-6.30 (m, 1 H), 8.14-8.17 (m, 1 H), 8.89-8.94 (m, 1 H).

EXAMPLE 30(64)

3-ethyl-5-isopropyl-2-mesityl-7-methylpyrrolo[2,1-f][1,2,4]triazin-4(3H)-one

TLC: Rf 0.57 (n-hexane/ethyl acetate=6/1);
$^1$H-NMR (CDCl$_3$): δ 1.06 (t, J=6.9 Hz, 3 H), 1.32 (d, J=7.0 Hz, 6 H), 2.21 (s, 6 H), 2.34 (s, 3 H), 2.37 (s, 3 H), 3.62-3.87 (m, 3 H), 6.24 (s, 1 H), 6.97 (s, 2 H).

EXAMPLE 30(65)

2-(2-chloro-6-fluoro-4-methoxyphenyl)-3-ethyl-5-isopropyl-7-methylpyrrolo[2,1-f][1,2,4]triazin-4(3H)-one TLC: Rf 0.50 (n-hexane/ethyl acetate=3/1);
$^1$H-NMR (CDCl$_3$): δ 1.12 (t, J=7.1 Hz, 3 H), 1.25-1.38 (m, 6 H), 2.38 (d, J=0.7 Hz, 3 H), 3.50-3.65 (m, 1 H), 3.70-3.82 (m, 1 H), 3.84-4.04 (m, 4 H), 6.26 (s, 1 H), 6.70 (dd, J=10.6, 2.4 Hz, 1 H), 6.89 (dd, J=2.4, 1.5 Hz, 1 H).

EXAMPLE 30(66)

2-(2-chloro-5-fluoro-4-methylphenyl)-3-ethyl-5-isopropyl-7-methylpyrrolo[2,1-f][1,2,4]triazin-4(3H)-one TLC: Rf 0.54 (n-hexane/ethyl acetate=3/1);
$^1$H-NMR (CDCl$_3$): δ 1.10 (t, J=7.0 Hz, 3 H), 1.27-1.34 (m, 6 H), 2.35 (d, J=1.6 Hz, 3 H), 2.37 (s, 3 H), 3.28-3.45 (m, 1 H), 3.66-3.82 (m, 1 H), 4.09-4.25 (m, 1 H), 6.24 (s, 1 H), 7.13 (d, J=8.8 Hz, 1 H), 7.33 (dd, J=8.8, 0.7 Hz, 1 H).

EXAMPLE 30(67)

2-[6-(dimethylamino)-4-methyl-3-pyridinyl]-3-ethyl-5-isopropyl-7-methylpyrrolo[2,1-f][1,2,4]triazin-4(3H)-one TLC: Rf 0.42 (n-hexane/ethyl acetate=9/1);
$^1$H-NMR (CDCl$_3$): δ 1.08 (t, J=7.0 Hz, 3 H), 1.30 (d, J=7.0 Hz, 6 H), 2.21 (s, 3 H), 2.30-2.48 (m, 3 H), 3.14 (s, 6 H), 3.26-3.58 (m, 1 H), 3.65-3.86 (m, 1 H), 3.99-4.29 (m, 1 H), 6.24 (s, 1 H), 6.41 (s, 1 H), 8.14 (s, 1 H).

EXAMPLE 30(68)

2-[2-chloro-4-(difluoromethoxy)-3,5-difluorophenyl]-3-ethyl-5-isopropyl-7-methylpyrrolo[2,1-f][1,2,4]triazin-4(3H)-one TLC: Rf 0.46 (ethyl acetate/n-hexane=1/6);
$^1$H-NMR (CDCl$_3$): δ 1.13 (t, J=7.0 Hz, 3 H), 1.30 (dd, J=6.9, 1.7 Hz, 6 H), 2.37 (d, J=0.7 Hz, 3 H), 3.25-3.46 (m, 1 H), 3.65-3.82 (m, 1 H), 4.05-4.28 (m, 1 H), 6.28 (s, 1 H), 6.69 (t, J=72.2 Hz, 1 H), 7.21 (dd, J=9.1, 2.3 Hz, 1 H).

EXAMPLE 30(69)

2-[4-(difluoromethoxy)-2,6-difluorophenyl]-3-ethyl-5-isopropyl-7-methylpyrrolo[2,1-f][1,2,4]triazin-4(3H)-one TLC: Rf 0.43 (ethyl acetate/n-hexane=1/6);
$^1$H-NMR (CDCl$_3$): δ 1.13 (t, J=7.0 Hz, 3 H), 1.30 (d, J=7.0 Hz, 6 H), 2.38 (d, J=0.7 Hz, 3H), 3.64-3.86 (m, 3 H), 6.26 (s, 1 H), 6.61 (t, J=71.9 Hz, 1 H), 6.88 (d, J=7.7 Hz, 2 H).

EXAMPLE 30(70)

2-(4-chloro-5-fluoro-2-methoxyphenyl)-3-ethyl-5-isopropyl-7-methylpyrrolo[2,1-f][1,2,4]triazin-4(3H)-one TLC: Rf 0.36 (ethyl acetate/n-hexane=1/6);
$^1$H-NMR (CDCl$_3$): δ 1.07 (t, J=7.0 Hz, 3 H), 1.30 (d, J=7.0 Hz, 6 H), 2.37 (s, 3 H), 3.27-3.44 (m, 1 H), 3.66-3.81 (m, 1 H), 3.82 (s, 3 H), 4.04-4.24 (m, 1 H), 6.24 (s, 1 H), 7.02 (d, J=5.9 Hz, 1 H), 7.21 (d, J=8.2 Hz, 1 H).

EXAMPLE 30(71)

2-[2-chloro-4-(difluoromethoxy)-6-fluorophenyl]-3-ethyl-5-isopropyl-7-methylpyrrolo[2,1-f][1,2,4]triazin-4(3H)-one TLC: Rf 0.66 (n-hexane/ethyl acetate=5/1);
$^1$H-NMR (CDCl$_3$): δ 1.14 (t, J=7.1 Hz, 3 H), 1.31 (d, J=6.8 Hz, 6 H), 2.38 (s, 3 H), 3.48-3.63 (m, 1 H), 3.70-3.82 (m, 1 H), 3.87-4.03 (m, 1 H), 6.27 (s, 1 H), 6.61 (t, J=71.9 Hz, 1H), 6.99 (dd, J=9.3, 1.8 Hz, 1 H), 7.16 (t, J=1.8 Hz, 1 H).

EXAMPLE 30(72)

2-(5-chloro-2,4-dimethoxyphenyl)-3-ethyl-5-isopropyl-7-methylpyrrolo[2,1-f][1,2,4]triazin-4(3H)-one TLC: Rf 0.23 (n-hexane/ethyl acetate=3/1);
$^1$H-NMR (CDCl$_3$): δ 1.06 (t, J=7.0 Hz, 3 H), 1.30 (d, J=6.8 Hz, 6 H), 2.38 (s, 3 H), 3.31-3.45 (m, 1 H), 3.66-3.82 (m, 1 H), 3.85 (s, 3 H), 3.98 (s, 3 H), 4.04-4.21 (m, 1 H), 6.22 (s, 1 H), 6.55 (s, 1 H), 7.36 (s, 1 H).

EXAMPLE 30(73)

3-ethyl-5-isopropyl-2-[4-methoxy-2-(methylthio)phenyl]-7-methylpyrrolo[2,1-f][1,2,4]triazin-4(3H)-one TLC: Rf 0.46 (n-hexane/ethyl acetate=5/1);
$^1$H-NMR (CDCl$_3$): δ 1.07 (t, J=7.0 Hz, 3 H), 1.30 (d, J=6.8 Hz, 6 H), 2.38 (s, 3 H), 2.45 (s, 3 H), 3.35-3.47 (m, 1 H), 3.69-3.82 (m, 1 H), 3.87 (s, 3 H), 4.04-4.17 (m, 1 H), 6.22 (s, 1H), 6.78 (dd, J=8.3, 2.5 Hz, 1 H), 6.86 (d, J=2.6 Hz, 1 H), 7.27 (d, J=8.4 Hz, 1 H).

EXAMPLE 30(74)

2-[4-chloro-2-(methylthio)phenyl]-3-ethyl-5-isopropyl-7-methylpyrrolo[2,1-f][1,2,4]triazin-4(3H)-one TLC: Rf 0.54 (n-hexane/ethyl acetate=4/1);
$^1$H-NMR (CDCl$_3$): δ 1.07 (t, J=7.0 Hz, 3 H), 1.30 (d, J=7.0 Hz, 6 H), 2.37 (s, 3 H), 2.48 (s, 3 H), 3.27-3.46 (m, 1 H), 3.68-3.82 (m, 1 H), 4.01-4.19 (m, 1 H), 6.23 (s, 1 H), 7.21-7.32 (m, 3 H).

EXAMPLE 30(75)

3-ethyl-5-isopropyl-7-methyl-2-[4-methyl-2-(methylthio)phenyl]pyrrolo[2,1-f][1,2,4]triazin-4(3H)-one TLC: Rf 0.38 (n-hexane/ethyl acetate=5/1);
$^1$H-NMR (CDCl$_3$): δ 1.07 (t, J=7.0 Hz, 3 H), 1.30 (d, J=7.0 Hz, 6 H), 2.38 (d, J=0.7 Hz, 3H), 2.43 (s, 3 H), 2.46 (s, 3 H), 3.27-3.50 (m, 1 H), 3.68-3.83 (m, 1 H), 4.00-4.20 (m, 1H), 6.23 (s, 1 H), 7.04-7.13 (m, 1 H), 7.17 (s, 1 H), 7.21-7.31 (m, 1 H).

EXAMPLE 30(76)

2-(3,5-dichloro-2-pyridinyl)-3-ethyl-5-isopropyl-7-methylpyrrolo[2,1-f][1,2,4]triazin-4(3H)-one TLC: Rf 0.40 (n-hexane/ethyl acetate=5/1);
$^1$H-NMR (CDCl$_3$): δ 1.14 (t, J=7.1 Hz, 3 H), 1.30 (d, J=7.0 Hz, 6 H), 2.37 (d, J=0.7 Hz, 3H), 3.65-3.83 (m, 3 H), 6.26 (s, 1 H), 7.92 (d, J=2.2 Hz, 1 H), 8.61 (d, J=2.2 Hz, 1 H).

EXAMPLE 30(77)

2-[2,5-dimethyl-4-(methylthio)phenyl]-3-ethyl-5-isopropyl-7-methylpyrrolo[2,1-f][1,2,4]triazin-4(3H)-one TLC: Rf 0.49 (n-hexane/ethyl acetate=4/1);
$^1$H-NMR (CDCl$_3$): δ 1.06 (t, J=7.0 Hz, 3 H), 1.30 (d, J=7.0 Hz, 6 H), 2.26 (s, 3 H), 2.32 (s, 3 H), 2.37 (d, J=0.7 Hz, 3 H), 2.51 (s, 3 H), 3.34-3.51 (m, 1 H), 3.68-3.83 (m, 1 H), 3.96-4.14 (m, 1 H), 6.23 (d, J=0.7 Hz, 1 H), 7.02 (s, 1 H), 7.09 (s, 1 H).

EXAMPLE 30(78)

2-[4-(dimethylamino)-5-fluoro-2-methylphenyl]-3-ethyl-5-isopropyl-7-methylpyrrolo[2,1-f][1,2,4]triazin-4(3H)-one TLC: Rf 0.50 (n-hexane/ethyl acetate=4/1);
$^1$H-NMR (CDCl$_3$): δ 1.08 (t, J=6.9 Hz, 3 H), 1.31 (d, J=7.0 Hz, 6 H), 2.22 (s, 3 H), 2.38 (s, 3 H), 2.92 (s, 6 H), 3.37-3.53 (m, 1 H), 3.68-3.83 (m, 1 H), 4.01-4.19 (m, 1 H), 6.24 (s, 1H), 6.74 (d, J=9.0 Hz, 1 H), 7.00 (d, J=13.0 Hz, 1 H).

EXAMPLE 30(79)

3-ethyl-5-isopropyl-2-[4-(isopropylthio)-2,5-dimethylphenyl]-7-methylpyrrolo[2,1-f][1,2,4]triazin-4(3H)-one TLC: Rf 0.48 (n-hexane/ethyl acetate=4/1);
$^1$H-NMR (CDCl$_3$): δ 1.06 (t, J=7.0 Hz, 3 H), 1.30 (d, J=6.9 Hz, 6 H), 1.35-1.45 (m, 6 H), 2.24 (s, 3 H), 2.37 (s, 3 H), 2.38 (s, 3 H), 3.33-3.56 (m, 2 H), 3.69-3.82 (m, 1 H), 3.97-4.15 (m, 1 H), 6.23 (s, 1 H), 7.14 (s, 1 H), 7.22 (s, 1 H).

EXAMPLE 30(80)

2-[4-(difluoromethoxy)-2-ethyl-6-methylphenyl]-3-ethyl-5-isopropyl-7-methylpyrrolo[2,1-f][1,2,4]triazin-4(3H)-one TLC: Rf 0.51 (ethyl acetate/n-hexane=1/6);
$^1$H-NMR (CDCl$_3$): δ 1.01-1.09 (m, 3 H), 1.19-1.26 (m, 3 H), 1.31 (d, J=1.1 Hz, 6 H), 2.25 (s, 3 H), 2.37 (d, J=0.7 Hz, 3 H), 2.45-2.59 (m, 2 H), 3.46-3.62 (m, 1 H), 3.67-3.83 (m, 2H), 6.25 (s, 1 H), 6.56 (t, J=73.6 Hz, 1 H), 6.91 (d, J=2.0 Hz, 1 H), 6.95 (d, J=2.0 Hz, 1H).

EXAMPLE 30(81)

2-[4-(difluoromethoxy)-2-isopropylphenyl]-3-ethyl-5-isopropyl-7-methylpyrrolo[2,1-f][1,2,4]triazin-4(3H)-one TLC: Rf 0.49 (ethyl acetate/n-hexane=1/6);
$^1$H-NMR (CDCl$_3$): δ 1.08 (t, J=7.0 Hz, 3 H), 1.19-1.28 (m, 6 H), 1.29-1.36 (m, 6 H), 2.36 (s, 3 H), 2.76-2.99 (m, 1 H), 3.37-3.54 (m, 1 H), 3.66-3.84 (m, 1 H), 3.88-4.05 (m, 1 H), 6.24 (s, 1 H), 6.58 (t, J=73.3 Hz, 1 H), 7.06 (dd, J=8.4, 2.4 Hz, 1 H), 7.16 (d, J=2.4 Hz, 1H), 7.32 (d, J=8.4 Hz, 1 H).

EXAMPLE 30(82)

2-[2-(difluoromethyl)-4-methoxyphenyl]-3-ethyl-5-isopropyl-7-methylpyrrolo[2,1-f][1,2,4]triazin-4(3H)-one TLC: Rf 0.38 (n-hexane/ethyl acetate=4/1);
$^1$H-NMR (CDCl$_3$): δ 1.10 (t, J=7.0 Hz, 3 H), 1.30 (d, J=7.0 Hz, 6 H), 2.36 (s, 3 H), 3.49-3.69 (m, 1 H), 3.68-3.83 (m, 1 H), 3.82-4.04 (m, 4 H), 6.25 (s, 1 H), 6.82 (t, J=55.4 Hz, 1H), 7.07-7.16 (m, 1 H), 7.29 (d, J=2.4 Hz, 1H), 7.39 (d, J=8.4 Hz, 1 H).

EXAMPLE 30(83)

2-[2-chloro-5-methyl-4-(methylthio)phenyl]-3-ethyl-5-isopropyl-7-methylpyrrolo[2,1-f][1,2,4]triazin-4(3H)-one TLC: Rf 0.38 (n-hexane/ethyl acetate=9/1);
$^1$H-NMR (CDCl$_3$): δ 1.09 (t, J=7.0 Hz, 3 H), 1.25-1.36 (m, 6 H), 2.33 (s, 3 H), 2.34-2.42 (m, 3 H), 2.53 (s, 3 H), 3.31-3.53 (m, 1 H), 3.67-3.87 (m, 1 H), 4.05-4.26 (m, 1 H), 6.25 (s, 1 H), 7.18 (s, 1 H), 7.19-7.22 (m, 1 H).

EXAMPLE 30(84)

2-(2,5-dichloro-4-methoxyphenyl)-3-ethyl-5-isopropyl-7-methylpyrrolo[2,1-f][1,2,4]triazin-4(3H)-one TLC: Rf 0.43 (n-hexane/ethyl acetate=5/1);
$^1$H-NMR (CDCl$_3$): δ 1.05-1.15 (m, 3 H), 1.30 (dd, J=6.9, 1.0 Hz, 6 H), 2.38 (d, J=0.7 Hz, 3H), 3.31-3.47 (m, 1 H), 3.67-3.80 (m, 1 H), 3.97 (s, 3 H), 4.07-4.22 (m, 1 H), 6.24 (s, 1H), 7.04 (s, 1 H), 7.47 (s, 1 H).

EXAMPLE 30(85)

3-ethyl-5-isopropyl-2-[4-isopropyl-2-(methylthio)phenyl]-7-methylpyrrolo[2,1-f][1,2,4]triazin-4(3H)-one TLC: Rf 0.55 (n-hexane/ethyl acetate=4/1);
$^1$H-NMR (CDCl$_3$): δ 1.07 (t, J=6.9 Hz, 3 H), 1.30 (d, J=7.0 Hz, 12 H), 2.38 (s, 3 H), 2.47 (s, 3 H), 2.89-3.06 (m, 1 H), 3.32-3.46 (m, 1 H), 3.68-3.83 (m, 1 H), 4.02-4.16 (m, 1 H), 6.22 (s, 1 H), 7.13 (dd, J=7.8, 1.6 Hz, 1 H), 7.18-7.22 (m, 1 H), 7.25-7.29 (m, 1 H).

EXAMPLE 30(86)

3-ethyl-2-[5-fluoro-2-methyl-4-(methylthio)phenyl]-5-isopropyl-7-methylpyrrolo[2,1-f][1,2,4]triazin-4(3H)-one TLC: Rf 0.44 (n-hexane/ethyl acetate=5/1);
$^1$H-NMR (CDCl$_3$): δ 1.03-1.12 (m, 3 H), 1.31 (d, J=7.0 Hz, 6 H), 2.26 (s, 3 H), 2.37 (d, J=0.7 Hz, 3 H), 2.52 (s, 3 H), 3.28-3.48 (m, 1 H), 3.69-3.84 (m, 1 H), 3.97-4.17 (m, 1 H), 6.25 (s, 1 H), 7.05 (d, J=9.7 Hz, 1 H), 7.15 (d, J=7.1 Hz, 1 H).

EXAMPLE 30(87)

2-{2-chloro-4-[(difluoromethyl)thio]phenyl}-3-ethyl-5-isopropyl-7-methylpyrrolo[2,1-f][1,2,4]triazin-4(3H)-one TLC: Rf 0.56 (n-hexane/ethyl acetate=4/1);
$^1$H-NMR (CDCl$_3$): δ 1.09 (t, J=7.0 Hz, 3 H), 1.31 (dd, J=7.0, 1.5 Hz, 6 H), 2.38 (d, J=0.7 Hz, 3 H), 3.34 (dd, J=14.1, 7.1 Hz, 1 H), 3.67-3.84 (m, 1 H), 4.17 (dd, J=14.1, 7.0 Hz, 1H), 6.27 (s, 1 H), 6.94 (t, J=56.2 Hz, 1 H), 7.47-7.54 (m, 1 H), 7.59-7.67 (m, 1 H), 7.75 (d, J=1.8 Hz, 1 H).

EXAMPLE 30(88)

3-ethyl-5-isopropyl-7-methyl-2-(2,4,5-trimethylphenyl)pyrrolo[2,1-f][1,2,4]triazin-4(3H)-one TLC: Rf 0.65 (n-hexane/ethyl acetate=4/1);
$^1$H-NMR (CDCl$_3$): δ 1.06 (t, J=7.0 Hz, 3 H), 1.27-1.37 (m, 6 H), 2.21 (s, 3 H), 2.27 (s, 3H), 2.29 (s, 3 H), 2.38 (s, 3 H), 3.35-3.49 (m, 1 H), 3.68-3.83 (m, 1 H), 3.95-4.13 (m, 1H), 6.23 (s, 1 H), 7.08 (s, 1 H), 7.11 (s, 1 H).

EXAMPLE 30(89)

2-[2-chloro-4-(1-hydroxy-1-methylethyl)phenyl]-3-ethyl-5-isopropyl-7-methylpyrrolo[2,1-f][1,2,4]triazin-4(3H)-one TLC: Rf 0.21 (n-hexane/ethyl acetate=3/1);
$^1$H-NMR (CDCl$_3$): δ 1.08 (t, J=7.0 Hz, 3 H), 1.31 (dd, J=6.8, 1.5 Hz, 6 H), 1.63 (s, 6 H), 1.80 (s, 1 H), 2.38 (d, J=0.7 Hz, 3 H), 3.29-3.44 (m, 1 H), 3.69-3.84 (m, 1 H), 4.07-4.26 (m, 1 H), 6.22-6.27 (m, 1 H), 7.40-7.46 (m, 1 H), 7.47-7.54 (m, 1 H), 7.65 (d, J=1.6 Hz, 1H).

EXAMPLE 30(90)

2-(5-chloro-4-methoxy-2-methylphenyl)-3-ethyl-5-isopropyl-7-methylpyrrolo[2,1-f][1,2,4]triazin-4(3H)-one TLC: Rf 0.31 (n-hexane/ethyl acetate=4/1);
$^1$H-NMR (CDCl$_3$): δ 1.07 (t, J=6.8 Hz, 3 H), 1.31 (d, J=6.8 Hz, 6 H), 2.28 (s, 3 H), 2.38 (s, 3 H), 3.33-3.50 (m, 1 H), 3.68-3.82 (m, 1 H), 3.96 (s, 3 H), 4.00-4.18 (m, 1 H), 6.25 (s, 1H), 6.85 (s, 1 H), 7.37 (s, 1 H).

EXAMPLE 30(91)

3-ethyl-5-isopropyl-7-methyl-2-[2-methyl-4-(trifluoromethyl)phenyl]pyrrolo[2,1-f][1,2,4]triazin-4(3H)-one TLC: Rf 0.56 (n-hexane/ethyl acetate=5/1);
$^1$H-NMR (CDCl$_3$): δ 1.07 (t, J=7.0 Hz, 3 H), 1.31 (dd, J=7.0, 1.1 Hz, 6 H), 2.37 (s, 6 H), 3.23-3.43 (m, 1 H), 3.65-3.84 (m, 1 H), 3.99-4.16 (m, 1 H), 6.27 (s, 1 H), 7.47-7.54 (m, 1H), 7.57-7.64 (m, 2 H).

EXAMPLE 30(92)

2-[2,5-dimethyl-4-(1-pyrrolidinyl)phenyl]-3-ethyl-5-isopropyl-7-methylpyrrolo[2,1-f][1,2,4]triazin-4(3H)-one TLC: Rf 0.38 (n-hexane/ethyl acetate=5/1);
$^1$H-NMR (CDCl$_3$): δ 1.06 (t, J=7.0 Hz, 3 H), 1.31 (d, J=7.0 Hz, 6 H), 1.90-2.02 (m, 4 H), 2.21 (s, 3 H), 2.33 (s, 3 H), 2.38 (s, 3 H), 3.23-3.36 (m, 4 H), 3.39-3.58 (m, 1 H), 3.68-3.86 (m, 1 H), 3.96-4.17 (m, 1 H), 6.23 (s, 1 H), 6.69 (s, 1 H), 7.04 (s, 1 H).

EXAMPLE 30(93)

2-[5-chloro-4-(dimethylamino)-2-methylphenyl]-3-ethyl-5-isopropyl-7-methylpyrrolo[2,1-f][1,2,4]triazin-4(3H)-one TLC: Rf 0.33 (n-hexane/ethyl acetate=5/1);
$^1$H-NMR (CDCl$_3$): δ 1.09 (t, J=7.0 Hz, 3 H), 1.31 (d, J=6.8 Hz, 6 H), 2.24 (s, 3 H), 2.38 (s, 3 H), 2.88 (s, 6 H), 3.34-3.51 (m, 1 H), 3.67-3.84 (m, 1 H), 3.97-4.16 (m, 1 H), 6.25 (s, 1H), 6.94 (s, 1 H), 7.34 (s, 1 H).

EXAMPLE 30(94)

2-[5-chloro-4-(difluoromethoxy)-2-methylphenyl]-3-ethyl-5-isopropyl-7-methylpyrrolo[2,1-f][1,2,4]triazin-4(3H)-one TLC: Rf 0.61 (n-hexane/ethyl acetate=3/1);
$^1$H-NMR (CDCl$_3$): δ 1.09 (t, J=6.8 Hz, 3 H), 1.30 (d, J=6.8 Hz, 6 H), 2.29 (s, 3 H), 2.37 (s, 3 H), 3.29-3.46 (m, 1 H), 3.66-3.83 (m, 1 H), 4.00-4.18 (m, 1 H), 6.26 (s, 1 H), 6.61 (t, J=72.9 Hz, 1 H), 7.21 (s, 1 H), 7.47 (s, 1 H).

EXAMPLE 30(95)

2-[4-(dimethylamino)-2,5-dimethylphenyl]-3-ethyl-5-isopropyl-7-methylpyrrolo[2,1-f][1,2,4]triazin-4(3H)-one TLC: Rf 0.33 (ethyl acetate/n-hexane=1/6);
$^1$H-NMR (CDCl$_3$): δ 0.99-1.12 (m, 3 H), 1.31 (d, J=7.0 Hz, 6 H), 2.22 (s, 3 H), 2.32 (s, 3H), 2.38 (d, J=0.7 Hz, 3 H), 2.75 (s, 6 H), 3.36-3.54 (m, 1 H), 3.68-3.86 (m, 1 H), 3.96-4.15 (m, 1 H), 6.23 (s, 1 H), 6.88 (s, 1 H), 7.11 (s, 1 H).

EXAMPLE 30(96)

2-(4-chloro-2-methoxy-5-methylphenyl)-3-ethyl-5-isopropyl-7-methylpyrrolo[2,1-f][1,2,4]triazin-4(3H)-one TLC: Rf 0.57 (n-hexane/ethyl acetate=4/1);
$^1$H-NMR (CDCl$_3$): δ 1.05 (t, J=7.1 Hz, 3 H), 1.30 (d, J=7.0 Hz, 6 H), 2.36 (s, 3 H), 2.38 (s, 3 H), 3.30-3.47 (m, 1 H), 3.67-3.83 (m, 4 H), 4.02-4.18 (m, 1 H), 6.23 (s, 1 H), 7.00 (s, 1H), 7.22 (s, 1 H).

EXAMPLE 30(97)

2-[5-(dimethylamino)-3-methyl-2-pyridinyl]-3-ethyl-5-isopropyl-7-methylpyrrolo[2,1-f][1,2,4]triazin-4(3H)-one TLC: Rf 0.43 (n-hexane/ethyl acetate=1/1);
$^1$H-NMR (CDCl$_3$): δ 1.09 (t, J=7.0 Hz, 3 H), 1.30 (d, J=6.8 Hz, 6 H), 2.31 (s, 3 H), 2.38 (s, 3 H), 3.05 (s, 6 H), 3.66-3.92 (m, 3 H), 6.22 (s, 1 H), 6.85 (d, J=2.7 Hz, 1 H), 8.03 (d, J=2.7 Hz, 1 H).

EXAMPLE 30(98)

2-[3-chloro-5-(dimethylamino)-2-pyridinyl]-3-ethyl-5-isopropyl-7-methylpyrrolo[2,1-f][1,2,4]triazin-4(3H)-one TLC: Rf 0.57 (ethyl acetate/n-hexane=1/6);
$^1$H-NMR (CDCl$_3$): δ 1.07-1.18 (m, 3 H), 1.29 (d, J=6.8 Hz, 6 H), 2.38 (d, J=0.7 Hz, 3 H), 3.08 (s, 6 H), 3.63-3.90 (m, 3 H), 6.22 (s, 1 H), 7.00 (d, J=2.7 Hz, 1 H), 8.06 (d, J=2.7 Hz, 1 H).

EXAMPLE 30(99)

2-[3-chloro-5-(difluoromethoxy)-2-pyridinyl]-3-ethyl-5-isopropyl-7-methylpyrrolo[2,1-f][1,2,4]triazin-4(3H)-one TLC: Rf 0.42 (n-hexane/ethyl acetate=3/1);
$^1$H-NMR (CDCl$_3$): δ 1.14 (t, J=6.8 Hz, 3 H), 1.30 (d, J=6.8 Hz, 6 H), 2.38 (d, J=0.7 Hz, 3 H), 3.69-3.84 (m, 3 H), 6.23-6.30 (m, 1 H), 6.67 (t, J=71.4 Hz, 1 H), 7.72 (d, J=2.6 Hz, 1 H), 8.52 (d, J=2.6 Hz, 1 H).

EXAMPLES 31(1)~(27)

By the same procedure as a series of reactions of Example 5→Example 8, using the compound provided by using cyclopropylamine instead of an aqueous solution of 40% methylamine instead of the compound prepared in Example 4, and using the corresponding aldehydes instead of the compound prepared in Example 7, the compounds of the present invention having the following physical data were obtained.

EXAMPLE 31(1)

3-cyclopropyl-5-(1-ethylpropyl)-2-(4-methoxy-2-methylphenyl)-7-methylpyrrolo[2,1-f][1,2,4]triazin-4(3H)-one

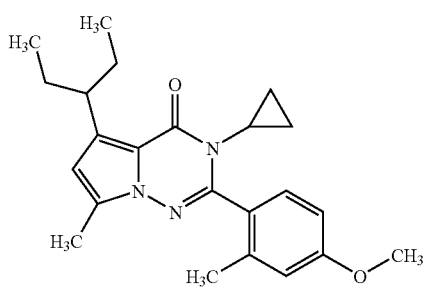 [SMILES: CCC(CC)c1cc(C)n2nc(-c3ccc(OC)cc3C)n(C3CC3)c(=O)c12]

TLC: Rf 0.38 (n-hexane/ethyl acetate=4/1);
$^1$H-NMR (CDCl$_3$): δ 0.43-0.62 (m, 2 H), 0.66-0.97 (m, 8 H), 1.52-1.88 (m, 4 H), 2.38 (s, 6H), 2.68 (m, 1 H), 3.40 (m, 1 H), 3.85 (s, 3 H), 6.13 (s, 1 H), 6.73-6.92 (m, 2 H), 7.24-7.37 (m, 1 H).

EXAMPLE 31(2)

3-cyclopropyl-2-(2-ethyl-4-methoxyphenyl)-5-(1-ethylpropyl)-7-methylpyrrolo[2,1-f][1,2,4]triazin-4(3H)-one TLC: Rf 0.31 (n-hexane/ethyl acetate=9/1);
$^1$H-NMR (CDCl$_3$): δ 0.41 (m, 1 H), 0.52-0.95 (m, 9 H), 1.30 (t, J=7.5 Hz, 3 H), 1.51-1.83 (m, 4 H), 2.38 (s, 3 H), 2.59-2.76 (m, 3 H), 3.31-3.48 (m, 1 H), 3.87 (s, 3 H), 6.13 (s, 1H), 6.83 (dd, J=8.4, 2.6 Hz, 1 H), 6.89 (d, J=2.6 Hz, 1 H), 7.26-7.33 (m, 1 H).

EXAMPLE 31(3)

2-[2-chloro-4-(difluoromethoxy)phenyl]-3-cyclopropyl-5-(1-ethylpropyl)-7-methylpyrrolo[2,1-f][1,2,4]triazin-4(3H)-one TLC: Rf 0.28 (n-hexane/ethyl acetate=9/1);
$^1$H-NMR (CDCl$_3$): δ 0.28-0.55 (m, 1 H), 0.57-1.04 (m, 9 H), 1.57-1.84 (m, 4 H), 2.29-2.44 (m, 3 H), 2.79-2.98 (m, 1 H), 3.29-3.47 (m, 1 H), 6.16 (s, 1 H), 6.59 (t, J=72.6 Hz, 1 H), 7.19 (dd, J=8.4, 2.4 Hz, 1 H), 7.30 (d, J=2.4 Hz, 1 H), 7.50 (d, J=8.4 Hz, 1 H).

EXAMPLE 31(4)

2-(4-chloro-2-methylphenyl)-3-cyclopropyl-5-(1-ethylpropyl)-7-methylpyrrolo[2,1-f][1,2,4]triazin-4(3H)-one TLC: Rf 0.42 (n-hexane/ethyl acetate=9/1);
$^1$H-NMR (CDCl$_3$): δ 0.38-0.62 (m, 2 H), 0.61-0.98 (m, 8 H), 1.40-1.88 (m, 4 H), 2.21-2.47 (m, 6 H), 2.55-2.79 (m, 1 H), 3.29-3.50 (m, 1 H), 6.15 (s, 1 H), 7.27-7.38 (m, 3 H).

EXAMPLE 31(5)

3-cyclopropyl-5-(1-ethylpropyl)-2-(5-fluoro-4-methoxy-2-methylphenyl)-7-methylpyrrolo[2,1-f][1,2,4]triazin-4(3H)-one TLC: Rf 0.50 (n-hexane/ethyl acetate=3/1);
$^1$H-NMR (CDCl$_3$): δ 0.51 (s, 2 H), 0.71-0.97 (m, 8 H), 1.46-1.83 (m, 4 H), 2.37 (s, 3 H), 2.38 (s, 3 H), 2.62-2.76 (m, 1 H), 3.29-3.50 (m, 1 H), 3.94 (s, 3 H), 6.14 (s, 1 H), 6.87 (d, J=8.42 Hz, 1 H), 7.11 (d, J=11.34 Hz, 1 H).

EXAMPLE 31(6)

2-(4-chloro-2-methoxyphenyl)-3-cyclopropyl-5-(1-ethylpropyl)-7-methylpyrrolo[2,1-f][1,2,4]triazin-4(3H)-one TLC: Rf 0.56 (n-hexane/ethyl acetate=3/1);
$^1$H-NMR (CDCl$_3$): δ 0.16-0.34 (m, 1 H), 0.38-0.57 (m, 1 H), 0.63-0.79 (m, 1 H), 0.79-1.10 (m, 7 H), 1.48-1.82 (m, 4 H), 2.38 (d, J=0.73 Hz, 3 H), 2.76-2.92 (m, 1 H), 3.30-3.52 (m, 1H), 3.85 (s, 3 H), 6.13 (s, 1 H), 6.97 (d, J=1.83 Hz, 1 H), 7.08 (dd, J=8.05, 1.83 Hz, 1 H), 7.35 (d, J=8.05 Hz, 1 H).

EXAMPLE 31(7)

3-cyclopropyl-5-(1-ethylpropyl)-2-(6-methoxy-2-methyl-3-pyridinyl)-7-methylpyrrolo[2,1-f][1,2,4]triazin-4(3H)-one TLC: Rf 0.29 (n-hexane/ethyl acetate=9/1);
$^1$H-NMR (CDCl$_3$): δ 0.38-0.61 (m, 2 H), 0.69-1.00 (m, 8 H), 1.46-1.83 (m, 4 H), 2.38 (s, 3H), 2.53 (s, 3 H), 2.60-2.81 (m, 1 H), 3.29-3.47 (m, 1 H), 3.99 (s, 3 H), 6.15 (s, 1 H), 6.67 (d, J=8.4 Hz, 1 H), 7.55 (d, J=8.4 Hz, 1 H).

EXAMPLE 31(8)

3-cyclopropyl-5-(1-ethylpropyl)-2-(4-methoxy-2,5-dimethylphenyl)-7-methylpyrrolo[2,1-f][1,2,4]triazin-4(3H)-one TLC: Rf 0.47 (n-hexane/ethyl acetate=4/1);
$^1$H-NMR (CDCl$_3$): δ 0.39-0.63 (m, 2 H), 0.64-0.94 (m, 8 H), 1.57-1.80 (m, 4 H), 2.21 (s, 3H), 2.36-2.41 (m, 6 H), 2.64-2.75 (m, 1 H), 3.33-3.46 (m, 1 H), 3.87 (s, 3 H), 6.13 (s, 1H), 6.72 (s, 1 H), 7.12 (s, 1 H).

EXAMPLE 31(9)

3-cyclopropyl-2-(4,5-difluoro-2-methoxyphenyl)-5-(1-ethylpropyl)-7-methylpyrrolo[2,1-f][1,2,4]triazin-4(3H)-one TLC: Rf 0.37 (n-hexane/ethyl acetate=4/1);
$^1$H-NMR (CDCl$_3$): δ 0.44-0.58 (m, 2 H), 0.85 (t, J=7.3 Hz, 8 H), 1.48-1.82 (m, 3 H), 2.39 (s, 3 H), 2.90-3.00 (m, 1 H), 3.31-3.46 (m, 1 H), 3.95 (s, 3 H), 6.15 (s, 1 H), 6.79 (dd, J=10.8, 7.0 Hz, 1 H), 7.21-7.31 (m, 2 H).

EXAMPLE 31(10)

2-(2-chloro-4-methoxy-6-methylphenyl)-3-cyclopropyl-5-(1-ethylpropyl)-7-methylpyrrolo[2,1-f][1,2,4]triazin-4(3H)-one TLC: Rf 0.46 (n-hexane/ethyl acetate=2/1);
$^1$H-NMR (CDCl$_3$): δ 0.34-0.50 (m, 1 H), 0.54-0.68 (m, 1 H), 0.73-0.96 (m, 8 H), 1.48-1.82 (m, 4 H), 2.32 (s, 3 H), 2.38 (s, 3 H), 2.69-2.81 (m, 1 H), 3.32-3.47 (m, 1 H), 3.84 (s, 3H), 6.15 (s, 1 H), 6.77 (d, J=2.4 Hz, 1 H), 6.88 (d, J=2.4 Hz, 1 H).

EXAMPLE 31(11)

3-cyclopropyl-2-(2,4-dichlorophenyl)-5-(1-ethylpropyl)-7-methylpyrrolo[2,1-f][1,2,4]triazin-4(3H)-one TLC: Rf 0.69 (n-hexane/ethyl acetate=2/1);
$^1$H-NMR (CDCl$_3$): δ 0.31-0.50 (m, 1 H), 0.56-1.01 (m, 9 H), 1.44-1.81 (m, 4 H), 2.38 (s, 3H), 2.77-2.95 (m, 1 H), 3.30-3.46 (m, 1 H), 6.16 (s, 1 H), 7.35-7.47 (m, 2 H), 7.53 (d, J=1.3 Hz, 1 H).

EXAMPLE 31(12)

3-cyclopropyl-2-(2,4-dimethylphenyl)-5-(1-ethylpropyl)-7-methylpyrrolo[2,1-f][1,2,4]triazin-4(3H)-one TLC: Rf 0.65 (n-hexane/ethyl acetate=2/1);
$^1$H-NMR (CDCl$_3$): δ 0.42-0.58 (m, 2 H), 0.66-0.81 (m, 2 H), 0.87 (t, J=7.4 Hz, 6 H), 1.50-1.81 (m, 4 H), 2.36 (s, 3 H), 2.38 (d, J=0.7 Hz, 3 H), 2.38 (s, 3 H), 2.61-2.78 (m, 1 H), 3.29-3.49 (m, 1 H), 6.13 (s, 1 H), 7.02-7.16 (m, 2 H), 7.20-7.30 (m, 1 H).

EXAMPLE 31(13)

3-cyclopropyl-5-(1-ethylpropyl)-2-(2-fluoro-4-methoxyphenyl)-7-methylpyrrolo[2,1-f][1,2,4]triazin-4(3H)-one TLC: Rf 0.53 (n-hexane/ethyl acetate=5/1);
$^1$H-NMR (CDCl$_3$): δ 0.49 (s, 1 H), 0.66-1.03 (m, 7 H), 1.46-1.83 (m, 4 H), 2.39 (s, 3 H), 2.85-3.01 (m, 1 H), 3.31-3.50 (m, 1 H), 3.87 (s, 3 H), 6.14 (s, 1 H), 6.72 (dd, J=11.80, 2.47 Hz, 1 H), 6.82 (dd, J=8.60, 2.47 Hz, 1 H), 7.43 (t, J=8.60 Hz, 1 H).

EXAMPLE 31(14)

2-(2-chloro-4-methoxy-5-methylphenyl)-3-cyclopropyl-5-(1-ethylpropyl)-7-methylpyrrolo[2,1-f][1,2,4]triazin-4(3H)-one TLC: Rf 0.50 (n-hexane/ethyl acetate=5/1);
$^1$H-NMR (CDCl$_3$): δ 0.30-0.50 (m, 1 H), 0.55-0.78 (m, 2 H), 0.77-0.98 (m, 7 H), 1.47-1.81 (m, 4 H), 2.23 (s, 3 H), 2.39 (d, J=0.73 Hz, 3 H), 2.82-2.95 (m, 1 H), 3.30-3.51 (m, 1 H), 3.89 (s, 3 H), 6.14 (s, 1 H), 6.90 (s, 1 H), 7.22 (d, J=0.73 Hz, 1 H).

EXAMPLE 31(15)

2-(2-chloro-5-fluoro-4-methoxyphenyl)-3-cyclopropyl-5-(1-ethylpropyl)-7-methylpyrrolo[2,1-f][1,2,4]triazin-4(3H)-one TLC: Rf 0.35 (n-hexane/ethyl acetate=5/1);
$^1$H-NMR (CDCl$_3$): δ 0.44 (s, 1 H), 0.57-1.05 (m, 9 H), 1.46-1.82 (m, 4 H), 2.38 (d, J=0.73 Hz, 3 H), 2.82-2.97 (m, 1 H), 3.30-3.49 (m, 1 H), 3.96 (s, 3 H), 6.15 (s, 1 H), 7.06 (d, J=7.68 Hz, 1 H), 7.22 (d, J=10.79 Hz, 1 H).

EXAMPLE 31(16)

3-cyclopropyl-5-(1-ethylpropyl)-7-methyl-2-[2-methyl-4-(trifluoromethoxy)phenyl]pyrrolo[2,1-f][1,2,4]triazin-4(3H)-one TLC: Rf 0.55 (n-hexane/ethyl acetate=5/1);
$^1$H-NMR (CDCl$_3$): δ 0.33-0.64 (m, 2 H), 0.76 (s, 2 H), 0.87 (t, J=7.41 Hz, 6 H), 1.49-1.83 (m, 4 H), 2.38 (d, J=0.73 Hz, 3 H), 2.43 (s, 3 H), 2.60-2.75 (m, 1 H), 3.30-3.48 (m, 1 H), 6.16 (s, 1 H), 7.09-7.21 (m, 2 H), 7.42 (dd, J=7.78, 1.19 Hz, 1 H).

EXAMPLE 31(17)

3-cyclopropyl-5-(1-ethylpropyl)-2-(4-methoxy-2,6-dimethylphenyl)-7-methylpyrrolo[2,1-f][1,2,4]triazin-4(3H)-one TLC: Rf 0.33 (n-hexane/ethyl acetate=5/1);
$^1$H-NMR (CDCl$_3$): δ 0.50-0.61 (m, 2 H), 0.66-0.79 (m, 2 H), 0.88 (t, J=7.41 Hz, 6 H), 1.50-1.82 (m, 4 H), 2.27 (s, 6 H), 2.38 (s, 3 H), 2.49-2.64 (m, 1 H), 3.30-3.52 (m, 1 H), 3.83 (s, 3 H), 6.14 (s, 1 H), 6.67 (s, 2 H).

EXAMPLE 31(18)

3-cyclopropyl-2-[4-(dimethylamino)-2-methylphenyl]-5-(1-ethylpropyl)-7-methylpyrrolo[2,1-f][1,2,4]triazin-4(3H)-one TLC: Rf 0.36 (n-hexane/ethyl acetate=5/1);
$^1$H-NMR (CDCl$_3$): δ 0.41-0.60 (m, 2 H), 0.68-0.96 (m, 8 H), 1.49-1.85 (m, 4 H), 2.37 (s, 3H), 2.38 (s, 3 H), 2.65-2.79 (m, 1 H), 3.01 (s, 6 H), 3.33-3.48 (m, 1 H), 6.12 (s, 1 H), 6.56-6.68 (m, 2 H), 7.21 (d, J=8.23 Hz, 1 H).

EXAMPLE 31(19)

2-[2-chloro-4-(methylthio)phenyl]-3-cyclopropyl-5-(1-ethylpropyl)-7-methylpyrrolo[2,1-f][1,2,4]triazin-4(3H)-one TLC: Rf 0.54 (n-hexane/ethyl acetate=2/1);
$^1$H-NMR (CDCl$_3$): δ 0.35-0.48 (m, 1 H), 0.60-0.96 (m, 9 H), 1.52-1.80 (m, 4 H), 2.38 (d, J=0.7 Hz, 3 H), 2.53 (s, 3 H), 2.81-2.96 (m, 1 H), 3.32-3.46 (m, 1 H), 6.11-6.16 (m, 1 H), 7.20-7.24 (dd, J=8.2, 1.8 Hz, 1 H), 7.30 (d, J=1.8 Hz, 1 H), 7.36 (d, J=8.2 Hz, 1 H).

EXAMPLE 31(20)

3-cyclopropyl-2-[4-(difluoromethoxy)-2-methylphenyl]-5-(1-ethylpropyl)-7-methylpyrrolo[2,1-f][1,2,4]triazin-4(3H)-one TLC: Rf 0.58 (n-hexane/ethyl acetate=4/1);
$^1$H-NMR (CDCl$_3$): δ 0.40-0.62 (m, 2 H), 0.66-0.93 (m, 8 H), 1.57-1.81 (m, 4 H), 2.38 (s, 3H), 2.42 (s, 3 H), 2.62-2.73 (m, 1 H), 3.32-3.46 (m, 1 H), 6.15 (s, 1 H), 6.57 (t, J=73.6 Hz, 1 H), 7.03-7.11 (m, 2 H), 7.38 (d, J=8.1 Hz, 1 H).

EXAMPLE 31(21)

3-cyclopropyl-5-(1-ethylpropyl)-2-(2-isopropyl-4-methoxyphenyl)-7-methylpyrrolo[2,1-f][1,2,4]triazin-4(3H)-one TLC: Rf 0.63 (n-hexane/ethyl acetate=4/1);
$^1$H-NMR (CDCl$_3$): δ 0.28-0.46 (m, 1 H), 0.54-0.72 (m, 2 H), 0.78-0.96 (m, 7 H), 1.29 (d, J=6.0 Hz, 6 H), 1.58-1.82 (m, 3 H), 2.36 (s, 3 H), 2.60-2.71 (m, 1 H), 2.95-3.09 (m, 1 H), 3.33-3.45 (m, 1 H), 3.86 (s, 3 H), 6.12 (s, 1 H), 6.81 (dd, J=8.6, 2.6 Hz, 1 H), 6.94 (d, J=2.6 Hz, 1 H), 7.21-7.28 (m, 2 H).

EXAMPLE 31(22)

2-(2-chloro-4-ethoxy-5-fluorophenyl)-3-cyclopropyl-5-(1-ethylpropyl)-7-methylpyrrolo[2,1-f][1,2,4]triazin-4(3H)-one TLC: Rf 0.53 (n-hexane/ethyl acetate=4/1);
$^1$H-NMR (CDCl$_3$): δ 0.29-0.54 (m, 1 H), 0.58-1.04 (m, 9 H), 1.42-1.89 (m, 7 H), 2.38 (s, 3H), 2.83-2.96 (m, 1 H), 3.31-3.46 (m, 1 H), 4.09-4.24 (m, 2 H), 6.11-6.17 (m, 1 H), 7.04 (d, J=7.5 Hz, 1 H), 7.20 (d, J=10.8 Hz, 1 H).

EXAMPLE 31(23)

2-(2-chloro-4-ethoxyphenyl)-3-cyclopropyl-5-(1-ethylpropyl)-7-methylpyrrolo[2,1-f][1,2,4]triazin-4(3H)-one TLC: Rf 0.51 (n-hexane/ethyl acetate=5/1);
$^1$H-NMR (CDCl$_3$): δ 0.31-0.50 (m, 1 H), 0.57-0.78 (m, 2 H), 0.78-1.02 (m, 7 H), 1.46 (t, J=7.0 Hz, 3 H), 1.50-1.83 (m, 4 H), 2.39 (s, 3 H), 2.81-2.96 (m, 1 H), 3.31-3.48 (m, 1 H), 4.09 (q, J=7.0 Hz, 2 H), 6.14 (s, 1 H), 6.91 (dd, J=8.6, 2.4 Hz, 1 H), 7.01 (d, J=2.4 Hz, 1H), 7.37 (d, J=8.6 Hz, 1 H).

EXAMPLE 31(24)

3-cyclopropyl-2-[4-(difluoromethoxy)-2,5-dimethylphenyl]-5-(1-ethylpropyl)-7-methylpyrrolo[2,1-f][1,2,4]triazin-4(3H)-one TLC: Rf 0.59 (ethyl acetate/n-hexane=1/6);
$^1$H-NMR (CDCl$_3$): δ 0.35-0.93 (m, 10 H), 1.46-1.87 (m, 4 H), 2.30 (s, 3 H), 2.35-2.41 (m, 6H), 2.63-2.74 (m, 1 H), 3.31-3.46 (m, 1 H), 6.14 (s, 1 H), 6.55 (t, J=73.6 Hz, 1 H), 7.01 (s, 1 H), 7.24 (s, 1 H).

EXAMPLE 31(25)

3-cyclopropyl-2-[4-(difluoromethoxy)-5-fluoro-2-methylphenyl]-5-(1-ethylpropyl)-7-methylpyrrolo[2,1-f][1,2,4]triazin-4(3H)-one TLC: Rf 0.37 (n-hexane/ethyl acetate=9/1);
$^1$H-NMR (CDCl$_3$): δ 0.38-0.64 (m, 2 H), 0.68-1.04 (m, 8 H), 1.51-1.83 (m, 4 H), 2.28-2.41 (m, 6 H), 2.61-2.77 (m, 1 H), 3.30-3.48 (m, 1 H), 6.16 (s, 1 H), 6.61 (t, J=73.1 Hz, 1 H), 7.12-7.25 (m, 2 H).

EXAMPLE 31(26)

2-(2-chloro-4-isopropylphenyl)-3-cyclopropyl-5-(1-ethylpropyl)-7-methylpyrrolo[2,1-f][1,2,4]triazin-4(3H)-one TLC: Rf 0.41 (n-hexane/ethyl acetate=7/1);
$^1$H-NMR (CDCl$_3$): δ 0.29-0.49 (m, 1 H), 0.51-0.78 (m, 2 H), 0.78-1.01 (m, 7 H), 1.29 (d, J=6.8 Hz, 6 H), 1.49-1.81 (m, 4 H), 2.39 (d, J=0.7 Hz, 3 H), 2.82-3.06 (m, 2 H), 3.32-3.48 (m, 1 H), 6.15 (s, 1 H), 7.21-7.29 (m, 1 H), 7.34 (d, J=1.6 Hz, 1 H), 7.39 (d, J=7.9 Hz, 1H).

EXAMPLE 31(27)

3-cyclopropyl-5-(1-ethylpropyl)-2-[4-methoxy-2-(trifluoromethyl)phenyl]-7-methylpyrrolo[2,1-f][1,2,4]triazin-4(3H)-one TLC: Rf 0.31 (n-hexane/ethyl acetate=4/1);
$^1$H-NMR (CDCl$_3$): δ 0.42-0.73 (m, 3 H), 0.77-1.02 (m, 7 H), 1.47-1.81 (m, 4 H), 2.35 (s, 3H), 2.64-2.74 (m, 1 H), 3.32-3.45 (m, 1 H), 3.92 (s, 3 H), 6.14 (s, 1 H), 7.16 (dd, J=8.6, 2.7 Hz, 1 H), 7.30 (d, J=2.7 Hz, 1 H), 7.48 (d, J=8.6 Hz, 1 H).

EXAMPLES 32(1)~(3)

By the same procedure as a series of reactions of Example 2→Example 3→Example 4→Example 5→Example 8, using methylmagnesium bromide instead of ethylmagnesium bromide, using cyclopropylamine instead of an aqueous solution of 40% methylamine, and using the corresponding aldehydes instead of the compound prepared in Example 7, the compounds of the present invention having the following physical data were obtained.

EXAMPLE 32(1)

2-(2-chloro-4-methoxyphenyl)-3-cyclopropyl-5-isopropyl-7-methylpyrrolo[2,1-f][1,2,4]triazin-4(3H)-one

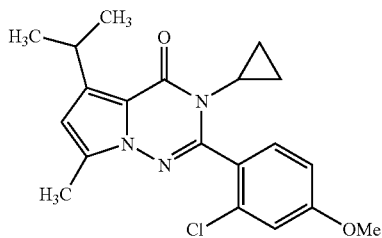 [SMILES: COc1ccc(-c2nn3c(C)cc(C(C)C)c3c(=O)n2C2CC2)c(Cl)c1]

TLC: Rf 0.41 (n-hexane/ethyl acetate=1/1);
$^1$H-NMR (CDCl$_3$): δ 0.33-0.46 (m, 1 H), 0.58-0.79 (m, 2 H), 0.82-0.97 (m, 1 H), 1.29 (d, J=4.9 Hz, 6 H), 2.39 (s, 3 H), 2.82-2.95 (m, 1 H), 3.64-3.82 (m, 1 H), 3.87 (s, 3 H), 6.22 (s, 1 H), 6.93 (dd, J=8.4, 2.4 Hz, 1 H), 7.02 (d, J=2.4 Hz, 1 H), 7.36 (d, J=8.4 Hz, 1 H).

EXAMPLE 32(2)

2-[2-chloro-4-(difluoromethoxy)phenyl]-3-cyclopropyl-5-isopropyl-7-methylpyrrolo[2,1-f][1,2,4]triazin-4(3H)-one TLC: Rf 0.50 (n-hexane/ethyl acetate=1/1);
$^1$H-NMR (CDCl$_3$): δ 0.32-0.46 (m, 1 H), 0.58-1.00 (m, 3 H), 1.24-1.34 (m, 6 H), 2.38 (s, 3H), 2.81-2.94 (m, 1 H), 3.64-3.82 (m, 1 H), 6.24 (s, 1 H), 6.59 (t, J=72.6 Hz, 1 H), 7.18 (dd, J=8.4, 2.4 Hz, 1 H), 7.30 (d, J=2.4 Hz, 1 H), 7.47 (d, J=8.4 Hz, 1 H).

EXAMPLE 32(3)

3-cyclopropyl-2-[4-(difluoromethoxy)-2,6-dimethylphenyl]-5-isopropyl-7-methylpyrrolo[2,1-f][1,2,4]triazin-4(3H)-one TLC: Rf 0.56 (n-hexane/ethyl acetate=1/1);
$^1$H-NMR (CDCl$_3$): δ 0.51-0.61 (m, 2 H), 0.67-0.77 (m, 2 H), 1.30 (d, J=6.8 Hz, 6 H), 2.29 (s, 6 H), 2.37 (s, 3 H), 2.49-2.60 (m, 1 H), 3.64-3.83 (m, 1 H), 6.23 (s, 1 H), 6.54 (t, J=73.6 Hz, 1 H), 6.90 (s, 2 H).

EXAMPLES 33(1)~(30)

By the same procedure as a series of reactions of Example 4→Example 5→Example 8, using the compound prepared in Example 18 instead of the compound prepared in Example 3, using cyclopropylamine instead of an aqueous solution of 40% methylamine, and using the corresponding aldehydes instead of the compound prepared in Example 7, the compounds of the present invention having the following physical data were obtained.

EXAMPLE 33(1)

5-sec-butyl-2-(4-chloro-2-methylphenyl)-3-cyclopropyl-7-methylpyrrolo[2,1-f][1,2,4]triazin-4(3H)-one

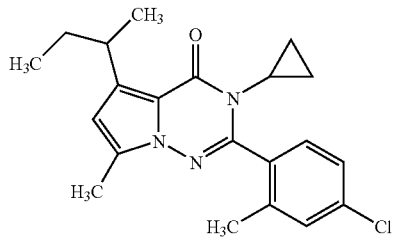 [SMILES: CCC(C)c1cc(C)n2nc(-c3ccc(Cl)cc3C)n(C3CC3)c(=O)c12]

TLC: Rf 0.57 (n-hexane/ethyl acetate=3/1);
$^1$H-NMR (CDCl$_3$): δ 0.40-0.64 (m, 2 H), 0.69-0.86 (m, 2 H), 0.91 (t, J=7.4 Hz, 3 H), 1.26 (d, J=7.0 Hz, 3 H), 1.58-1.73 (m, 2 H), 2.37 (d, J=0.5 Hz, 3 H), 2.38 (s, 3 H), 2.63-2.70 (m, 1 H), 3.47-3.58 (m, 1 H), 6.17-6.18 (m, 1 H), 7.27-7.28 (m, 2 H), 7.31-7.32 (m, 1 H).

EXAMPLE 33(2)

5-sec-butyl-2-(2-chloro-5-fluoro-4-methoxyphenyl)-3-cyclopropyl-7-methylpyrrolo[2,1-f][1,2,4]triazin-4(3H)-one TLC: Rf 0.41 (n-hexane/ethyl acetate=3/1);
$^1$H-NMR (CDCl$_3$): δ 0.38-0.48 (m, 1 H), 0.65-0.76 (m, 2 H), 0.87-0.95 (m, 4 H), 1.26 (d, J=6.8 Hz, 3 H), 1.57-1.72 (m, 2 H), 2.38 (s, 3 H), 2.86-2.93 (m, 1 H), 3.46-3.59 (m, 1 H), 3.95 (s, 3 H), 6.18 (s, 1 H), 7.05 (d, J=7.7 Hz, 1 H), 7.19 (d, J=10.6 Hz, 1 H).

EXAMPLE 33(3)

5-sec-butyl-3-cyclopropyl-2-(4-methoxy-2,6-dimethylphenyl)-7-methylpyrrolo[2,1-f][1,2,4]triazin-4(3H)-one TLC: Rf 0.43 (n-hexane/ethyl acetate=3/1);
$^1$H-NMR (CDCl$_3$): δ 0.49-0.79 (m, 4 H), 0.93 (t, J=7.3 Hz, 3 H), 1.27 (d, J=7.0 Hz, 3 H), 1.57-1.78 (m, 2 H), 2.25 (s, 3 H), 2.26 (s, 3 H), 2.37 (s, 3 H), 2.52-2.59 (m, 1 H), 3.47-3.60 (m, 1 H), 3.82 (s, 3 H), 6.17 (s, 1 H), 6.66 (s, 2 H).

EXAMPLE 33(4)

5-sec-butyl-2-(2-chloro-4-methoxy-5-methylphenyl)-3-cyclopropyl-7-methylpyrrolo[2,1-f][1,2,4]triazin-4(3H)-one TLC: Rf 0.49 (n-hexane/ethyl acetate=3/1);
$^1$H-NMR (CDCl$_3$): δ 0.35-0.47 (m, 1 H), 0.59-0.75 (m, 2 H), 0.83-0.95 (m, 4 H), 1.24-1.28 (m, 3 H), 1.57-1.72 (m, 2 H), 2.23 (s, 3 H), 2.38 (s, 3 H), 2.85-2.92 (m, 1 H), 3.48-3.59 (m, 1 H), 3.88 (s, 3 H), 6.17 (s, 1 H), 6.89 (s, 1 H), 7.19 (s, 1 H).

EXAMPLE 33(5)

5-sec-butyl-2-[2-chloro-4-(difluoromethoxy)phenyl]-3-cyclopropyl-7-methylpyrrolo[2,1-f][1,2,4]triazin-4(3H)-one TLC: Rf 0.39 (ethyl acetate/n-hexane=1/6);
$^1$H-NMR (CDCl$_3$): δ 0.26-0.51 (m, 1 H), 0.55-0.81 (m, 2 H), 0.83-1.01 (m, 4 H), 1.19-1.33 (m, 3 H), 1.64 (d, 2 H), 2.38 (d, J=0.7 Hz, 3 H), 2.78-2.98 (m, 1 H), 3.45-3.65 (m, 1 H), 6.20 (s, 1 H), 6.59 (t, J=72.6 Hz, 1 H), 7.19 (dd, J=8.4, 2.4 Hz, 1 H), 7.30 (d, J=2.4 Hz, 1 H), 7.48 (d, J=8.4 Hz, 1 H).

EXAMPLE 33(6)

5-sec-butyl-3-cyclopropyl-2-(6-methoxy-2-methyl-3-pyridinyl)-7-methylpyrrolo[2,1-f][1,2,4]triazin-4(3H)-one TLC: Rf 0.28 (ethyl acetate/n-hexane=1/6);
$^1$H-NMR (CDCl$_3$): δ 0.36-0.68 (m, 2 H), 0.69-0.99 (m, 5 H), 1.26 (d, J=7.0 Hz, 3 H), 1.51-1.79 (m, 2 H), 2.38 (s, 3 H), 2.51 (s, 3 H), 2.64-2.74 (m, 1 H), 3.45-3.61 (m, 1 H), 3.98 (s, 3 H), 6.19 (s, 1 H), 6.67 (d, J=8.4 Hz, 1 H), 7.54 (d, J=8.4 Hz, 1 H).

EXAMPLE 33(7)

5-sec-butyl-3-cyclopropyl-2-[4-(difluoromethoxy)-2,6-dimethylphenyl]-7-methylpyrrolo[2,1-f][1,2,4]triazin-4(3H)-one TLC: Rf 0.46 (ethyl acetate/n-hexane=1/6);
$^1$H-NMR (CDCl$_3$): δ 0.46-0.84 (m, 4 H), 0.88-1.00 (m, 3 H), 1.27 (d, J=7.0 Hz, 3 H), 1.52-1.80 (m, 2 H), 2.30 (d, J=1.6 Hz, 6 H), 2.38 (s, 3 H), 2.49-2.62 (m, 1 H), 3.44-3.62 (m, 1H), 6.20 (s, 1 H), 6.55 (t, J=73.7 Hz, 1 H), 6.91 (s, 2 H).

EXAMPLE 33(8)

5-sec-butyl-3-cyclopropyl-2-(2,4-dichlorophenyl)-7-methylpyrrolo[2,1-f][1,2,4]triazin-4(3H)-one TLC: Rf 0.56 (ethyl acetate/n-hexane=1/6);
$^1$H-NMR (CDCl$_3$): δ 0.18-0.54 (m, 1 H), 0.56-0.81 (m, 2 H), 0.83-1.03 (m, 4 H), 1.19-1.32 (m, 3 H), 1.49-1.79 (m, 2 H), 2.38 (s, 3 H), 2.71-3.00 (m, 1 H), 3.42-3.64 (m, 1 H), 6.20 (s, 1 H), 7.33-7.46 (m, 2 H), 7.50-7.56 (m, 1 H).

EXAMPLE 33(9)

5-sec-butyl-3-cyclopropyl-2-(2-fluoro-4-methoxyphenyl)-7-methylpyrrolo[2,1-f][1,2,4]triazin-4(3H)-one TLC: Rf 0.30 (n-hexane/ethyl acetate=5/1);
$^1$H-NMR (CDCl$_3$): δ 0.41-0.61 (m, 2 H), 0.70-1.00 (m, 5 H), 1.26 (d, J=6.95 Hz, 3 H), 1.52-1.81 (m, 2 H), 2.39 (d, J=0.73 Hz, 3 H), 2.86-3.01 (m, 1 H), 3.54 (m, 1 H), 3.87 (s, 3H), 6.16-6.20 (m, 1 H), 6.71 (dd, J=11.89, 2.38 Hz, 1 H), 6.82 (dd, J=8.05, 2.38 Hz, 1 H), 7.42 (t, J=8.05 Hz, 1 H).

EXAMPLE 33(10)

5-sec-butyl-2-(2-chloro-4-methoxyphenyl)-3-cyclopropyl-7-methylpyrrolo[2,1-f][1,2,4]triazin-4(3H)-one TLC: Rf 0.28 (n-hexane/ethyl acetate=5/1);
$^1$H-NMR (CDCl$_3$): δ 0.26-0.51 (m, 1 H), 0.56-0.82 (m, 2 H), 0.81-1.02 (m, 4 H), 1.26 (d, J=7.14 Hz, 3 H), 1.49-1.84 (m, 2 H), 2.39 (s, 3 H), 2.78-2.99 (m, 1 H), 3.41-3.66 (m, 1 H), 3.87 (s, 3 H), 6.18 (s, 1 H), 6.93 (dd, J=8.42, 2.38 Hz, 1 H), 7.02 (d, J=2.38 Hz, 1 H), 7.37 (d, J=8.42 Hz, 1 H).

EXAMPLE 33(11)

5-sec-butyl-3-cyclopropyl-7-methyl-2-[2-methyl-4-(trifluoromethoxy)phenyl]pyrrolo[2,1-f][1,2,4]triazin-4(3H)-one TLC: Rf 0.53 (n-hexane/ethyl acetate=5/1);
$^1$H-NMR (CDCl$_3$): δ 0.33-0.63 (m, 2 H), 0.64-0.87 (m, 2 H), 0.92 (t, J=7.41 Hz, 3 H), 1.27 (d, J=6.95 Hz, 3 H), 1.52-1.82 (m, 2 H), 2.38 (s, 3 H), 2.42 (s, 3 H), 2.60-2.73 (m, 1 H), 3.43-3.63 (m, 1 H), 6.14-6.22 (m, 1 H), 7.13-7.20 (m, 2 H), 7.40 (d, J=8.78 Hz, 1 H).

EXAMPLE 33(12)

5-sec-butyl-2-[2-chloro-4-(trifluoromethyl)phenyl]-3-cyclopropyl-7-methylpyrrolo[2,1-f][1,2,4]triazin-4(3H)-one TLC: Rf 0.45 (n-hexane/ethyl acetate=5/1);
$^1$H-NMR (CDCl$_3$): δ 0.26-0.53 (m, 1 H), 0.53-0.83 (m, 2 H), 0.84-1.01 (m, 4 H), 1.21-1.34 (m, 3 H), 1.52-1.80 (m, 2 H), 2.38 (d, J=0.73 Hz, 3 H), 2.79-3.01 (m, 1 H), 3.46-3.65 (m, 1H), 6.19-6.25 (m, 1 H), 7.60-7.66 (m, 1 H), 7.66-7.72 (m, 1 H), 7.77-7.80 (m, 1 H).

EXAMPLE 33(13)

5-sec-butyl-2-(2-chloro-4-methoxy-6-methylphenyl)-3-cyclopropyl-7-methylpyrrolo[2,1-f][1,2,4]triazin-4(3H)-one TLC: Rf 0.50 (n-hexane/ethyl acetate=2/1);
$^1$H-NMR (CDCl$_3$): δ 0.33-0.51 (m, 1 H), 0.53-0.70 (m, 1 H), 0.75-0.99 (m, 5 H), 1.20-1.33 (m, 3 H), 1.51-1.80 (m, 2 H), 2.31 (d, J=1.3 Hz, 3 H), 2.38 (s, 3 H), 2.69-2.83 (m, 1 H), 3.47-3.63 (m, 1 H), 3.85 (s, 3 H), 6.19 (s, 1 H), 6.77 (d, J=2.4 Hz, 1 H), 6.88 (d, J=2.4 Hz, 1 H).

EXAMPLE 33(14)

5-sec-butyl-3-cyclopropyl-2-[4-(difluoromethoxy)-2-methylphenyl]-7-methylpyrrolo[2,1-f][1,2,4]triazin-4(3H)-one TLC: Rf 0.58 (n-hexane/ethyl acetate=2/1);
$^1$H-NMR (CDCl$_3$): δ 0.39-0.62 (m, 2 H), 0.64-0.86 (m, 2 H), 0.92 (t, J=7.3 Hz, 3 H), 1.26 (d, J=7.0 Hz, 3 H), 1.50-1.78 (m, 2 H), 2.38 (s, 3 H), 2.40 (s, 3 H), 2.60-2.75 (m, 1 H), 3.45-3.61 (m, 1 H), 6.19 (s, 1 H), 6.57 (t, J=73.6 Hz, 1 H), 7.02-7.10 (m, 2 H), 7.37 (d, J=8.4 Hz, 1 H).

EXAMPLE 33(15)

5-sec-butyl-2-[2-chloro-4-(trifluoromethoxy)phenyl]-3-cyclopropyl-7-methylpyrrolo[2,1-f][1,2,4]triazin-4(3H)-one TLC: Rf 0.58 (n-hexane/ethyl acetate=4/1);
$^1$H-NMR (CDCl$_3$): δ 0.26-0.52 (m, 1 H), 0.53-1.03 (m, 6 H), 1.20-1.34 (m, 3 H), 1.57-1.79 (m, 2 H), 2.38 (s, 3 H), 2.81-2.95 (m, 1 H), 3.44-3.62 (m, 1 H), 6.16-6.24 (m, 1 H), 7.27-7.34 (m, 1 H), 7.35-7.44 (m, 1 H), 7.51 (d, J=8.2 Hz, 1 H).

EXAMPLE 33(16)

5-sec-butyl-2-[2-chloro-4-(methylthio)phenyl]-3-cyclopropyl-7-methylpyrrolo[2,1-f][1,2,4]triazin-4(3H)-one TLC: Rf 0.43 (n-hexane/ethyl acetate=4/1);
$^1$H-NMR (CDCl$_3$): δ 0.29-0.53 (m, 1 H), 0.59-0.99 (m, 6 H), 1.21-1.31 (m, 3 H), 1.57-1.78 (m, 2 H), 2.38 (s, 3 H), 2.54 (s, 3 H), 2.82-2.95 (m, 1 H), 3.47-3.60 (m, 1 H), 6.19 (s, 1H), 7.20-7.25 (m, 1 H), 7.31 (d, J=1.8 Hz, 1 H), 7.33-7.39 (m, 1 H).

EXAMPLE 33(17)

5-sec-butyl-2-(4-chloro-2-methoxyphenyl)-3-cyclopropyl-7-methylpyrrolo[2,1-f][1,2,4]triazin-4(3H)-one TLC: Rf 0.38 (n-hexane/ethyl acetate=4/1);
$^1$H-NMR (CDCl$_3$): δ 0.15-0.35 (m, 1 H), 0.40-0.57 (m, 1 H), 0.64-0.82 (m, 1 H), 0.83-1.07 (m, 4 H), 1.21-1.30 (m, 3 H), 1.58-1.80 (m, 2 H), 2.38 (s, 3 H), 2.77-2.90 (m, 1 H), 3.46-3.64 (m, 1 H), 3.85 (s, 3 H), 6.17 (s, 1 H), 6.97 (d, J=1.9 Hz, 1 H), 7.08 (dd, J=8.1, 1.9 Hz, 1 H), 7.33 (d, J=8.1 Hz, 1 H).

EXAMPLE 33(18)

5-sec-butyl-2-[2-chloro-4-(difluoromethoxy)-5-fluorophenyl]-3-cyclopropyl-7-methylpyrrolo[2,1-f][1,2,4]triazin-4(3H)-one TLC: Rf 0.55 (n-hexane/ethyl acetate=4/1);
$^1$H-NMR (CDCl$_3$): δ 0.33-0.55 (m, 1 H), 0.59-1.05 (m, 6 H), 1.20-1.33 (m, 3 H), 1.57-1.78 (m, 2 H), 2.38 (s, 3 H), 2.84-2.97 (m, 1 H), 3.44-3.61 (m, 1 H), 6.20 (s, 1 H), 6.63 (t, J=72.2 Hz, 1 H), 7.32 (d, J=9.9 Hz, 1 H), 7.41 (d, J=7.0 Hz, 1 H).

EXAMPLE 33(19)

5-sec-butyl-3-cyclopropyl-2-(2-ethyl-4-methoxyphenyl)-7-methylpyrrolo[2,1-f][1,2,4]triazin-4(3H)-one TLC: Rf 0.34 (n-hexane/ethyl acetate=9/1);
$^1$H-NMR (CDCl$_3$): δ 0.27-0.50 (m, 1 H), 0.50-0.77 (m, 2 H), 0.75-1.06 (m, 4 H), 1.14-1.35 (m, 6 H), 1.57-1.83 (m, 2 H), 2.37 (s, 3 H), 2.55-2.75 (m, J=7.6, 7.6, 7.6 Hz, 3 H), 3.38-3.71 (m, 1 H), 3.86 (s, 3 H), 6.16 (s, 1 H), 6.81 (dd, J=8.5, 2.6 Hz, 1 H), 6.88 (d, J=2.6 Hz, 1 H), 7.16-7.33 (m, 1 H).

EXAMPLE 33(20)

5-sec-butyl-3-cyclopropyl-2-(2,4-dimethylphenyl)-7-methylpyrrolo[2,1-f][1,2,4]triazin-4(3H)-one TLC: Rf 0.43 (n-hexane/ethyl acetate=9/1);
$^1$H-NMR (CDCl$_3$): δ 0.35-0.62 (m, 2 H), 0.62-0.86 (m, 2 H), 0.92 (t, J=7.3 Hz, 3 H), 1.20-1.33 (m, 3 H), 1.58-1.79 (m, 2 H), 2.29-2.43 (m, 9 H), 2.61-2.76 (m, 1 H), 3.44-3.62 (m, 1H), 6.16 (s, 1 H), 7.00-7.15 (m, 2 H), 7.18-7.27 (m, 1 H).

EXAMPLE 33(21)

5-sec-butyl-3-cyclopropyl-2-(4-methoxy-2,5-dimethylphenyl)-7-methylpyrrolo[2,1-f][1,2,4]triazin-4(3H)-one TLC: Rf 0.42 (n-hexane/ethyl acetate=9/1);
$^1$H-NMR (CDCl$_3$): δ 0.34-0.63 (m, 2 H), 0.64-0.87 (m, 2 H), 0.92 (t, J=7.4 Hz, 3 H), 1.16-1.33 (m, 3 H), 1.59-1.82 (m, 2 H), 2.20 (s, 3 H), 2.29-2.47 (m, 6 H), 2.59-2.89 (m, 1 H), 3.38-3.70 (m, 1 H), 3.87 (s, 3 H), 6.16 (s, 1 H), 6.71 (s, 1 H), 7.09 (s, 1 H).

EXAMPLE 33(22)

5-sec-butyl-3-cyclopropyl-2-(4-methoxy-2-methylphenyl)-7-methylpyrrolo[2,1-f][1,2,4]triazin-4(3H)-one TLC: Rf 0.25 (n-hexane/ethyl acetate=9/1);
$^1$H-NMR (CDCl$_3$): δ 0.36-0.63 (m, 2 H), 0.65-0.87 (m, 2 H), 0.92 (t, J=7.3 Hz, 3 H), 1.18-1.34 (m, 3 H), 1.57-1.83 (m, 2 H), 2.28-2.44 (m, J=3.1 Hz, 6 H), 2.56-2.83 (m, 1 H), 3.40-3.65 (m, 1 H), 3.85 (s, 3 H), 6.16 (s, 1 H), 6.73-6.92 (m, 2 H), 7.19-7.35 (m, 1 H).

EXAMPLE 33(23)

5-sec-butyl-3-cyclopropyl-2-(2-isopropyl-4-methoxyphenyl)-7-methylpyrrolo[2,1-f][1,2,4]triazin-4(3H)-one TLC: Rf 0.53 (n-hexane/ethyl acetate=4/1);
$^1$H-NMR (CDCl$_3$): δ 0.27-0.49 (m, 1 H), 0.55-0.74 (m, 2 H), 0.83-1.00 (m, 4 H), 1.22-1.34 (m, 9 H), 1.58-1.78 (m, 2 H), 2.36 (s, 3 H), 2.59-2.71 (m, 1 H), 2.94-3.08 (m, 1 H), 3.47-3.61 (m, 1 H), 3.87 (s, 3 H), 6.17 (s, 1 H), 6.82 (dd, J=8.5, 2.6 Hz, 1 H), 6.95 (d, J=2.6 Hz, 1 H), 7.23 (d, J=8.5 Hz, 1 H).

EXAMPLE 33(24)

5-sec-butyl-3-cyclopropyl-2-(5-fluoro-4-methoxy-2-methylphenyl)-7-methylpyrrolo[2,1-f][1,2,4]triazin-4(3H)-one TLC: Rf 0.43 (toluene/ethyl acetate=20/1);
$^1$H-NMR (CDCl$_3$): δ 0.39-0.63 (m, 2 H), 0.68-0.91 (m, 2 H), 0.91 (t, J=7.4 Hz, 3 H), 1.26 (d, J=7.0 Hz, 3 H), 1.51-1.79 (m, 2 H), 2.35 (s, 3 H), 2.37 (s, 3 H), 2.63-2.75 (m, 1 H), 3.44-3.60 (m, 1 H), 3.93 (s, 3 H), 6.17 (s, 1 H), 6.86 (d, J=8.2 Hz, 1 H), 7.08 (d, J=11.3 Hz, 1 H).

EXAMPLE 33(25)

5-sec-butyl-3-cyclopropyl-2-[4-(difluoromethoxy)-2-ethylphenyl]-7-methylpyrrolo[2,1-f][1,2,4]triazin-4(3H)-one TLC: Rf 0.61 (toluene/ethyl acetate=20/1);
$^1$H-NMR (CDCl$_3$): δ 0.30-1.02 (m, 7 H), 1.23-1.35 (m, 6 H), 1.59-1.79 (m, 2 H), 2.37 (s, 3H), 2.58-2.78 (m, 3 H), 3.46-3.63 (m, 1 H), 6.19 (s, 1 H), 6.58 (t, J=73.6 Hz, 1 H), 7.06 (dd, J=8.6, 2.4 Hz, 1 H), 7.13 (d, J=2.4 Hz, 1 H), 7.36 (d, J=8.6 Hz, 1 H).

EXAMPLE 33(26)

5-sec-butyl-2-(2-chloro-4-ethoxy-5-fluorophenyl)-3-cyclopropyl-7-methylpyrrolo[2,1-f][1,2,4]triazin-4(3H)-one TLC: Rf 0.45 (n-hexane/ethyl acetate=4/1);
$^1$H-NMR (CDCl$_3$): δ 0.31-0.53 (m, 1 H), 0.58-1.05 (m, 6 H), 1.25 (d, J=5.7 Hz, 3 H), 1.44-1.79 (m, 6 H), 2.37 (s, 3 H), 2.83-2.98 (m, 1 H), 3.46-3.61 (m, 1 H), 4.09-4.23 (m, 1 H), 6.14-6.22 (m, 1 H), 6.98-7.08 (m, 1 H), 7.18 (d, J=8.8 Hz, 1 H).

EXAMPLE 33(27)

5-sec-butyl-2-(2-chloro-4-ethoxyphenyl)-3-cyclopropyl-7-methylpyrrolo[2,1-f][1,2,4]triazin-4(3H)-one TLC: Rf 0.53 (n-hexane/ethyl acetate=5/1);
$^1$H-NMR (CDCl$_3$): δ 0.28-0.51 (m, 1 H), 0.55-0.80 (m, 2 H), 0.80-1.06 (m, 4 H), 1.26 (d, J=6.8 Hz, 3 H), 1.46 (t, J=7.0 Hz, 3 H), 1.53-1.79 (m, 2 H), 2.39 (s, 3 H), 2.80-2.99 (m, 1H), 3.45-3.65 (m, 1 H), 4.09 (q, J=7.0 Hz, 2 H), 6.18 (s, 1 H), 6.91 (dd, J=8.4, 2.4 Hz, 1H), 7.01 (d, J=2.4 Hz, 1 H), 7.35 (d, J=8.4 Hz, 1 H).

EXAMPLE 33(28)

5-sec-butyl-3-cyclopropyl-2-[4-(difluoromethoxy)-2,5-dimethylphenyl]-7-methylpyrrolo[2,1-f][1,2,4]triazin-4(3H)-one TLC: Rf 0.54 (ethyl acetate/n-hexane=1/6);
$^1$H-NMR (CDCl$_3$): δ 0.33-0.87 (m, 4 H), 0.91 (t, J=7.4 Hz, 3 H), 1.26 (d, J=7.0 Hz, 3 H), 1.46-1.80 (m, 2 H), 2.29 (s, 3 H), 2.35 (s, 3 H), 2.37 (s, 3 H), 2.61-2.76 (m, 1 H), 3.43-3.63 (m, 1 H), 6.17 (s, 1 H), 6.54 (t, J=73.6 Hz, 1 H), 7.00 (s, 1 H), 7.22 (s, 1 H).

EXAMPLE 33(29)

5-sec-butyl-2-(2-chloro-4-isopropylphenyl)-3-cyclopropyl-7-methylpyrrolo[2,1-f][1,2,4]triazin-4(3H)-one TLC: Rf 0.41 (n-hexane/ethyl acetate=7/1);
$^1$H-NMR (CDCl$_3$): δ 0.27-0.50 (m, 1 H), 0.50-1.03 (m, 6 H), 1.18-1.40 (m, 9 H), 1.50-1.78 (m, 2 H), 2.39 (s, 3 H), 2.81-3.06 (m, 2 H), 3.45-3.65 (m, 1 H), 6.19 (s, 1 H), 7.21-7.28 (m, 1 H), 7.34 (d, J=1.6 Hz, 1 H), 7.38 (d, J=7.9 Hz, 1 H).

EXAMPLE 33(30)

5-sec-butyl-3-cyclopropyl-2-[4-methoxy-2-(trifluoromethyl)phenyl]-7-methylpyrrolo[2,1-f][1,2,4]triazin-4(3H)-one TLC: Rf 0.29 (n-hexane/ethyl acetate=4/1);
$^1$H-NMR (CDCl$_3$): δ 0.40-0.73 (m, 3 H), 0.86-1.00 (m, 4 H), 1.26 (d, J=7.0 Hz, 3 H), 1.58-1.76 (m, 2 H), 2.35 (s, 3 H), 2.63-2.75 (m, 1 H), 3.45-3.61 (m, 1 H), 3.92 (s, 3 H), 6.17 (s, 1 H), 7.11-7.19 (m, 1 H), 7.28-7.32 (m, 1 H), 7.42-7.51 (m, 1 H).

EXAMPLES 34(1)~(4)

By the same procedure as a series of reactions of Example 2→Example 3→Example 4→Example 5→Example 8, using propylmagnesium bromide instead of ethylmagnesium bromide, using cyclopropylamine instead of an aqueous solution of 40% methylamine, and using the corresponding aldehydes instead of the compound prepared in Example 7, the compounds of the present invention having the following physical data were obtained.

EXAMPLE 34(1)

2-[2-chloro-4-(trifluoromethoxy)phenyl]-3-cyclopropyl-7-methyl-5-(1-propylbutyl)pyrrolo[2,1-f][1,2,4]triazin-4(3H)-one

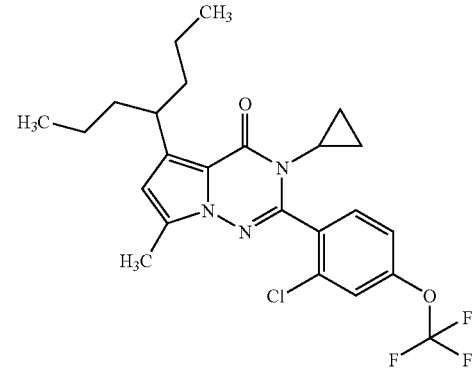 [SMILES: CCCC(CCC)c1cc(C)n2nc(-c3ccc(OC(F)(F)F)cc3Cl)n(C3CC3)c(=O)c12]

TLC: Rf 0.57 (n-hexane/ethyl acetate=9/1);
$^1$H-NMR (CDCl$_3$): δ 0.25-0.48 (m, 1 H), 0.57-0.97 (m, 9 H), 1.13-1.40 (m, 4 H), 1.46-1.74 (m, 4 H), 2.38 (s, 3 H), 2.75-2.97 (m, 1 H), 3.46-3.70 (m, 1 H), 6.16 (s, 1 H), 7.23-7.33 (m, 1 H), 7.34-7.43 (m, 1 H), 7.54 (d, J=8.6 Hz, 1 H).

EXAMPLE 34(2)

2-(4-chloro-2-methylphenyl)-3-cyclopropyl-7-methyl-5-(1-propylbutyl)pyrrolo[2,1-f][1,2,4]triazin-4(3H)-one TLC: Rf 0.56 (n-hexane/ethyl acetate=9/1);
$^1$H-NMR (CDCl$_3$): δ 0.37-0.62 (m, 2 H), 0.66-0.93 (m, 8 H), 1.16-1.37 (m, 4 H), 1.43-1.73 (m, 4 H), 2.36 (s, 3 H), 2.39 (s, 3 H), 2.59-2.74 (m, 1 H), 3.50-3.64 (m, 1 H), 6.14 (s, 1H), 7.27-7.34 (m, 3 H).

EXAMPLE 34(3)

2-(2-chloro-4-methoxyphenyl)-3-cyclopropyl-7-methyl-5-(1-propylbutyl)pyrrolo[2,1-f][1,2,4]triazin-4(3H)-one TLC: Rf 0.33 (n-hexane/ethyl acetate=9/1);
$^1$H-NMR (CDCl$_3$): δ 0.33-0.53 (m, 1 H), 0.58-0.98 (m, 9 H), 1.11-1.40 (m, 4 H), 1.45-1.72 (m, 4 H), 2.37 (s, 3 H), 2.74-2.94 (m, 1 H), 3.45-3.68 (m, 1 H), 3.86 (s, 3 H), 6.13 (s, 1H), 6.91 (dd, J=8.6, 2.4 Hz, 1 H), 7.01 (d, J=2.4 Hz, 1 H), 7.37 (d, J=8.6 Hz, 1 H).

EXAMPLE 34(4)

3-cyclopropyl-2-(2-ethyl-4-methoxyphenyl)-7-methyl-5-(1-propylbutyl)pyrrolo[2,1-f][1,2,4]triazin-4(3H)-one TLC: Rf 0.35 (n-hexane/ethyl acetate=9/1);
$^1$H-NMR (CDCl$_3$): δ 0.23-0.75 (m, 4 H), 0.87 (t, J=7.3 Hz, 6 H), 1.15-1.41 (m, 7 H), 1.45-1.73 (m, 4 H), 2.36 (s, 3 H), 2.56-2.76 (m, 3 H), 3.45-3.65 (m, 1 H), 3.86 (s, 3 H), 6.12 (s, 1 H), 6.81 (dd, J=8.4, 2.6 Hz, 1 H), 6.88 (d, J=2.6 Hz, 1 H), 7.26 (d, J=8.4 Hz, 1 H).

EXAMPLE 35

1-amino-3-(1-ethylpropyl)-5-methyl-1H-pyrrole-2-carboxamide

By the same procedure as a reaction of Example 5, using 3-(1-ethylpropyl)-5-methyl-1H-pyrrole-2-carboxamide (which was provided by the same procedure as a reaction of Example 4, using a saturated aqueous solution of ammonia instead of an aqueous solution of 40% methylamine) instead of the compound prepared in Example 4, using cyclopropylamine instead of 40% aqueous solution of methylamine, and using the corresponding aldehydes instead of the compound prepared in Example 7, the title compound (1.988 g) having the following physical data was obtained.
TLC: Rf 0.23 (n-hexane/ethyl acetate=1/2);
$^1$H-NMR (CDCl$_3$): δ 0.83 (t, J=7.4 Hz, 6 H), 1.29-1.80 (m, 4 H), 2.25 (d, J=0.7 Hz, 3 H), 2.81-3.08 (m, 1 H), 5.19 (s, 2 H), 5.69 (s, 1 H), 5.99 (s, 2 H).

EXAMPLE 36

2-(2-chloro-4-methoxyphenyl)-5-(1-ethylpropyl)-7-methylpyrrolo[2,1-f][1,2,4]triazin-4(3H)-one The compound prepared in Example 35 (175 mg) and 2-chloro-4-methoxybenzaldehyde (146 mg) were dissolved with Xylene (1.8 mL). Darco-KB (89 mg) was added to the reaction mixture. The reaction mixture was substituted in oxygen, and stirred for 2 days under reflux. The reaction mixture was subjected to filtration with Celite (trade name) while it was hot, and was concentrated under reduced pressure. The obtained residue was perspired with Xylene (2 mL) and was washed. The title compound (227 mg) having the following physical data was obtained.
TLC: Rf 0.17 (n-hexane/ethyl acetate=4/1);
$^1$H-NMR (DMSO-D$_6$): δ 0.76 (t, J=7.41 Hz, 6 H), 1.34-1.74 (m, 4 H), 2.33 (s, 3 H), 3.13-3.31 (m, 1 H), 3.84 (s, 3 H), 6.24 (s, 1 H), 7.03 (dd, J=8.60, 2.56 Hz, 1 H), 7.18 (d, J=2.56 Hz, 1 H), 7.59 (d, J=8.60 Hz, 1 H), 11.54 (s, 1 H).

EXAMPLE 37

Methyl [2-(2-chloro-4-methoxyphenyl)-5-(1-ethylpropyl)-7-methyl-4-oxopyrrolo[2,1-f][1,2,4]triazin-3(4H)-yl]acetate Methyl bromoacetate (0.14 mL), potassium carbonate (66 mg) and tetrabutylammonium iodide (12 mg) were added to the N,N-dimethylformamide solution (3 mL) of the compound prepared in Example 36 (109 mg), and the reaction mixture was stirred at room temperature overnight. Water was added to the reaction mixture, and the reaction mixture was extracted with ethyl acetate. The organic layer was washed by a saturated aqueous solution of sodium chloride, and dried with anhydrous sodium sulfate. The organic layer was concentrated under reduced pressure. The obtained residue was purified by column chromatography on silica gel (with an automatic purifying equipment made in Yamazen corporation) to obtain a title compound (95 mg) having the following physical data.
TLC: Rf 0.26 (n-hexane/ethyl acetate=4/1);
$^1$H-NMR (CDCl$_3$): δ 0.61-1.08 (m, 6 H), 1.47-1.82 (m, 4 H), 2.41 (s, 3 H), 3.22-3.45 (m, 1H), 3.64 (s, 3 H), 3.77-4.00 (m, 4 H), 5.05 (d, J=17.56 Hz, 1 H), 6.19 (s, 1 H), 6.90 (dd, J=8.60, 2.56 Hz, 1 H), 7.02 (d, J=2.56 Hz, 1 H), 7.40 (d, J=8.60 Hz, 1 H).

EXAMPLE 38

[2-(2-chloro-4-methoxyphenyl)-5-(1-ethylpropyl)-7-methyl-4-oxopyrrolo[2,1-f][1,2,4]triazin-3(4H)-yl] acetic acid 2N aqueous solution of sodium hydroxide (0.21 mL) was added to the mixed solution of methanol (0.4 mL) and tetrahydrofuran (0.6 mL) of the compound prepared in Example 37 (91 mg), and the reaction mixture was stirred at room temperature for 2 hours. The reaction mixture was neutralized with 1N hydrochloric acid (0.42 mL) on ice bath, and extracted with ethyl acetate. The organic layer was washed by a saturated aqueous solution of sodium chloride, and dried with anhydrous sodium sulfate. The organic layer was concentrated under reduced pressure. The title compound (85 mg) having the following physical data was obtained.
TLC: Rf 0.33 (chloroform/methanol=9/1);
$^1$H-NMR (CDCl$_3$): δ 0.75-0.98 (m, 6 H), 1.48-1.81 (m, 4 H), 2.40 (s, 3 H), 3.21-3.49 (m, 1H), 3.81-4.01 (m, 4 H), 5.00 (d, J=17.56 Hz, 1 H), 6.19 (s, 1 H), 6.94 (dd, J=8.60, 2.56 Hz, 1 H), 7.02 (d, J=2.56 Hz, 1 H), 7.38 (d, J=8.60 Hz, 1 H).

EXAMPLE 39

2-[2-(2-chloro-4-methoxyphenyl)-5-(1-ethylpropyl)-7-methyl-4-oxopyrrolo[2,1-f][1,2,4]triazin-3(4H)-yl] acetamide N-hydroxysuccinimide (24 mg) and 1-ethyl-3-(3-dimethylaminopropyl)carbodiimide/hydrochloride (63 mg) were added to the acetonitrile solution (2 mL) of the compound prepared in Example 38 (85 mg). The reaction mixture was stirred at 0° C. for an hour. A saturated aqueous solution of ammonia (1 mL) was added to the reaction mixture, and the reaction mixture was stirred at 0° C. for 30 minutes. Water was added to the reaction mixture, and the reaction mixture was extracted with ethyl acetate. The organic layer was washed by a saturated aqueous solution of sodium chloride, and dried with, anhydrous sodium sulfate. The organic layer was concentrated under reduced pressure. The obtained residue was purified by column chromatography on silica gel (with an automatic purifying equipment made in Yamazen corporation) to obtain the compound of the present invention (65 mg) having the following physical data.
TLC: Rf 0.38 (n-hexane/ethyl acetate=1/2);

¹H-NMR (CDCl₃): δ 0.63-1.03 (m, 6 H), 1.44-1.87 (m, 4 H), 2.40 (s, 3 H), 3.16-3.46 (m, 1H), 3.69-3.99 (m, 4 H), 4.88 (d, J=16.1 Hz, 1 H), 5.52 (s, 1 H), 5.94 (s, 1 H), 6.20 (s, 1 H), 6.91 (dd, J=8.6, 2.6 Hz, 1 H), 7.01 (d, J=2.6 Hz, 1 H), 7.49 (d, J=8.6 Hz, 1 H).

EXAMPLE 40

2-(2-chloro-4-methoxyphenyl)-5-(1-ethylpropyl)-3-(2-hydroxyethyl)-7-methylpyrrolo[2,1-f][1,2,4]triazin-4(3H)-one Potassium carbonate (60 mg), 2-(2-bromoethoxy)tetrahydro-2H-pyran (175 µL) and n-butylammonium iodide (20 mg) were added to the N,N-dimethylformamide solution (2 mL) of the compound prepared in Example 36 (104 mg). The reaction mixture was stirred at room temperature for 4 hours 10 minutes. Ethyl acetate (50 mL) was added to the reaction mixture. The reaction mixture was washed twice with water and washed once with a saturated aqueous solution of sodium chloride. The reaction mixture was dried with anhydrous sodium sulfate. The organic layer was concentrated under reduced pressure. A rough product of the title compound was obtained. The obtained rough product was purified by column chromatography on silica gel (Yamazen corporation, high flash L, n-hexane→ethyl acetate/n-hexane=1/1) to obtain the compound of the present invention (82 mg) having the following physical data.

TLC: Rf 0.48 (ethyl acetate/n-hexane=1/1);

¹H-NMR (CDCl₃): δ 0.76-0.95 (m, 6 H), 1.44-1.91 (m, 4 H), 2.39 (s, 3 H), 2.81 (t, J=5.4 Hz, 1 H), 3.31-3.46 (m, 1 H), 3.45-3.66 (m, 2 H), 3.67-3.82 (m, 1 H), 3.87 (s, 3 H), 4.21-4.35 (m, 1 H), 6.20 (s, 1 H), 6.94 (dd, J=8.5, 2.5 Hz, 1 H), 7.03 (d, J=2.5 Hz, 1 H), 7.41 (d, J=8.5 Hz, 1 H).

EXAMPLES 41(1)~(18)

By the same procedure as a series of reactions of Example 2→Example 3→Example 4→Example 5→Example 8, using methylmagnesium bromide instead of ethylmagnesium bromide, using cyclopropanemethylamine instead of an aqueous solution of 40% methylamine, and using the corresponding aldehydes instead of the compound prepared in Example 7, the compounds of the present invention having the following physical data were obtained.

EXAMPLE 41(1)

3-(cyclopropylmethyl)-2-(5-fluoro-4-methoxy-2-methylphenyl)-5-isopropyl-7-methylpyrrolo[2,1-f][1,2,4]triazin-4(3H)-one

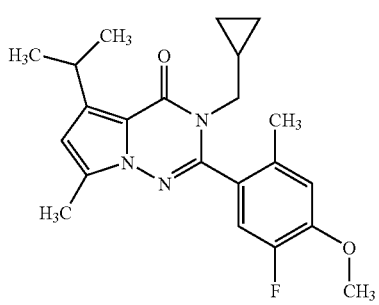 [SMILES: COc1cc(C)c(-c2nn3c(C)cc(C(C)C)c3c(=O)n2CC2CC2)cc1F]

TLC: Rf 0.50 (n-hexane/ethyl acetate=3/1);

¹H-NMR (CDCl₃): δ 0.01-0.27 (m, 2 H), 0.31-0.46 (m, 2 H), 0.79-0.98 (m, 1 H), 1.29-1.34 (m, 6 H), 2.26 (s, 3 H), 2.39 (d, J=0.73 Hz, 3 H), 3.38 (dd, J=14.09, 6.95 Hz, 1 H), 3.67-3.81 (m, 1 H), 3.88 (dd, J=14.09, 7.14 Hz, 1 H), 3.94 (s, 3 H), 6.25 (s, 1 H), 6.87 (d, J=8.42 Hz, 1 H), 7.11 (d, J=10.98 Hz, 1 H).

EXAMPLE 41(2)

3-(cyclopropylmethyl)-5-isopropyl-2-(4-methoxy-2-methylphenyl)-7-methylpyrrolo[2,1-f][1,2,4]triazin-4(3H)-one TLC: Rf 0.58 (n-hexane/ethyl acetate=3/1);

¹H-NMR (CDCl₃): δ −0.03-0.09 (m, 1 H), 0.09-0.24 (m, 1 H), 0.24-0.45 (m, 2 H), 0.80-0.99 (m, 1 H), 1.31 (dd, J=6.86, 1.56 Hz, 6 H), 2.27 (s, 3 H), 2.39 (s, 3 H), 3.36 (dd, J=14.09, 6.95 Hz, 1 H), 3.69-3.81 (m, 1 H), 3.82-3.96 (m, 4 H), 6.24 (s, 1 H), 6.80-6.88 (m, 2 H), 7.27-7.35 (m, 1 H).

EXAMPLE 41(3)

3-(cyclopropylmethyl)-5-isopropyl-7-methyl-2-[2-methyl-4-(trifluoromethoxy)phenyl]pyrrolo[2,1-f][1,2,4]triazin-4(3H)-one TLC: Rf 0.52 (ethyl acetate/n-hexane=1/6);

¹H-NMR (CDCl₃): δ −0.03-0.23 (m, 2 H), 0.29-0.47 (m, 2 H), 0.77-0.95 (m, 1 H), 1.30 (t, J=6.8 Hz, 6 H), 2.33 (s, 3 H), 2.39 (s, 3 H), 3.34 (dd, J=14.2, 6.8 Hz, 1 H), 3.67-3.82 (m, 1H), 3.87 (dd, J=14.2, 6.8 Hz, 1 H), 6.26 (s, 1 H), 7.14-7.22 (m, 2 H), 7.39-7.47 (m, 1 H).

EXAMPLE 41(4)

2-[2-chloro-4-(methylthio)phenyl]-3-(cyclopropylmethyl)-5-isopropyl-7-methylpyrrolo[2,1-f][1,2,4]triazin-4(3H)-one TLC: Rf 0.52 (ethyl acetate/n-hexane=1/6);

¹H-NMR (CDCl₃): δ −0.05-0.08 (m, 1 H), 0.19-0.47 (m, 3 H), 0.78-1.00 (m, 1 H), 1.30 (d, J=7.0 Hz, 6 H), 2.39 (d, J=0.7 Hz, 3 H), 2.54 (s, 3 H), 3.20 (dd, J=14.5, 7.0 Hz, 1 H), 3.67-3.85 (m, 1 H), 4.07-4.17 (m, 1 H), 6.26 (s, 1 H), 7.21-7.26 (m, 1 H), 7.31 (d, J=1.8 Hz, 1 H), 7.41 (d, J=8.1 Hz, 1 H).

EXAMPLE 41(5)

3-(cyclopropylmethyl)-2-(2,4-dichlorophenyl)-5-isopropyl-7-methylpyrrolo[2,1-f][1,2,4]triazin-4(3H)-one TLC: Rf 0.63 (ethyl acetate/n-hexane=1/6);

¹H-NMR (CDCl₃): δ −0.06-0.05 (m, 1 H), 0.19-0.50 (m, 3 H), 0.77-0.95 (m, 1 H), 1.30 (d, J=7.0 Hz, 6 H), 2.38 (d, J=0.7 Hz, 3 H), 3.16 (dd, J=14.5, 7.0 Hz, 1 H), 3.69-3.80 (m, 1H), 4.11 (dd, J=14.5, 7.0 Hz, 1 H), 6.26 (s, 1 H), 7.39-7.44 (m, 1 H), 7.45-7.50 (m, 1 H), 7.53 (d, J=1.8 Hz, 1 H).

EXAMPLE 41(6)

2-(2-chloro-4-methoxy-5-methylphenyl)-3-(cyclopropylmethyl)-5-isopropyl-7-methylpyrrolo[2,1-f][1,2,4]triazin-4(3H)-one TLC: Rf 0.41 (ethyl acetate/n-hexane=1/6);
$^1$H-NMR (CDCl$_3$): δ −0.05-0.04 (m, 1 H), 0.18-0.48 (m, 3 H), 0.81-1.00 (m, 1 H), 1.30 (d, J=7.0 Hz, 6 H), 2.23 (s, 3 H), 2.40 (d, J=0.7 Hz, 3 H), 3.23 (dd, J=14.3, 7.0 Hz, 1 H), 3.70-3.81 (m, 1 H), 3.89 (s, 3 H), 4.05-4.14 (m, 1 H), 6.25 (s, 1 H), 6.90 (s, 1 H), 7.25 (d, J=0.7 Hz, 1 H).

EXAMPLE 41(7)

3-(cyclopropylmethyl)-5-isopropyl-2-[4-methoxy-2-(trifluoromethyl)phenyl]-7-methylpyrrolo[2,1-f][1,2,4]triazin-4(3H)-one TLC: Rf 0.41 (ethyl acetate/n-hexane=1/6);
$^1$H-NMR (CDCl$_3$): δ −0.01-0.12 (m, 1 H), 0.14-0.26 (m, 1 H), 0.29-0.50 (m, 2 H), 0.78-0.99 (m, 1 H), 1.29-1.34 (m, 6 H), 2.36 (d, J=0.7 Hz, 3 H), 3.34 (dd, J=14.3, 7.0 Hz, 1 H), 3.68-3.80 (m, 1 H), 3.84 (dd, J=14.3, 7.0 Hz, 1 H), 3.93 (s, 3 H), 6.24 (s, 1 H), 7.17 (dd, J=8.3, 2.5 Hz, 1 H), 7.29 (d, J=2.5 Hz, 1 H), 7.48 (d, J=8.3 Hz, 1 H).

EXAMPLE 41(8)

3-(cyclopropylmethyl)-2-(2,4-dimethylphenyl)-5-isopropyl-7-methylpyrrolo[2,1-f][1,2,4]triazin-4(3H)-one TLC: Rf 0.59 (ethyl acetate/n-hexane=1/6);
$^1$H-NMR (CDCl$_3$): δ −0.04-0.10 (m, 1 H), 0.07-0.23 (m, 1 H), 0.26-0.48 (m, 2 H), 0.77-1.00 (m, 1 H), 1.29-1.36 (m, 6 H), 2.25 (s, 3 H), 2.39 (s, 6 H), 3.36 (dd, J=14.0, 7.0 Hz, 1 H), 3.69-3.82 (m, 1 H), 3.88 (dd, J=14.0, 7.0 Hz, 1 H), 6.24 (s, 1 H), 7.07-7.16 (m, 2 H), 7.22-7.30 (m, 1 H).

EXAMPLE 41(9)

2-(4-chloro-2-methoxyphenyl)-3-(cyclopropylmethyl)-5-isopropyl-7-methylpyrrolo[2,1-f][1,2,4]triazin-4(3H)-one TLC: Rf 0.37 (ethyl acetate/n-hexane=1/6);
$^1$H-NMR (CDCl$_3$): δ −0.12-0.04 (m, 1 H), 0.16-0.44 (m, 3 H), 0.73-0.94 (m, 1 H), 1.25-1.33 (m, 6 H), 2.38 (d, J=0.7 Hz, 3 H), 3.07 (dd, J=14.5, 7.0 Hz, 1 H), 3.66-3.87 (m, 4 H), 4.15 (dd, J=14.5, 7.1 Hz, 1 H), 6.22 (s, 1 H), 6.97 (d, J=1.8 Hz, 1 H), 7.07 (dd, J=8.1, 1.8 Hz, 1H), 7.35 (d, J=8.1 Hz, 1 H).

EXAMPLE 41(10)

2-(2-chloro-4-methoxyphenyl)-3-(cyclopropylmethyl)-5-isopropyl-7-methylpyrrolo[2,1-f][1,2,4]triazin-4(3H)-one TLC: Rf 0.59 (n-hexane/ethyl acetate=3/1);
$^1$H-NMR (CDCl$_3$): δ −0.08-0.05 (m, 1 H), 0.17-0.47 (m, 3 H), 0.79-0.99 (m, 1 H), 1.31 (d, J=7.0 Hz, 6 H), 2.39 (d, J=0.7 Hz, 3 H), 3.20 (dd, J=14.2, 7.1 Hz, 1 H), 3.67-3.83 (m, 1 H), 3.87 (s, 3 H), 4.12 (dd, J=14.2, 7.0 Hz, 1 H), 6.25 (s, 1 H), 6.93 (dd, J=8.6, 2.4 Hz, 1H), 7.02 (d, J=2.4 Hz, 1 H), 7.42 (d, J=8.6 Hz, 1 H).

EXAMPLE 41(11)

2-(4-chloro-2-methylphenyl)-3-(cyclopropylmethyl)-5-isopropyl-7-methylpyrrolo[2,1-f][1,2,4]triazin-4(3H)-one TLC: Rf 0.79 (n-hexane/ethyl acetate=3/1);
$^1$H-NMR (CDCl$_3$): δ 0.02-0.11 (m, 1 H), 0.12-0.22 (m, 1 H), 0.28-0.46 (m, 2 H), 0.74-0.95 (m, 1 H), 1.28-1.34 (m, 6 H), 2.29 (s, 3 H), 2.38 (d, J=0.5 Hz, 3 H), 3.34 (dd, J=14.1, 7.0 Hz, 1 H), 3.67-3.81 (m, 1 H), 3.86 (dd, J=14.1, 7.0 Hz, 1 H), 6.26 (s, 1 H), 7.29-7.37 (m, 3H).

EXAMPLE 41(12)

3-(cyclopropylmethyl)-2-(2-ethyl-4-methoxyphenyl)-5-isopropyl-7-methylpyrrolo[2,1-f][1,2,4]triazin-4(3H)-one TLC: Rf 0.63 (n-hexane/ethyl acetate=3/1);
$^1$H-NMR (CDCl$_3$): δ 0.02-0.20 (m, 2 H), 0.24-0.44 (m, 2 H), 0.78-0.97 (m, 1 H), 1.23 (t, J=7.5 Hz, 3 H), 1.31 (dd, J=6.9, 2.8 Hz, 6 H), 2.39 (s, 3 H), 2.47-2.64 (m, 2 H), 3.43 (dd, J=14.1, 6.8 Hz, 1 H), 3.67-3.84 (m, 2 H), 3.87 (s, 3 H), 6.24 (s, 1 H), 6.84 (dd, J=8.4, 2.4 Hz, 1 H), 6.88 (d, J=2.4 Hz, 1 H), 7.28 (d, J=8.4 Hz, 1 H).

EXAMPLE 41(13)

2-[2-chloro-4-(trifluoromethoxy)phenyl]-3-(cyclopropylmethyl)-5-isopropyl-7-methylpyrrolo[2,1-f][1,2,4]triazin-4(3H)-one TLC: Rf 0.74 (n-hexane/ethyl acetate=3/1);
$^1$H-NMR (CDCl$_3$): δ −0.11-0.04 (m, 1 H), 0.15-0.55 (m, 3 H), 0.73-0.96 (m, 1 H), 1.28-1.35 (d, J=7.0 Hz, 6 H), 2.39 (s, 3 H), 3.17 (dd, J=14.4, 6.9 Hz, 1 H), 3.68-3.84 (m, 1 H), 4.12 (dd, J=14.5, 7.0 Hz, 1 H), 6.27 (s, 1 H), 7.27-7.33 (m, 1 H), 7.40 (dd, J=2.0, 0.9 Hz, 1 H), 7.58 (d, J=8.4 Hz, 1 H).

EXAMPLE 41(14)

2-[2-chloro-4-(difluoromethoxy)phenyl]-3-(cyclopropylmethyl)-5-isopropyl-7-methylpyrrolo[2,1-f][1,2,4]triazin-4(3H)-one TLC: Rf 0.62 (n-hexane/ethyl acetate=3/1);
$^1$H-NMR (CDCl$_3$): δ −0.06-0.03 (m, 1 H), 0.19-0.51 (m, 3 H), 0.77-0.96 (m, 1 H), 1.31 (d, J=7.0 Hz, 6 H), 2.39 (s, 3 H), 3.18 (dd, J=14.6, 7.1 Hz, 1 H), 3.67-3.86 (m, 1 H), 4.12 (dd, J=14.6, 7.0 Hz, 1 H), 6.27 (s, 1 H), 6.60 (t, J=72.5 Hz, 1 H), 7.20 (dd, J=8.4, 2.4 Hz, 1 H), 7.30 (d, J=2.4 Hz, 1 H), 7.54 (d, J=8.4 Hz, 1 H).

EXAMPLE 41(15)

3-(cyclopropylmethyl)-2-[4-(difluoromethoxy)-2-methylphenyl]-5-isopropyl-7-methylpyrrolo[2,1-f][1,2,4]triazin-4(3H)-one TLC: Rf 0.32 (ethyl acetate/n-hexane=1/6);
$^1$H-NMR (CDCl$_3$): δ −0.05-0.10 (m, 1 H), 0.11-0.24 (m, 1 H), 0.27-0.45 (m, 2 H), 0.75-0.98 (m, 1 H), 1.20-1.37 (m, 6 H), 2.31 (s, 3 H), 2.39 (s, 3 H), 3.34 (dd, J=14.2, 6.9 Hz, 1 H), 3.67-3.81 (m, 1 H), 3.81-3.94 (m, 1 H), 6.26 (s, 1 H), 6.58 (t, J=73.4 Hz, 1 H), 6.99-7.16 (m, 2 H), 7.34-7.46 (m, 1 H).

EXAMPLE 41(16)

2-(2-chloro-4-methoxy-6-methylphenyl)-3-(cyclopropylmethyl)-5-isopropyl-7-methylpyrrolo[2,1-f][1,2,4]triazin-4(3H)-one TLC: Rf 0.62 (n-hexane/ethyl acetate=3/1);
$^1$H-NMR (CDCl$_3$): δ −0.02-0.12 (m, 1 H), 0.16-0.28 (m, 1 H), 0.33-0.45 (m, 2 H), 0.79-0.96 (m, 1 H), 1.28-1.36 (m, 6 H), 2.31 (s, 3 H), 2.39 (d, J=0.73 Hz, 3 H), 3.32 (dd, J=14.36, 7.23 Hz, 1 H), 3.69-3.82 (m, 1 H), 3.82-3.96 (m, 4 H), 6.26 (s, 1 H), 6.77 (dd, J=2.47, 0.64 Hz, 1 H), 6.88 (d, J=2.47 Hz, 1 H).

EXAMPLE 41(17)

3-(cyclopropylmethyl)-5-isopropyl-2-(4-methoxy-2,6-dimethylphenyl)-7-methylpyrrolo[2,1-f][1,2,4]triazin-4(3H)-one TLC: Rf 0.58 (n-hexane/ethyl acetate=3/1);
$^1$H-NMR (CDCl$_3$): δ 0.04-0.17 (m, 2 H), 0.30-0.43 (m, 2 H), 0.76-1.00 (m, 1 H), 1.32 (d, J=6.95 Hz, 6 H), 2.24 (s, 6 H), 2.39 (s, 3 H), 3.55 (d, J=6.95 Hz, 2 H), 3.70-3.81 (m, 1 H), 3.83 (s, 3 H), 6.25 (s, 1 H), 6.67 (s, 2 H).

EXAMPLE 41(18)

2-[4-chloro-2-(difluoromethoxy)phenyl]-3-(cyclopropylmethyl)-5-isopropyl-7-methylpyrrolo[2,1-f][1,2,4]triazin-4(3H)-one TLC: Rf 0.42 (n-hexane/ethyl acetate=9/1);
$^1$H-NMR (CDCl$_3$): δ −0.09-0.07 (m, 1 H), 0.14-0.30 (m, 1 H), 0.29-0.45 (m, 2 H), 0.68-0.94 (m, 1 H), 1.28-1.34 (m, 6 H), 2.37 (s, 3 H), 3.26 (dd, J=14.5, 7.0 Hz, 1 H), 3.63-3.85 (m, 1H), 4.03 (dd, J=14.5, 7.0 Hz, 1 H), 6.26 (s, 1 H), 6.28-6.83 (m, 1 H), 7.31-7.39 (m, 2 H), 7.44-7.52 (m, 1 H).

EXAMPLE 43

Ethyl 3-isobutyl-2-nitro-5-oxohexanoate

Diisopropylethylamine (7.9 mL) was added to the acetonitrile solution (50 mL) of (3E)-6-methylhept-3-en-2-one (6.25 g) and nitro ethyl acetate (5 mL) under argon gas atmosphere, and the reaction mixture was stirred at room temperature overnight. 1N hydrochloric acid was added to the reaction mixture, and the reaction mixture was extracted with ethyl acetate. The organic layer was washed by water and a saturated aqueous solution of sodium chloride, and dried with anhydrous magnesium sulfate. The organic layer was concentrated under reduced pressure. The obtained residue was purified by column chromatography on silica gel (n-hexane/ethyl acetate=95/5→75/25) to obtain the title compound (9.88 g) having the following physical data.
TLC: Rf 0.38 (n-hexane/ethyl acetate=3/1);
$^1$H-NMR (CDCl$_3$): δ 0.89-0.95 (m, 6 H), 1.25-1.35 (m, 5 H), 1.49-1.63 (m, 1 H), 2.16-2.16 (m, 3 H), 2.55-2.88 (m, 2 H), 2.94-3.03 (m, 1 H), 4.24-4.32 (m, 2 H), 5.34-5.38 (m, 1 H).

EXAMPLE 44

Ethyl 3-isobutyl-5-methyl-1H-pyrrole-2-carboxylate

Formamidinesulfinic acid (13.8 g) and ammonium acetate (4.93 g) were added to the isopropanol solution (200 mL) of the compound prepared in Example 43 (9.88 g) under argon gas atmosphere, and the reaction mixture was stirred at 100° C. for 9 hours. The reaction mixture was concentrated under reduced pressure. Water was added to the obtained residue, and the mixture was extracted with ethyl acetate. The organic layer was washed by water and a saturated aqueous solution of sodium chloride, and dried with anhydrous magnesium sulfate. The organic layer was concentrated under reduced pressure. The obtained residue was washed by methanol/water (50/50). The title compound (2.08 g) having the following physical data was obtained.
TLC: Rf 0.57 (n-hexane/ethyl acetate=3/1);
$^1$H-NMR (CDCl$_3$): δ 0.91 (d, J=6.6 Hz, 6 H), 1.35 (t, J=7.1 Hz, 3 H), 1.77-1.91 (m, 1 H), 2.25 (s, 3 H), 2.60 (d, J=7.1 Hz, 2 H), 4.28 (q, J=7.1 Hz, 2 H), 5.79 (d, J=2.9 Hz, 1 H), 8.56-8.65 (m, 1 H).

EXAMPLE 45

4-isobutyl-2-methyl-1H-pyrrole 1N aqueous solution of sodium hydroxide (20 mL) was added to the ethanol solution (20 mL) of the compound prepared in Example 44 (2.08 g), and the reaction mixture was stirred at 90° C. for 2 days. The reaction mixture was cooled to room temperature. 2N hydrochloric acid (15 mL) and ethyl acetate (20 mL) were added to the reaction mixture, and the reaction mixture was stirred at room temperature for an hour. The reaction mixture was extracted with ethyl acetate. The organic layer was washed by water, a saturated aqueous solution of sodium bicarbonate and a saturated aqueous solution of sodium chloride. The organic layer was dried with anhydrous magnesium sulfate, and concentrated under reduced pressure. The title compound (1.69 g) having the following physical data was obtained.
TLC: Rf 0.47 (n-hexane/ethyl acetate=6/1);
$^1$H-NMR (CDCl$_3$): δ 0.91 (d, J=6.6 Hz, 6 H), 1.68-1.81 (m, 1 H), 2.24 (s, 3 H), 2.28 (d, J=7.0 Hz, 2 H), 5.73 (s, 1 H), 6.39 (s, 1 H), 7.56-7.68 (m, 1 H).

EXAMPLE 46

2-(2-chloro-4-methoxyphenyl)-5-isobutyl-3,7-dimethylpyrrolo[2,1-f][1,2,4]triazin-4(3H)-one By the same procedure as a series of reactions of Example 4→Example 5→Example 8, using the compound prepared in Example 45 instead of the compound prepared in Example 3, and using 2-chloro-4-methoxybenzaldehyde instead of the compound prepared in Example 7, the compound of the present invention (130 mg) having the following physical data was obtained.
TLC: Rf 0.50 (n-hexane/ethyl acetate=3/1);
$^1$H-NMR (CDCl$_3$): δ 0.97 (d, J=6.8 Hz, 6 H), 1.91-2.05 (m, 1 H), 2.39 (s, 3 H), 2.81 (dd, J=13.7, 6.9 Hz, 1 H), 2.87 (dd, J=13.7, 7.1 Hz, 1 H), 3.20 (s, 3 H), 3.87 (s, 3 H), 6.15 (s, 1H), 6.94 (dd, J=8.5, 2.6 Hz, 1 H), 7.04 (d, J=2.6 Hz, 1 H), 7.37 (d, J=8.5 Hz, 1 H).

EXAMPLE 47

5-isobutyl-2-(4-methoxy-2,6-dimethylphenyl)-3,7-dimethylpyrrolo[2,1-f][1,2,4]triazin-4(3H)-one By the same procedure as a series of reactions of Example 4→Example 5→Example 8, using the compound prepared in Example 45 instead of the compound prepared in Example 3, and using 2,2-dimethyl-4-methoxybenzaldehyde instead of the compound prepared in Example 7, the compound of the present invention having the following physical data was obtained.

TLC: Rf 0.39 (n-hexane/ethyl acetate=6/1);
$^1$H-NMR (CDCl$_3$): δ 0.99 (d, J=6.6 Hz, 6 H), 1.92-2.06 (m, 1 H), 2.20 (s, 6 H), 2.38 (s, 3H), 2.85 (d, J=7.1 Hz, 2 H), 3.10 (s, 3 H), 3.83 (s, 3 H), 6.15 (s, 1 H), 6.69 (s, 2 H).

EXAMPLE 48

(3E)-6,6,6-trifluoro-5-methylhex-3-en-2-one 1-(triphenylphosphoranylidene)acetone (15.3 g) was added to the dichloromethane solution (50 mL) of 3,3,3-trifluoro-2-methylpropanal (5 g) under argon gas atmosphere, and the reaction mixture was stirred at room temperature for 2 days. The reaction mixture was concentrated under reduced pressure. n-Hexane was added to the obtained residue. Insoluble substance was filtrated, and removed. The obtained filtrate was concentrated under reduced pressure. The title compound (5.1 g) having the following physical data was obtained.

TLC: Rf 0.52 (n-hexane/ethyl acetate=3/1);
$^1$H-NMR (CDCl$_3$): δ 1.31 (d, J=7.0 Hz, 3 H), 2.30 (s, 3 H), 2.99-3.12 (m, 1 H), 6.23 (d, J=16.1 Hz, 1 H), 6.67 (dd, J=16.1, 7.5 Hz, 1 H).

EXAMPLES 49(1)~(2)

By the same procedure as a series of reactions of Example 43→Example 44→Example 45→Example 4→Example 5→Example 8, using the compound prepared in Example 48 instead of (3E)-6-methylhept-3-en-2-one, and using the corresponding aldehydes instead of the compound prepared in Example 7, the compounds of the present invention having the following physical data were obtained.

EXAMPLE 49(1)

2-(2-chloro-4-methoxyphenyl)-3,7-dimethyl-5-(2,2,2-trifluoro-1-methylethyl)pyrrolo[2,1-f][1,2,4]triazin-4(3H)-one TLC: Rf 0.21 (n-hexane/ethyl acetate=9/1);
$^1$H-NMR (CDCl$_3$): δ 1.39-1.53 (m, 3 H), 2.41 (s, 3 H), 3.23 (s, 3 H), 3.88 (s, 3 H), 4.50-4.81 (m, 1 H), 6.39 (s, 1 H), 6.85-7.00 (m, 1 H), 7.00-7.14 (m, 1 H), 7.30-7.45 (m, 1 H).

EXAMPLE 49(2)

2-[2-chloro-4-(difluoromethoxy)phenyl]-3,7-dimethyl-5-(2,2,2-trifluoro-1-methylethyl)pyrrolo[2,1-f][1,2,4]triazin-4(3H)-one TLC: Rf 0.45 (n-hexane/ethyl acetate=4/1);
$^1$H-NMR (CDCl$_3$): δ 1.42-1.53 (m, 3 H), 2.41 (s, 3 H), 3.23 (s, 3 H), 4.49-4.83 (m, 1 H), 6.29-6.89 (m, 2 H), 7.14-7.26 (m, 1 H), 7.30-7.39 (m, 1 H), 7.42-7.58 (m, 1 H).

EXAMPLE 50

Allyl 3,3-dimethylpentanoate

Allyl bromide (14 mL) and potassium carbonate (22.2 g) were added to the N,N-dimethylformamide (160 mL) of 3,3-dimethylpentane acid (21 g) under argon gas atmosphere, and the reaction mixture was stirred at room temperature for 2 hours. Water was added to the reaction mixture, and the reaction mixture was extracted with tert-butyl methyl ether. The organic layer was washed by water and a saturated aqueous solution of sodium chloride. The organic layer was dried with anhydrous magnesium sulfate, and concentrated under reduced pressure. The title compound (26 g) having the following physical data was obtained.

TLC: Rf 0.56 (n-hexane/ethyl acetate=9/1);
$^1$H-NMR (CDCl$_3$): δ 0.86 (t, J=7.5 Hz, 3 H), 0.98 (s, 6 H), 1.35 (q, J=7.5 Hz, 2 H), 2.22 (s, 2 H), 4.55-4.58 (m, 2 H), 5.21-5.25 (m, 1 H), 5.29-5.36 (m, 1 H), 5.86-5.99 (m, 1 H).

EXAMPLE 51

2-(1,1-dimethylpropyl)pent-4-enoic acid

Trimethylsilyl trifluoromethanesulfonate (41 mL) and triethylamine (32 mL) were added to the dichloroethane (230 mL) of the compound prepared in Example 50 (26 g) under argon gas atmosphere, and the reaction mixture was stirred at 95° C. overnight. 2N hydrochloric acid was added to the reaction mixture, and the mixture was extracted with tert-butylmethylether. The organic layer was washed by water. The organic layer was extracted with 0.5N aqueous solution of sodium hydroxide reversely. The extract was washed by tert-butyl methyl ether. The water layer was considered to be the acidity with 2N hydrochloric acid, and extracted with tert-butyl methyl ether. The organic layer was washed by water and a saturated aqueous solution of sodium chloride. The organic layer was dried with anhydrous magnesium sulfate, and concentrated under reduced pressure.

The title compound (15 g) having the following physical data was obtained. TLC: Rf 0.43 (n-hexane/ethyl acetate=3/1);
$^1$H-NMR (CDCl$_3$): δ 0.86 (t, J=7.4 Hz, 3 H), 0.95 (s, 3 H), 0.96 (s, 3 H), 1.31-1.44 (m, 2 H), 2.20-2.38 (m, 3 H), 4.99-5.03 (m, 1 H), 5.06-5.12 (m, 1 H), 5.69-5.82 (m, 1 H), 10.29-10.79 (m, 1 H).

EXAMPLE 52

2-(1,1-dimethylpropyl)-N-methoxy-N-methylpent-4-enamide

Oxalylchloride (9 mL) and N,N-dimethylformamide (1 drop) were added to the dichloromethane (90 mL) of the compound prepared in Example 51 (15 g) under argon gas atmosphere, and the reaction mixture was stirred at room temperature for 30 minutes. The reaction mixture was concentrated under reduced pressure, and the acid chloride was obtained.

The acid chloride was dissolved with acetonitrile (300 mL) under argon gas atmosphere, and N,O-dimethylhydroxyamine hydrochloride (11.3 g) and triethylamine (31 mL) were added to the solution. The reaction mixture was stirred at room temperature overnight. Water was added to the reaction mixture, the mixture was extracted with diethyl ether. The organic layer was washed by 1N hydrochloric acid, water and a saturated aqueous solution of sodium chloride. The organic layer was dried with anhydrous magnesium sulfate, and concentrated under reduced pressure. The obtained residue was purified by column chromatography on silica gel (n-hexane/ethyl acetate=95/5→75/25) to obtain the title compound (17 g) having the following physical data.

TLC: Rf 0.57 (n-hexane/ethyl acetate=3/1);

$^1$H-NMR (CDCl$_3$): δ 0.84 (t, J=7.5 Hz, 3 H), 0.90 (s, 3 H), 0.94 (s, 3 H), 1.31-1.42 (m, 2H), 2.13-2.21 (m, 1 H), 2.41-2.52 (m, 1 H), 2.83-2.88 (m, 1 H), 3.16 (s, 3 H), 3.64 (s, 3H), 4.93-4.97 (m, 1 H), 5.01-5.08 (m, 1 H), 5.63-5.76 (m, 1 H).

EXAMPLE 53

2-(1,1-dimethylpropyl)pent-4-enal

Lithium aluminum hydride (1.23 g) was suspended with diethyl ether (30 mL) under argon gas atmosphere, and the reaction mixture was cooled to 0° C. The diethyl ether (15 mL) of the compound prepared in Example 52 (6.09 g) was dropped to the reaction mixture, and the reaction mixture was stirred at same temperature for 15 minutes. 10% aqueous solution of potassium hydrogensulfate was added to the reaction mixture, and the mixture was extracted with diethyl ether. The organic layer was washed by 1N hydrochloric acid, water and a saturated aqueous solution of sodium chloride. The organic layer was dried with anhydrous magnesium sulfate, and concentrated under reduced pressure. The title compound (3 g) having the following physical data was obtained.
TLC: Rf 0.75 (n-hexane/ethyl acetate=4/1);
$^1$H-NMR (CDCl$_3$): δ 0.87 (t, J=7.4 Hz, 3 H), 0.96 (s, 3 H), 0.98 (s, 3 H), 1.28-1.45 (m, 2H), 2.19-2.26 (m, 2 H), 2.40-2.52 (m, 1 H), 4.96-5.06 (m, 2 H), 5.60-5.74 (m, 1 H), 9.69 (d, J=4.2 Hz, 1 H).

EXAMPLE 54

3,3-dimethyl-2-(2-oxopropyl)pentanal

Palladium chloride (199 mg) and copper chloride (151 mg) were added to the mixed solution of 1,2-dimethoxyethane (12 mL) and water (1.8 mL), and the reaction mixture was stirred for 5 minutes under oxygen gas atmosphere. The 1,2-dimethoxyethane (7.7 mL) of the compound prepared in Example 53 (1.73 g) was added to the reaction mixture, and the reaction mixture was stirred for 2 hours 50 minutes. The reaction mixture was poured into 1N hydrochloric acid, and extracted twice with ethyl acetate. The organic layer was washed by water and a saturated aqueous solution of sodium chloride. The organic layer was dried with anhydrous sodium sulfate, and concentrated under reduced pressure. The title compound (3.27 g) having the following physical data was obtained. This compound was used for the next reaction without being purified.
TLC: Rf 0.57 (n-hexane/ethyl acetate=3/1);
$^1$H-NMR (CDCl$_3$): δ 0.90 (t, J=7.5 Hz, 3 H), 0.93 (s, 3 H), 1.01 (s, 3 H), 1.36 (q, J=7.3 Hz, 2 H), 2.20 (s, 3 H), 2.23-2.42 (m, 1 H), 2.92-3.09 (m, 2 H), 9.84-10.08 (m, 1 H).

EXAMPLE 55

2-[4-(1,1-dimethylpropyl)-2-methyl-1H-pyrrol-1-yl]-1H-isoindole-1,3(2H)-dione

N-aminophthalimide (476 mg) and 5N hydrochloric acid (5 drops) were added to the tetrahydrofuran solution (20 mL) of the compound prepared in Example 54 (1 g). The reaction mixture was stirred for 20 minutes under argon gas atmosphere. Ethyl acetate (100 mL) was added to the reaction mixture. The reaction mixture was washed by a saturated aqueous solution of sodium bicarbonate and a saturated aqueous solution of sodium chloride. The organic layer was dried with anhydrous sodium sulfate, and concentrated under reduced pressure. The obtained residue was purified by column chromatography on silica gel (Yamazen corporation, high flash 2 L, n-hexane→ethyl acetate/n-hexane=1/4) to obtain the title compound (675 mg) having the following physical data.
TLC: Rf 0.50 (n-hexane/ethyl acetate=3/1);
$^1$H-NMR (CDCl$_3$): δ 0.80 (t, J=7.4 Hz, 3 H), 1.18 (s, 6 H), 1.52 (q, J=7.4 Hz, 2 H), 2.04 (d, J=0.7 Hz, 3 H), 5.92-5.97 (m, 1 H), 6.32-6.39 (m, 1 H), 7.80-7.91 (m, 2 H), 7.92-8.05 (m, 2 H).

EXAMPLE 56

3-(1,1-dimethylpropyl)-1-(1,3-dioxo-1,3-dihydro-2H-isoindol-2-yl)-5-methyl-1H-pyrrole-2-carbaldehyde The N,N-dimethylformamide (3 mL) of phosphorus oxychloride (690 μL) was added to the N,N-dimethylformamide (6 mL) of the compound prepared in Example 55 (780 mg), and the reaction mixture was stirred at 75° C. overnight. The reaction mixture was cooled to room temperature, poured into a saturated aqueous solution of sodium bicarbonate which been cooled with ice, and extracted twice with ethyl acetate. The obtained organic layer was washed by water twice and washed by a saturated aqueous solution of sodium chloride once. The organic layer was dried with anhydrous sodium sulfate, and concentrated under reduced pressure. The obtained residue was purified by column chromatography on silica gel (Yamazen corporation, high flash L, n-hexane→ethyl acetate/n-hexane=3/7) to obtain the title compound (424 mg) having the following physical data.
TLC: Rf 0.38 (n-hexane/ethyl acetate=3/1);
$^1$H-NMR (CDCl$_3$): δ 0.79-0.90 (m, 3 H), 1.39 (s, 6 H), 1.74 (q, J=7.4 Hz, 2 H), 2.16 (d, J=0.7 Hz, 3 H), 6.08 (d, J=0.7 Hz, 1 H), 7.79-7.90 (m, 2 H), 7.93-8.05 (m, 2 H), 9.88 (s, 1H).

EXAMPLE 57

3-(1,1-dimethylpropyl)-1-(1,3-dioxo-1,3-dihydro-2H-isoindol-2-yl)-5-methyl-1H-pyrrole-2-carboxylic acid Potassium permanganate (824 mg) was added to the mixed solution of acetone (6 mL) and water (4 mL) of the compound prepared in Example 56 (423 mg). The reaction mixture was stirred for 30 minutes under argon gas atmosphere, and purified by sodium sulfate-column chromatography on silica gel (Merck-5744) (ethyl acetate/n-hexane=1/2→3/1). The obtained solution was concentrated under reduced pressure, and purified by column chromatography on silica gel (ethyl acetate/n-hexane=1/2→43/1) again to obtain the title compound (85 mg) having the following physical data.
TLC: Rf 0.43 (n-hexane/ethyl acetate=1/1);
$^1$H-NMR (CDCl$_3$): δ 0.69 (t, J=7.4 Hz, 3 H), 1.27 (s, 6 H), 1.73 (q, J=7.4 Hz, 2 H), 2.11 (s, 3 H), 6.10 (d, J=0.7 Hz, 1 H), 7.76-7.86 (m, 2 H), 7.88-7.97 (m, 2 H), 8.37-10.89 (m, 1 H).

EXAMPLE 58

1-amino-3-(1,1-dimethylpropyl)-N,5-dimethyl-1H-pyrrole-2-carboxamide

The compound prepared in Example 57 (85 mg) was dissolved with thionyl chloride (3 mL), and the mixture was stirred for 40 minutes under reflux. The reaction mixture was concentrated under reduced pressure. The obtained acid chloride was dissolved with methylene chloride (3 mL), and methylamine (41 µL) was added to the solution. The reaction mixture was stirred for 30 minutes, and concentrated under reduced pressure. The obtained residue was dissolved with ethanol (3 mL), and hydrazine monohydrate (63 pt) was added to the solution. The reaction mixture was refluxed for 30 minutes. Even more particularly, hydrazine monohydrate (150 µL) was added to the reaction mixture, and the reaction mixture was stirred for 2 hours under reflux. The reaction mixture was cooled to room temperature, and ethyl acetate (50 mL) was added to the reaction mixture. The obtained organic layer was washed by a saturated aqueous solution of sodium bicarbonate twice and washed by a saturated aqueous solution of sodium chloride once. The organic layer was dried with anhydrous sodium sulfate, and concentrated under reduced pressure. The obtained residue was purified by column chromatography on silica gel (Merck5744, n-hexane→ethyl acetate/n-hexane=2/1) to obtain the title compound (33 mg) having the following physical data.

TLC: Rf 0.41 (n-hexane/ethyl acetate=1/4);
$^1$H-NMR (CDCl$_3$): δ 0.76 (t, J=7.5 Hz, 3 H), 1.25 (s, 6 H), 1.65 (q, J=7.5 Hz, 2 H), 2.20 (d, J=0.7 Hz, 3 H), 2.96 (d, J=4.9 Hz, 3 H), 4.72 (s, 2 H), 5.68 (d, J=0.7 Hz, 1 H), 6.48 (s, 1H).

EXAMPLE 59

2-(2-chloro-4-methoxyphenyl)-5-(1,1-dimethylpropyl)-3,7-dimethylpyrrolo[2,1-f][1,2,4]triazin-4(3H)-one By the same procedure as a reaction of Example 8, using the compound prepared in Example 58 instead of the compound prepared in Example 5, and using 2-chloro-4-methoxybenzaldehyde instead of the compound prepared in Example 7, the compound of the present invention having the following physical data was obtained.

TLC: Rf 0.46 (ethyl acetate/n-hexane=1/6);
$^1$H-NMR (CDCl$_3$): δ 0.76 (t, J=7.5 Hz, 3 H), 1.42 (s, 3 H), 1.43 (s, 3 H), 1.84-2.09 (m, 2 H), 2.38 (s, 3 H), 3.22 (s, 3 H), 3.86 (s, 3 H), 6.25 (d, J=0.7 Hz, 1 H), 6.93 (dd, J=8.4, 2.4 Hz, 1 H), 7.03 (d, J=2.4 Hz, 1 H), 7.36 (d, J=8.4 Hz, 1 H).

EXAMPLE 60

Ethyl 2-(2-chloro-4-methoxyphenyl)-3,7-dimethyl-4-oxo-3,4-dihydropyrrolo[2,1-f][1,2,4]triazin-5-carboxylate By the same procedure as a series of reactions of Example 4→Example 5→Example 8, using Ethyl 5-methyl-1H-pyrrole-3-carboxylate instead of the compound prepared in Example 3, and using 2-chloro-4-methoxybenzaldehyde instead of the compound prepared in Example 7, the title compound having the following physical data was obtained.

TLC: Rf 0.68 (n-hexane/ethyl acetate=1/2);
$^1$H-NMR (CDCl$_3$): δ 1.42 (t, J=7.2 Hz, 3 H), 2.41 (s, 3 H), 3.29 (s, 3 H), 3.88 (s, 3 H), 4.41 (q, J=7.2 Hz, 2 H), 6.83 (s, 1 H), 6.96 (dd, J=2.7, 8.4 Hz, 1 H), 7.06 (d, J=2.7 Hz, 1 H), 7.38 (d, J=8.4 Hz, 1 H).

EXAMPLE 61

2-(2-chloro-4-methoxyphenyl)-3,7-dimethyl-4-oxo-3,4-dihydropyrrolo[2,1-f][1,2,4]triazin-5-carboxylic acid 2N aqueous solution of sodium hydroxide (12.4 mL) was added to the mixed solution of methanol (30 mL) and tetrahydrofuran (30 mL) of the compound prepared in Example 60 (3.11 g), and the reaction mixture was stirred at 50° C. for 25 hours. After the reaction mixture was cooled, 2N hydrochloric acid (12.4 mL) was added to the reaction mixture. The solid which was precipitated was removed. The filtrate was extracted with ethyl acetate. The obtained organic layer was washed by water and a saturated aqueous solution of sodium chloride. The organic layer was dried with anhydrous sodium sulfate, and concentrated under reduced pressure. The obtained residue was matched with the solid which was filtered, and they were dried under vacuum. The title compound (2.65 g) having the following physical data was obtained.

TLC: Rf 0.62 (n-hexane/ethyl acetate=1/2);
$^1$H-NMR (CDCl$_3$): δ 2.46 (s, 3 H), 3.38 (s, 3 H), 3.90 (s, 3 H), 7.00 (dd, J=2.4, 8.4 Hz, 1H), 7.09-7.10 (m, 1 H), 7.41 (d, J=8.4 Hz, 1 H), 13.8 (s, 1 H).

EXAMPLE 62 tert-Butyl [2-(2-chloro-4-methoxyphenyl)-3,7-dimethyl-4-oxo-3,4-dihydropyrrolo[2,1-f][1,2,4]triazin-5-yl]carbamate tert-Butanol (2.9 mL), diphenylphosphoric acid azide (65 pt) and triethylamine (42 µL) were added to the toluene solution (2.9 mL) of the compound prepared in Example 61 (100 mg), and the reaction mixture was stirred at 130° C. overnight. The reaction mixture was concentrated under reduced pressure after having been cooled. The obtained residue was purified by column chromatography on silica gel (Yamazen corporation, high flash 2 L, n-hexane/ethyl acetate=92/8→71/29) to obtain the title compound (51.7 mg) having the following physical data.

TLC: Rf 0.56 (n-hexane/ethyl acetate=2/1);
$^1$H-NMR (CDCl$_3$): δ 1.52 (s, 9 H), 2.37 (s, 3 H), 3.16 (s, 3 H), 3.87 (s, 3 H), 6.81 (brs, 1 H), 6.81 (dd, J=2.7, 8.4 Hz, 1 H), 7.04 (d, J=2.7 Hz, 1 H), 7.37 (d, J=8.4 Hz, 1 H), 8.08 (brs, 1 H).

EXAMPLE 63 tert-Butyl [2-(2-chloro-4-methoxyphenyl)-3,7-dimethyl-4-oxo-3,4-dihydropyrrolo[2,1-f][1,2,4]triazin-5-yl]ethylcarbamate Sodium hydride (10.9 mg) was added to the anhydrous N,N-dimethylformamide (0.7 mL) of the compound prepared in Example 62 (56.9 mg) on ice bath, and the reaction mixture was stirred for 30 minutes. Subsequently, ethyl iodide (22 µL) was added to the reaction mixture, and the reaction was stirred at room temperature for 2 hours. Water was added to the reaction mixture, and the reaction mixture was extracted with ethyl acetate. The obtained organic layer was washed by water and a saturated aqueous solution of sodium chloride. The organic layer was dried with anhydrous sodium sulfate, and concentrated under reduced pressure. The obtained residue was purified by column chromatography on silica gel (Yamazen corporation, high flash M, n-hexane/ethyl acetate=78/22→57/43) to obtain the title compound (56.2 mg) having the following physical data.

TLC: Rf 0.36 (n-hexane/ethyl acetate=2/1);
$^1$H-NMR (CDCl$_3$): δ 1.20-1.00 (m, 3 H), 1.25-1.56 (m, 9 H), 2.38 (s, 3 H), 3.18 (s, 3 H), 3.60-3.80 (m, 2 H), 3.87 (s, 3 H), 6.26 (brs, 1 H), 6.93 (dd, J=2.4, 8.4 Hz, 1 H), 7.03 (d, J=2.4 Hz, 1 H), 7.26-7.35 (m, 1 H).

EXAMPLE 64

2-(2-chloro-4-methoxyphenyl)-5-(ethylamino)-3,7-dimethylpyrrolo[2,1-f][1,2,4]triazin-4(3H)-one Trifluoroacetic acid (0.5 mL) was added to the compound prepared in Example 63 (48.1 mg), and the reaction mixture was stirred for 10 minutes. The reaction mixture was extracted with ethyl acetate. The obtained organic layer was washed by a saturated aqueous solution of sodium bicarbonate, water, and a saturated aqueous solution of sodium chloride. The organic layer was dried with anhydrous sodium sulfate, and concentrated under reduced pressure. The title compound (37.1 mg) having the following physical data was obtained.

TLC: Rf 0.31 (n-hexane/ethyl acetate=2/1);
$^1$H-NMR (CDCl$_3$): δ 1.26 (t, J=7.2 Hz, 3 H), 2.33 (s, 3 H), 3.10 (s, 3 H), 3.20 (q, J=6.9 Hz, 2 H), 3.86 (s, 3 H), 5.72 (s, 1 H), 6.92 (dd, J=2.4, 8.7 Hz, 1 H), 7.02 (d, J=2.4 Hz, 1 H), 7.35 (d, J=8.7 Hz, 1 H).

EXAMPLE 65

2-(2-chloro-4-methoxyphenyl)-5-(diethylamino)-3,7-dimethylpyrrolo[2,1-f][1,2,4]triazin-4(3H)-one Acetaldehyde (36 mg) and sodium tri(acetoxy)borohydride (132 mg) were added to the 5% acetic acid-dichloromethane solution (3 mL) of the compound prepared in Example 64 (14.3 mg), and the reaction mixture was stirred overnight. Water was added to the reaction mixture, and the reaction mixture was extracted with ethyl acetate. The obtained organic layer was washed by a saturated aqueous solution of sodium bicarbonate, water, and a saturated aqueous solution of sodium chloride. The organic layer was dried with anhydrous sodium sulfate, and concentrated under reduced pressure. The obtained residue was purified by preparative TLC (n-hexane/ethyl acetate=2/1) to obtain the compound of the present invention (12.7 mg) having the following physical data.

TLC: Rf 0.43 (n-hexane/ethyl acetate=2/1);
$^1$H-NMR (CDCl$_3$): δ 1.07 (t, J=7.1 Hz, 6 H), 2.27 (s, 3 H), 3.08 (s, 3 H), 3.32 (q, J=7.1 Hz, 4 H), 3.79 (s, 3 H), 5.83 (s, 1 H), 6.86 (dd, J=8.4, 2.4 Hz, 1 H), 6.96 (d, J=2.4 Hz, 1 H), 7.30 (d, J=8.4 Hz, 1 H).

EXAMPLE 66

N-methoxy-N,2,3-trimethylbutanamide 1-ethyl-3-(3-dimethylaminopropyl)carbodiimide/hydrochloride (10.1 g), 1-hydroxybenzotriazole/monohydrate (9.7 g), N,O-dimethylhydroxylamine/hydrochloride (5.2 g) and triethylamine (14.7 mL) were added to the N,N-dimethylformamide solution (47 mL) of 2,3-dimethylbutane acid (4.73 g) at 0° C., and the reaction mixture was stirred at room temperature for 14 hours. After the reaction mixture was cooled to 0° C., 1N hydrochloric acid (100 mL) was added to the reaction mixture. The reaction mixture was poured into water, and extracted with diethyl ether. The obtained organic layer was washed by a saturated aqueous solution of sodium bicarbonate, water, and a saturated aqueous solution of sodium chloride. The organic layer was dried with anhydrous magnesium sulfate, and concentrated under reduced pressure. The title compound (6 g) having the following physical data was obtained.

TLC: Rf 0.12 (dichloromethane/methanol=9/1);
$^1$H-NMR (CDCl$_3$): δ 3.67 (d, J=0.6 Hz, 3 H), 3.19 (s, 3 H), 2.60 (m, 1 H), 1.88 (m, 1 H), 1.09 (d, J=6.9 Hz, 3 H), 0.96-0.87 (m, 6 H).

EXAMPLE 67

2,3-dimethylbutanal

Lithium aluminum hydride (2.3 mL) was added to the diethyl ether solution (80 mL) of the compound prepared in Example 66 (6 g) at 0° C., and the reaction mixture was stirred for 30 minutes. 5% aqueous solution of potassium hydrogensulfate was added to the reaction mixture, and the reaction was stopped. The obtained organic layer was washed by a saturated aqueous solution of sodium chloride. The organic layer was dried with anhydrous magnesium sulfate, and concentrated under reduced pressure. The title compound (3.2 g) having the following physical data was obtained.

TLC: Rf 0.72 (n-hexane/ethyl acetate=5/1);
$^1$H-NMR (CDCl$_3$): δ 9.66 (d, J=2.1 Hz, 1 H), 2.09 (m, 1 H), 1.80-1.42 (m, 1 H), 1.06-0.86 (m, 9 H).

EXAMPLE 68

2-(2-chloro-4-methoxyphenyl)-5-(1,2-dimethylpropyl)-3,7-dimethylpyrrolo[2,1-f][1,2,4]triazin-4(3H)-one By the same procedure as a series of reactions of Example 48→Example 43→Example 44→Example 45→Example 4→Example 5→Example 8, using the compound prepared in Example 67 instead of 3,3,3-trifluoro-2-methylpropanal, and using 2-chloro-4-methoxybenzaldehyde instead of the compound prepared in Example 7, the compound of the present invention (139 mg) having the following physical data was obtained.

TLC: Rf 0.19 (n-hexane/ethyl acetate=7/1);
$^1$H-NMR (CDCl$_3$): δ 0.78-1.05 (m, 6 H), 1.12-1.36 (m, 3 H), 1.76-2.03 (m, 1 H), 2.39 (s, 3 H), 3.21 (s, 3 H), 3.38-3.60 (m, 1 H), 3.87 (s, 3 H), 6.20 (s, 1 H), 6.89-6.99 (m, 1 H), 7.04 (d, J=2.6 Hz, 1 H), 7.29-7.50 (m, 1 H).

EXAMPLE 69

2-(2-chloro-4-methoxyphenyl)-5-(1-ethylbutyl)-3,7-dimethylpyrrolo[2,1-f][1,2,4]triazin-4(3H)-one By the same procedure as a series of reactions of Example 66→Example 67→Example 48→Example 43→Example 44→Example 45→Example 4→Example 5→Example 8, using 2-ethylpentanoic acid instead of 2,3-dimethylbutane acid, and using 2-chloro-4-methoxybenzaldehyde instead of the compound prepared in Example 7, the compound of the present invention having the following physical data was obtained.

TLC: Rf 0.28 (n-hexane/ethyl acetate=5/1);
$^1$H-NMR (CDCl$_3$): δ 0.73-0.99 (m, 6 H), 1.14-1.39 (m, 2 H), 1.44-1.77 (m, 4 H), 2.39 (s, 3H), 3.20 (s, 3 H), 3.38-3.59 (m, 1 H), 3.86 (s, 3 H), 6.16 (s, 1 H), 6.93 (dd, J=8.6, 2.6 Hz, 1 H), 7.03 (d, J=2.6 Hz, 1 H), 7.36 (dd, J=8.6 Hz, 1 H).

EXAMPLE 70

(3R)-3-methyl-2-(2-oxopropyl)hexanal

By the same procedure as a series of reactions of Example 50→Example 51→Example 52→Example 53→Example 54, using (3R)-3-methylhexanoic acid instead of 3,3-dimethylpentane acid, the title compound having the following physical data was obtained.

TLC: Rf 0.27 (n-hexane/ethyl acetate=9/1);
$^1$H-NMR (CDCl$_3$): δ 9.74 and 9.68 (s, total 1 H), 3.04 (m, 1 H), 2.90 (m, 1H), 2.30 (m, 1H), 2.22 and 2.21 (s, total 3 H), 2.19-1.90 (m, 2 H), 1.48-1.05 (m, 4 H), 0.98-0.80 (m, 6H).

EXAMPLE 71

2-methyl-4-[(1R)-1-methylbutyl]-1H-pyrrole

Ammonium acetate (65 g) was added to the ethanol solution (300 ml) of the compound prepared in Example 70 (49.6 g), the reaction mixture was heated and refluxed for 6 hours. The reaction mixture was added to the mixed solution of tert-butyl methyl ether and cold water after having been cooled. The organic layer was separated. The obtained organic layer was washed by a saturated aqueous solution of sodium bicarbonate, and a saturated aqueous solution of sodium chloride. The organic layer was dried with anhydrous sodium sulfate, and concentrated under reduced pressure. The title compound (37 g) having the following physical data was obtained.

TLC: Rf 0.47 (n-hexane/ethyl acetate=9/1);
$^1$H-NMR (CDCl$_3$): δ 7.60 (m, 1 H), 6.40 (m, 1 H), 5.78 (m, 1 H), 2.59 (m, 1 H), 2.24 (m, 3H), 1.58-1.05 (m, 7 H), 0.88 (t, J=7.2 Hz, 3 H).

EXAMPLE 72

1-amino-N,5-dimethyl-3-[(1R)-1-methylbutyl]-1H-pyrrole-2-carboxamide

By the same procedure as a series of reactions of Example 4→Example 5, using the compound prepared in Example 71 instead of the compound prepared in Example 3, the title compound having the following physical data was obtained.

TLC: Rf 0.30 (n-hexane/isopropanol=3/1);
$^1$H-NMR (CDCl$_3$): δ 0.86 (t, J=7.5 Hz, 3 H), 1.18 (d, J=6.9 Hz, 3 H), 1.35-1.45 (m, 2 H), 1.40-1.55 (m, 2 H), 2.23 (s, 3 H), 2.95 (d, J=5.1 Hz, 3 H), 3.14-3.25 (m, 1 H), 5.13 (s, 2H), 5.72 (s, 1 H), 6.74 (brs, 1 H).

EXAMPLE 73

1-{[2-chloro-4-(methylthio)benzoyl]amino}-N,5-dimethyl-3-[(1R)-1-methylbutyl]-1H-pyrrole-2-carboxamide Pyridine (2.19 mL) and an anhydrous tetrahydrofuran solution (10 mL) of 2-chloro-4-methylthiobenzoyl chloride (5.51 g) were added to the anhydrous tetrahydrofuran solution (50 mL) of the compound prepared in Example 72 (5.05 g), and the reaction mixture was stirred for 2 hours. The reaction mixture was extracted with dichloromethane. The obtained organic layer was washed by 1N hydrochloric acid, water, and a saturated aqueous solution of sodium chloride. The organic layer was dried with anhydrous sodium sulfate, and filtered. The filtrate was concentrated under reduced pressure. The title compound (8.02 g) having the following physical data was obtained.

TLC: Rf 0.72 (n-hexane/ethyl acetate=1/1);
$^1$H-NMR (CDCl$_3$): δ 0.87 (t, J=7.2 Hz, 3 H), 1.18-1.29 (m, 5 H), 1.46-1.53 (m, 2 H), 2.22 (s, 3 H), 2.51 (s, 3 H), 2.84-2.90 (m, 4 H), 5.75-5.77 (m, 1 H), 5.83 (s, 1 H), 7.18 (dd, J=2.1, 8.4 Hz, 1 H), 7.26-7.27 (m, 1 H), 7.68 (d, J=8.4 Hz, 1 H), 9.32 (s, 1 H).

EXAMPLE 74

2-[2-chloro-4-(methylthio)phenyl]-3,7-dimethyl-5-[(1R)-1-methylbutyl]pyrrolo[2,1-f][1,2,4]triazin-4(3H)-one p-toluenesulfonic acid monohydrate (3.62 g) was added to the toluene solution (80 mL) of the compound prepared in Example 73 (7.75 g), and the reaction mixture was heated and refluxed for 14 hours. After the reaction mixture was cooled, ethyl acetate was added to the reaction mixture. The obtained organic layer was washed by water, a saturated aqueous solution of sodium bicarbonate and a saturated aqueous solution of sodium chloride. The organic layer was dried with anhydrous sodium sulfate, and concentrated under reduced pressure. The obtained residue was purified by column chromatography on silica gel (n-hexane/ethyl acetate=100/0→79/21) to obtain the compound of the present invention (6 g) having the following physical data.

TLC: Rf 0.52 (n-hexane/ethyl acetate=4/1);
$^1$H-NMR (CDCl$_3$): δ 0.86-0.95 (m, 3 H), 1.23-1.43 (m, 5 H), 1.48-1.72 (m, 2 H), 2.38 (d, J=0.55 Hz, 3 H), 2.53 (s, 3 H), 3.21 (s, 3 H), 3.58-3.72 (m, 1 H), 6.21 (s, 1 H), 7.20-7.27 (m, 1 H), 7.30-7.37 (m, 2 H).

EXAMPLE 75

Methyl 2-chloro-4-(methylthio)benzoate 2-chloro-4-(methylthio)benzoic acid (5 g) was suspended with methanol (75 mL). Thionyl chloride (3.6 mL) was dropped to the reaction mixture, and the reaction mixture was stirred at 60° C. for 4 hours. The reaction mixture was concentrated under reduced pressure. A saturated aqueous solution of sodium bicarbonate was added to the reaction mixture, and the reaction mixture was extracted with ethyl acetate. The obtained organic layer was washed by water and a saturated aqueous solution of sodium chloride. The organic layer was dried with anhydrous magnesium sulfate, and concentrated under reduced pressure. The title compound (4.42 g) having the following physical data was obtained.

TLC: Rf 0.52 (n-hexane/ethyl acetate=3/1);
$^1$H-NMR (CDCl$_3$): δ 2.51 (s, 3 H), 3.91 (s, 3 H), 7.12 (dd, J=8.3, 2.0 Hz, 1 H), 7.25 (d, J=2.0 Hz, 1 H), 7.79 (d, J=8.3 Hz, 1 H).

EXAMPLE 76

2-chloro-4-(methylthio)benzohydrazide

Hydrazine/monohydrate (5 mL) was added to the ethanol solution (20 mL) of the compound prepared in Example 75 (4.42 g), and the reaction mixture was stirred at 100° C. for 3 hours. Water was added to the reaction mixture, and the reaction mixture was extracted with ethyl acetate. The obtained organic layer was washed by water and a saturated aqueous solution of sodium chloride. The organic layer was dried with anhydrous magnesium sulfate, and concentrated under reduced pressure. The obtained residue was washed by hexane/ethyl acetate (50/50). The title compound (3.51 g) having the following physical data was obtained.

TLC: Rf 0.33 (ethyl acetate);

¹H-NMR (CDCl₃): δ 2.50 (s, 3 H), 4.13 (d, J=4.2 Hz, 2 H), 7.16 (dd, J=8.1, 1.7 Hz, 1 H), 7.22 (d, J=1.7 Hz, 1 H), 7.49-7.55 (m, 1 H), 7.63 (d, J=8.1 Hz, 1 H).

EXAMPLE 77

2-chloro-N-{2-methyl-4-[(1S)-1-methylbutyl]-1H-pyrrol-1-yl}-4-(methylthio)benzamide The compound prepared in Example 76 (1.65 g) and (3S)-3-methyl-2-(2-oxopropyl)hexanal (1.86 g) were dissolved with tetrahydrofuran (10 mL), and 5N hydrochloric acid (0.2 mL) was added to the reaction mixture. The reaction mixture was stirred at room temperature for 6 hours. A saturated aqueous solution of sodium bicarbonate and water were added to the reaction mixture, and the reaction mixture was extracted with ethyl acetate. The obtained organic layer was washed by water and a saturated aqueous solution of sodium chloride. The organic layer was dried with anhydrous magnesium sulfate, and concentrated under reduced pressure. The obtained residue was purified by column chromatography on silica gel (n-hexane/ethyl acetate=85/15→65/35) to obtain the title compound (1.6 g) having the following physical data.

TLC: Rf 0.34 (n-hexane/ethyl acetate=3/1);
¹H-NMR (CDCl₃): δ 0.89 (t, J=7.1 Hz, 3 H), 1.17 (d, J=7.0 Hz, 3 H), 1.28-1.54 (m, 4 H), 2.18 (s, 3 H), 2.52 (s, 3 H), 2.56-2.65 (m, 1 H), 5.83 (s, 1 H), 6.44 (d, J=2.0 Hz, 1 H), 7.21 (dd, J=8.2, 1.7 Hz, 1 H), 7.25-7.26 (m, 1 H), 7.76 (d, J=8.2 Hz, 1 H), 8.55 (s, 1 H).

EXAMPLE 78

2-[2-chloro-4-(methylthio)phenyl]-3,7-dimethyl-5-[(1S)-1-methylbutyl]pyrrolo[2,1-f][1,2,4]triazin-4(3H)-one By the same procedure as a series of reactions of Example 4→Example 74, using the compound prepared in Example 77, the compound of the present invention having the following physical data was obtained.

TLC: Rf 0.48 (n-hexane/ethyl acetate=6/1);
¹H-NMR (CDCl₃): δ 0.87-0.93 (m, 3 H), 1.25-1.28 (m, 3 H), 1.29-1.42 (m, 2 H), 1.50-1.70 (m, 2 H), 2.39 (s, 3 H), 2.54 (s, 3 H), 3.21 (s, 3 H), 3.58-3.72 (m, 1 H), 6.22 (s, 1 H), 7.23-7.26 (m, 1 H), 7.33-7.37 (m, 2 H).

EXAMPLE 79

2-[2-chloro-4-(methylthio)phenyl]-5-(1,2-dimethylpropyl)-3,7-dimethylpyrrolo[2,1-f][1,2,4]triazin-4(3H)-one By the same procedure as a series of reactions of Example 48→Example 43→Example 44→Example 45→Example 4→Example 5→Example 8, using the compound prepared in Example 67 instead of 3,3,3-trifluoro-2-methylpropanal, and using 2-chloro-4-methylthiobenzaldehyde instead of the compound prepared in Example 7, the compound of the present invention having the following physical data was obtained.

TLC: Rf 0.54 (n-hexane/ethyl acetate=5/1);
¹H-NMR (CDCl₃): δ 0.81-1.02 (m, 6 H), 1.17-1.30 (m, 3 H), 1.77-2.01 (m, 1 H), 2.39 (s, 3 H), 2.54 (s, 3 H), 3.21 (s, 3 H), 3.40-3.56 (m, 1 H), 6.21 (s, 1 H), 7.20-7.29 (m, 1 H), 7.30-7.41 (m, 2 H).

EXAMPLE 80

2-[2-chloro-4-(methylthio)phenyl]-5-isopropyl-7-methylpyrrolo[2,1-f][1,2,4]triazin-4(3H)-one By the same procedure as a series of reactions of Example 35→Example 36, using 3-isopropyl-5-methyl-1H-pyrrole-2-carboxamide (which was provided by the same procedure as a series of reactions of Example 2→Example 3→Example 4, using methylmagnesium bromide instead of ethylmagnesium bromide, and using a saturated aqueous solution of ammonia instead of an aqueous solution of 40% methylamine) instead of the compound prepared in Example 4, and using 2-chloro-4-methylthiobenzaldehyde instead of 2-chloro-4-methoxybenzaldehyde, the title compound having the following physical data was obtained.

TLC: Rf 0.74 (n-hexane/ethyl acetate=1/1);
¹H-NMR (CDCl₃): δ 9.33 (s, 1 H), 7.60 (d, J=8.1 Hz, 1 H), 7.30 (d, J=1.5 Hz, 1 H), 7.22 (dd, J=8.1, 1.5 Hz, 1 H), 6.27 (s, 1 H), 3.62 (m, 1 H), 2.53 (s, 3 H), 2.45 (s, 3 H), 1.27 (d, J=6.9 Hz, 6 H).

EXAMPLE 81

2-[2-chloro-4-(methylthio)phenyl]-5-isopropyl-7-methyl-3-[2-(tetrahydro-2H-pyran-2-yloxy)ethyl]pyrrolo[2,1-f][1,2,4]triazin-4(3H)-one Potassium carbonate (60 mg), n-butylammonium iodide (20 mg) and 2-(2-bromoethoxy)tetrahydro-2H-pyran (0.174 mL) were added to the N,N-dimethylformamide solution (2 mL) of the compound prepared in Example 80 (100 mg), and the reaction mixture was stirred at 40° C. for 24 hours. The reaction mixture was washed by water and a saturated aqueous solution of sodium chloride after having been diluted with ethyl acetate. The obtained organic layer was dried with anhydrous magnesium sulfate, and concentrated under reduced pressure. The obtained residue was purified by column chromatography on silica gel (n-hexane/ethyl acetate=100/0→44/1) to obtain the title compound (100 mg) having the following physical data.

TLC: Rf 0.47 (n-hexane/ethyl acetate=3/1);
¹H-NMR (CDCl₃): δ 1.30 (d, J=7.0 Hz, 6 H), 1.36-1.78 (m, 6 H), 2.38 (s, 3 H), 2.53 (s, 3H), 3.24-3.92 (m, 6 H), 4.39 (m, 2 H), 6.25 (d, J=3.1 Hz, 1 H), 7.17-7.25 (m, 1 H), 7.27-7.32 (m, 1 H), 7.42 (dd, J=8.1, 4.9 Hz, 1 H).

EXAMPLE 82

2-[2-chloro-4-(methylthio)phenyl]-3-(2-hydroxyethyl)-5-isopropyl-7-methylpyrrolo[2,1-f][1,2,4]triazin-4(3H)-one The 80% acetic acid solution of the compound prepared in Example 81 (90 mg) was stirred at 60° C. for 5 hours. The reaction mixture was diluted with ethyl acetate after having been cooled. The reaction mixture was washed by a saturated aqueous solution of sodium bicarbonate and a saturated aqueous solution of sodium chloride. The obtained organic layer was dried with anhydrous magnesium sulfate, and concentrated under reduced pressure. The obtained residue was purified by column chromatography on silica gel (n-hexane/ethyl acetate=13/2→13/7) to obtain the compound of the present invention (64 mg) having the following physical data.

TLC: Rf 0.33 (n-hexane/ethyl acetate=2/1);

¹H-NMR (CDCl₃): δ 1.30 (m, 6 H), 2.39 (s, 3 H), 2.53 (s, 3 H), 2.69 (t, J=5.40 Hz, 1 H), 3.50-3.83 (m, 4 H), 4.29 (m, 1 H), 6.28 (s, 1 H), 7.19-7.26 (m, 1 H), 7.31 (d, J=1.65 Hz, 1 H), 7.37 (d, J=8.05 Hz, 1 H).

EXAMPLES 83(1)~(11)

By the same procedure as a series of reactions of Example 35→Example 36→Example 81→Example 82, using the corresponding aldehydes instead of 2-chloro-4-methoxybenzaldehyde, and using the corresponding halogen or tosylate compounds instead of 2-(2-bromoethoxy)tetrahydro-2H-pyran, the compounds of the present invention having the following physical data were obtained.

EXAMPLE 83(1)

2-[2-chloro-4-(trifluoromethoxy)phenyl]-3-(2-hydroxyethyl)-5-(1-ethylpropyl)-7-methylpyrrolo[2,1-f][1,2,4]triazin-4(3H)-one TLC: Rf 0.33 (n-hexane/ethyl acetate=3/1);
¹H-NMR (CDCl₃): δ 0.80-0.94 (m, 6 H), 1.52-1.80 (m, 4 H), 2.39 (s, 3 H), 2.52 (t, J=5.3 Hz, 1 H), 3.30-3.44 (m, 1 H), 3.45-3.55 (m, 1 H), 3.56-3.68 (m, 1 H), 3.73-3.85 (m, 1 H), 4.25-4.37 (m, 1 H), 6.22 (s, 1 H), 7.25-7.32 (m, 1 H), 7.40 (d, J=1.5 Hz, 1 H), 7.59 (d, J=8.6 Hz, 1 H).

EXAMPLE 83(2)

2-(2-chloro-4-methoxyphenyl)-3-[(2S)-2,3-dihydroxypropyl]-5-(1-ethylpropyl)-7-methylpyrrolo[2,1-f][1,2,4]triazin-4(3H)-one TLC: Rf 0.24 (n-hexane/ethyl acetate=1/2);
¹H-NMR (CDCl₃): δ 0.79-0.93 (m, 6 H), 1.49-1.82 (m, 4 H), 2.40 (s, 3 H), 2.80-3.76 (m, 7H), 3.87 (s, 3 H), 4.02-4.29 (m, 1 H), 6.19-6.26 (m, 1 H), 6.90-6.98 (m, 1 H), 7.04 (d, J=2.6 Hz, 1 H), 7.34-7.49 (m, 1 H).

EXAMPLE 83(3)

2-[2-chloro-4-(trifluoromethoxy)phenyl]-3-[(2S)-2,3-dihydroxypropyl]-5-(1-ethylpropyl)-7-methylpyrrolo[2,1-f][1,2,4]triazin-4(3H)-one TLC: Rf 0.61 (n-hexane/ethyl acetate=1/2);
¹H-NMR (CDCl₃): δ 0.79-0.93 (m, 6 H), 1.48-1.82 (m, 4 H), 2.40 (s, 3 H), 2.73-2.85 (m, 1H), 2.91-3.24 (m, 1 H), 3.31-3.71 (m, 5 H), 4.07-4.31 (m, 1 H), 6.22-6.28 (m, 1 H), 7.25-7.35 (m, 1 H), 7.38-7.44 (m, 1 H), 7.57 (d, J=8.4 Hz, 1 H).

EXAMPLE 83(4)

2-[2-chloro-4-(methylthio)phenyl]-3-[(2S)-2,3-dihydroxypropyl]-5-(1-ethylpropyl)-7-methylpyrrolo[2,1-f][1,2,4]triazin-4(3H)-one TLC: Rf 0.40 (n-hexane/ethyl acetate=1/2);
¹H-NMR (CDCl₃): δ 0.78-0.92 (m, 6 H), 1.48-1.82 (m, 4 H), 2.39 (s, 3 H), 2.54 (s, 3 H), 2.81-3.29 (m, 2 H), 3.31-3.75 (m, 5 H), 4.04-4.32 (m, 1 H), 6.21-6.25 (m, 1 H), 7.21-7.28 (m, 1 H), 7.32 (d, J=1.8 Hz, 1 H), 7.34-7.43 (m, 1 H).

EXAMPLE 83(5)

2-[6-(dimethylamino)-4-methyl-3-pyridinyl]-3-(2-hydroxyethyl)-5-(1-ethylpropyl)-7-methylpyrrolo[2,1-f][1,2,4]triazin-4(3H)-one TLC: Rf 0.31 (n-hexane/ethyl acetate=1/2);
¹H-NMR (CDCl₃): δ 0.87 (t, J=7.1 Hz, 6 H), 1.48-1.84 (m, 4 H), 2.22 (s, 3 H), 2.39 (s, 3H), 2.79-2.89 (m, 1 H), 3.14 (s, 6 H), 3.30-3.44 (m, 1 H), 3.62-3.77 (m, 3 H), 4.11-4.38 (m, 1 H), 6.19 (s, 1 H), 6.40 (s, 1 H), 8.13 (s, 1 H).

EXAMPLE 83(6)

2-[2-(dimethylamino)-4,6-dimethyl-5-pyrimidinyl]-3-(2-hydroxyethyl)-5-(1-ethylpropyl)-7-methylpyrrolo[2,1-f][1,2,4]triazin-4(3H)-one TLC: Rf 0.53 (n-hexane/ethyl acetate=1/1);
¹H-NMR (CDCl₃): δ 0.87 (t, J=7.4 Hz, 6 H), 1.51-1.82 (m, 4 H), 2.28 (s, 6 H), 2.39 (s, 3 H), 2.89-2.95 (m, 1 H), 3.23 (s, 6 H), 3.30-3.45 (m, 1 H), 3.68 (q, J=5.1 Hz, 2 H), 3.93 (t, J=5.1 Hz, 2 H), 6.21 (s, 1 H).

EXAMPLE 83(7)

2-[6-(dimethylamino)-2-methyl-3-pyridinyl]-3-(2-hydroxyethyl)-5-(1-ethylpropyl)-7-methylpyrrolo[2,1-f][1,2,4]triazin-4(3H)-one TLC: Rf 0.37 (n-hexane/ethyl acetate=1/2);
¹H-NMR (CDCl₃): δ 0.77-0.94 (m, 6 H), 1.52-1.82 (m, 4 H), 2.37 (s, 3 H), 2.39 (s, 3 H), 2.87 (t, J=5.0 Hz, 1 H), 3.14 (s, 6 H), 3.31-3.45 (m, 1 H), 3.57-3.80 (m, 3 H), 4.13-4.28 (m, 1 H), 6.19 (s, 1 H), 6.42 (d, J=8.8 Hz, 1 H), 7.39 (d, J=8.8 Hz, 1 H).

EXAMPLE 83(8)

2-[6-(dimethylamino)-2,4-dimethyl-3-pyridinyl]-3-(2-hydroxyethyl)-5-(1-ethylpropyl)-7-methylpyrrolo[2,1-f][1,2,4]triazin-4(3H)-one TLC: Rf 0.33 (n-hexane/ethyl acetate=1/2);
¹H-NMR (CDCl₃): δ 0.88 (t, J=7.4 Hz, 6 H), 1.52-1.82 (m, 4 H), 2.17 (s, 3 H), 2.32 (s, 3 H), 2.39 (s, 3 H), 3.09-3.17 (m, 7 H), 3.30-3.45 (m, 1 H), 3.55-3.74 (m, 2 H), 3.92 (t, J=5.3 Hz, 2 H), 6.20 (s, 1 H), 6.26 (s, 1 H).

EXAMPLE 83(9)

2-(2-chloro-4-methoxyphenyl)-3-[(2R)-2,3-dihydroxypropyl]-5-(1-ethylpropyl)-7-methylpyrrolo[2,1-f][1,2,4]triazin-4(3H)-one TLC: Rf 0.33 (n-hexane/ethyl acetate=3/1);
¹H-NMR (CDCl₃): δ 0.78-0.95 (m, 6 H), 1.47-1.84 (m, 4 H), 2.40 (s, 3 H), 2.81-3.75 (m, 7 H), 3.87 (s, 3 H), 4.01-4.30

(m, 1 H), 6.17-6.27 (m, 1 H), 6.87-6.98 (m, 1 H), 7.03 (d, J=2.6 Hz, 1 H), 7.34-7.43 (m, 1 H).

EXAMPLE 83(10)

N-{4-[5-(1-ethylpropyl)-3-(2-hydroxyethyl)-7-methyl-4-oxo-3,4-dihydropyrrolo[2,1-f][1,2,4]triazin-2-yl]-3-methylphenyl}-N-methylmethanesulfonamide TLC: Rf 0.23 (n-hexane/ethyl acetate=1/2);
$^1$H-NMR (CDCl$_3$): δ 0.79-0.96 (m, 6 H), 1.50-1.83 (m, 4 H), 2.33 (s, 3 H), 2.39 (s, 3 H), 2.72 (t, J=5.3 Hz, 1 H), 2.92 (s, 3 H), 3.30-3.46 (m, 4 H), 3.54-3.75 (m, 3 H), 4.12-4.24 (m, 1 H), 6.21 (s, 1 H), 7.30-7.39 (m, 2 H), 7.41 (d, J=8.1 Hz, 1 H).

EXAMPLE 83(11)

2-[2-chloro-4-(methylthio)phenyl]-5-(1-ethylpropyl)-3-(2-hydroxyethyl)-7-methylpyrrolo[2,1-f][1,2,4]triazin-4(3H)-one TLC: Rf 0.65 (n-hexane/ethyl acetate=1/1);
$^1$H-NMR (CDCl$_3$): δ 0.78-0.95 (m, 6 H), 1.49-1.82 (m, 4 H), 2.31-2.47 (m, 3 H), 2.54 (s, 3 H), 2.72 (t, J=5.4 Hz, 1 H), 3.30-3.44 (m, 1 H), 3.51-3.67 (m, 2 H), 3.70-3.82 (m, 1 H), 4.24-4.35 (m, 1 H), 6.21 (s, 1 H), 7.24 (dd, J=8.1, 1.6 Hz, 1 H), 7.32 (d, J=1.6 Hz, 1 H), 7.40 (d, J=8.1 Hz, 1 H).

EXAMPLE 84

2-[2-chloro-4-(methylthio)phenyl]-3-(2-hydroxyethyl)-7-methyl-5-(1-methylbutyl)pyrrolo[2,1-f][1,2,4]triazin-4(3H)-one By the same procedure as a series of reactions of Example 35→Example 36→Example 81→Example 82, using 3-(1-methylbutyl)-5-methyl-1H-pyrrole-2-carboxamide (which was provided by the same procedure as a series of reactions of Example 21→Example 15→Example 16→Example 17→Example 18→Example 4, using a saturated aqueous solution of ammonia instead of an aqueous solution of 40% methylamine) instead of the compound prepared in Example 4, and using 2-chloro-4-methylthiobenzaldehyde instead of 2-chloro-4-methoxybenzaldehyde, the compound of the present invention having the following physical data was obtained.

EXAMPLE 85

2-[2-chloro-4-(methylthio)phenyl]-3-(2-hydroxyethyl)-7-methyl-5-[(1S)-1-methylbutyl]pyrrolo[2,1-f][1,2,4]triazin-4(3H)-one By the same procedure as a series of reactions of Example 4→Example 74→Example 81→Example 82, using the compound prepared in Example 77 instead of the compound prepared in Example 3, and using a saturated aqueous solution of ammonia instead of an aqueous solution of 40% methylamine, the compound of the present invention having the following physical data was obtained.
TLC: Rf 0.13 (n-hexane/ethyl acetate=3/1);
$^1$H-NMR (CDCl$_3$): δ 0.84-0.96 (m, 3 H), 1.19-1.44 (m, 5 H), 1.47-1.76 (m, 2 H), 2.30-2.43 (m, 3 H), 2.53 (s, 3 H), 2.61-2.76 (m, 1 H), 3.48-3.69 (m, 3 H), 3.69-3.85 (m, 1 H), 4.21-4.37 (m, 1 H), 6.18-6.30 (m, 1 H), 7.21-7.26 (m, 1 H), 7.31 (d, J=1.6 Hz, 1 H), 7.34-7.42 (m, 1 H).

EXAMPLE 86

2-(2-chloro-4-methoxyphenyl)-3-(2-hydroxyethyl)-7-methyl-5-[(1R)-1-methylbutyl]pyrrolo[2,1-f][1,2,4]triazin-4(3H)-one By the same procedure as a series of reactions of Example 4→Example 5→Example 73→Example 74→Example 81→Example 82, using the compound prepared in Example 71 instead of the compound prepared in Example 3, using a saturated aqueous solution of ammonia instead of an aqueous solution of 40% methylamine, and using 2-chloro-4-methoxybenzoyl chloride instead of 2-chloro-4-methylthiobenzoyl chloride, the compound of the present invention having the following physical data was obtained.
TLC: Rf 0.16 (n-hexane/ethyl acetate=3/1);
$^1$H-NMR (CDCl$_3$): δ 0.86-0.96 (m, 3 H), 1.20-1.43 (m, 5 H), 1.45-1.74 (m, 2 H), 2.31-2.46 (m, 3 H), 2.68-2.80 (m, 1 H), 3.50-3.68 (m, 3 H), 3.70-3.81 (m, 1 H), 3.87 (s, 3 H), 4.22-4.36 (m, 1 H), 6.24 (s, 1 H), 6.90-6.97 (m, 1 H), 7.03 (d, J=2.6 Hz, 1 H), 7.36-7.44 (m, 1 H).

PHARMACOLOGIC EXPERIMENT EXAMPLE

It was confirmed that the compound of the present invention represented by the formula (I) has a CRF receptor antagonistic activity by the following experiments.

Experiment Example 1

Binding Assay

[Membrane Preparation]
The forced-expression cell strain of the human CRF receptor I (parent strain is CHO-K1 cell) was cultured until the cell was confluent and collected with a scraper. The collected cells were washed twice with PBS, and were suspended with an ice-colded binding assay buffer (Tris-HCl (50 mM, pH 7.0), EDTA (2 mM, pH 8.0), and MgCl$_2$ (10 mM)). After fractured with a dounce-type homogenizer, the suspended cells were centrifuged at 10,000 g, and a membrane fraction was collected. The collected membrane fraction was resuspended with a little amount of the binding assay buffer, thereafter diluted with the binding assay buffer so as to have a concentration of 1 mg/mL. The obtained membrane fraction was used for a binding assay.
[Binding Assay]
$^{125}$I-CRF was diluted with the binding assay buffer so as to have a concentration of 0.5 nM, whereby 50 µL of the diluted $^{125}$I-CRF was added to a siliconized 1.5 mL tube. Next, evaluation compounds diluted at appropriate times, DMSO (for general binding), or 100 µM of CRF (for non-specific binding), was added to a 1 µL tube. Finally, 50 µL of the membrane fraction was added thereto and the reaction was started (final concentration of $^{125}$I-CRF was 0.25 nM). The tube was incubated at room temperature for 2 hours. After the reaction, the tube was centrifuged at 20,000 g in order to collect the membrane fraction. The supernatant was discarded, and the pellet was washed with an ice-colded PBS/ 0.01% TritonX-100. A membrane binding count was measured using a γ counter. The specific binding count was obtained by subtracting the non-specific count from the measured count.
As a result, it was revealed that the compound of the present invention had a strong receptor binding activity (IC$_{50}$ value <1 µM). About concrete IC$_{50}$ value of the compound of the present invention, they are shown in table 1.

TABLE 1

| Compound | IC$_{50}$ (nM) |
| --- | --- |
| Compound of example 8 | 6.1 |
| Compound of example 8 (25) | 3.6 |
| Compound of example 8 (27) | 14.7 |
| Compound of example 8 (38) | 23.5 |
| Compound of example 8 (44) | 7.8 |
| Compound of example 8 (48) | 7.2 |
| Compound of example 13 | 5.3 |
| Compound of example 14 (2) | 4.5 |
| Compound of example 22 | 2.1 |
| Compound of example 23 | 11 |
| Compound of example 24 (21) | 5.2 |
| Compound of example 28 (10) | 20.7 |
| Compound of example 65 | 4.9 |

Experiment Example 2

Receptor Antagonistic Activity (Cyclic AMP Assay)

The forced expression cell strain of the human CRF receptor I was cultured at 37° C. under 5% carbon dioxide and 95% air by using a Ham's F-12 medium (F-12 nutrient mixture) containing 10% bovine fetal serum and 1% antibiotic substance-antifungal agent. On the previous day before the cyclic AMP was measured, the cells were inoculated into a 96-well plate in an amount of $1 \times 10^4$ cell/well. On the measurement day, the cells were washed twice with a Ham's F-12 medium, whereby a solution of Ham's F-12 medium/1 mM 3-isobutyl-1-methylxanthine (assay medium) (178 µL) was added to each well. After the incubation at 37° C. for 15 minutes, the solutions (2 µL) of evaluation compound in various concentrations were added thereto, or DMSO (2 µL) was added to a CRF group and a blank group. An assay medium (20 µL) containing 10 nM human/rat CRF was added to wells of an evaluation compound group and the CRF group. An assay medium (20 µL) containing 0.00001% acetic acid was added to the blank group. Each group was further incubated at 37° C. for 15 minutes. The supernatant was removed and ice-colded to stop the reaction. Note that the reactions of 2 wells were the same in all reactions. The measurement for accumulated cyclic AMP amount in cells was carried out by using a cyclic AMP Biotrak enzyme immunoassay system (manufactured by GE Healthcare). The accumulated cyclic AMP amounts were calculated by subtracting mean values of corresponding 2 wells in the blank group from that of 2 wells. The IC$_{50}$ values were calculated with non-linear regression analysis by defining logarithm concentration of the evaluation compound as independent variable and an accumulated cyclic AMP amount as dependent variable.

As a result, it was revealed that the compound of the present invention has a strong antagonistic activity against CRF (IC$_{50}$ value <1 µM). About concrete IC$_{50}$ value of the compound of the present invention, they are shown in table 2.

TABLE 2

| Compound | IC$_{50}$ (nM) |
| --- | --- |
| Compound of example 8 | 1.8 |
| Compound of example 8 (25) | 1.7 |
| Compound of example 8 (27) | 9.4 |
| Compound of example 8 (38) | 34.8 |
| Compound of example 8 (44) | 4.2 |
| Compound of example 8 (48) | 1.2 |
| Compound of example 13 | 3.2 |
| Compound of example 14 (2) | 2.1 |
| Compound of example 22 | 1.9 |
| Compound of example 23 | 9.6 |
| Compound of example 24 (21) | 5.8 |
| Compound of example 28 (10) | 17.1 |
| Compound of example 65 | 3.5 |

The fact that the compounds of the present invention have an antianxiety effect was confirmed by the following test.

Experiment Example 3

Elevated Plus Maze Test with Swim-Stressed Rat 2 open arms with the same lengths (50×10 cm) and 2 close arms (a 30 cm wall was provided) with the same lengths (50×10 cm) were arranged in orthogonal manner at a height of 50 cm from the floor to provide an elevated crossroad maze system. In 70 cm above the both open arms, white light was provided, whereby illuminance was maintained at constant.

SD rats of 7 weeks of age (CHARLES RIVER LABORATORIES JAPAN) were forcedly made to swim for 120 seconds in a pool (40×30×38 cm) at 22° C. of water temperature and 25 cm of water depth. After 9 minutes of soaking stress loading, the rat was put on the center of the system. The activity for 5 minutes of the rat was analyzed with an automatic activity-tracking analysis system (EthoVision Version 3.0, Noldus Information Technology) to calculate the dwell time (second) on the open arm.

Note that no soaking stress was loaded on the control group. In addition, 20% Wellsolve (registered trademark) (5 mL/kg) was orally administered to the vehicle group and evaluation compounds in various concentrations were orally administrated to the evaluation compound administration group 1 hour before the test.

As a result, the dwell time on the open arm was favorably elongated owing to the compound of the present invention at a dose of 10 mg/kg or less compared to that of the vehicle group. For example, administration group of 10 mg/kg of the compound of Example 8 and Example 23 favorably elongated the mean dwell time on the open arm compared to that of the vehicle group. In addition, administration group of 3 mg/g of the compound of Example 8 (25) and Example 28 (10) favorably elongated the mean dwell time on the open arm compared to that of the vehicle group. Accordingly, it was confirmed that the compound of the present invention has strong effects of preventing and/or treating a neuropsychiatric disease, and in particular, an antianxiety effect.

The fact that the compound of the present invention has an anti-depression effect was confirmed by the following test.

Experiment Example 4

Rat Learned Helplessness Test

The learned helplessness test was carried out using a two-way shuttle box which is partitioned into two by a gate which can be opened and closed so that travel to right and left becomes possible. On the 1$^{st}$ day of the learned helplessness test, rats were put into the device under un-escapable condition by closing the gate, and a total of 90 times of an electric shock (0.5 mA) was applied to them through a floor grid for 10 seconds at 2 seconds' intervals (shock training). Rats of the control group were left as they are for the same period of time (for 18 minutes) without applying the electric shock. After 24 hours of the shock training, rats were put into the device under escapable condition by opening the gate to carry out an escape test. After 5 minutes of acclimatization, a light stimulus and a sound stimulus (conditioning stimuli) were applied simultaneously for 5 seconds, and subsequent electric shock (unconditioning stimulus) was applied for 10 seconds. This was regarded as one trial. A case of continuously receiving the electric shock without escape was regarded as escape failure. A total of 40 trials were carried out by setting the interval between respective trials to 5 seconds, and frequency of the escape failure was recorded.

In this connection, the vehicle (20% solvent) and evaluation compound were repeatedly administered once a day for 6 days and further orally administered 1 hour before the shock training.

As a result, the compound of the present invention significantly inhibited increase of the frequency of escape failure for the vehicle group at a dose of 10 mg/kg or less. For example, the compounds of Example 8 and Example 24(21) significantly inhibited increase of the frequency of escape failure for the vehicle group in a 10 mg/kg administration group. Additionally, the compounds of Example 13 and Example 22 significantly inhibited increase of the frequency of escape failure for the vehicle group in a 3 mg/kg administration group. Accordingly, it was confirmed that the compound of the present invention has strong effects of preventing and/or treating a neuropsychiatric disease, and in particular, an anti-depression effect.

The fact that the compound of the present invention has an anti-stress effect was confirmed by the following test.

Experiment Example 5

Water Aversive Stress Model in Rats

Male Wistar rats of 7 weeks of age were used in the test. A platform of 8.5 cm in diameter and 11 cm in height was arranged in the center of a plastic container (30 cm in length, 45 cm in width, 37 cm in height), and water was filled therein to a depth of about 10 cm. Each rat was put on the platform, and the number of evacuations was counted 5, 30 and 60 minutes thereafter. To the vehicle group, 20% Wellsolve (registered trademark) was orally administered, and an evaluation compound having varied concentrations was orally administered to the evaluation compound group, once 30 minutes before loading the water aversive stress. The dose was set to be 5 ml/kg for both cases.

As a result, 60 minutes after loading the water aversive stress, the compound of the present invention significantly inhibited increase of the number of evacuations by the stress loading for the vehicle group at a dose of 10 mg/kg or less. For example, in the case of the compound of Example 14(2), it significantly inhibited increase of the number of evacuations for the vehicle group in a 3 mg/kg administration group. Accordingly, it was confirmed that the compound of the present invention has strong effects of preventing and/or treating a digestive disease such as irritable bowel syndrome and the like, particularly an anti-stress effect.

The fact that the compound of the present invention has a chemical stability was confirmed by the following test.
Stability Test:
1) Stability Test Under Acidic Condition A 1 mg/ml ethanol solution of an evaluation compound and the test liquid first liquid of the disintegration test of The Pharmacopoeia of Japan (to be referred to as Pharmacopoeia first liquid hereinafter) were mixed at a ratio of 1 to 1 (0.5 ml for each) and stirred at 37° C. for 24 hours. Amount of the evaluation compound at 0 minute or after 24 hours was determined by an HPLC apparatus. Survival rate (%) of the evaluation compound was calculated by the following formula.

Survival rate of evaluation compound (%)=amount of evaluation compound after 24 hours of treatment with Pharmacopoeia first liquid/amount of evaluation compound just after treatment with Pharmacopoeia first liquid×100

<HPLC Conditions>
Apparatus: A 1200 series (manufactured by Agilent Technologies, Inc.),
Column: YMC-Pack C4, A-802, 150×4.6 mm I.D., S-5 μm, 120 A (manufactured by YMC),
Mobile phase: A: water, B: acetonitrile, A/B: 35/65,
Column temperature: room temperature,
Flow rate: 1.0 mL/min.

As a result, it was found that the compound of the present invention is stable under an acidic condition. For example, while residual ratio of the compound of Example 8 described in WO2007/069671 was 27%, residual ratio of a compound of Example 8(1) which is the compound of the present invention, was 90%.
2) Light Stability Test After weighing 5 mg of an evaluation compound, it was put into a test tube made of glass which was then sealed with a stop cock. Said test tube was stored at 25° C. for 11 days or 20 days under irradiation of 2500 Lux (a D65 lamp was used as the light source). The evaluation compound after 11 days or 20 days of irradiation was determined by an HPLC apparatus. Survival rate (%) of the evaluation compound was calculated by the following formula.

Survival rate of evaluation compound (%)=amount of evaluation compound after 11 days or 20 days of irradiation (mg)/weighed value of evaluation compound (mg)×100

<HPLC Conditions>
Apparatus: A 1200 series (manufactured by Agilent Technologies, Inc.),
Column: YMC-Pack C4, A-802, 150×4.6 mm I.D., S-5 μm, 120 A (manufactured by YMC),
Mobile phase: A: water, B: acetonitrile, A/B: 35/65,
Column temperature: room temperature,
Flow rate: 1.0 mL/min.

As a result, it was found that the compound of the present invention is stable to light. For example, while residual ratio after 20 days of the compound of Example 8 described in WO2007/069671 was 34%, residual ratios after 20 days of compounds of Example 8 and Example 8(1) which are the compound of the present invention, were 99% and 93%, respectively.

PREPARATION EXAMPLES

Preparation Example 1

The following components were mixed by known method, and thereafter formed into a tablet to obtain 10,000 tablets each containing 10 mg of active ingredient per tablet.

| | |
|---|---|
| 2-[2-chloro-4-(trifluoromethoxy)phenyl]-5-(1-ethylpropyl)-3,7-dimethylpyrrolo[2,1-f][1,2,4]triazin-4(3H)-one (Compound of example 8) | 100 g |
| Carboxymethyl cellulose calcium (disintegrator) | 20 g |
| Magnesium stearate (lubricator) | 10 g |
| Microcrystalline cellulose | 870 g |

Preparation Example 2

The following components were mixed by known method, followed by filtration with a dust-removing filter. The resultant filtrate in an amount of 5 mL was loaded into an ampule, and the resultant mixture was sterilized by heat with an autoclave to obtain 10,000 ampules containing 20 mg of active ingredient per ampule.

| | |
|---|---|
| 2-[2-chloro-4-(trifluoromethoxy)phenyl]-5-(1-ethylpropyl)-3,7-dimethylpyrrolo[2,1-f][1,2,4]triazin-4(3H)-one (Compound of example 8) | 200 g |
| Mannitol | 20 g |
| Distilled water | 50 L |

Industrial Applicability

The compound of the present invention has a CRF antagonist action, and therefore is effective for preventing and/or treating CRF mediated diseases, for example, neuropsychiatric diseases or digestive diseases, and can be used as a medicament.

The invention claimed is:

1. A compound of a formula (I):

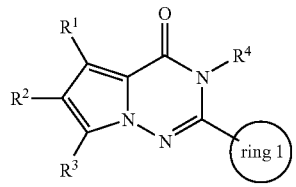

wherein $R^1$ represents
(1) a C3-10 branched alkyl group which may be substituted or
(2) a —$(CH_2)_m$—$NR^5R^6$ group,
$R^5$ and $R^6$ each independently represent a C1-6 alkyl group which may be substituted, or $R^5$ represents a hydrogen atom and $R^6$ represents a C3-6 branched alkyl group which may be substituted,
m represents 0 or an integer of 1 to 3;
$R^2$ represents a hydrogen atom or a C1-4 alkyl group which may be substituted;
$R^3$ represents a C1-4 alkyl group which may be substituted or a halogen atom;
$R^4$ represents a C1-4 alkyl group which may be substituted or a C3-6 cycloalkyl group which may be substituted; and
ring 1 represents a cyclic group which has planarity and may have a substituent group,
a salt thereof, or an N-oxide thereof.

2. The compound according to claim 1, wherein the ring 1 is

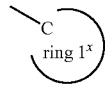

wherein ring $1^x$ represents a cyclic group which has planarity; binds to pyrrolo[2,1-f][1,2,4]triazin-4(3H)-one ring through the carbon atom; and may have a substituent group.

3. The compound according to claim 1, wherein $R^1$ is isopropyl, 1-methylbutyl, 1-ethylpropyl, 1-methylpentyl, 1-ethylbutyl, 1-methylhexyl, 1-ethylpentyl, 1-propylbutyl, 1-methylheptyl, 1-ethylhexyl, 1-propylpentyl, (1S)-1-methylbutyl or (1R)-1-methylbutyl.

4. The compound according to claim 2, wherein ring 1 is benzene, indane, imidazole, pyrazole, pyrazine, pyridine, pyrimidine, pyridazine, thiophene, oxazole, thiazole, isothiazole, indole, benzothiophene, benzoxazole, benzothiazole, benzimidazole, benzofurazan, benzothiadiazole or benzotriazole having 1-3 substituent(s).

5. The compound according to claim 4, wherein ring 1 is benzene, pyridine, pyrimidine or thiazole having 1-3 substituent(s).

6. The compound according to claim 5, wherein ring 1 represents the ring represented by one of the following formulae:

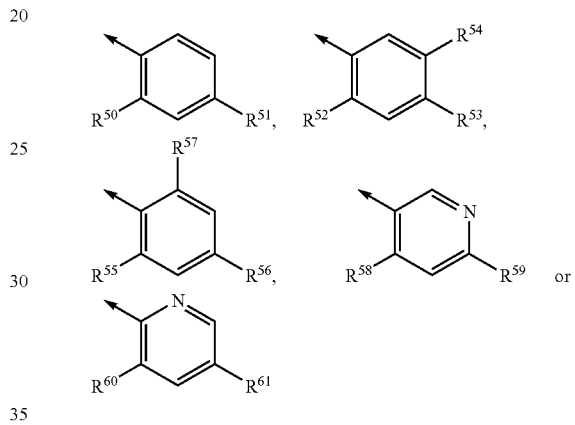

wherein $R^{50}$, $R^{51}$, $R^{52}$, $R^{53}$, $R^{54}$, $R^{55}$, $R^{56}$, $R^{57}$, $R^{58}$, $R^{59}$, $R^{60}$ and $R^{61}$ represent the substituent of ring 1, and arrowhead represents a bond with pyrrolo[2,1-f][1,2,4]triazin-4(3H)-one ring.

7. The compound according to claim 6, wherein $R^{50}$, $R^{51}$, $R^{52}$, $R^{53}$, $R^{54}$, $R^{55}$, $R^{56}$, $R^{57}$, $R^{58}$, $R^{59}$, $R^{60}$ and $R^{61}$ are each independently C1-6 alkyl, C1-6 alkoxy, difluoromethoxy, trifluoromethoxy, C1-6 alkylthio, a halogen atom, or a cyclic group which may be substituted.

8. The compound according to claim 1, wherein the compound is:
<1> 2-[6-(difluoromethoxy)-4-methyl-3-pyridinyl]-5-(1-ethylpropyl)-3,7-dimethylpyrrolo[2,1-f][1,2,4]triazin-4(3H)-one,
<2> 2-[2-chloro-4-(trifluoromethoxy)phenyl]-5-isopropyl-3,7-dimethylpyrrolo[2,1-f][1,2,4]triazin-4(3H)-one,
<3> 2-[2-chloro-4-(methylthio)phenyl]-3-ethyl-5-isopropyl-7-methylpyrrolo[2,1-f][1,2,4]triazin-4(3H)-one,
<4> 2-[2-chloro-4-(trifluoromethoxy)phenyl]-5-(1-ethylpropyl)-3,7-dimethylpyrrolo[2,1-f][1,2,4]triazin-4(3H)-one,
<5> 3-ethyl-5-isopropyl-7-methyl-2-[2-methyl-4-(methylthio)phenyl]pyrrolo[2,1-f][1,2,4]triazin-4(3H)-one,
<6> 2-[2-chloro-4-(methylthio)phenyl]-3,7-dimethyl-5-(1-methybutyl)pyrrolo[2,1-f][1,2,4]triazin-4(3H)-one,
<7> 5-(1-ethylpropyl)-2-(5-fluoro-4-methoxy-2-methylphenyl)-3,7-dimethylpyrrolo[2,1-f][1,2,4]triazin-4(3H)-one,
<8> 2-(4-chloro-2-methylphenyl)-5-(1-ethylpropyl)-3,7-dimethylpyrrolo[2,1-f][1,2,4]triazin-4(3H)-one, <9> 2-[2-chloro-4-(difluoromethoxy)phenyl]-5-(1-ethylpropyl)-3,7-dimethylpyrrolo[2,1-f][1,2,4]triazin-4(3H)-one, <10> 2-(2-ethyl-4-methoxyphenyl)-5-(1-ethylpropyl)-3,7-dimethylpyrrolo[2,1-f][1,2,4]triazin -4(3H)-one, <11> 5-(1-ethylpropyl)-3,7-dimethyl-2-[2-methyl-4-(1H-pyrazol-1-yl)phenyl]pyrrolo[2,1-f][1,2,4]triazin-4(3H)-one, <12> 2-[2-chloro-4-(methylthio)phenyl]-5-(1-ethylpropyl)-3,7-dimethylpyrrolo[2,1-f][1,2,4]triazin-4(3H)-one, <13> 2-(2-chloro-4-methoxyphenyl)-3-cyclopropyl-5-(1-ethylpropyl)-7-methylpyrrolo[2,1-f][1,2,4]triazin-4(3H)-one, <14> 2-(2-chloro-4-methoxy-6-methylphenyl)-5-(1 -ethylpropyl)-3,7-dimethylpyrrolo[2,1-f][1,2,4]triazin-4(3H)-one, <15> 5-(1-ethylpropyl)-2-[4-(1H-imidazol-1-yl)-2-methylphenyl]-3,7-dimethylpyrrolo[2,1-f][1,2,4]triazin-4(3H)-one, <16> 2-(3-chloro-5-methoxy-2-pyridinyl)-5-(1-ethylpropyl)-3,7-dimethylpyrrolo[2,1-f][1,2,4]triazin-4(3H)-one, <17> 2-(2-chloro-5-fluoro-4-methoxyphenyl)-5-(1-ethylpropyl)-3,7-dimethylpyrrolo[2,1-f][1,2,4]triazin-4(3H)-one, <18> 3-ethyl-5-(1-ethylpropyl)-2-(2-fluoro-4-methoxyphenyl)-7-methylpyrrolo[2,1-f][1,2,4]triazin-4(3H)-one, <19> 5-sec-butyl-2-(2-chloro-5-fluoro-4-methoxyphenyl)-3,7-dimethylpyrrolo[2,1-f][1,2,4]triazin-4(3H)-one, <20> 5-sec-butyl-2-[2-chloro-4-(difluoromethoxy)phenyl]-3,7-dimethylpyrrolo[2,1-f][1,2,4]triazin-4(3H)-one, <21> 2-[4-(difluoromethoxy)-5-fluoro-2-methylphenyl]-3-ethyl-5-isopropyl-7-methypyrrolo[2,1-f][1,2,4]triazin-4(3H)-one, <22> 2-[4-(difluoromethoxy)-2-methylphenyl]-3-ethyl-5-isopropyl-7-methylpyrrolo[2,1-f][1,2,4]triazin-4(3H)-one, <23> 2-[2-chloro-4-(difluoromethoxy)-6-fluorophenyl]-3-ethyl-5-isopropyl-7-methylpyrrolo[2,1-f][1,2,4]triazin-4(3H)-one, <24> 2-[2-chloro-4-(difluoromethoxy)phenyl]-3,7-dimethyl-5-(1-methylbutyl)pyrrolo[2,1-f][1,2,4]triazin-4(3H)-one, <25> 2-(2-chloro-5-fluoro-4-methoxyphenyl)-3,7-dimethyl-5-(1-methylbutyl)pyrrolo[2,1-f][1,2,4]triazin-4(3H)-one, <26> 2[6-(difluoromethoxy)-4-methyl-3-pyridinyl]-3,7-dimethyl-5-(1-methylbutyl)pyrrolo[2,1-f][1,2,4]triazin-4(3H)-one, <27> 2-[5-chloro-4-(difluoromethoxy)-2-methylphenyl]-3-ethyl-5-isopropyl-7-methylpyrrolo [2,1-f][1,2,4]triazin-4(3H)-one, <28> 2-[2-chloro-4-(methylthio)phenyl]-3,7-dimethyl-5-[(1S)-1-methylbutyl]pyrrolo[2,1-f][1,2,4]triazin-4(3H)-one, or <29> 2-[2-chloro-4-(methylthio)phenyl]-3,7-dimethyl-5-[(1R)-1-methylbutyl]pyrrolo[2,1-f][1,2,4]triazin-4(3H)-one.

9. A pharmaceutical composition containing as an active ingredient the compound of the formula (I) described in claim 1, a salt thereof, or an N-oxide thereof.

10. The pharmaceutical composition according to claim 9, which is a CRF antagonist.

11. The pharmaceutical composition according to claim 9, which is an agent for treating depression, anxiety, obesity, or irritable bowel syndrome.

12. The pharmaceutical composition according to claim 11, wherein the anxiety is associated with generalized anxiety disorder, panic disorder, posttraumatic stress disorder, obsessive compulsive disorder, social anxiety disorder, or phobic disorder.

13. A method for treating depression, anxiety, obesity, or irritable bowel syndrome, comprising administering an effective amount of the compound of the formula (I) described in claim 1, a salt thereof, or an N-oxide thereof, to a mammal in need thereof.

14. The method according to claim 13, wherein said anxiety is associated with generalized anxiety disorder, panic disorder, posttraumatic stress disorder, obsessive compulsive disorder, social anxiety disorder, or phobic disorder.

15. A method for treating a stress-related disorder, comprising administering an effective amount of the compound of formula (I) described in claim 1, a salt thereof, or an N-oxide thereof, to mammal with a stress-related disorder, wherein the administration of said compound treats said disorder by reducing the mammal's stress level.

16. The method for treating a stress-related disorder according to claim 15, wherein the stress-related disorder is a gastrointestinal disorder caused by stress.

17. A method for treating alcoholism or drug intoxication, comprising administering an effective amount of the compound of the formula (I) described in claim 1, a salt thereof, or an N-oxide thereof, to a mammal in need thereof.

18. A method for treating bipolar disorder or premenstrual dysphoric disorder comprising administering an effective amount of the compound of the formula (I) described in claim 1, a salt thereof, or an N-oxide thereof, to a mammal in need thereof.

* * * * *